(12) United States Patent
Wentzler et al.

(10) Patent No.: US 7,528,147 B2
(45) Date of Patent: May 5, 2009

(54) PYRROLO (2,3-B)PYRIDINE DERIVATIVES, THE PREPARATION AND THE PHARMACEUTICAL USE THEREOF IN THE FORM OF KINASE INHIBITORS

(75) Inventors: Sylvie Wentzler, Fresnes (FR); Youssef El-Ahmad, Creteil (FR); Bruno Filoche-Rommé, Creteil (FR); Conception Nemecek, Thiais (FR); Corinne Venot, Paris (FR); Augustin Hittinger, Igny (FR)

(73) Assignee: Aventis Pharma S.A., Antony (FR)

( * ) Notice: Subject to any disclaimer, the term of this patent is extended or adjusted under 35 U.S.C. 154(b) by 238 days.

(21) Appl. No.: 11/541,051

(22) Filed: Sep. 29, 2006

(65) Prior Publication Data

US 2007/0093480 A1 Apr. 26, 2007

Related U.S. Application Data

(63) Continuation of application No. PCT/FR05/000773, filed on Mar. 30, 2005.

(30) Foreign Application Priority Data

Mar. 31, 2004 (FR) .................... 04 03354

(51) Int. Cl.
```
A01N 43/42    (2006.01)
A61K 31/44    (2006.01)
C07D 471/02   (2006.01)
C07D 491/02   (2006.01)
C07D 498/02   (2006.01)
C07D 513/02   (2006.01)
C07D 515/02   (2006.01)
```
(52) U.S. Cl. .................... 514/300; 546/113
(58) Field of Classification Search ........... 546/113; 514/300
See application file for complete search history.

(56) References Cited

U.S. PATENT DOCUMENTS

| 6,770,643 B2 | 8/2004 | Cox |
| 6,897,207 B2 | 5/2005 | Cox |
| 7,227,020 B2 | 6/2007 | Cox et al. |
| 2005/0267304 A1 | 12/2005 | Cox et al. |

FOREIGN PATENT DOCUMENTS

| WO | 01/47922 | * | 7/2001 |
| WO | 03/000688 | * | 1/2003 |
| WO | 03/000690 | * | 1/2003 |
| WO | WO03/000688 | | 1/2003 |

OTHER PUBLICATIONS

Daaka et al., Biochimica et Biophysica Acta, Molecular and Cell Biology of Lipids (2002), 1582(1-3), 265-269.*

* cited by examiner

*Primary Examiner*—D. Margaret Seaman
*Assistant Examiner*—Niloofar Rahmani
(74) *Attorney, Agent, or Firm*—Kelly L. Bender

(57) ABSTRACT

Novel compounds of formula (I):

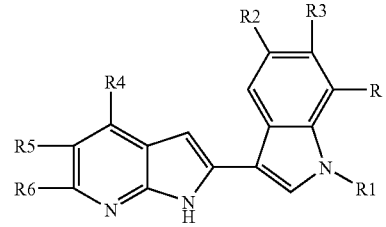

(I)

or pharmaceutically acceptable salts thereof, wherein R, R1, R2, R3, R4, R5, and R6 have the meanings given in the description, pharmaceutical compositions comprising said compounds and use thereof as protein kinase inhibitors.

42 Claims, 6 Drawing Sheets

Pathway A: For obtaining 2-(1H-Indol-3-yl)-1H-pyrrolo[2,3-b]pyridine derivatives Introduction of the substituents in the R3 position Introduction of the 2-(1H-Indol-3-yl)-1H-pyrrolo[2,3-b]pyridine-4-carboxaldehyde derivatives

PYRROLO (2,3-B)PYRIDINE DERIVATIVES, THE PREPARATION AND THE PHARMACEUTICAL USE THEREOF IN THE FORM OF KINASE INHIBITORS

The present invention relates to novel pyrrolo(2,3-b)pyridine derivatives, to a process for preparing them, to their use as medicinal products, to pharmaceutical compositions containing them and to the pharmaceutical use of such derivatives for preventing and treating conditions that may be modulated by inhibiting the activity of protein kinases.

The present invention relates to novel pyrrolo(2,3-b)pyridine derivatives that have inhibitory effects on protein kinases.

The compounds of the present invention may thus be used in particular for preventing or treating conditions that may be modulated by inhibiting the activity of protein kinases.

The inhibition and regulation of protein kinases in particular constitute a powerful new mechanism of action for treating a large number of solid tumors.

Such conditions that can be treated by the compounds of the present application are therefore most particularly solid tumors.

Such protein kinases belong in particular to the following group:
IGF1, Raf, EGF, PDGF, VEGF, Tie2, KDR, Fltl-3, FAK, Src, Abl, cKit, cdk1-9, Aurora 1-2, cdc7, Akt, Pdk, S6K, Jnk, IR, FLK-1, FGFR1, FGFR2, FGFR3, FGFR4, FGFR5, PLK, Pyk2

Such protein kinases belong more particularly to the following group: IGF1, cdc7, Aurora 1-2, Src, Jnk, FAK, KDR, IR, Tie2

The protein kinase IGF1 (Insulin Growth Factor-1) is particularly indicated.

The present invention thus relates particularly to novel inhibitors of the IGF-1R receptor which can be used for oncology treatments.

Cancer remains a disease for which the existing treatments are clearly insufficient. Certain protein kinases play an important role in many cancers. The inhibition of such protein kinases is potentially important in the chemotherapy of cancers, in particular for suppressing tumor growth or survival. The present invention therefore relates to the identification of novel compounds which inhibit such protein kinases.

Protein kinases participate in signaling events that control the activation, growth and differentiation of cells in response either to extracellular mediators or to changes in the environment. In general, these kinases belong to two groups: those which preferentially phosphorylate serine and/or threonine residues and those which preferentially phosphorylate tyrosine residues [S. K. Hanks and T. Hunter, FASEB, J., 1995, 9, pages 576-596]. Serine/threonine kinases are, for example, the isoforms of the protein kinases C [A. C. Newton, J. Biol. Chem., 1995, 270, pages 28495-28498] and a group of cycline-dependent kinases, such as cdc2 [J. Pines, Trends in Biochemical Sciences, 1995, 18, pages 195-197]. Tyrosine kinases comprise growth factor receptors, such as the epidermal growth factor (EGF) receptor [S. Iwashita and M. Kobayashi, Cellular Signalling, 1992, 4, pages 123-132], and cytosolic kinases such as p56tck, p59fYn, ZAP-70 and the csk kinases [C. Chan et al., Ann. Rev. Immunol., 1994, 12, pages 555-592].

Abnormally high levels of protein kinase activity have been implicated in many diseases, resulting from abnormal cellular functions. This may arise either directly or indirectly from a dysfunction in the mechanisms controlling the kinase activity, linked, for example, to a mutation, an overexpression or an inappropriate activation of the enzyme, or an over- or underproduction of cytokines or of growth factors, also involved in transduction of the signals upstream or downstream of the kinases. In all these cases, selective inhibition of the action of the kinases offers hope of a beneficial effect.

The type 1 receptor for insulin-like growth factor (IGF-I-R) is a transmembrane receptor with tyrosine kinase activity which binds firstly to IGFI, but also to IGFII and to insulin with lower affinity. The binding of IGFI to its receptor results in oligomerization of the receptor, activation of the tyrosine kinase, intermolecular autophosphorylation and phosphorylation of cell substrates (main substrates: IRS1 and Shc). The receptor activated by its ligand induces mitogenic activity in normal cells. However, IGF-I-R plays an important role in "abnormal" growth.

Several clinical reports underline the important role of the IGF-I pathway in the development of human cancers:

IGF-I-R is often found to be overexpressed in many tumor types (breast, colon, lung, sarcoma, etc.) and its presence is often associated with a more aggressive phenotype.

High concentrations of circulating IGF1 are strongly correlated with a risk of prostate cancer, lung cancer and breast cancer.

In addition, it has been widely documented that IGF-I-R is necessary for establishing and maintaining the transformed phenotype in vitro as in vivo [Baserga R, Exp. Cell, Res., 1999, 253, 253, pages 1-6]. The kinase activity of IGF-I-R is essential to the transforming activity of several oncogenes: EGFR, PDGFR, SV40 virus large T antigen, activated Ras, Raf, and v-Src. The expression of IGF-I-R in normal fibroblasts induces a neoplastic phenotype, which may then result in the formation of a tumor in vivo. The expression of IGF-I-R plays an important role in substrate-independent growth. IGF-I-R has also been shown to be a protector in chemotherapy-induced and radiation-induced apoptosis, and cytokine-induced apoptosis. In addition, the inhibition of endogenous IGF-I-R by means of a dominant negative, the formation of a triple helix or the expression of an antisense brings about suppression of the transforming activity in vitro and reduction of tumor growth in animal models.

Figure 1:
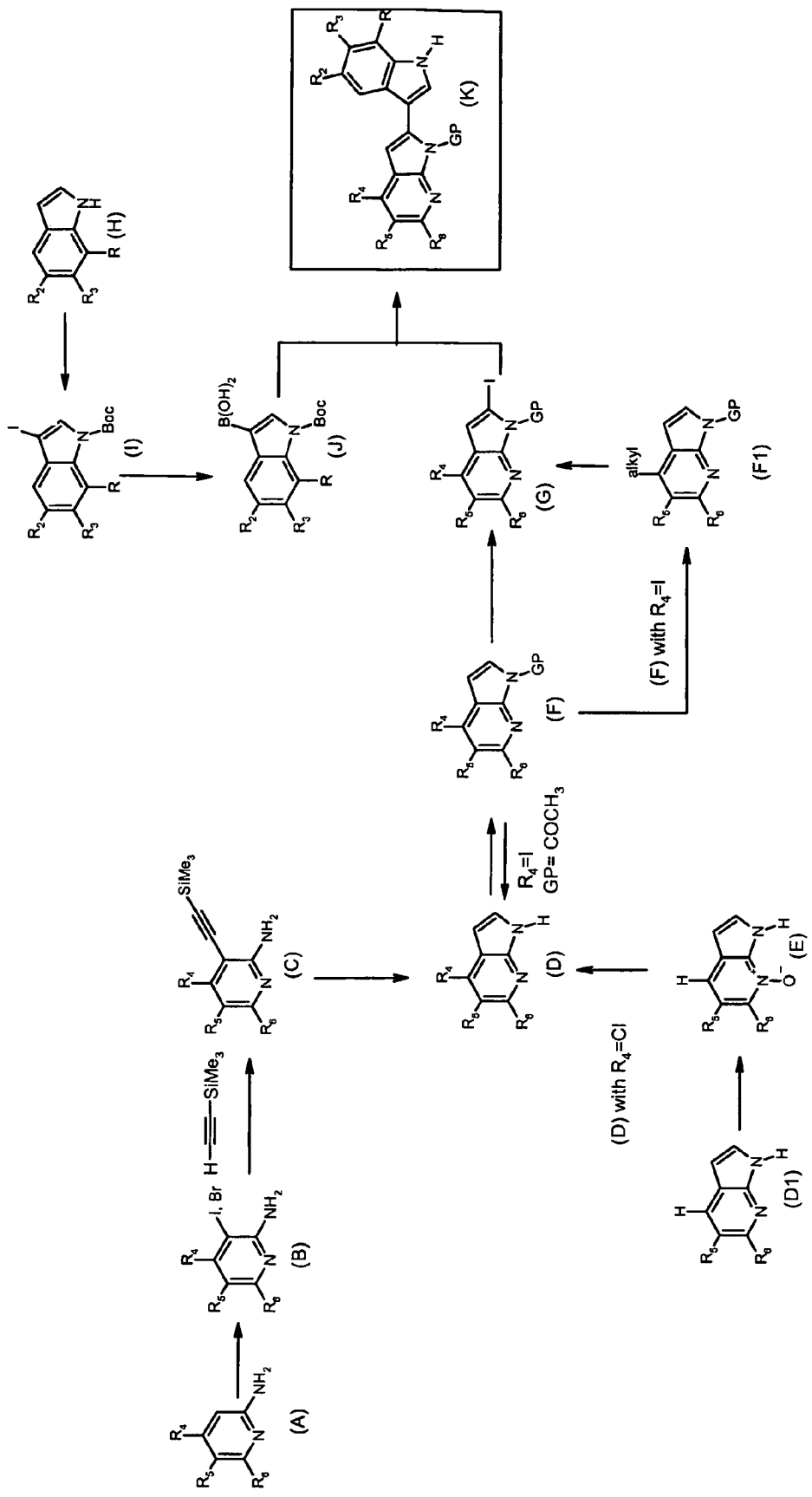
FIG. 1 (Scheme 1) describes a pathway "A" for obtaining the compounds of formula (I): 2-(1H-indol-3-yl)-1H-pyrrolo [2,3-b]pyridine.

A subject of the present invention is the compounds of formula (I):

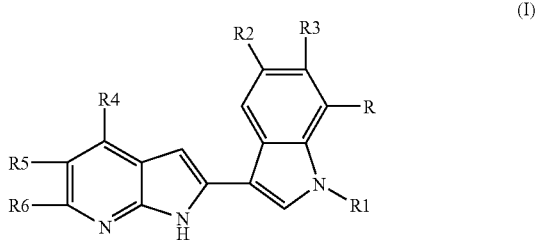

in which:
R represents hydrogen or is selected from the values of R2 and R3,
R1 represents alkenyl or alkyl optionally substituted with —CO—NR7R8, —NR7R8, free or esterified carboxyl, hydroxyl, alkoxy or a halogen atom,
R2 and R3, which may be identical or different, represent alkyl or —O-alkyl optionally substituted with —CO—NR7R8,
—NR7R8, alkoxy, alkoxy-NR7R8, free or esterified carboxyl, or phenyl, which is itself optionally substituted,
R4, R5 and R6, which may be identical or different, are selected from a hydrogen atom, halogen atoms and cyano, amino, and optionally substituted alkoxy or alkyl radicals, R4 also possibly being selected from the following values: carboxaldehyde —CH=O, formaldoxime —CH=N—OH and methylhydroxylamine —CH2NHOH;
R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted,
all the above alkyl, alkenyl, cycloalkyl, cycloalkenyl, heterocycloalkyl, aryl and heteroaryl radicals, which may be monocyclic or bicyclic, and also the heterocyclic radical formed by R7 and R8 with the nitrogen atom to which they are attached, being optionally substituted with one or more radicals, which may be identical or different, selected from halogen atoms and cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)-C(=O)—R9, —N(R11)-C(=O)—OR10, —NR12R13, —C(=O)—NR12R13, —N(R11)-C(=O)—NR12R13, —S(O)n-R9, —N(R11)-S(O)n-R9, —S(O)n-NR12R13 and —N(R11)-S(O)n-NR12R13 radicals,
n represents an integer from 0 to 2,
the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from halogen atoms and hydroxyl, alkyl, alkoxy, —NR12R13, free or esterified carboxyl, CF3, nitro, cyano, phenyl and phenylalkyl radicals in which the phenyl radical is itself optionally substituted with one or more radicals, which may be identical or different, selected from halogen atoms and hydroxyl, alkyl, alkoxy, free or esterified carboxyl, CF3, nitro, cyano and pyridyl radicals;

R9 represents alkyl, alkenyl, cycloalkyl, heterocycloalkyl, aryl, heteroaryl, cycloalkylalkyl, heterocycloalkylalkyl, arylalkyl and heteroarylalkyl, all these radicals being optionally substituted,
R10 represents the values of R9 and hydrogen,
R11 represents hydrogen or optionally substituted alkyl,
R12 and R13, which may be identical or different, represent hydrogen, acyl, alkyl, cycloalkyl, heterocycloalkyl, heteroaryl, SO2-heteroaryl, —SO2-alkyl, —SO2-phenyl, —CO—NH-phenyl and phenyl radicals, all these radicals being optionally substituted,
or alternatively R12 and R13 form, with the nitrogen atom to which they are attached, an unsaturated or partially or totally saturated 3- to 10-membered heterocyclic radical containing one or more hetero atoms selected from O, S, N and NR14, this radical being optionally substituted,
R14 represents the values of R9 and hydrogen, acyl and free and esterified carboxyl,
the radicals R9, R10, R11, R12, R13 and R14 above, and also the cyclic radical that may be formed by R12 and R13 with the nitrogen atom to which they are attached, being optionally substituted with one or more radicals, which may be identical or different, selected from halogen atoms and alkyl, alkyl-NH2, alkyl-NHCO2alkyl, NH2, NHCO2alkyl, hydroxyl, alkoxy, hydroxyalkoxy, free or esterified carboxyl, CF3, SCF3, OCF3, OCHF2, SO2CF3, nitro, cyano, heterocycloalkyl, heteroaryl and phenyl radicals, the latter cyclic radicals themselves being optionally substituted with one or more radicals, which may be identical or different, selected from halogen atoms and alkyl, hydroxyl, alkoxy, free or esterified carboxyl, CF3, SCF3, OCF3, OCHF2, SO2CF3, NH2, NHCO2alkyl, nitro and cyano radicals,
all the above aryl, heteroaryl and heterocycloalkyl radicals moreover being optionally substituted with an alkylenedioxy radical,
all the above alkyl, alkenyl, alkoxy or —O-alkyl and alkylthio radicals being linear or branched and containing no more than 6 carbon atoms,
all the above cycloalkyl radicals containing no more than 7 carbon atoms,
all the above aryl, heteroaryl and heterocycloalkyl radicals containing no more than 10 carbon atoms,
said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which:
R represents hydrogen or is selected from the values of R2 and R3,
R1 represents alkenyl or alkyl optionally substituted with —CO—NR7R8, —NR7R8, free or esterified carboxyl, hydroxyl, alkoxy or a halogen atom,
R2 and R3, which may be identical or different, represent alkyl or —O-alkyl optionally substituted with —CO—NR7R8,
—NR7R8, alkoxy, alkoxy-NR7R8, free or esterified carboxyl, or phenyl, which is itself optionally substituted,
R4, R5 and R6, which may be identical or different, are selected from a hydrogen atom, halogen atoms and cyano, amino, and optionally substituted alkoxy or alkyl radicals, R4 also possibly being selected from the following values: carboxaldehyde —CH=O, formaldoxime —CH=N—OH and methylhydroxylamine —CH2NHOH;

R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted, all the above alkyl, alkenyl, cycloalkyl, cycloalkenyl, heterocycloalkyl, aryl and heteroaryl radicals, which may be monocyclic or bicyclic, and also the heterocyclic radical formed by R7 and R8 with the nitrogen atom to which they are attached, being optionally substituted with one or more radicals, which may be identical or different, selected from halogen atoms and cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)-C(=O)—R9, —N(R11)-C(=O)—OR10, —NR12R13, —C(=O)—NR12R13, —N(R11)-C(=O)—NR12R13, —S(O)n-R9, —N(R11)-S(O)n-R9, —S(O)n-NR12R13 and —N(R11)-S(O)n-NR12R13 radicals, n represents an integer from 0 to 2, the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from halogen atoms and hydroxyl, alkyl, alkoxy, —NR12R13, free or esterified carboxyl, CF3, nitro, cyano, phenyl and phenylalkyl radicals in which the phenyl radical is itself optionally substituted with one or more radicals, which may be identical or different, selected from halogen atoms and hydroxyl, alkyl, alkoxy, free or esterified carboxyl, CF3, nitro, cyano and pyridyl radicals;

R9 represents alkyl, alkenyl, cycloalkyl, heterocycloalkyl, aryl, heteroaryl, cycloalkylalkyl, heterocycloalkylalkyl, arylalkyl and heteroarylalkyl, all these radicals being optionally substituted, R10 represents the values of R9 and hydrogen, R11 represents hydrogen or optionally substituted alkyl, R12 and R13, which may be identical or different, represent hydrogen, acyl, alkyl, cycloalkyl, piperidyl, piperazinyl, pyrrolidinyl, azetidinyl, pyrazolyl, pyridyl, imidazolyl, pyrimidyl, thiazolyl, thiazolidinyl, —SO2-thienyl, —SO2-pyridyl, —SO2-alkyl, —SO2-phenyl, —CO—NH-phenyl and phenyl radicals, all these radicals being optionally substituted, or alternatively R12 and R13 form, with the nitrogen atom to which they are attached, an unsaturated or partially or totally saturated 3- to 10-membered heterocyclic radical containing one or more hetero atoms selected from O, S, N and NR14, this radical being optionally substituted, R14 represents the values of R9 and hydrogen, acyl and free and esterified carboxyl, the radicals R9, R10, R11, R12, R13 and R14 above, and also the cyclic radical that may be formed by R12 and R13 with the nitrogen atom to which they are attached, being optionally substituted with one or more radicals, which may be identical or different, selected from halogen atoms and alkyl, —CH2-NH2, —CH2-NHCO2alkyl, NH2, NHCO2alkyl, hydroxyl, alkoxy, hydroxyalkoxy, free or esterified carboxyl, CF3, SCF3, OCF3, OCHF2, SO2CF3, nitro, cyano, piperidyl, morpholinyl, piperazinyl, thienyl, pyridyl, imidazolyl, thiazolyl, thiazolidinyl and phenyl radicals, the latter cyclic radicals themselves being optionally substituted with one or more radicals, which may be identical or different, selected from halogen atoms and alkyl, hydroxyl, alkoxy, free or esterified carboxyl, CF3, SCF3, OCF3, OCHF2, SO2CF3, NH2, NHCO2alkyl, nitro and cyano radicals, all the above aryl, heteroaryl and heterocycloalkyl radicals moreover being optionally substituted with an alkylenedioxy radical, all the above alkyl, alkenyl, alkoxy or —O-alkyl and alkylthio radicals being linear or branched and containing no more than 6 carbon atoms, all the above cycloalkyl radicals containing no more than 7 carbon atoms, all the above aryl, heteroaryl and heterocycloalkyl radicals containing no more than 10 carbon atoms, said compounds of formula (I) being in any possible racemic, enantiomeric or diastereoisomeric isomer form, and also the addition salts with mineral and organic acids or with mineral and organic bases of said compounds of formula (I).

A subject of the present invention is the compounds of formula (I):

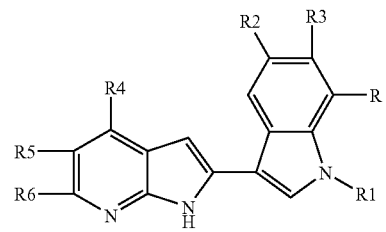

in which:

R represents hydrogen or is selected from the values for R2 and R3,

R1 represents alkenyl or alkyl optionally substituted with —CO—NR7R8, —NR7R8, free or esterified carboxyl, hydroxyl, alkoxy or a halogen atom, R2 and R3, which may identical or different, represent alkyl or —O-alkyl optionally substituted with —CO—NR7R8, —NR7R8, hydroxyl, alkoxy, alkoxy-NR7R8, free or esterified carboxyl, or phenyl which is itself optionally substituted, R4, R5 and R6, which may be identical or different, are selected from the hydrogen atom, the halogen atoms and the radicals: cyano, amino, alkoxy or alkyl, which is optionally substituted, R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated heterocyclic radical consisting of 3 to 10 ring members and containing one or more hetero atoms selected from O, S, N and NR14, this radical being optionally substituted, all the above radicals: alkyl, alkenyl, cycloalkyl, cycloalkenyl, heterocycloalkyl, aryl and heteroaryl, which may be monocyclic or bicyclic, and also the heterocyclic radical formed by R7 and R8 with the nitrogen atom to which they are attached, being optionally substituted with one or more radicals, which may be identical or different, selected from the halogen atoms and the radicals: cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)-C(=O)—R9, —N(R11)-C(=O)—OR10, —NR12R13, —C(=O)—NR12R13, —N(R11)-C(=O)—NR12R13, —S(O)n-R9, —N(R11)-S(O)n-R9, —S(O)n-NR12R13 and —N(R11)-S(O)n-NR12R13, n represents an integer from 0 to 2, the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from the halogen atoms and the radicals: hydroxyl, alkyl, alkoxy, —NR12R13, free or esterified carboxyl, CF$_3$, nitro, cyano, pyrrolidinyl, and phenyl and phenylalkyl in which the phenyl radical is itself optionally substituted with one or more radicals, which may be identical or different, selected from the halogen atoms and the radicals: hydroxyl, alkyl, alkoxy, free or esterified carboxyl, CF$_3$, nitro, cyano and pyridyl, R9 represents alkyl, alkenyl, cycloalkyl, heterocycloalkyl, aryl, heteroaryl, cycloalkylalkyl, heterocycloalkylalkyl, arylalkyl, and heteroarylalkyl, all these radicals being optionally substituted, R10 represents the values of R9 and hydrogen, R11 represents hydrogen or optionally substituted alkyl, R12 and R13, which may be identical or different, represent hydrogen, acyl, alkyl, cycloalkyl and phenyl, these radicals being optionally substituted, or alternatively R12 and R13 form, with the nitrogen atom to which they are attached, an unsaturated or partially or totally saturated heterocyclic radical consisting of 3 to 10 ring members and containing one or more hetero atoms selected from O, S, N and NR14, the radical being optionally substituted, R14 represents the values for R9 and hydrogen, acyl and free and esterified carboxyl, the radicals R9, R10, R11, R12, R13 and R14 above being optionally substituted with one or more radicals, which may be identical or different, selected from the halogen atoms and the radicals: alkyl, hydroxyl, alkoxy, hydroxyalkoxy, free or esterified carboxyl, CF$_3$, nitro, cyano and phenyl, itself optionally substituted with one or more radicals, which may be identical or different, selected from the halogen atoms and the radicals: alkyl, hydroxyl, alkoxy, free or esterified carboxyl, CF$_3$, nitro and cyano, all the aryl, heteroaryl and heterocycloalkyl radicals above being, in addition, optionally substituted with an alkylenedioxy radical, all the alkyl, alkenyl, alkoxy or —O-alkyl and alkylthio radicals above being linear or branched and containing no more than 6 carbon atoms, all the cycloalkyl radicals above containing no more than 7 carbon atoms, all the aryl, heteroaryl and heterocycloalkyl radicals above containing no more than 10 carbon atoms, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R2 and R3, which may be identical or different, represent —O-alkyl containing no more than 4 carbon atoms, optionally substituted with —CO—NR7R8, —NR7R8, alkoxy, alkoxy-NR7R8 or free or esterified carboxyl, the other substituents of said compounds of formula (I) having the values defined above in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R2 and R3, which may be identical or different, represent —O-alkyl containing no more than 4 carbon atoms, optionally substituted with —CO—NR7R8, —NR7R8, alkoxy, alkoxy-NR7R8, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R2 and R3, which may be identical or different, represent —O-alkyl containing at most 4 carbon atoms, optionally substituted with —CO—NR7R8 or —NR7R8, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R1 represents alkyl optionally substituted with —CO—NR7R8, —NR7R8, free or esterified carboxyl, hydroxyl, alkoxy, or a halogen atom, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R1 represents alkyl containing no more than 4 carbon atoms, optionally substituted with —CO—NR7R8, —NR7R8, free or esterified carboxyl, or hydroxyl, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R1 represents alkyl containing no more than 4 carbon atoms, optionally substituted with —CO—NR7R8, —NR7R8 or hydroxyl, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined in any one of the other claims, in which R1 represents alkyl containing no more than 4 carbon atoms, optionally substituted with —CO—NR7R8 or —NR7R8, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R1 represents alkyl containing no more than 4 carbon atoms, optionally substituted with NR7R8, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which:

R4, R5 and R6 are such that one represents hydrogen and the others, which may be identical or different, are selected from the hydrogen atom, the halogen atoms and the radicals: cyano, amino or alkyl which may be optionally substituted, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 are such that R5 and R6, which may be identical or different, are selected from a hydrogen atom and halogen atoms, and R4, which may be identical to or different from R5 and R6, is selected from halogen atoms and amino, carboxaldehyde —CH=O, formaldoxime —CH=N—OH, methylhydroxylamine —CH2NHOH and alkyl radicals, optionally substituted with one or more radicals, which may be identical or different, selected from halogen atoms and cyano, hydroxyl, alkoxy, cycloalkyl, heterocycloalkyl, phenyl, heteroaryl and —NR12R13 radicals;

R, R1, R2, R3, R12 and R13 having the values defined in any one of the other claims, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which:

R4, R5 and R6 represent hydrogen or are such that two of them represent hydrogen and the third represents a halogen atom or the cyano radical, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 represent hydrogen, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 are such that two of them represent hydrogen and the third represents a halogen atom or the cyano radical, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 are such that two of them represent hydrogen and the third represents a halogen atom, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 are such that two of them represent hydrogen and the third represents a chlorine or fluorine atom, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4, R5 and R6 are such that two of them represent hydrogen and the third represents the cyano radical, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R6 represents hydrogen, the other substituents of said compounds of formula (I) having the values defined above and in the present invention, said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R5 and R6 represent hydrogen and R4 represents a halogen atom or the cyano radical, the other substituents of said compounds of formula (I) having the values defined above and in the present invention,
said compounds of formula (I) being in any possible racemic, enantiomeric or diastereoisomeric isomer form, and also the addition salts with mineral and organic acids or with mineral and organic bases of said compounds of formula (I).

A subject of the present invention is thus the compounds of formula (I) as defined above and in the present invention, in which R4 and R6 represent hydrogen and R5 represents a fluorine atom, the other substituents of said compounds of formula (I) having the values defined above and in the present invention,
said compounds of formula (I) being in any possible racemic, enantiomeric or diastereoisomeric isomer form, and also the addition salts with mineral and organic acids or with mineral and organic bases of said compounds of formula (I).

In the compounds of formula (I) and in the following text, the terms indicated have the following meanings:

the term "Hal", "Halo" or "halogen" denotes fluorine, chlorine, bromine or iodine atoms;

the term "alkyl radical" or "alk radical" denotes a linear or branched radical containing no more than 12 carbon atoms, selected from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl and also heptyl, octyl, nonyl, decyl, undecyl and dodecyl radicals, and also the linear or branched positional isomers thereof.

Mention is made more particularly of alkyl radicals having no more than 6 carbon atoms, and in particular methyl, ethyl, propyl, isopropyl, n-butyl, isobutyl, tert-butyl, linear or branched pentyl and linear or branched hexyl radicals;

the term "alkylene radical", denotes a linear or branched radical containing no more than 12 carbon atoms, and preferably 4 carbon atoms, selected, for example, from the following values: ethenyl or vinyl, propenyl or allyl, 1-propenyl, n-butenyl, i-butenyl, 3-methylbut-2-enyl, n-pentenyl, hexenyl, heptenyl, octenyl, cyclohexylbutenyl and decenyl, and also the linear or branched positional isomers thereof.

Among the alkenyl values, mention may be made more particularly of the allyl or butenyl values:

the term "alkoxy radical" or "O-alkyl radical" denotes a linear or branched radical containing no more than 12 carbon atoms, and preferably 6 carbon atoms, selected, for example, from methoxy, ethoxy, propoxy, isopropoxy, linear, secondary or tertiary butoxy, pentoxy, hexoxy and heptoxy radicals, and also the linear or branched positional isomers thereof;

the term "alkoxycarbonyl radical", or "alkyl-O—CO— radical", denotes a linear or branched radical containing no more than 12 carbon atoms, in which the alkyl radical has the meaning given above; mention may be made, for example, of methoxycarbonyl and ethoxycarbonyl radicals;

the term "alkylenedioxy radical" or "—O-alkylene-O— radical" denotes a linear or branched radical containing no more than 12 carbon atoms, in which the alkylene radical has the meaning given above; mention may be made, for example, of methylenedioxy and ethylenedioxy radicals;

the term "alkylsulfinyl" or "alkyl-SO—" denotes a linear or branched radical containing no more than 12 carbon atoms, in which the alkyl radical has the meaning given above and preferably contains 4 carbon atoms;

the term "alkylsulfonyl" or "alkyl-SO$_2$-" denotes a linear or branched radical containing no more than 12 carbon atoms, in which the alkyl radical has the meaning given above and preferably contains 4 carbon atoms;

the term "alkylsulfonylcarbamoyl" or "alkyl-SO$_2$—NH—C(=O)-" denotes a linear or branched radical containing no more than 12 carbon atoms, in which the alkyl radical has the meaning given above and preferably contains 4 carbon atoms;

the term "alkylthio" or "alkyl-S-" denotes a linear or branched radical containing no more than 12 carbon atoms and represents in particular methylthio, ethylthio, isopropylthio and heptylthio radicals;

the term "cycloalkyl radical" denotes a 3- to 10-membered monocyclic or bicyclic carbocyclic radical and denotes in particular cyclopropyl, cyclobutyl, cyclopentyl and cyclohexyl radicals;

the term "—O-cycloalkyl radical" denotes a radical in which the cycloalkyl radical has the meaning given above;

the term "cycloalkenyl radical" denotes a monocyclic or bicyclic nonaromatic carbocyclic radical containing at least one double bond and having from 3 to 10 ring members, and denotes in particular cyclobutenyl, cyclopentenyl or cyclohexenyl radicals;

the term "cycloalkylalkyl radical" denotes a radical in which the cycloalkyl and alkyl are selected from the values indicated above; this radical thus denotes, for example, cyclopropylmethyl, cyclopentylmethyl, cyclohexylmethyl and cycloheptylmethyl radicals;

the term "acyl radical" or "r-CO— radical" denotes a linear or branched radical containing no more than 12 carbon atoms, in which the radical r represents a hydrogen atom or an alkyl, cycloalkyl, cycloalkenyl, cycloalkyl, heterocycloalkyl, aryl or heteroaryl radical, these radicals having the optionally substituted values indicated above and hereinafter; thus, the acyl radical represents in particular CO-alkyl, CO-aryl or CO-heteroaryl. Mention may be made, for example, of formyl, acetyl, propionyl, butyryl or benzoyl radicals, or else valeryl, hexanoyl, acryloyl, crotonoyl, carbamoyl, pyrrolidinylcarboxyl or furylcarboxyl radicals;

the term "acyloxy radical" is intended to mean acyl-O- radicals in which acyl has the meaning given above; mention may be made, for example, of acetoxy or propionyloxy radicals;

the term "acylamino radical" is intended to mean acyl-NH radicals in which acyl has the meaning given above;

the term "aryl radical" denotes unsaturated monocyclic radicals or unsaturated radicals consisting of fused carbocyclic rings. As examples of such aryl radicals, mention may be made of phenyl or naphthyl radicals.

Mention is more particularly made of the phenyl radical.

The term "arylalkyl" is intended to mean radicals resulting from the combination of the optionally substituted alkyl radicals mentioned above and the optionally substituted aryl radicals also mentioned above; mention may be made, for example, of benzyl, phenylethyl, 2-phenylethyl, triphenylmethyl or naphthalenemethyl radicals;

the term "heterocyclic radical" denotes a saturated carbocyclic radical (heterocycloalkyl) or unsaturated carbocyclic radical (heteroaryl) which is at most 6-membered, interrupted with one or more hetero atoms, which may be identical or different, selected from oxygen, nitrogen and sulfur atoms.

Heterocycloalkyl radicals which may be in particular be mentioned include dioxolane, dioxane, dithiolane, thiooxolane, thiooxane, oxiranyl, oxolanyl, dioxolanyl, piperazinyl, piperidyl, pyrrolidyl, imidazolidinyl, pyrazolidinyl, morpholinyl, or tetrahydrofuryl, tetrahydrothienyl, chromanyl, dihydrobenzofuranyl, indolinyl, piperidyl, perhydropyranyl, pyrindolinyl, tetrahydroquinolyl, tetrahydroisoquinolyl or thio-azolidinyl, piperidyl, tetrahydrofuran-2-yl, imidazolinyl, dihydropyrrolyl, tetrahydropyrrolyl, diazepine, perhydro-1,4-diazepine, tetrahydropyrrolo[3,4-c]pyrrol-2-one, tetrahydropyrrolo[3,4-c]pyrrol-1,3-dione and 1,4-dioxa-8-azaspiro[4.5]decane radicals, all these radicals being optionally substituted.

Among the heterocycloalkyl radicals, mention may in particular be made of piperazinyl, piperidyl, pyrrolidinyl, imidazolidinyl, pyrazolidinyl, morpholinyl, thioazolidinyl, piperidyl radicals; tetrahydrofuran-2-yl, imidazolinyl, dihydropyrrolyl, tetrahydropyrrolyl, diazepine, perhydro-1,4-diazepine, tetrahydropyrrolo[3,4-c]pyrrol-2-one, tetrahydropyrrolo-[3,4-c]pyrrol-1,3-dione and 1,4-dioxa-8-azaspiro [4.5]decane radicals, all these radicals being optionally substituted.

the term "heterocycloalkylalkyl radical" is intended to mean radicals in which the heterocycloalkyl and alkyl residues have the above meanings.

Among the 5-membered heteroaryl radicals, mention may be made of furyl radicals such as 2-furyl, thienyl radicals such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl radicals.

Among the 6-membered heteroaryl radicals, mention may in particular be made of pyridyl radicals such as 2-pyridyl, 3-pyridyl and 4-pyridyl, and pyrimidyl, pyrimidinyl, pyridazinyl, pyrazinyl and tetrazolyl radicals.

As fused heteroaryl radicals containing at least one hetero atom selected from sulfur, nitrogen and oxygen, mention may be made, for example, of benzothienyl such as 3-benzothienyl, benzofuryl, benzopyranyl, benzofuranyl, benzopyrrolyl, benzimidazolyl, benzoxazolyl, thionaphthyl, indolyl, purinyl, quinolyl, isoquinolyl and naphthyridinyl.

Among the fused heteroaryl radicals, mention may be made more particularly of benzothienyl, benzofuranyl, indolyl, quinolyl, benzimidazolyl, benzothiazolyl, furyl, imidazolyl, indolizinyl, isoxazolyl, isoquinolyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl, and thienyl radicals and triazolyl groups, these radicals being optionally substituted as indicated for the heteroaryl radicals.

the term "cyclic amine" denotes 3- to 8-membered cycloalkyl radical in which one carbon atom is replaced with a nitrogen atom, the cycloalkyl radical having the meaning given above and also possibly containing one or more other hetero atoms selected from O, S, $SO_2$, N or $NR9$ with R9 as defined above; as examples of such cyclic amines, mention may be made, for example, of pyrrolidinyl, piperidyl, morpholinyl, piperazinyl, indolinyl, pyrindolinyl and tetrahydroquinolyl radicals, these radicals being optionally substituted.

The term "patient" denotes human beings, but also other mammals.

The term "prodrug" denotes a compound which may be converted in vivo via metabolic mechanisms (such as hydrolysis) into a compound of formula (I). For example, an ester of a compound of formula (I) containing a hydroxyl group may be converted by hydrolysis in vivo into its parent molecule. Alternatively, an ester of a compound of formula (I) containing a carboxyl group may be converted by hydrolysis in vivo into its parent molecule.

Examples of esters of compounds of formula (I) containing a hydroxyl group which may be mentioned include the acetates, citrates, lactates, tartrates, malonates, oxalates, salicylates, propionates, succinates, fumarates, maleates, methylenebis-beta-hydroxynaphthoates, gentisates, isethionates, di-p-tolyltartrates, methanesulfonates, ethanesulfonates, benzenesulfonates, p-toluenesulfonates, cyclohexylsulfamates and quinates.

Esters of compounds of formula (I) which are particularly useful, containing a hydroxyl group, may be prepared from acid residues such as those described by Bundgaard et al., J. Med. Chem., 1989, 32, page 2503-2507; these esters include in particular substituted (aminomethyl)benzoates, dialkylaminomethylbenzoates in which the two alkyl groups may be linked together or may be interrupted with an oxygen atom or with an optionally substituted nitrogen atom, i.e. an alkylated nitrogen atom, or alternatively (morpholinomethyl)benzoates, e.g. 3- or 4-(morpholinomethyl)benzoates, and (4-alkylpiperazin-1-yl)benzoates, e.g. 3- or 4-(4-alkylpiperazin-1-yl)benzoates.

The carboxyl radical(s) of the compounds of formula (I) may be salified or esterified with various groups known to those skilled in the art, among which mention may be made, as non-limiting examples, of the following compounds:

among the salification compounds, mineral bases such as, for example, one equivalent of sodium, potassium, lithium, calcium, magnesium or ammonium, or organic bases such as, for example, methylamine, propylamine, trimethylamine, diethylamine, triethylamine, N,N-dimethylethanolamine, tris(hydroxymethyl)-aminomethane, ethanolamine, pyridine, picoline, dicyclohexylamine, morpholine, benzylamine, procaine, lysine, arginine, histidine or N-methylglucamine, among the esterification compounds, alkyl radicals to form alkoxycarbonyl groups such as, for example, methoxycarbonyl, ethoxycarbonyl, tert-butoxycarbonyl or benzyloxycarbonyl, these alkyl radicals possibly being substituted with radicals selected, for example, from halogen atoms, and hydroxyl, alkoxy, acyl, acyloxy, alkylthio, amino or aryl radicals, such as, for example, in chloromethyl, hydroxypropyl, methoxymethyl, propionyloxymethyl, methylthiomethyl, dimethylaminoethyl, benzyl or phenethyl groups.

The term "esterified carboxyl" is intended to mean, for example, radicals such as alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl; alkyloxycarbonyloxy alkyl radicals such as methoxycarbonyloxy methyl or ethyl radicals, and isopropyloxycarbonyloxy methyl or ethyl radicals.

A list of such ester radicals may be found, for example, in European patent EP 0 034 536.

The term "amidated carboxyl" is intended to mean radicals of the type —CONR7R8 as defined above or hereinafter.

The term "alkylamino radical" or "dialkylamino radical" is intended to mean radicals in which the alkyl radical(s) preferably contain(s) 1 to 4 carbon atoms, such as methyl, ethyl, propyl, isopropyl, butyl, isobutyl, sec-butyl or tert-butyl radicals; this gives, for example, methylamino, ethylamino, propylamino or butylamino radicals, which may be linear or branched, and dimethylamino, diethylamino and methylethylamino radicals.

The amino radicals may also contain one or two heterocycles which may optionally contain an additional hetero atom. Mention may be made, for example, of pyrrolyl, imidazolyl, indolyl, piperidyl, morpholinyl and piperazinyl radicals, and particularly piperidyl, morpholinyl or piperazinyl radicals.

The term "salified carboxyl" is intended to mean the salts formed, for example, with one equivalent of sodium, potassium, lithium, calcium, magnesium or ammonium. Mention may also be made of the salts formed with organic bases such as methylamine, propylamine, trimethylamine, diethylamine or triethylamine. The sodium salt is preferred.

When the compounds of formula (I) comprise an amino radical that may be salified with an acid, it is clearly understood that these acid salts also form part of the invention. Mention may be made of the salts obtained, for example, with hydrochloric acid or methanesulfonic acid.

The addition salts with mineral or organic acids of the compounds of formula (I) may be, for example, the salts formed with hydrochloric acid, hydrobromic acid, hydroiodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as, for example, methanesulfonic acid, ethanesulfonic acid or propanesulfonic acid, alkyldisulfonic acids such as, for example, methanedisulfonic acid, or alpha,beta-ethanedisulfonic acid, arylmonosulfonic acids such as benzenesulfonic acid, and aryldisulfonic acids.

It may be recalled that the stereoisomerism may be defined in its broad sense as the isomerism of compounds having the same structural formulae but whose various groups are arranged differently in space, especially such as in monosubstituted cyclohexanes whose substituent may be in the axial or equatorial position, and the various possible rotational conformations of ethane derivatives. However, there is another type of stereoisomerism, due to the different spatial arrangements of fixed substituents, either on double bonds or on rings, which is often referred to as geometrical isomerism or cis-trans isomerism. The term "stereoisomer" is used in the present patent application in its broadest sense and thus relates to all the compounds indicated above.

A subject of the present invention is thus the compounds of formula (I) as defined above and in the present invention, in which the substituents R, R1, R2, R3, R4, R5 and R6 of said compounds of formula (I) have the values defined above and in the present invention, in which the radical —NR12R13 is such that R12 and R13, which may be identical or different, represent a hydrogen atom; and acyl, alkyl, cycloalkyl, piperidyl, piperazinyl, pyrrolidinyl, azetidinyl, pyrazolyl, pyridyl, imidazolyl, pyrimidyl, thiazolyl, thiazolidinyl, —SO2-thienyl, —SO2-pyridyl, —SO2-alkyl, —SO2-phenyl, —CO—NH-phenyl and phenyl radicals, all these radicals being optionally substituted with one or more radicals, which may be identical or different, selected from halogen atoms and the following radicals: alkyl; CH2-NH2; CH2—NHCO2alkyl; NH2; NHCO2alkyl; hydroxyl; alkoxy; hydroxyalkoxy; free or esterified carboxyl; CF3; SCF3; OCF3; OCHF2; SO2CF3; nitro; cyano; thienyl; piperidyl; morpholino, which is itself optionally substituted with one or two alkyl radicals; and phenyl, which is itself optionally substituted with one or more radicals, which may be identical or different, selected from halogen atoms and alkyl, hydroxyl, alkoxy, free or esterified carboxyl, CF3, SCF3, OCH3, OCHF2, SO2CF3, NH2, NHCO2alkyl, nitro and cyano radicals;

or alternatively R12 and R13 form, with the nitrogen atom to which they are attached, an unsaturated or partially or totally saturated 3- to 10-membered heterocyclic radical containing one or more hetero atoms selected from O, S, N and NR11, this radical being optionally substituted with one or more radicals, which may be identical or different, selected from halogen atoms and the following radicals: alkyl; —CH2-NH2; CH2-NHCO2alkyl; NH2; NHCO2alkyl; hydroxyl; alkoxy; hydroxyalkoxy; free or esterified carboxyl; CF3; SCF3; OCF3; OCHF2; SO2CF3; nitro; cyano; and piperidyl; morpholinyl; piperazinyl; thienyl; pyridyl, imidazolyl, thiazolyl, thiazolidinyl and phenyl radicals, which are themselves optionally substituted with one or more radicals, which may be identical or different, selected from halogen atoms and alkyl, hydroxyl, alkoxy, free or esterified carboxyl, CF3, SCF3, NH2, NHCO2alkyl, nitro and cyano radicals, said compounds of formula (I) being in any possible racemic, enantiomeric or diastereoisomeric isomer form, and also the addition salts with mineral and organic acids or with mineral and organic bases of said compounds of formula (I).

In particular, R12 and R13, which may be identical or different, may represent hydrogen; acyl, for instance alkyl-CO—, phenyl-CO-pyrazolyl-CO—, pyridyl-CO—, imidazolyl-CO—, pyrimidyl-CO— or thiazolyl-CO—; alkyl optionally substituted with thienyl, alkoxy or phenyl, which is itself optionally substituted with OCH3, SCF3, NHCO2ALK or NH2; cycloalkyl; piperidyl optionally substituted with alkyl; piperazinyl, pyrrolidinyl, azetidinyl; pyrazolyl optionally substituted with alkyl; pyridyl, imidazolyl, pyrimidyl, thiazolyl, thiazolidinyl; —SO2-thienyl; —SO2-pyridyl; —SO2-alkyl; —SO2-phenyl optionally substituted with OCF3; —CO—NH-phenyl optionally substituted with OCF3; and phenyl, which is itself optionally substituted with OCH3, SCF3, piperidyl or morpholino, the latter radical itself being optionally substituted with one or two alkyl radicals.

A subject of the present invention is thus the compounds of formula (I) as defined above and in the present invention, in which R, R1, R2, R3, R4, R5 and R6 have the meanings given above and in the present invention, and R7 and R8, which may be identical or different, are selected from hydrogen, alkyl, cycloalkyl, phenyl, heterocycloalkyl and heteroaryl, which may be monocyclic or bicyclic, all these radicals being optionally substituted, or alternatively R7 and R8 form, with the nitrogen atom to which they are attached, an unsaturated or partially or totally saturated heterocyclic radical consisting of 3 to 10 ring-members and containing one or more hetero atoms selected from O, S, N and NR14, this radical being optionally substituted, all the above radicals: alkyl, cycloalkyl, phenyl, heterocycloalkyl and heteroaryl, which may be monocyclic or bicyclic, and also the heterocyclic radical formed by R7 and R8 with the nitrogen atom to which they are attached, being optionally substituted with one or more radicals, which may be identical or different, selected from the halogen atoms and the radicals hydroxyl, oxo, nitro, alkyl, alkoxy, alkylthio, cycloalkyl, phenyl, heterocycloalkyl, heteroaryl, —C(=O)—R9, —C(=O)—OR10, —N(R11)-C(=O)—R9, —N(R11)-C(=O)—OR10, —NR12R13, —C(=O)—NR12R13, and —N(R11)-C(=O)—NR12R13, the latter alkyl, alkoxy, cycloalkyl, phenyl, heterocycloalkyl and heteroaryl radicals themselves being optionally substituted with one or more radicals, which may be identical or different, selected from the halogen atoms and the radicals: hydroxyl, alkyl, alkoxy, —NR12R13, free or esterified carboxyl, pyrrolidinyl, and phenyl and phenylalkyl in which the phenyl radical is itself optionally substituted with one or more radicals, which may be identical or different, selected from the halogen atoms and the radicals: hydroxyl, alkyl, alkoxy, free or esterified carboxyl, $CF_3$, nitro, cyano and pyridyl, R9 represents alkyl, cycloalkyl, phenyl, heterocycloalkyl and heteroaryl, all these radicals being optionally substituted, R10 represents the values for R9 and hydrogen, R11 represents hydrogen or optionally substituted alkyl, R12 and R13, which may be identical or different, represent hydrogen, acyl, alkyl, cycloalkyl and phenyl, these radicals being optionally substituted, or alternatively R12 and R13 form, with the nitrogen atom to which they are attached, an unsaturated or partially or totally saturated heterocyclic radical consisting of 3 to 10 ring members and containing one or more hetero atoms selected from O, S, N and NR11, this radical being optionally substituted, R14 represents hydrogen, acyl, free and esterified carboxyl, alkyl, cycloalkyl and phenyl, which may be optionally substituted, the radicals R9, R10, R11, R12, R13 and R14 above being optionally substituted with one or more radicals, which may be identical or different, selected from the halogen atoms and the radicals: alkyl, hydroxyl, alkoxy, hydroxyalkoxy, free or esterified carboxyl, $CF_3$, nitro, cyano and phenyl, itself optionally substituted with one or more radicals, which may be identical or different, selected from the halogen atoms and the radicals: alkyl, hydroxyl, alkoxy, free or esterified carboxyl, $CF_3$, nitro and cyano, all the phenyl and heteroaryl radicals above being, in addition, optionally substituted with a dioxol radical, all the alkyl, alkenyl, alkoxy or —O-alkyl and alkylthio radicals above being linear or branched and containing no more than 4 carbon atoms, all the cycloalkyl radicals above containing no more than 7 carbon atoms, all the heteroaryl and heterocycloalkyl radicals above containing no more than 10 carbon atoms, said compounds of formula (I) being in any possible racemic, enantiomeric or diastereoisomeric isomer form, and also the addition salts with mineral and organic acids or with mineral and organic bases of said compounds of formula (I).

For example, R14 may represent a hydrogen atom; a cycloalkyl radical; an alkyl radical optionally substituted, for example, with hydroxyl, alkoxy, hydroxyalkoxy or phenyl, itself optionally substituted with one or more radicals selected from the halogen atoms and $CF_3$, alkoxy and dioxol radicals; a heterocyclic radical such as, for example, piperidyl or pyridyl; a phenyl radical, itself optionally substituted with alkoxy, $CF_3$ or halogen; a free or esterified carboxyl radical; an acyl radical such as, for example, —CO—$CH_3$ or —CO-furyl.

Examples of heterocyclic radicals that the above radicals may represent are given hereinafter: among these heterocyclic radicals hereinafter, those comprising at least one nitrogen atom constitute examples of radicals that R7 and R8 may form with the nitrogen atom to which they are attached and also that R12 and R13 may form with the nitrogen atom to which they are attached. Mention may thus be made, in a nonlimiting manner, of the following radicals:

pyrrolidinyl, piperidyl, pyrimidinyl, thienyl, thiazolyl, pyran, furyl, tetrahydrofuryl, tetrahydrofur-2-yl, imidazolinyl, imidazolyl, piperazinyl, indolyl, pyrrole, benzopyran, quinolyl, pyridyl, purinyl, morpholinyl, thiomorpholinyl, azetidinyl, azepanyl, diazepine, spiro[4.5]decane, pyrrolyl, 2H-pyrrolyl, piperidyl, indolinyl, pyrindolinyl, tetrahydroquinolyl, thiazolidinyl, naphthyridinyl, quinazolinyl, dihydropyrrolyl, 1,4-dioxa-8-azaspiro[4.5]decane and tetrahydropyrrolo[3,4-c]-pyrrolyl, all these radicals being optionally substituted.

More particularly, when R12 and R13 form a cyclic radical with the nitrogen atom to which they are attached, this cyclic radical may be selected from pyrrolidinyl, morpholinyl, piperazinyl, piperidyl and azetidinyl radicals, all these radicals being optionally substituted as indicated above.

In particular when R12 and R13 form a cyclic radical with the nitrogen atom to which they are attached, this cyclic radical may be selected from the following radicals: piperidyl, which is itself optionally substituted with a piperidyl radical or a hydroxyl radical; azetidinyl, which is itself optionally substituted with NH—CO2alk, CH2-NH2-CO2alk, CH2-NH2 and NH2; and piperazinyl, which is itself optionally substituted with an alkyl, phenylalkyl or phenyl radical, in which the phenyl radical is itself optionally substituted with one or more radicals selected from OCF3, OCHF2, SCF3 and SO2CF3.

A subject of the present invention is particularly the compounds of formula (I) as defined above and in the present invention, in which R, R1, R2, R3, R4, R5 and R6 have the meanings given above and in the present invention, and R7 and R8, which may be identical or different, are selected from hydrogen, cycloalkyl, optionally substituted alkyl, optionally substituted phenyl, heterocycloalkyl and monocyclic or bicyclic heteroaryl, which may be optionally substituted, or alternatively R7 and R8 form, with the nitrogen atom to which they are attached, an optionally substituted heterocyclic radical containing one or more hetero atoms, all the alkyl, phenyl and heterocyclic radicals above, and also the heterocyclic radical that R7 and R8 may form with the nitrogen atom to which they are attached, being optionally substituted with one or more radicals selected from the halogen atoms and the radicals: hydroxyl; oxo; nitro; cycloalkyl; alkoxy; $OCF_3$; hydroxyalkoxy; alkylthio; acyl; free or esterified carboxyl; optionally substituted phenyl; optionally substituted amino; alkyl optionally substituted with one or more radicals selected from the halogen atoms and the radicals: hydroxyl, alkoxy, pyrrolidinyl, phenyl and amino, themselves optionally substituted; and pyrrolidinyl, piperidyl, pyridyl and piperazinyl, themselves optionally substituted with one or more radicals selected from the radicals: hydroxyl, alkyl, alkoxy, free or esterified carboxyl, phenyl and phenylalkyl, themselves optionally substituted, the amino radicals being optionally substituted with one or two radicals, which may be identical or different, selected from alkyl, hydroxyalkyl, alkoxyalkyl, acyl, phenyl and phenylalkyl, themselves optionally substituted, the phenyl and phenylalkyl radicals being optionally substituted with one or more radicals selected from the halogen atoms and the radicals: hydroxyl, alkyl, alkoxy, $CF_3$, free or esterified carboxyl, pyridyl and dioxol, all the alkyl and alkoxy radicals being linear or branched and containing no more than 4 carbon atoms, said compounds of formula (I) being in any possible racemic, enantiomeric or diastereoisomeric isomer form, and also the addition salts with mineral and organic acids or with mineral and organic bases of said compounds of formula (I).

The radicals R7 and R8, which may be identical or different, may thus in particular represent hydrogen and optionally substituted alkyl, cycloalkyl, phenyl radicals and an optionally substituted heterocyclic radical: among the values for R7 and R8, mention may be made, for example, of pyrimidinyl; thienyl; pyridyl; quinolyl; thiazolyl optionally substituted with one or two halogen atoms; pyran optionally substituted with one or more OCOAlk; phenyl optionally substituted with one or more radicals selected from the halogen atoms and the radicals: alkyl, alkoxy, amino, alkylamino, dialkylamino and free carboxyl or carboxyl esterified with an alkyl radical; alkyl substituted with phenyl, itself optionally substituted with one or more radicals selected from the halogen atoms, alkyl, alkoxy, amino, alkylamino, dialkylamino, and free carboxyl or carboxyl esterified with an alkyl radical; alkyl substituted with piperazinyl, itself optionally substituted with one or more radicals selected from Alk, Alk-OH and pyridyl; alkyl substituted with imidazolyl; alkyl substituted with one or more radicals selected from $NH_2$, NHAlk, $N(Alk)_2$, N(Alk) (phenylalkyl), N(Alk) (aminoalkyl), N(Alk)-(alkylaminoalkyl) and N(Alk)(dialkylaminoalkyl); alkyl substituted with morpholinyl optionally substituted with one or two Alk; alkyl substituted with pyrrolidinyl; alkyl substituted with piperidyl, itself optionally substituted with one or two Alk; alkyl substituted with thiomorpholinyl; alkyl substituted with azetidinyl; alkyl substituted with azepanyl optionally substituted with oxo.

As radical that R7 and R8 may form with the nitrogen atom to which they are attached, mention may also be made of dihydropyrrolyl, 1,4-dioxa-8-azaspiro[4.5]decane or tetrahydropyrrolo[3,4-c]pyrrolyl radicals, these radicals all being optionally substituted.

The radical that R7 and R8 may form with the nitrogen atom to which they are attached can in particular be optionally substituted with one or more radicals, which may be identical or different, selected from the halogen atoms and the radicals: alkyl, hydroxyl, alkoxy and phenyl, itself optionally substituted with one or more radicals selected from the halogen atoms and alkyl and alkoxy radicals.

The pyrrolidinyl and quinazolinyl radicals may in particular be optionally substituted with oxo or thioxo.

The piperazinyl radical may in particular be optionally substituted with one or more radicals selected from Alk, Alk-OH and pyridyl.

The acyl radical represents in particular the —CO-alkyl radicals with alkyl containing no more than 4 carbon atoms, the —CO-furyl radical or the —CO-pyrrolidinyl radical.

A subject of the present invention is more particularly the compounds of formula (I) as defined above and in the present invention, in which R, R1, R2, R3, R4, R5 and R6 have the meanings given above and in the present invention, and R7 and R8, which may be identical or different, are selected from hydrogen and alkyl, cycloalkyl, phenyl and heterocyclic radicals, such as pyrrolidinyl, piperidyl, pyrimidinyl, thienyl, thiazolyl, pyran, furyl, tetrahydrofuryl, tetrahydrofur-2-yl, imidazolinyl, piperazinyl, indolyl, pyrrole, benzopyran, quinolyl, pyridyl, purinyl and morpholinyl, these radicals being optionally substituted, or alternatively R7 and R8 form, with the nitrogen atom to which they are attached, a heterocyclic radical selected from pyrrolidinyl, imidazolyl, morpholinyl, piperazinyl, piperidyl, thiazolyl, diazepine, spiro[4.5]decane, pyrrolyl, dihydropyrrolyl, tetrahydropyrrolyl, tetrahydropyrrolo[3,4-c]pyrrolyl, piperidyl, indolinyl, pyrindolinyl, tetrahydroquinolyl, thiazolidinyl, naphthyridyl, azetidine or quinazolinyl radicals, these radicals all being optionally substituted, all the above alkyl, phenyl and heterocyclic radicals being optionally substituted with one or more radicals selected from the halogen atoms and the radicals: hydroxyl; oxo; nitro; cycloalkyl; alkoxy; $OCF_3$; hydroxyalkoxy; alkylthio; acyl; free or esterified carboxyl; optionally substituted phenyl; optionally substituted amino; alkyl optionally substituted with one or more radicals selected from halogen atoms and the radicals: hydroxyl, alkoxyl, pyrrolidinyl, phenyl and amino, themselves optionally substituted; and pyrrolidinyl, piperidyl, pyridyl and piperazinyl, themselves optionally substituted with one or more radicals selected from the radicals: hydroxyl, alkyl, alkoxy, free or esterified carboxyl, phenyl and phenylalkyl, themselves optionally substituted, the amino radicals being optionally substituted with one or two radicals, which may be identical or different, selected from alkyl, hydroxyalkyl, alkoxyalkyl, acyl, phenyl and phenylalkyl, themselves optionally substituted, the phenyl and phenylalkyl radicals being optionally substituted with one or more radicals selected from the halogen atoms and the radicals: hydroxyl, alkyl, alkoxy, $CF_3$, free or esterified carboxyl, pyridyl and dioxol, all the alkyl and alkoxy radicals being linear or branched and containing no more than 4 carbon atoms, said compounds of formula (I) being in any possible racemic, enantiomeric or diastereoisomeric isomer form, and also the addition salts with mineral and organic acids or with mineral and organic bases of said compounds of formula (I).

A subject of the present invention is in particular the compounds; of formula (I) as defined above and in the present invention, in which R, R1, R2, R3, R4, R5 and R6 have the meanings given above and in the present invention, and R7 and R8, which may be identical or different, are selected from hydrogen, cycloalkyl radicals and alkyl, phenyl and heterocyclic radicals such as pyrrolidinyl, piperidyl, furyl, tetrahydrofuryl, tetrahydrofur-2-yl, imidazolinyl, piperazinyl, indolyl, pyrrolyl, benzopyranyl, benzopyran-8-carboxylic, pyridyl, purinyl and morpholinyl, all these radicals being optionally substituted, or alternatively R7 and R8 form, with the nitrogen atom to which they are attached, a heterocyclic radical selected from pyrrolidinyl, imidazolyl, morpholinyl, piperazinyl, piperidyl, thiazolyl, diazepine, spiro[4.5]decane, pyrrolyl, dihydropyrrolyl, tetrahydropyrrolyl and tetrahydropyrrolo [3,4-c]pyrrolyl radicals, all these radicals being optionally substituted, all the above alkyl, phenyl and heterocyclic radicals that R7 and R8 represent or that R7 and R8 may form with the nitrogen atom to which they are attached being optionally substituted with one or more radicals selected from the radicals: oxo; cycloalkyl; CO-alkyl; —CO-furyl; hydroxyl; alkoxy; hydroxyalkoxy; alkylthio; free or esterified carboxyl; optionally substituted phenyl; alkyl optionally substituted with a radical selected from hydroxyl, alkoxyl, pyrrolidinyl, optionally substituted phenyl and amino optionally substituted with one or two radicals selected from alkyl and optionally substituted phenyl; amino optionally substituted with one or two radicals, which may be identical or different, selected from alkyl, hydroxyalkyl, alkoxyalkyl, CO-alkyl and phenyl, itself optionally substituted; pyrrolidinyl, piperidinyl, pyridyl and piperazinyl, optionally substituted with one or more radicals selected from free or esterified carboxyl, alkyl, alkoxy, hydroxyl, phenylalkyl and optionally substituted phenyl, all the phenyl radicals being optionally substituted with one or more radicals, which may be identical or different, selected from the halogen atoms and the radicals: hydroxyl, alkyl, alkoxy, $CF_3$, free or esterified carboxyl, pyridyl and dioxol, said compounds of formula (I) being in any possible racemic, enantiomeric or diastereoisomeric isomer form, and also the addition salts with mineral and organic acids or with mineral and organic bases of said compounds of formula (I).

Thus, R7 and R8 form in particular, with the nitrogen atom to which they are attached, a radical selected from the following radicals: pyrrolidinyl; imidazolyl; dihydropyrrolyl; 1,4-dioxa-8-azaspiro[4.5]decane; morpholinyl; piperazinyl; piperidyl; thiazolyl; diazepine; perhydro-1,4-diazepine; 4-methylperhydro-1,4-diazepin-1-yl; tetrahydropyrrolo[3,4-c]pyrrol-2-one; tetrahydropyrrolo[3,4-c]pyrrol-1,3-dione, these radicals being optionally substituted with one or more radicals: as indicated above or else illustrated in the experimental section.

A subject of the present invention is more particularly the compounds of formula (I) as defined above and in the present invention, in which R, R1, R2, R3, R4, R5 and R6 have the meanings given above and in the present invention, and R7 and R8, which may be identical or different, are selected from the following radicals:
hydrogen;
benzopyran;
pyridyl itself optionally substituted with hydroxyl;
piperidyl optionally substituted with alkyl, itself optionally substituted with phenyl;
purinyl;
alkyl optionally substituted with one or more radicals selected from hydroxyl; alkoxy; alkylthio; pyridyl; imidazolinyl, indolyl; pyrrolyl; furyl; tetrahydrofuryl; amino optionally substituted with one or two radicals, which may be identical or different, selected from alkyl, hydroxyalkyl, alkoxyalkyl and phenyl, itself optionally substituted with alkyl; pyrrolidinyl, itself optionally substituted with an alkyl radical; piperidyl, itself optionally substituted with alkyl or phenylalkyl; piperazinyl, itself optionally substituted with alkyl; phenyl optionally substituted with dioxol or free or esterified carboxyl;
phenyl optionally substituted with one or more radicals selected from alkoxyl, piperidyl and piperazinyl, itself optionally substituted with an alkyl radical;
or alternatively R7 and R8 form, with the nitrogen atom to which they are attached, a heterocyclic radical selected from the following radicals:
imidazolyl;
dihydropyrrolyl;
1,4-dioxa-8-azaspiro[4.5]decane;
thiazolyl;
tetrahydropyrrolo[3,4-c]pyrrol-2-one;
tetrahydropyrrolo[3,4-c]pyrrole-1,3-dione;
pyrrolidinyl optionally substituted with a radical selected from pyridyl; amino, itself optionally substituted with an alkyl radical and an acyl radical; and alkyl, itself optionally substituted with a radical selected from hydroxyl, alkoxy, pyrrolidinyl and amino, itself optionally substituted with a phenyl radical;
morpholinyl optionally substituted with one or more alkyl radicals;
piperazinyl optionally substituted with one or more radicals, which may be identical or different, selected from the radicals: oxo; cycloalkyl; acyl; carboxyl; pyridyl; alkyl containing no more than 4 carbon atoms, itself optionally substituted with a radical: hydroxyl, alkoxy, hydroxyalkoxy containing no more than 4 carbon atoms and phenyl, itself optionally substituted with a dioxol radical; phenyl, itself optionally substituted with one or more radicals selected from the halogen atoms and hydroxyl, alkoxy and $CF_3$ radicals;
piperidyl optionally substituted with one or more substituents selected from hydroxyl, alkyl, hydroxyalkyl and piperidyl;
diazepine or perhydro-1,4-diazepine optionally substituted with an alkyl radical; itself optionally substituted with pyrrolidinyl;
said compounds of formula (I) being in any possible racemic, enantiomeric or diastereoisomeric isomer form, and also the addition salts with mineral and organic acids or with mineral and organic bases of said compounds of formula (I).

A subject of the present invention is more particularly the compounds of formula (I) as defined above and in the present invention, in which R, R1, R2, R3, R4, R5 and R6 have the meanings given above and in the present invention, and R7 and R8, which may be identical or different, are selected from the radicals: hydrogen, alkyl, itself optionally substituted with a pyrrolidinyl or piperidyl radical and phenyl, itself optionally substituted with one or more radicals selected from the piperazinyl radical, itself optionally substituted with an alkyl radical, or alternatively R7 and R8 form, together with the nitrogen atom to which they are attached, a radical selected from the following radicals: morpholinyl; thiazolyl; diazepine or perhydro-1,4-diazepine optionally substituted with an alkyl radical; 1-tetrahydropyrrolo[3,4-c]pyrrol-2-one; piperazinyl optionally substituted with one or more radicals, which may be identical or different, selected from the radicals: oxo and alkyl, itself optionally substituted with a hydroxyl, alkoxy or hydroxyalkoxy radical; piperidyl optionally substituted with hydroxyl, alkyl, hydroxyalkyl or piperidyl;

the alkyl and alkoxy radicals containing no more than 4 carbon atoms, said compounds of formula (I) being in any possible racemic, enantiomeric or diastereoisomeric isomer form, and also the addition salts with mineral and organic acids or with mineral and organic bases of said compounds of formula (I).

A subject of the present invention is more particularly the compounds of formula (I) as defined above, in which:

R and R6 represent a hydrogen atom,

R1 represents alkyl containing no more than 2 carbon atoms, optionally substituted with —CO—NR7R8 or —NR7R8, R2 and R3, which may be identical or different, represent —O-alkyl containing no more than 3 carbon atoms, optionally substituted with —CO—NR7R8 or —NR7R8, R4 and R5 are such that one represents hydrogen and the other represents a halogen atom or a cyano radical, R7 and R8 having the meanings given above, said compounds of formula (I) being in any possible racemic, enantiomeric or diastereoisomeric isomer form, and also the addition salts with mineral and organic acids or with mineral and organic bases of said compounds of formula (I).

A subject of the present invention is more particularly the compounds of formula (I) as defined above and in the present invention, in which R, R1, R2, R3, R4, R5, R6, R7 and R8 have the meanings given above and in the present invention, it being understood that R7 and R8 do not both represent hydrogen, said compounds of formula (I) being in any possible racemic, enantiomeric or diastereoisomeric isomer form, and also the addition salts with mineral and organic acids or with mineral and organic bases of said compounds of formula (I).

A subject of the present invention is more particularly the compounds of formula (I) as defined above and in the present invention, in which:

R, R1, R2, R3, R4, R5 and R6 have the meanings given in any one of the other claims, and R7 and R8 are such that either one of R7 and R8 represents hydrogen or alkyl and the other is selected from the values for R7 and R8 as defined in any one of the other claims, or R7 and R8 form, with the nitrogen atom to which they are attached, a heterocyclic radical as defined in any one of the other claims, said compounds of formula (I) being in any possible racemic, enantiomeric or diastereoisomeric isomer form, and also the addition salts with mineral and organic acids or with mineral and organic bases of said compounds of formula (I).

Among the preferred compounds of the invention, mention may be made more particularly of the compounds of formula (I) as defined above, the names of which are given below:

2-{5,6-dimethoxy-1-[2-(4-methylpiperazin-1-yl)ethyl]-1H-indol-3-yl}-1H-pyrrolo[2,3-b]pyridine 2-(4-{2-[5,6-dimethoxy-3-(1H-pyrrolo[2,3-b]pyrid-2-yl)indol-1-yl]ethyl}piperazin-1-yl)ethanol 2-(1-{2-[5,6-dimethoxy-3-(1H-pyrrolo[2,3-b]pyrid-2-yl)indol-1-yl]ethyl}piperid-4-yl)ethanol 1'-{2-[5,6-dimethoxy-3-(1H-pyrrolo[2,3-b]pyrid-2-yl)indol-1-yl]ethyl}-[1,4']bipiperidyl 1-{2-[5,6-dimethoxy-3-(1H-pyrrolo[2,3-b]pyrid-2-yl)indol-1-yl]ethyl}piperid-3-ol 2-{5,6-dimethoxy-1-[2-(4-methylperhydro-1,4-diazepin-1-yl)ethyl]-1H-indol-3-yl}-1H-pyrrolo[2,3-b]pyridine 2-[5,6-dimethoxy-3-(1H-pyrrolo[2,3-b]pyrid-2-yl)indol-1-yl]-1-(4-hydroxypiperid-1-yl)ethanone 2-[5,6-dimethoxy-3-(1H-pyrrolo[2,3-b]pyrid-2-yl)indol-1-yl]-1-thiazolidin-3-ylethanone 4-{[5,6-dimethoxy-3-(1H-pyrrolo[2,3-b]pyrid-2-yl)indol-1-yl]acetyl}-1-methylpiperazin-2-one 4-Chloro-2-(5,6-dimethoxy-1-methyl-1H-indol-3-yl)-1H-pyrrolo[2,3-b]pyridine 2-(5,6-dimethoxy-1-methyl-1H-indol-3-yl)-1H-pyrrolo[2,3-b]pyridine-4-carbonitrile 4-chloro-2-[5,6-dimethoxy-1-(2-morpholin-4-ylethyl)-1H-indol-3-yl]-1H-pyrrolo[2,3-b]pyridine 2-(1-{2-[3-(4-chloro-1H-pyrrolo[2,3-b]pyrid-2-yl)-5,6-dimethoxyindol-1-yl]ethyl}piperid-4-yl)ethanol 4-chloro-2-{5,6-dimethoxy-1-[2-(4-methylpiperazin-1-yl)ethyl]-1H-indol-3-yl}-1H-pyrrolo[2,3-b]pyridine 2-{5,6-dimethoxy-1-[2-(4-methylpiperazin-1-yl)ethyl]-1H-indol-3-yl}-1H-pyrrolo[2,3-b]pyridine-4-carbonitrile 2-(5,6-dimethoxy-1-methyl-1H-indol-3-yl)-5-fluoro-1H-pyrrolo[2,3-b]pyridine 2-[5,6-dimethoxy-1-(2-morpholin-4-ylethyl)-1H-indol-3-yl]-5-fluoro-1H-pyrrolo[2,3-b]pyridine 2-{5,6-dimethoxy-1-[2-(4-methylpiperazin-1-yl)ethyl]-1H-indol-3-yl}-5-fluoro-1H-pyrrolo[2,3-b]pyridine 2-[5-Methoxy-1-methyl-3-(1H-pyrrolo[2,3-b]pyrid-2-yl)-1H-indol-6-yloxy]-1-morpholin-4-ylethanone 2-[5-Methoxy-1-methyl-3-(1H-pyrrolo[2,3-b]pyrid-2-yl)-1H-indol-6-yloxy]-1-(4-methyl[1,4]diazepan-1-yl)ethanone 2-[5-Methoxy-1-methyl-3-(1H-pyrrolo[2,3-b]pyrid-2-yl)-1H-indol-6-yloxy]-N-[4-(4-methylpiperazin-1-yl)phenyl]acetamide 2-[5-Methoxy-1-methyl-3-(1H-pyrrolo[2,3-b]pyrid-2-yl)-1H-indol-6-yloxy]-1-(4-methylpiperazin-1-yl)ethanone 1-{4-[2-(2-Hydroxyethoxy)ethyl]piperazin-1-yl}-2-[5-methoxy-1-methyl-3-(1H-pyrrolo[2,3-b]pyrid-2-yl)-1H-indol-6-yloxy]ethanone 3aS,6aS)-5-{2-[5-Methoxy-1-methyl-3-(1H-pyrrolo[2,3-b]pyrid-2-yl)-1H-indol-6-yloxy]acetyl}hexahydropyrrolo[3,4-c]pyrrol-1-one trifluoroacetate 2-{5-Methoxy-1-methyl-6-[3-(4-methylperhydro-1,4-diazepin-1-yl)propoxy]-1H-indol-3-yl}-1H-pyrrolo[2,3-b]pyridine 4-Chloro-2-{1-methyl-5-methoxy-6-[2-(4-methylpiperazin-1-yl)ethoxy]-1H-indol-3-yl}-1H-pyrrolo[2,3-b]pyridine 4-Chloro-2-{1-methyl-5-methoxy-6-[2-(4-piperidylpiperid-1-yl) ethoxy]-1H-indol-3-yl}-1H-pyrrolo[2,3-b]pyridine 4-Chloro-2-{5-Methoxy-1-methyl-6-[2-(2-pyrrolidinethylamino)ethoxy]-1H-indol-3-yl}-1H-pyrrolo[2,3-b]pyridine 4-Chloro-2-{1-methyl-5-methoxy-6-[2-(2-piperidinethylamino)ethoxy]-1H-indol-3-yl}-1H-pyrrolo[2,3-b]pyridine, said compounds of formula (I) being in any possible racemic, enantiomeric or diastereoisomeric isomer form, and also the addition salts with mineral and organic acids, or with mineral and organic bases of said compounds of formula (I).

Among the preferred compounds of the invention, mention may more particularly be made of the compounds of formula (I) as defined above, the names of which are given below:

2-{5,6-Dimethoxy-1-[2-(4-methylpiperazin-1-yl)ethyl]-1H-indol-3-yl}-1H-pyrrolo[2,3-b]pyridine 2-(4-{2-[5,6-Dimethoxy-3-(1H-pyrrolo[2,3-b]pyridin-2-yl)indol-1-yl]ethyl}piperazin-1-yl)ethanol 2-(1-{2-[5,6-Dimethoxy-3-(1H-pyrrolo[2,3-b]pyridin-2-yl)indol-1-yl]ethyl}piperidin-4-yl)ethanol 1'-{2-[5,6-Dimethoxy-3-(1H-pyrrolo[2,3-b]pyridin-2-yl)indol-1-yl]ethyl}-[1,4']bipiperidinyl 1-{2-[5,6-Dimethoxy-3-(1H-pyrrolo[2,3-b]pyridin-2-yl)indol-1-yl]ethyl}piperidin-3-ol 2-{5,6-Dimethoxy-1-[2-(4-methylperhydro-1,4-diazepin-1-yl)ethyl]-1H-indol-3-yl}-1H-pyrrolo[2,3-b]pyridine 2-[5,6-Dimethoxy-3-(1H-pyrrolo[2,3-b]pyridin-2-yl)indol-1-yl]-1-(4-hydroxypiperidin-1-yl)ethanone 2-[5,6-Dimethoxy-3-(1H-pyrrolo[2,3-b]pyridin-2-yl)indol-1-yl]-1-thiazolidin-3-ylethanone 4-{[5,6-Dimethoxy-3-(1H-pyrrolo[2,3-b]pyridin-2-yl)indol-1-yl]acetyl}-1-methylpiperazin-2-one 4-Chloro-2-(5,6-dimethoxy-1-methyl-1H-indol-3-yl)-1H-pyrrolo[2,3-b]pyridine 2-(5,6-Dimethoxy-1-methyl-1H-indol-3-yl)-1H-pyrrolo[2,3-b]pyridine-4-carbonitrile 4-Chloro-2-[5,6-dimethoxy-1-(2-morpholin-4-ylethyl)-1H-indol-3-yl]-1H-pyrrolo[2,3-b]pyridine 2-(1-{2-[3-(4-chloro-1H-pyrrolo[2,3-b]pyridin-2-yl)-5,6-dimethoxyindol-1-yl]ethyl}piperidin-4-yl)ethanol 4-Chloro-2-{5,6-dimethoxy-1-[2-(4-methylpiperazin-1-yl)ethyl]-1H-indol-3-yl}-1H-pyrrolo[2,3-b]pyridine 2-{5,6-Dimethoxy-1-[2-(4-methylpiperazin-1-yl)ethyl]-1H-indol-3-yl}-1H-pyrrolo[2,3-b]pyridine-4-carbonitrile
2-{5,6-Dimethoxy-1-methyl-1H-indol-3-yl)-5-fluoro-1H-pyrrolo[2,3-b]pyridine
2-[5,6-Dimethoxy-1-[2-morpholin-4-ylethyl)-1H-indol-3-yl]-5-fluoro-1H-pyrrolo[2,3-b]pyridine
2-{5,6-Dimethoxy-1-[2-(4-methylpiperazin-1-yl)ethyl]-1H-indol-3-yl}-5-fluoro-1H-pyrrolo[2,3-b]pyridine
2-[5-Methoxy-1-methyl-3-(1H-pyrrolo[2,3-b]pyridin-2-yl)-1H-indol-6-yloxy]-1-morpholin-4-ylethanone
2-[5-Methoxy-1-methyl-3-(1H-pyrrolo[2,3-b]pyridin-2-yl)-1H-indol-6-yloxy]-1-(4-methyl-[1,4]diazepan-1-yl)ethanone
2-[5-Methoxy-1-methyl-3-(1H-pyrrolo[2,3-b]pyridin-2-yl)-1H-indol-6-yloxy]-N-[4-(4-methylpiperazin-1-yl)phenyl]acetamide
2-[5-Methoxy-1-methyl-3-(1H-pyrrolo[2,3-b]pyridin-2-yl)-1H-indol-6-yloxy]-1-(4-methylpiperazin-1-yl)ethanone
1-{4-[2-(2-Hydroxyethoxy)ethyl]piperazin-1-yl}-2-[5-methoxy-1-methyl-3-(1H-pyrrolo[2,3-b]pyridin-2-yl)-1H-indol-6-yloxy]ethanone
(3aS,6aS)-5-{2-[5-Methoxy-1-methyl-3-(1H-pyrrolo[2,3-b]pyridin-2-yl)-1H-indol-6-yloxy]acetyl}hexahydropyrrolo[3,4-c]pyrrol-1-one trifluoroacetate
2-{5-Methoxy-1-methyl-6-[3-(4-methylperhydro-1,4-diazepin-1-yl)propoxy]-1H-indol-3-yl}-1H-pyrrolo[2,3-b]pyridine
4-Chloro-2-{1-methyl-5-methoxy-6-[2-(4-methylpiperazin-1-yl)ethoxy-1H-indol-3-yl}-1H-pyrrolo[2,3-b]pyridine
4-Chloro-2-{1-methyl-5-methoxy-6-[2-(4-piperidylpiperidin-1-yl)ethoxy-1H-indol-3-yl}-1H-pyrrolo[2,3-b]pyridine
4-Chloro-2-{5-methoxy-1-methyl-6-[2-(2-pyrrolidinethylamino)ethoxy]-1H-indol-3-yl}-1H-pyrrolo[2,3-b]pyridine
4-Chloro-2-{1-methyl-5-methoxy-6-[2-(2-piperidinethylamino)ethoxy-1H-indol-3-yl}-1H-pyrrolo[2,3-b]pyridine, said compounds of formula (I) being in any possible racemic, enantiomeric or diastereoisomeric isomer form, and also the addition salts with mineral and organic acids or with mineral and organic bases of said compounds of formula (I).

A subject of the present invention is also a process for preparing the compounds of formula (I) as described above.

Figure 2:
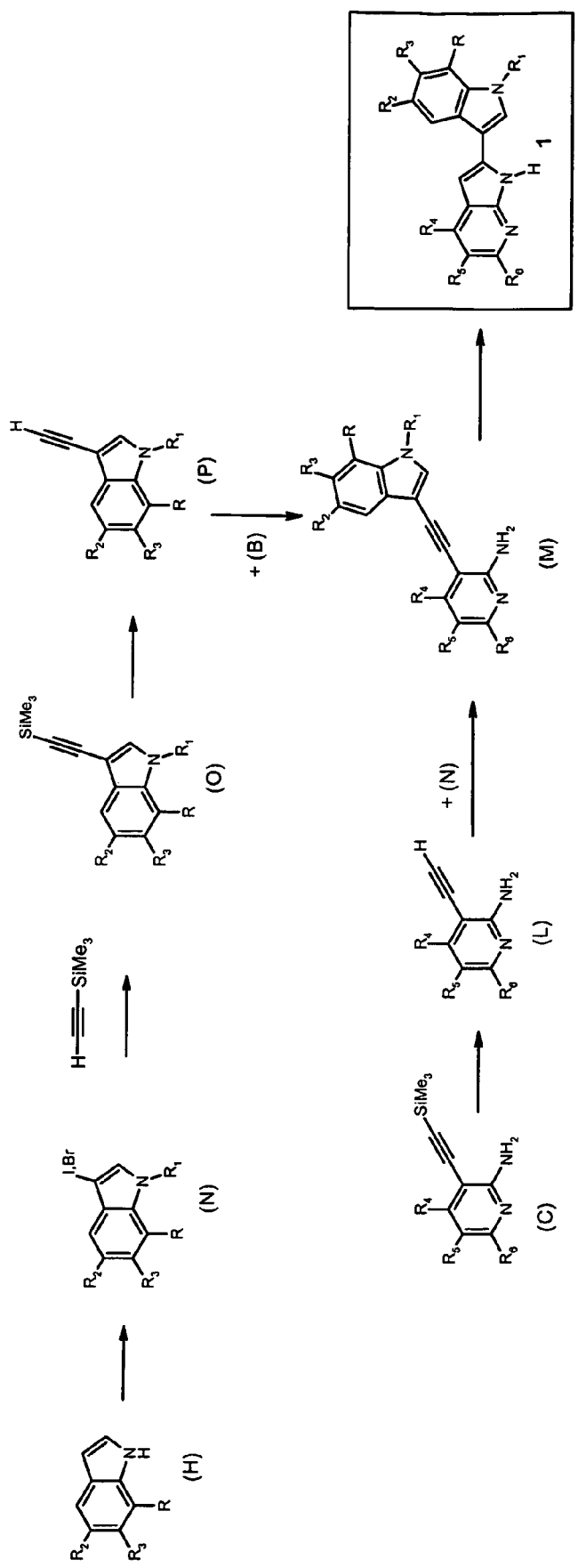
FIG. 2 (Scheme 2) describes a pathway "B" for obtaining the compounds of formula (I): 2-(indol-3-yl)-1H-pyrrolo[2,3-b]pyridine.
Figure 3:
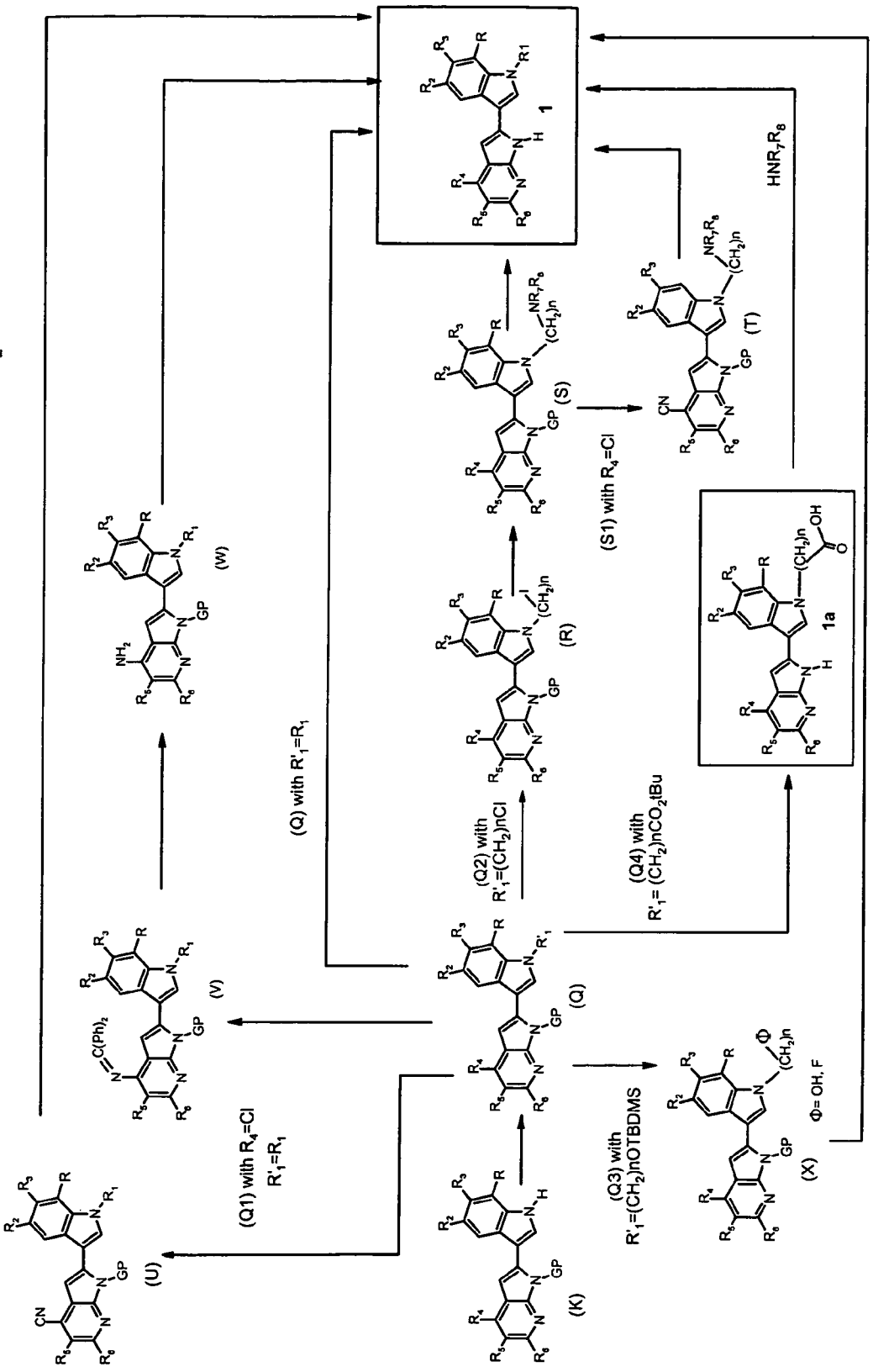
FIG. 3 (Scheme 3) describes pathways for introducing substituents in the R1 position, in the synthesis of the compounds of formula (I) of the present invention.
Figure 4:
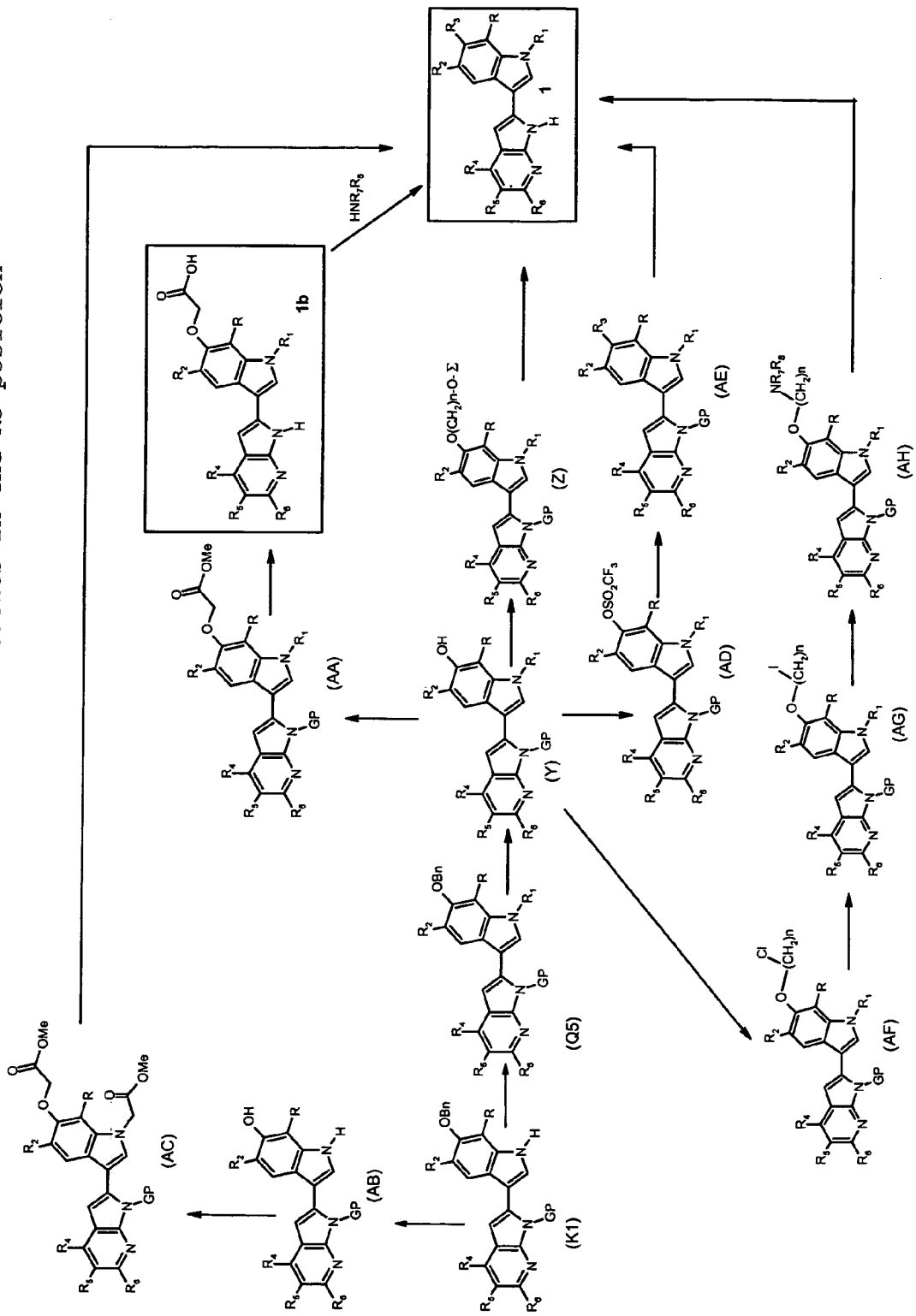
FIG. 4 (Scheme 4) describes pathways for introducing substituents in the R3 position, in the synthesis of the compounds of formula (I) of the present invention.
Figure 5:
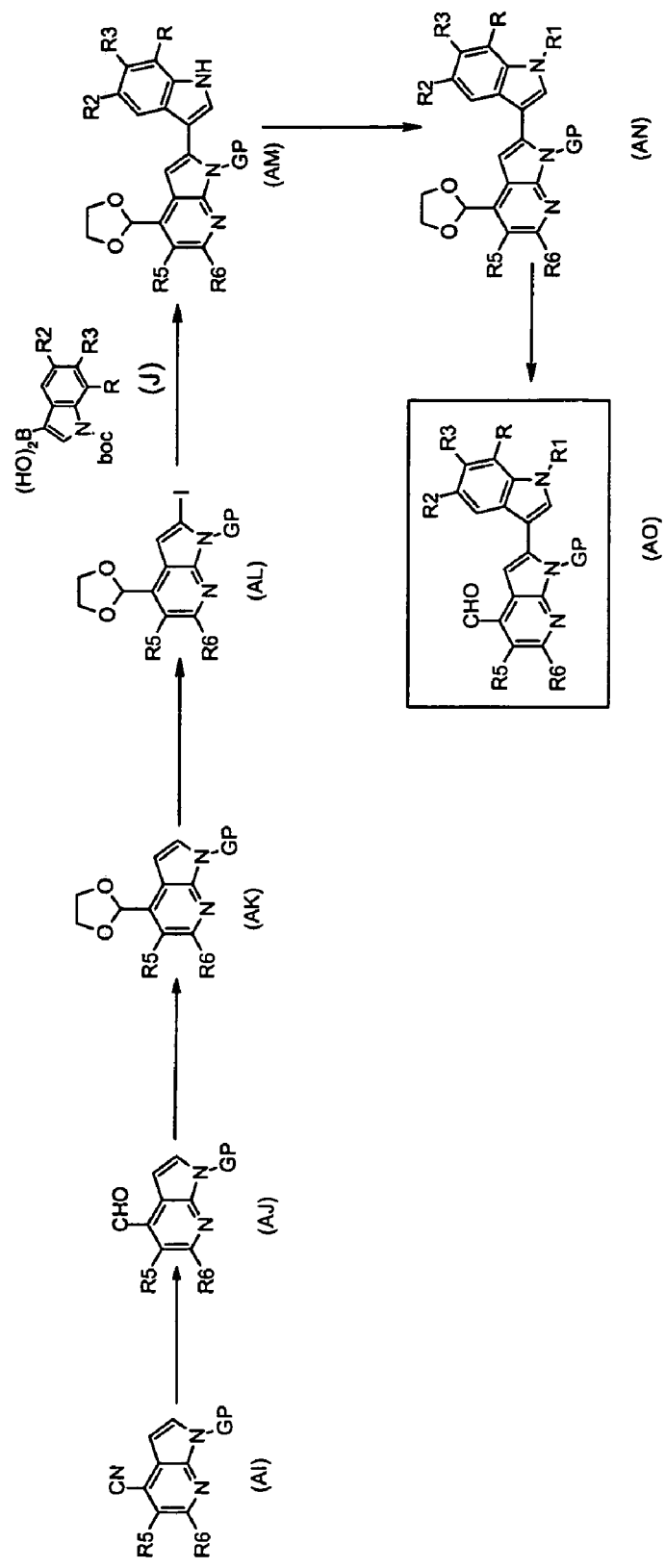
FIG. 5 (Scheme 5) describes a synthetic route for gaining access to the 2-(1H-indol-3-yl)-1H-pyrrolo[2,3-b]pyridine-4-carboxaldehyde derivatives.
Figure 6:
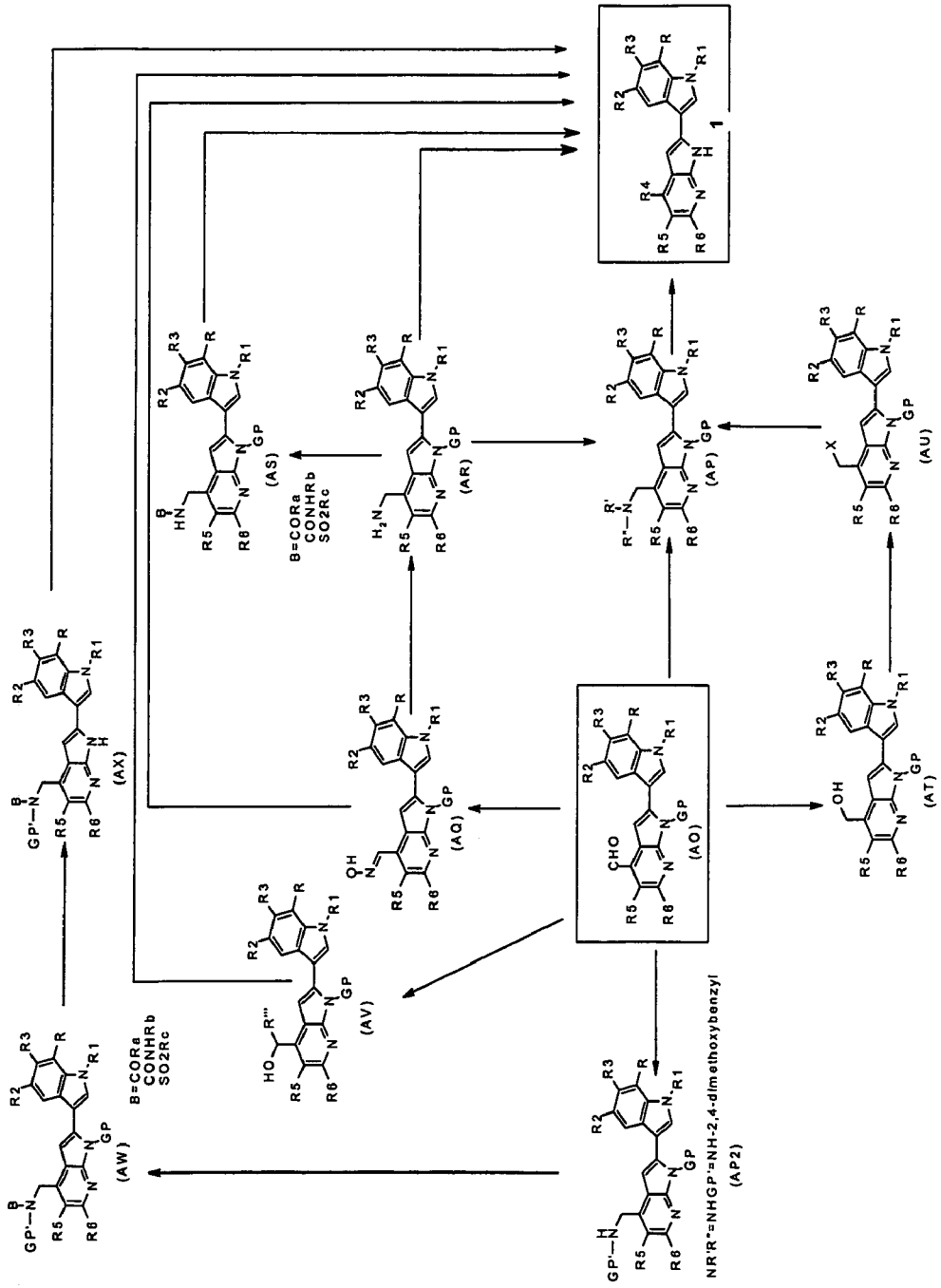
FIG. 6 (Scheme 6) describes a synthetic route for introducing substituents R4 into the compounds of formula (I).

The compounds of formula (I) of the present invention as described above can be prepared as indicated in Schemes 1 to 6 (FIGS. 1 to 6) described hereinafter; these schemes thus describe stages for synthesizing the compounds of formula (I) of the present invention and are part of the present invention.

The 1H-pyrrolo[2,3-b]pyridines of formula 1 according to the present invention:

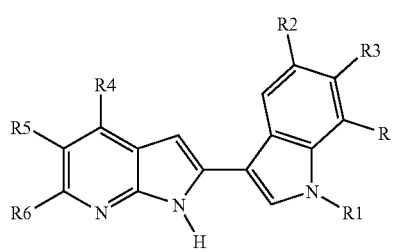

1 in which R1, R2, R3, R4, R5, R6 and R are defined as above, can be prepared according to schemes 1 to 4 in FIGS. 1 to 4; these schemes are part of the present invention.

In scheme 1 (FIG. 1), more particularly, the treatment of the 2-aminopyridines of formula (A) with $R_5 \neq H$, with N-iodosuccinimide or N-bromosuccinimide in a solvent such as acetic acid at a temperature of between 20° C. and 80° C., for instance under the conditions described by A. Fuss and V. Koch (Synthesis, 1990, 8, 681-5), results in the 3-halo-2-aminopyridines of formula (B).

More particularly, the 3-trimethylsilanylethynylpyridin-2-ylamines of formula (C) can be obtained by Sonogashira-type coupling with ethynyltrimethylsilane, for instance under the conditions described by P. Knochel et al., (Tetrahedron, 2003, 59, 1571-1587) using the 3-halo-2-aminopyridines of formula (B) in the presence of catalysts such as [1,1'-bis(diphenylphosphino)ferrocene] palladium(II) chloride or bis(triphenylphosphine) palladium(II) chloride, of copper iodide, of a base such as triethylamine and, optionally, of lithium chloride in a solvent such as dimethylformamide at a temperature of between 20° C. and 120° C.

More particularly, the 1H-pyrrolo[2,3-b]pyridines of formula (D) may be obtained by cyclization of the derivatives of formula (C) in the presence of a strong base such as potassium tert-butoxide or potassium hydride, in a solvent such as 1-methyl-2-pyrrolidinone at a temperature between 20° C. and 120° C.

More particularly, the 1H-pyrrolo[2,3-b]pyridine 7-oxides of formula (E) may be obtained by treating the derivatives of formula (D1) with 3-chloroperoxybenzoic acid in an ethereal solvent such as 1,2-dimethoxyethane at a temperature in the region of 20° C. under the conditions described in patent WO 03/000688 A1; the 1H-pyrrolo[2,3-b]pyridines of formula (D) with $R_4=Cl$ may be obtained from the 1H-pyrrolo[2,3-b]pyridine 7-oxides of formula (E) by treatment with phosphorus oxychloride at a temperature of between 20° C. and 50° C.

More particularly, the 1H-pyrrolo[2,3-b]pyridines of formula (F) may be obtained under the conditions described in patent WO 03/000688 A1 by protection of the nitrogen atom of the derivatives of formula (D) with a group such as, for example, p-toluenesulfonyl or benzenesulfonyl by treatment with the corresponding sulfonyl chlorides in the presence of a strong base such as sodium hydroxide and of a quaternary ammonium salt such as tetrabutylammonium hydrogen sulfate in a mixture of water and a solvent such as toluene at a temperature in the region of 20° C.

The 1H-pyrrolo[2,3-b]pyridines of formula (G) may be obtained as under the conditions described in the patent mentioned above, by treatment of the derivatives of formula (F) with a strong base such as N-butyllithium or tert-butyllithium in an ethereal solvent such as tetrahydrofuran, followed by the addition of iodine in solution in a solvent such as tetrahydrofuran, at a temperature in the region of −78° C.

More particularly, the 1H-pyrrolo[2,3-b]pyridines of formula (F), with $R_4=I$ and GP=acetyl may be prepared from the 1H-pyrrolo[2,3-b]pyridines of formula (D) with $R_4=Cl$, as under the conditions described by M. Allegretti et al., (Synlett, 2001, 5, 609-612) by treatment with acetyl chloride in the presence of sodium iodide in a solvent such as acetonitrile at a temperature between 20° C. and the reflux temperature of the solvent.

The 1H-pyrrolo[2,3-b]pyridines of formula (F), with $R_4=I$ and GP=acetyl, can result in the derivatives of formula (D) with $R_4=I$ by treatment in a solvent such as methanol at a temperature of between 20° C. and the reflux temperature of the solvent, under the conditions described in the above-mentioned reference.

More particularly, the 1H-pyrrolo[2,3-b]pyridines of formula (F) may be prepared from the derivatives of formula (F) with $R_4$=I by Stille coupling as under the conditions described by Javier Form et al., (Synth Commun, 23(21), 2965, 1993) by treatment with a stannic derivative, such as, for example, tetramethyl tin, in the presence of a catalyst such as bis(triphenylphosphine) palladium(II) chloride, of lithium chloride, of a phosphine such as triphenylphosphine in a solvent such as dimethylformamide at a temperature of between 20° C. and 120° C.

More particularly, the 1H-indoles of formula (I) may be obtained from the derivatives of formula (H) as under the conditions described in patent WO 03/000688 A1 by treatment with iodine in the presence of a strong base such as, for example, potassium hydroxide and of an organic base such as, for example, 4-(dimethylamino)pyridine, followed by the addition of di-tert-butyl dicarbonate in a solvent such as dimethylformamide at a temperature of between 20° C. and 60° C.

More particularly, the 1H-indoles of formula (J) may be prepared from the derivatives of formula (I) as under the conditions described in patent WO 03/000688 A1 by treatment with a strong base such as, for example, N-butyllithium and a boronic ester such as, for example, tributyl borate in an ethereal solvent such as tetrahydrofuran at a temperature of between −100° C. and 20° C.

More particularly, the 1H-pyrrolo[2,3-b]pyridines of formula (K) may be obtained by Suzuki-type coupling between the derivatives of formula (J) and the derivatives of formula (G), as, for example, under the conditions described in patent WO 03/000688 A1, in the presence of a catalyst such as tetrakis(triphenylphosphine)palladium, and of a base such as sodium hydrogen sulfate in aqueous solution, in a solvent such as dimethylformamide at a temperature of between 20° C. and the reflux temperature of the solvent.

In scheme 2 (FIG. 2), more particularly, treatment of the 1H-indoles of formula (H) with a strong base such as, for example, potassium hydroxide in a solvent such as dimethylformamide, followed by the addition of iodine or of bromine and then, for example, of an alkyl halide (preferably methyl iodide), at a temperature in the region of 20° C., results in the 3-halo-1H-indoles of formula (N) as under the conditions described by Gordon W. Gribble (J. Nat. Prod, 2002, 65, 748-749).

The 3-(trimethylsilanylethynyl-1H-indoles of formula (O) may be prepared from the derivatives of formula (N) by Sonogashira-type coupling as under the conditions described above for the derivatives of formula (C).

The 3-ethynyl-1H-indoles of formula (P) are obtained by treatment of the derivatives of formula (O) by treatment with a fluoro derivative such as, for example, potassium fluoride in a solvent such as methanol or tetrabutylammonium fluoride in a solvent such as tetrahydrofuran, at a temperature of between 20° C. and the reflux temperature of the solvent.

More particularly, the 3-ethynylpyridin-2-ylamines of formula (L) may be obtained, as under the conditions described above for the derivatives of formula (P), from the derivatives of formula (C).

More particularly, the 3-(1H-indol-3-ethynyl)pyridin-2-ylamines of formula (M) may be obtained by Sonogashira-type coupling under the conditions described above:
either between the 3-halo-2-aminopyridines of formula (B) and the 3-ethynyl-1H-indoles of formula (P)
or between the 3-halo-1H-indoles of formula (N) and the 3-ethynylpyridin-2-ylamines of formula (L).

The 1H-pyrrolo[2,3-b]pyridines of formula 1 may be prepared by treatment of the derivatives of formula (M) with a strong base such as, for example, potassium tert-butoxide or potassium hydride, in a solvent such as 1-methyl-2-pyrrolidinone, at a temperature of between 20° C. and 120° C. as under the conditions described by P. Knochel et al., (Tetrahedron, 2003, 59, 1571-1587).

In scheme 3 (FIG. 3), more particularly, the 1H-pyrrolo[2,3-b]pyridines of formula (Q) may be obtained by alkylation of the derivatives of formula (K) with an alkyl halide optionally substituted at the end position with:
a cyclic or acyclic, optionally substituted amine,
a halogen so as to give the derivatives of formula (Q2),
an alkoxy group so as to give the derivatives of formula (Q3),
an alkoxycarbonyl group so as to give the derivatives of formula (Q4),
as, for example, under the conditions described by D. Oelgen et al., (Pharmazie, 57(4), 238, 2002), in the presence of a base such as sodium hydride, in a solvent such as dimethylformamide, at a temperature between 20° C. and the reflux temperature of the solvent.

In the case of the derivatives of the formula (Q2), the conditions described by D. Bogdal et al., (Synthetic Communication, 30 (18), 3341-3352, 2000) in dichloroethane in the presence of bases such as potassium hydroxide, potassium carbonate, a quaternary ammonium such as tetrabutylammonium bromide, at a temperature in the region of 20° C., may optionally be used.

Alternatively, the 1H-pyrrolo[2,3-b]pyridines of formula (Q4), with $R'_1$=2-$(CH_2)_2CO_2tBu$ may be obtained by alkylation of the derivatives of formula (K) with a tert-butyl acrylate, as, for example, under the conditions described by M. V. R. Reddy et al., (J. Org. Chem, 67(15), 5382, 2002), in the presence of a base such as potassium carbonate, in a solvent such as dimethylformamide, at a temperature between 20° C. and the reflux temperature of the solvent.

More particularly, the 1H-pyrrolo[2,3-b]pyridines of formula (1a) may be obtained by simultaneous deprotection of the p-toluenesulfonyl group and of the ester of the derivatives of formula (Q4), as, for example, under the conditions described by A. V. Samet et al., (Synth Commun, 31(9), 1441, 2001), in the presence of a base such as potassium hydroxide, in a solvent such as methanol, at a temperature of between 20° C. and the reflux temperature of the solvent.

More particularly, the 1H-pyrrolo[2,3-b]pyridines of formula (1), where $R_1$=$(CH_2)_nCONR_7R_8$, may be obtained by amidation of the derivatives of formula (1a) with amines $HNR_7R_8$, using peptide coupling agents such as, for example, O-benzotriazolyl-N,N,N',N'-tetramethyluronium hexafluorophosphate (HBTU) or O-(7-azabenzotriazol-1-yl)-N,N,N', N'-tetramethyluronium hexafluorophosphate (HAUT), under the conditions described by V. Dourtoglou and B. Gross (Synthesis, 572, 1984), in a solvent such as dimethylformamide, at a temperature of between 20° C. and the reflux temperature of the solvent.

More particularly, the 1H-pyrrolo[2,3-b]pyridines of formula (R) may be obtained by reaction of the derivatives of formula (Q2) with sodium iodide or potassium iodide, as, for example, under the conditions described by C. F. H. Allen et al., (J. Org Chem, 14, 754, 1949), in a solvent such as methyl ethyl ketone, at a temperature of between 20° C. and the reflux temperature of the solvent.

More particularly, the 1H-pyrrolo[2,3-b]pyridines of formula (S) may be obtained by reaction of the derivatives of formula (R) with amines $HNR_7R_8$, as, for example, under the conditions described by M. D. Pujol et al., (Eur. J. Med. Chem., 31(11), 889, 1996), in the presence of a base such as potassium carbonate, in a solvent such as methyl ethyl ketone, at a temperature of between 20° C. and the reflux temperature of the solvent.

More particularly, the 1H-pyrrolo[2,3-b]pyridines of the formula (U) or (T) may be obtained from the 4-chloro-1H-pyrrolo[2,3-b]pyridines of formula (Q1) or (S1) by means of the action of zinc cyanide, in the presence of zinc, and of a catalyst such as, for example, 1,1'-bis(diphenylphosphino) ferrocene palladium(II) dichloride in a solvent such as, for example, dimethylacetamide, at a temperature of between 20 and 150° C., for instance under the conditions described by Fuqiang Jin et al., (Tetrahedron Letters 41, 2000, 3271-3273).

More particularly, the 1H-pyrrolo[2,3-b]pyridines of formula (V) may be obtained from the derivatives of formula (Q1) by Buchwald-type coupling with benzophenone imine in the presence of a base such as cesium carbonate, of a catalyst such as palladium(II) acetate, and of a ligand, such as, for example, 2,2'-bis(diphenylphosphino)-1,1'-binaphthyl, in a solvent such as toluene, at a temperature of between 20° C. and the reflux temperature of the solvent, for instance under the conditions described by L. Buchwald et al., (J. Org. Chem, 61, 1996, 7240-7241).

The 1H-pyrrolo[2,3-b]pyridines of formula (W) may be obtained from the derivatives of formula (V) under conventional conditions described by Greene and Wuts in Protective Groups in Organic Synthesis, 3rd edition, Wiley-Interscience, by hydrolysis of the imine in acid medium, for instance in aqueous hydrochloric acid in a solvent such as tetrahydrofuran, at a temperature of between 20° C. and the reflux temperature of the solvent.

More particularly, the 1H-pyrrolo[2,3-b]pyridines of formula (X) with $\Phi$=OH, may be obtained from the derivatives of formula (Q3) with $R'_1$=$(CH_2)_n OSiMe_2tBu$ [$(CH_2)_n OTB\text{-}DMS$], for instance under the conditions described by E. J. Corey and A. Venkateswarlu (J Am Chem Soc, 94, 6190, 1972), by reaction with a fluoro derivative such as, for example, tetrabutylammonium fluoride, in a solvent such as tetrahydrofuran, at a temperature of between 20° C. and the reflux temperature of the solvent. During this reaction, the derivatives of formula (X) with $\Phi$=F are also obtained.

More particularly, the 1H-pyrrolo[2,3-b]pyridines of formula (1) may be obtained by deprotection of the derivatives of formulae (S), (T), (U), (W), (X) and (Q) under conventional conditions described by Greene and Wuts in Protective Groups in Organic Synthesis, 3rd edition, Wiley-Interscience, 1999.

When the protective group is a p-toluenesulfonyl group, the N-deprotection of the derivatives of formulae (S), (T), (U), (W), (X) and (Q) is carried out for instance under the conditions described above for the derivatives of formula (1a) or else, for example, in the presence of tetrabutylammonium fluoride in a solvent such as tetrahydrofuran at a temperature of between 20° C. and the reflux temperature of the solvent.

In scheme 4 (FIG. 4), more particularly, the 1H-pyrrolo[2,3-b]pyridines of formula (Q5) may be obtained from the derivatives of formula (K1) as described above for the derivatives of formula (Q).

More particularly, the 1H-pyrrolo[2,3-b]pyridines of formula (Y) may be obtained by debenzylation of the derivatives of formula (Q5), for example under the conditions described by M. E. Jung and M. A. Lyster (J Org Chem, 42, 3761, 1977), in the presence of trimethylsilane iodide in a solvent such as acetonitrile at a temperature of between 20° C. and the reflux temperature of the solvent.

More particularly, the 1H-pyrrolo[2,3-b]pyridines derivatives of formula (Z) with $\Sigma$=CO-alkyl may be obtained by reaction of the derivatives of formula (Y) with a substituted alkyl halide such as $X(CH_2)_n OCO\text{-}alkyl$, for instance under the conditions described by J. C. Gonzalez-Gomez et al., in (Bioorg Med. Chem. Letters, 12, (2), 175, 2003), in the presence of a base such as sodium hydride, in a solvent such as dimethylformamide, at a temperature of between 20° C. and the reflux temperature of the solvent.

More particularly, the 1H-pyrrolo[2,3-b]pyridines of formula (1) with $\Sigma$=H may be obtained by simultaneous deprotection of the p-toluenesulfonyl and ester group of (Y) with $\Sigma$=CO-alkyl, for instance under the conditions described above for the derivatives of formula (1a).

Alternatively, the 1H-pyrrolo[2,3-b]pyridines of formula (Z) with $\Sigma$=alkyl may be obtained by reaction of the derivatives of formula (Y) with an alkyl ether halide such as $X(CH_2)_n O\text{-}alkyl$, for instance under the conditions described by A. Leschot et al., (Synth Commun, 32(20), 3219, 2002), in the presence of a base such as cesium carbonate or potassium carbonate, in a solvent such as acetone, acetonitrile or dimethylformamide, at a temperature of between 20° C. and the reflux temperature of the solvent.

Alternatively, the 1H-pyrrolo[2,3-b]pyridines of formula (Z) with $\Sigma$=$(CH_2)_n Cl$ may be obtained by reaction of the derivatives of formula (Y) with a dialkyl ether dihalide such as $X(CH_2)_n O\text{---}(CH_2)_n X$, for instance under the conditions above for the derivatives of formula (Z) with $\Sigma$=CO-alkyl.

Alternatively, the 1H-pyrrolo[2,3-b]pyridines of formula (Z) with $\Sigma$=$(CH_2)_n'' NR_7 R_8$ may be obtained by reaction of the derivatives of formula (Z) with $\Sigma$=$(CH_2)_n Cl$, with amines $HNR_7R_8$, for instance under the conditions described above for the derivatives of formula (S).

More particularly, the 1H-pyrrolo[2,3-b]pyridines of formula (AA) with GP=p-toluenesulfonyl may be obtained by alkylation of the derivatives of formula (Y) with an alkyl acetate halide, for instance under the conditions described above for the derivatives of formula (Z) with $\Sigma$=CO-alkyl.

More particularly, the 1H-pyrrolo[2,3-b]pyridines of formula (1b) may be obtained by simultaneous deprotection of the p-toluenesulfonyl and ester group of (AA), for instance under the conditions described above for the derivatives of formula (1a).

More particularly, the 1H-pyrrolo[2,3-b]pyridines of formula (1) with $R_3$=$OCH_2 CONR_7 R_8$ may be obtained by amidation of the derivatives of formula (1b), with amines $HNR_7R_8$, for instance under the conditions described in "Practical Guide to Combinatorial Chemistry", ISBN 0-8412-3485-x, p-51-97, in the presence of dicyclohexylcarbodiimide, or hydroxyazabenzotriazole and of a base in a solvent such as dimethylformamide at a temperature of between 20° C. and the reflux temperature of the solvent.

More particularly, the 6-hydroxy-1H-pyrrolo[2,3-b]pyridines of formula (AB) may be obtained by debenzylation of the derivatives of formula (K1), for instance under the conditions described above for the derivatives of formula (Y).

More particularly, the 1H-pyrrolo[2,3-b]pyridines of formula (AC) with GP=p-toluenesulfonyl may be obtained by bisalkylation of the derivatives of formula (AB) with an alkyl acetate halide, for instance under the conditions described above for the derivatives of formula (AA).

More particularly, the 1H-pyrrolo[2,3-b]pyridines of formula (AD) may be obtained by reaction of the derivatives of formula (Y) with triflic anhydride, for instance under the conditions described by K. A. Parker and Q. J. Ding (Tetrahedron, 56(52), 10249, 2000), in the presence of a base such as pyridine, in a solvent such as dichloromethane, at a temperature of between 0° C. and the reflux temperature of the solvent.

More particularly, the 1H-pyrrolo[2,3-b]pyridines of formula (AE) may be obtained by Suzuki-type coupling between the derivatives of formula (AD) and alkyl boronic acids, for instance under the conditions described by G. S. Cockerill (J Chem Soc, Perkin Trans. 1, 2591, 2000) in the presence of a catalyst such as tetrakis(triphenylphosphine)palladium, and of a base such as sodium hydrogen carbonate in aqueous solution, in a solvent such as dimethylformamide, at a temperature of between 20° C. and the reflux temperature of the solvent.

More particularly, the 1H-pyrrolo[2,3-b]pyridines of formula (AF) may be obtained by alkylation of the derivatives of formula (Y) with an alkyl dihalide, for instance under the conditions described above for the derivatives of formula (AA).

More particularly, the 1H-pyrrolo[2,3-b]pyridines of formula (AG) may be obtained by halogen exchange from the derivatives of formula (AF), for instance under the conditions described above for the derivatives of formula (R).

More particularly, the 1H-pyrrolo[2,3-b]pyridines of formula (AH) may be obtained by reaction of the derivatives of formula (AG) with amines $HNR_7R_8$, for instance under the conditions described above for the derivatives of formula (S).

More particularly, the 1H-pyrrolo[2,3-b]pyridines of formula (1) may be obtained by deprotection of the derivatives of formulae (AC), (AE), (AH) and (Z), under conventional conditions described by Greene and Wuts in Protective Groups in Organic Synthesis, 3rd edition, Wiley-Interscience, 1999.

When the protective group is a p-toluenesulfonyl group, the deprotection of the derivatives of formulae (AC), (AE), (AH) and (Z) is carried out, for instance, under the conditions described above for the derivatives of formula (1a).

Scheme 5 (FIG. 5) describes a synthetic route for gaining access to the 2-(1H-indol-3-yl)-1H-pyrrolo[2,3-b]pyridine-4-carboxaldehyde derivatives.

More particularly, treatment of the 4-cyano-1H-pyrrolo[2,3-b]pyridines of general formula (AI) with a reducing agent such as diisobutylaluminum hydride (DIBAH), in an aprotic solvent such as toluene, at a temperature of between –30° C. and 20° C., for instance under the conditions described by Anderson, B. A. et al. (J. Org. Chem., 1997, 62(25), 8634-8639), leads to the 4-carboxaldehyde-1H-pyrrolo[2,3-b]pyridines of general formula (AJ).

More particularly, the 4-(1,3-dioxolan)-1H-pyrrolo[2,3-b]pyridines of general formula (AK) may be obtained by reaction of the derivatives of general formula (AJ) with ethylene glycol in a solvent such as toluene, in the presence of an acidic catalyst such as para-toluenesulfonic acid, at a temperature of between 80° C. and 120° C., for instance under the conditions described by Pasto M. et al. (Tetrahedron: Asymmetry, 1995, 6(9), 2329-2342).

The 4-(1,3-dioxolan)-2-iodo-1H-pyrrolo[2,3-b]pyridines of general formula (AL) may be obtained as under the conditions described in patent WO 03/000688 A1, by treatment of the derivatives of general formula (AK) with a strong base, for instance n-butyllithium or tert-butyllithium, in an ether solvent such as tetrahydrofuran, followed by the addition of iodine as a solution in a solvent such as tetrahydrofuran, at a temperature in the region of –78° C.

More particularly, the 1H-pyrrolo[2,3-b]pyridines of general formula (AM) may be obtained via a Suzuki coupling between the derivatives of general formula (J) and the derivatives of general formula (AL) as described above for the derivatives of general formula (K).

More particularly, the 1H-pyrrolo[2,3-b]pyridines of general formula (AN) may be obtained from the derivatives of general formula (AM) as described above for the derivatives of general formula (Q).

More particularly, the 1H-pyrrolo[2,3-b]pyridines of general formula (AO) may be obtained by treatment of the derivatives of general formula (AN) in the presence of an acid such as hydrochloric acid, in a solvent such as tetrahydrofuran at a temperature of between 20° C. and 60° C., for instance under the conditions described by Ishimaru K. et al. (Heterocycles, 2001, 55(8), 1591-1597).

Scheme 6 (FIG. 6) describes a synthetic route for introducing substituents R4 into the compounds of formula (I).

More particularly, the 1H-pyrrolo[2,3-b]pyridines of general formula (AP) and (AP2) may be obtained by treatment of the derivatives of general formula (AO) with an amine, in the presence of a hydride such as sodium borohydride and a dehydrating agent such as magnesium sulfate, in a solvent such as methanol or ethanol, at a temperature in the region of 20° C., for instance under the conditions described by Patra, P. K. et al. (Eur. J. Org. Chem., 2001, 22, 4195-4206).

These 1H-pyrrolo[2,3-b]pyridines of general formula (AP) may also be obtained either:

by treatment of the derivatives of general formula (AR) with a halide or a mesylate, in the presence of a base such as sodium carbonate, in a solvent such as acetonitrile, at a temperature of between 20° C. and the boiling point of the solvent, for instance under the conditions described by Kaneko, T. et al. (Chem. Pharm. Bull., 2002, 50(7), 922-929);

or by treatment of the derivatives of general formula (AU) with an amine, in the presence of a base such as sodium carbonate, in a solvent such as acetonitrile, at a temperature of between 20° C. and the boiling point of the solvent, for instance under the conditions described above.

The 1H-pyrrolo[2,3-b]pyridines of general formula (AQ) may be obtained from the 1H-pyrrolo[2,3-b]pyridines of general formula (AO) by treatment with hydroxylamine hydrochloride, in a solvent such as pyridine, at a temperature of between 20° C. and 50° C., for instance under the conditions described by Schroeder, M. C. et al. (J. Heterocyclic Chem., 1992, 29(6), 1481-1498).

More particularly, the 4-aminomethyl-1H-pyrrolo[2,3-b]pyridines of general formula (AR) may be obtained by reduction of the oxime (AQ) with a metal such as zinc, in the presence of an acid such as acetic acid or formic acid, in a solvent such as water and/or ethanol and at a temperature in the region of 20° C., for instance under the conditions described by Prasitpan, N. et al. (Synth. Commun., 1990, 20(22), 3459-3466).

More particularly, the 1H-pyrrolo[2,3-b]pyridines of general formula (AS) may be obtained by treatment of the derivatives of general formula (AR) with substituted sulfonyl chlorides, substituted isocyanates or substituted acid chlorides, in the presence of a base such as triethylamine, in an aprotic solvent such as dichloromethane, at a temperature of between 0 and 20° C., as under the conditions described by Metz, P. et al. (Synlett, 1996, (8), 741-742), by Hergueta, A. R. et al. (Chem. Pharm. Bull., 2002, 50(10), 1379-1382) and by Coelho, P. J. et al. (Synlett, 2001, (9), 1455-1457).

The 1H-pyrrolo[2,3-b]pyridine-4-methanol compounds of general formula (AT) may be obtained by reduction of the derivatives of general formula (AO) with a hydride such as sodium borohydride, in an ether solvent such as tetrahydrofuran, at a temperature in the region of 20° C., for instance under the conditions described by Wang, E. C. et al. (Heterocycles, 2002, 57(11), 2021-2033).

More particularly, the 1H-pyrrolo[2,3-b]pyridines of general formula (AU), with X=Cl, may be obtained from the 1H-pyrrolo[2,3-b]pyridine-4-methanol compounds of general formula (AT), as under the conditions described by Fucase K. et al. (Tetrahedron Lett., 1991, 32(32), 4019-4022), by treatment with thionyl chloride in the presence of DMF in a solvent such as dichloromethane, at a temperature of between 0° C. and 20° C.

The 1H-pyrrolo[2,3-b]pyridines of general formula (AU), with X=OSO2Me, may be obtained from 1H-pyrrolo[2,3-b]pyridine-4-methanol compounds of general formula (AT), as under the conditions described by Altamura M. et al. (J. Org. Chem., 1993, 58(1), 272-274), by treatment with methanesulfonic anhydride in the presence of a base such as pyridine, in a solvent such as dichloromethane, at a temperature of between −10° C. and 20° C.

More particularly, the 1H-pyrrolo[2,3-b]pyridines of general formula (AV) may be obtained by treatment of the derivatives of general formula (AO) with Grignard reagents in a solvent such as tetrahydrofuran at a temperature of between 0 and 20° C., as under the conditions described by Labrosse, J. R. et al. (Synth. Commun., 2002, 32(23), 3667-3674).

More particularly, the 1H-pyrrolo[2,3-b]pyridines of general formula (AW), with B=CORa, CONHRb, SO2Rc), may be obtained from the derivatives of general formula (AP2) as described above for the derivatives of general formula (AS).

More particularly, the 1H-pyrrolo[2,3-b]pyridines of general formula (AX) may be obtained by deprotection of the derivatives of general formula (AW) under standard conditions described by Greene and Wuts in *Protective Groups in Organic Synthesis*, 3rd edition, Wiley-Interscience, 1999.

More particularly, the 1H-indoles of general formula (1) may be obtained from the derivatives of general formula (AX) as under the conditions described by Madar, D. J., et al. (Tetrahedron Lett., 2001, 42, 3681-3684), by treatment with an acid, for instance trifluoroacetic acid or para-toluenesulfonic acid, in a solvent such as dichloromethane or toluene, at a temperature of between 20° C. and 100° C.

More particularly, the 1H-pyrrolo[2,3-b]pyridines of general formula (1) may be obtained by deprotection of the derivatives of general formula (AP), (AQ), (AR), (AS) or (AV) under standard conditions described by Greene and Wuts in *Protective Groups in Organic Synthesis*, 3rd edition, Wiley-Interscience, 1999.

A subject of the present invention is also processes for preparing:
- the compounds of general formula (D) and most particularly the reactions using the 2-aminopyridines (A) according to scheme 1;
- the compounds of general formula (1) and most particularly the reactions according to scheme 2.

It may be noted that, in the reactions for preparing the compounds of formula (I) according to the present invention, and in particular in the reactions indicated in the schemes, the intermediate compounds or the compounds of formula (I) may, if necessary, be in protected form, the possible reactive functions being optionally protected with protective groups.

The intermediate compounds or the compounds of formula (I), which may or may not be in protected form, may be subjected, if desired and if necessary, in order to obtain compounds of formula (I) or other compounds of formula (I), to one or more of the following conversion reactions, in any order:

a) a reaction consisting of esterification of an acid function,
b) a reaction consisting of saponification of an ester function to an acid function,
c) a reaction consisting of oxidation of an alkylthio to a corresponding sulfoxide or sulfone,
d) a reaction consisting of conversion of a ketone function to an oxime function,
e) a reaction consisting of reduction of the free or esterified carboxyl function to an alcohol function,
f) a reaction consisting of conversion of an alkoxy function to a hydroxyl function, or alternatively of a hydroxyl function to an alkoxy function,
g) a reaction consisting of oxidation of an alcohol function to an aldehyde, acid or ketone function,
h) a reaction consisting of conversion of a nitrile radical to a tetrazolyl radical,
i) a reaction consisting of reduction of the nitrogenous compounds to amino compounds,
j) a reaction consisting of elimination of the protective groups that the protected reactive functions may bear,
k) a reaction consisting of salification with an mineral or organic acid or with a base in order to obtain the corresponding salt,
l) a reaction consisting of resolution of the racemic forms into resolved compounds, said compounds of formula (I) thus obtained being in any possible racemic, enantiomeric or diastereoisomeric isomer form.

It may be noted that such reactions for conversion of substituents to other substituents can also be carried out on the starting compounds and also on the intermediate compounds as defined above, before continuing the synthesis according to the reactions indicated in the process described above.

The compounds of formula (I) according to the present invention could also be prepared by applying or adapting known methods, and in particular the methods described in the literature, for instance those described by R. C. Larock in: Comprehensive Organic Transformations, VCH publishers, 1989.

In order to prepare the compounds of formula (I), it may therefore be necessary to protect reactive functional groups such as, for example, hydroxyl, amino, imino, thio or carboxyl groups, when these groups are desired in the final product but when their participation in the reactions to synthesize the compounds of formula (I) is not desired. Use may in particular be made of conventional protective groups in agreement with usual standard practices such as those described, for example, by T. W. Greene and P. G. M. Wuts in "Protective Groups in Organic Chemistry" John Wiley and Sons, 1991.

The various reactive functions that may be borne by certain compounds of the reactions defined above may, if necessary, be protected. These are, for example, free carboxyl, acyl or hydroxyl radicals, or else amino and monoalkylamino radicals, which can be protected with appropriate protective groups.

The following nonexhaustive list of examples of protection of reactive functions may be mentioned:
- the hydroxyl groups can be protected, for example, with alkyl radicals such as tert-butyl, trimethylsilyl, tert-butyldimethylsilyl, methoxymethyl, tetrahydropyrannyl, benzyl or acetyl,
- the amino groups can be protected, for example, with acetyl, trityl, benzyl, tert-butoxycarbonyl, benzyloxycarbonyl or phthalimido radicals or other radicals known in peptide chemistry,
- the acyl groups, such as the formyl group, can be protected, for example, in the form of cyclic or noncyclic acetals or thioacetals such as dimethyl or diethyl acetal or ethylene dioxyacetal, or diethyl thioacetal or ethylene dithioacetal, the acid functions of the compounds described above can, if desired, be amidated with a primary or secondary amine, for example in methylene chloride in the presence, for example, of 1-ethyl-3-(dimethylaminopropyl) carbodiimide hydrochloride at ambient temperature.

the acid functions can be protected, for example, in the form of esters formed with readily cleavable esters such as benzyl esters or tert-butyl esters or esters known in peptide chemistry.

These reactions a) to k) indicated above can be carried out, for example, as indicated hereinafter.

a) The compounds described above can, if desired, be the subject, on the possible carboxyl functions, of esterification reactions which can be carried out according to the usual methods known to those skilled in the art.

b) The optional conversions of an ester function to an acid function in the compounds described above can, if desired, be carried out under the usual conditions known to those skilled in the art, in particular by acid or alkaline hydrolysis, for example with sodium hydroxide or potassium hydroxide in alcoholic medium such as, for example, in methanol, or else with hydrochloric or sulfuric acid.

c) The possible alkylthio groups of the compounds described above, in which the alkyl radical is optionally substituted with one or more halogen atoms, in particular fluorine atoms, can, if desired, be converted into the corresponding sulfoxide or sulfone functions under the usual conditions known to those skilled in the art, such as, for example, with peracids, for instance peracetic acid or meta-chloroperbenzoic acid, or else with ozone, oxone, sodium periodate in a solvent such as, for example, methylene chloride, or dioxane, at ambient temperature.

Obtaining of the sulfoxide function can be promoted with an equimolar mixture of the compound containing an alkylthio group and of the reagent such as, in particular, a peracid.

Obtaining of the sulfone function can be promoted with a mixture of the compound containing an alkylthio group with an excess of the reagent such as, in particular, a peracid.

d) The reaction consisting of conversion of a ketone function to an oxime can be carried out under the usual conditions known to those skilled in the art, such as, in particular, action in the presence of an optionally O-substituted hydroxylamine in an alcohol such as, for example, ethanol, at ambient temperature or by heating.

e) The possible free or esterified carboxyl functions of the compounds described above can, if desired, be reduced to an alcohol function by the methods known to those skilled in the art; the possible esterified carboxyl functions can, if desired, be reduced to an alcohol function by the methods known to those skilled in the art, and in particular with lithium aluminum hydride in a solvent such as, for example, tetrahydrofuran or else dioxane or ethyl ether.

The possible free carboxyl functions of the compounds described above can, if necessary, be reduced to an alcohol function in particular with boron hydride.

f) The possible alkoxy functions, such as in particular methoxy functions, of the compounds described above can, if necessary, be converted into hydroxyl function under the usual conditions known to those skilled in the art, for example with boron tribromide in a solvent such as, for example, methylene chloride, with pyridine hydrobromide or hydrochloride or else with hydrobromic or hydrochloric acid in water or trifluoroacetic acid at reflux.

g) The possible alcohol functions of the compounds described above can, if desired, be converted into an aldehyde or acid function by oxidation under the usual conditions known to those skilled in the art, such as, for example, by the action of manganese oxide in order to obtain aldehydes, or of Jones reagent in order to obtain acids.

h) The possible nitrile functions of the compounds described above can, if desired, be converted into a tetrazolyl function under the usual conditions known to those skilled in the art, such as, for example, by cycloaddition of a metal azide such as, for example, sodium azide or a trialkyl tin azide, on the nitrile function as is indicated in the method described in the article mentioned below:

J. Organometallic Chemistry, 33, 337 (1971) S. Kozima et al.

It may be noted that the reaction for conversion of a carbamate to urea, and in particular of a sulfonyl carbamate to sulfonylurea, can be carried out, for example, at the reflux of the solvent such as, for example, toluene, in the presence of the appropriate amine.

It is understood that the reactions described above can be carried out as indicated or alternatively, where appropriate, according to other usual methods known to those skilled in the art.

i) The elimination of protective groups such as, for example, those indicated above can be carried out under the usual conditions known to those skilled in the art, in particular by acid or basic hydrolysis carried out with an acid such as hydrochloric acid, benzenesulfonic or para-toluenesulfonic acid, formic acid or trifluoroacetic acid, or else by catalytic hydrogenation or using a base such as potassium hydroxide, sodium hydroxide or tetrabutylammonium fluoride.

The phthalimido group can be eliminated with hydrazine.

A list of various protective groups which can be used will be found, for example, in patent BF 2 499 995.

j) The compounds described above can, if desired, be the subject of salification reactions, for example with an mineral or organic acid or with a mineral or organic base according to the usual methods known to those skilled in the art.

k) The possible optically active forms of the compounds described above can be prepared by resolution of the racemic mixtures according to the usual methods known to those skilled in the art.

The possible reactive functions may be hydroxyl or amino functions; the usual protective groups are used to protect these functions. Mention may be made, for example, of the following amino radical-protecting groups: tert-butyl, tert-amyl, trichloroacetyl, chloroacetyl, benzhydryl, trityl, formyl, benzyloxycarbonyl, para-toluenesulfonyl, acetyl, benzenesulfonyl or benzoyl.

As hydroxyl radical-protecting group, mention may be made of the radicals such as formyl, benzyl, acetyl, chloroacetyl, tetrahydropyranyl, trimethylsilyl and tert-butyldimethylsilyl.

It is clearly understood that the list above is not limiting and that other protective groups, for example known in peptide chemistry, can be used. A list of such protective groups can be found, for example, in French patent BF 2 499 995, the content of which is incorporated herein by way of reference.

The optional reactions for eliminating the protective groups are carried out as indicated in said patent BF 2 499 995. The preferred method of elimination is acid hydrolysis by means of acids selected from hydrochloric acid, benzenesulfonic acid or para-toluenesulfonic acid, formic acid or trifluoroacetic acid. Hydrochloric acid is preferred.

The optional reaction for hydrolysis of the group >C=NH to a ketone group is also preferably carried out by means of an acid, such as aqueous hydrochloric acid, for example at reflux.

The tert-butyldimethylsilyl protective group can be eliminated, for example, by means of hydrochloric acid.

The optional esterification of a free OH radical is carried out under conventional conditions. Use may be made, for example, of an acid or of a functional derivative, for example an anhydride such as acetic anhydride in the presence of a base such as pyridine.

The optional esterification or salification of a COOH group is carried out under the conventional conditions known to those skilled in the art.

The optional amidation of a COOH radical is carried out under conventional conditions. Use may be made of a primary or secondary amine on a functional derivative of the acid, for example a symmetric or mixed anhydride.

The compounds which are the subject of the present invention have advantageous pharmacological properties: it has been noted that they in particular possess protein kinase-inhibiting properties.

Among these protein kinases, mention may in particular be made of IGF1R.

Tests given in the experimental section hereinafter illustrate the inhibitory activity of the compounds of the present invention with respect to such protein kinases.

These properties therefore make the compounds of formula (I) of the present invention usable as medicinal products for the treatment of malignant tumors.

The compounds of formula (I) can also be used in the veterinary field.

A subject of the invention is therefore the application, as medicinal products, of the pharmaceutically acceptable compounds of formula (I).

A subject of the invention is particularly the application, as medicinal products, of the compounds of formula (I), the names of which are given below:

2-{5,6-dimethoxy-1-[2-(4-methylpiperazin-1-yl)ethyl]-1H-indol-3-yl}-1H-pyrrolo[2,3-b]pyridine
2-(4-{2-[5,6-dimethoxy-3-(1H-pyrrolo[2,3-b]pyrid-2-yl)indol-1-yl]ethyl}piperazin-1-yl)ethanol
2-(1-{2-[5,6-dimethoxy-3-(1H-pyrrolo[2,3-b]pyrid-2-yl)indol-1-yl]ethyl}piperid-4-yl)ethanol
1'-{2-[5,6-dimethoxy-3-(1H-pyrrolo[2,3-b]pyrid-2-yl)indol-1-yl]ethyl}-[1,4']bipiperidyl
1-{2-[5,6-dimethoxy-3-(1H-pyrrolo[2,3-b]pyrid-2-yl)indol-1-yl]ethyl}piperid-3-ol
2-{5,6-dimethoxy-1-[2-(4-methylperhydro-1,4-diazepin-1-yl)ethyl]-1H-indol-3-yl}-1H-pyrrolo[2,3-b]pyridine
2-[5,6-dimethoxy-3-(1H-pyrrolo[2,3-b]pyrid-2-yl)indol-1-yl]-1-(4-hydroxypiperid-1-yl)ethanone
2-[5,6-dimethoxy-3-(1H-pyrrolo[2,3-b]pyrid-2-yl)indol-1-yl]-1-thiazolidin-3-ylethanone
4-{[5,6-dimethoxy-3-(1H-pyrrolo[2,3-b]pyrid-2-yl)indol-1-yl]acetyl}-1-methylpiperazin-2-one
4-Chloro-2-(5,6-dimethoxy-1-methyl-1H-indol-3-yl)-1H-pyrrolo[2,3-b]pyridine
2-(5,6-dimethoxy-1-methyl-1H-indol-3-yl)-1H-pyrrolo[2,3-b]pyridine-4-carbonitrile
4-chloro-2-[5,6-dimethoxy-1-(2-morpholin-4-ylethyl)-1H-indol-3-yl]-1H-pyrrolo[2,3-b]pyridine
2-(1-{2-[3-(4-chloro-1H-pyrrolo[2,3-b]pyrid-2-yl)-5,6-dimethoxyindol-1-yl]ethyl}piperid-4-yl)ethanol
4-chloro-2-{5,6-dimethoxy-1-[2-(4-methylpiperazin-1-yl)ethyl]-1H-indol-3-yl}-1H-pyrrolo[2,3-b]pyridine
2-{5,6-dimethoxy-1-[2-(4-methylpiperazin-1-yl)ethyl]-1H-indol-3-yl}-1H-pyrrolo[2,3-b]pyridine-4-carbonitrile
2-(5,6-dimethoxy-1-methyl-1H-indol-3-yl)-5-fluoro-1H-pyrrolo[2,3-b]pyridine
2-[5,6-dimethoxy-1-(2-morpholin-4-ylethyl)-1H-indol-3-yl]-5-fluoro-1H-pyrrolo[2,3-b]pyridine
2-{5,6-dimethoxy-1-[2-(4-methylpiperazin-1-yl)ethyl]-1H-indol-3-yl}-5-fluoro-1H-pyrrolo[2,3-b]pyridine
2-[5-Methoxy-1-methyl-3-(1H-pyrrolo[2,3-b]pyrid-2-yl)-1H-indol-6-yloxy]-1-morpholin-4-ylethanone
2-[5-Methoxy-1-methyl-3-(1H-pyrrolo[2,3-b]pyrid-2-yl)-1H-indol-6-yloxy]-1-(4-methyl[1,4]diazepan-1-yl)ethanone
2-[5-Methoxy-1-methyl-3-(1H-pyrrolo[2,3-b]pyrid-2-yl)-1H-indol-6-yloxy]-N-[4-(4-methylpiperazin-1-yl)phenyl]acetamide
2-[5-Methoxy-1-methyl-3-(1H-pyrrolo[2,3-b]pyrid-2-yl)-1H-indol-6-yloxy]-1-(4-methylpiperazin-1-yl)ethanone
1-{4-[2-(2-Hydroxyethoxy)ethyl]piperazin-1-yl)-2-[5-methoxy-1-methyl-3-(1H-pyrrolo[2,3-b]pyrid-2-yl)-1H-indol-6-yloxy]ethanone
(3aS,6aS)-5-{2-[5-Methoxy-1-methyl-3-(1H-pyrrolo[2,3-b]pyrid-2-yl)-1H-indol-6-yloxy]acetyl}hexahydropyrrolo[3,4-c]pyrrol-1-one trifluoroacetate
2-{5-Methoxy-1-methyl-6-[3-(4-methylperhydro-1,4-diazepin-1-yl)propoxy]-1H-indol-3-yl}-1H-pyrrolo[2,3-b]pyridine
4-Chloro-2-{1-methyl-5-methoxy-6-[2-(4-methylpiperazin-1-yl)ethoxy]-1H-indol-3-yl}-1H-pyrrolo[2,3-b]pyridine
4-Chloro-2-{1-methyl-5-methoxy-6-[2-(4-piperidylpiperid-1-yl)ethoxy]-1H-indol-3-yl}-1H-pyrrolo[2,3-b]pyridine
4-Chloro-2-{5-methoxy-1-methyl-6-[2-(2-pyrrolidinethylamino)ethoxy]-1H-indol-3-yl}-1H-pyrrolo[2,3-b]pyridine
4-Chloro-2-[(1-methyl-5-methoxy-6-[2-(2-piperidinethylamino)ethoxy]-1H-indol-3-yl]-1H-pyrrolo[2,3-b]pyridine, and also the prodrugs thereof, said compounds of formula (I) being in any possible racemic, enantiomeric or diastereoisomeric isomer form, and also the pharmaceutically acceptable addition salts with mineral and organic acids or with mineral and organic bases of said compounds of formula (I).

A subject of the invention is particularly the application, as medicinal product, of the compounds of formula (I), the names of which are given below:

2-{5,6-Dimethoxy-1-[2-(4-methylpiperazin-1-yl)ethyl]-1H-indol-3-yl)-1H-pyrrolo[2,3-b]pyridine
2-(4-{2-[5,6-Dimethoxy-3-(1H-pyrrolo[2,3-b]pyridin-2-yl)indol-1-yl]ethyl}piperazin-1-yl)ethanol
2-(1-{2-[5,6-Dimethoxy-3-(1H-pyrrolo[2,3-b]pyridin-2-yl)indol-1-yl]ethyl}piperidin-4-yl)ethanol
1'-{2-[5,6-Dimethoxy-3-(1H-pyrrolo[2,3-b]pyridin-2-yl)indol-1-yl]ethyl}-[1,4']bipiperidinyl
1-{2-[5,6-Dimethoxy-3-(1H-pyrrolo[2,3-b]pyridin-2-yl)indol-1-yl]ethyl}piperidin-3-ol
2-{5,6-Dimethoxy-1-[2-(4-methylperhydro-1,4-diazepin-1-yl)ethyl]-1H-indol-3-yl}-1H-pyrrolo[2,3-b]pyridine
2-[5,6-Dimethoxy-3-(1H-pyrrolo[2,3-b]pyridin-2-yl)indol-1-yl]-1-(4-hydroxypiperidin-1-yl)ethanone
2-[5,6-Dimethoxy-3-(1H-pyrrolo[2,3-b]pyridin-2-yl)indol-1-yl]-1-thiazolidin-3-ylethanone
4-{[5,6-Dimethoxy-3-(1H-pyrrolo[2,3-b]pyridin-2-yl)indol-1-yl]acetyl}-1-methylpiperazin-2-one
4-Chloro-2-(5,6-dimethoxy-1-methyl-1H-indol-3-yl)-1H-pyrrolo[2,3-b]pyridine
2-(5,6-Dimethoxy-1-methyl-1H-indol-3-yl)-1H-pyrrolo[2,3-b]pyridine-4-carbonitrile 4-Chloro-2-[5,6-dimethoxy-1-(2-morpholin-4-ylethyl)-1H-indol-3-yl]-1H-pyrrolo[2,3-b]pyridine 2-(1-{2-[3-(4-chloro-1H-pyrrolo[2,3-b]pyridin-2-yl)-5,6-dimethoxyindol-1-yl]ethyl}piperidin-4-yl)ethanol 4-Chloro-2-{5,6-dimethoxy-1-[2-(4-methylpiperazin-1-yl)ethyl]-1H-indol-3-yl}-1H-pyrrolo[2,3-b]pyridine 2-{5,6-Dimethoxy-1-[2-(4-methylpiperazin-1-yl)ethyl]-1H-indol-3-yl}-1H-pyrrolo[2,3-b]pyridine-4-carbonitrile 2-{5,6-Dimethoxy-1-methyl-1H-indol-3-yl)-5-fluoro-1H-pyrrolo[2,3-b]pyridine 2-[5,6-Dimethoxy-1-[2-morpholin-4-ylethyl)-1H-indol-3-yl]-5-fluoro-1H-pyrrolo[2,3-b]pyridine 2-{5,6-Dimethoxy-1-[2-(4-methylpiperazin-1-yl)ethyl]-1H-indol-3-yl}-5-fluoro-1H-pyrrolo[2,3-b]pyridine 2-[5-Methoxy-1-methyl-3-(1H-pyrrolo[2,3-b]pyridin-2-yl)-1H-indol-6-yloxy]-1-morpholin-4-ylethanone 2-[5-Methoxy-1-methyl-3-(1H-pyrrolo[2,3-b]pyridin-2-yl)-1H-indol-6-yloxy]-1-(4-methyl-[1,4]diazepan-1-yl)ethanone 2-[5-Methoxy-1-methyl-3-(1H-pyrrolo[2,3-b]pyridin-2-yl)-1H-indol-6-yloxy]-N-[4-(4-methylpiperazin-1-yl)phenyl]acetamide 2-[5-Methoxy-1-methyl-3-(1H-pyrrolo[2,3-b]pyridin-2-yl)-1H-indol-6-yloxy]-1-(4-methylpiperazin-1-yl)ethanone 1-{4-[2-(2-Hydroxyethoxy)ethyl]piperazin-1-yl}-2-[5-methoxy-1-methyl-3-(1H-pyrrolo[2,3-b]pyridin-2-yl)-1H-indol-6-yloxy]ethanone (3aS,6aS)-5-{2-[5-Methoxy-1-methyl-3-(1H-pyrrolo[2,3-b]pyridin-2-yl)-1H-indol-6-yloxy]acetyl}hexahydropyrrolo[3,4-c]pyrrol-1-one trifluoroacetate 2-{5-methoxy-1-methyl-6-[3-(4-methylperhydro-1,4-diazepin-1-yl)propoxy]-1H-indol-3-yl}-1H-pyrrolo[2,3-b]pyridine 4-Chloro-2-{1-methyl-5-methoxy-6-[2-(4-methylpiperazin-1-yl)ethoxy-1H-indol-3-yl}-1H-pyrrolo[2,3-b]pyridine 4-Chloro 2-{1-methyl-5-methoxy-6-[2-(4-piperidylpiperidin-1-yl)ethoxy-1H-indol-3-yl}-1H-pyrrolo[2,3-b]pyridine 4-Chloro-2-(5-methoxy-1-methyl-6-[2-(2-pyrrolidinethylamino)ethoxy]-1H-indol-3-yl)-1H-pyrrolo[2,3-b]pyridine 4-Chloro-2-{1-methyl-5-methoxy-6-[2-(2-piperidinethylamino)ethoxy-1H-indol-3-yl}-1H-pyrrolo[2,3-b]pyridine, and also the prodrugs thereof, said compounds of formula (I) being in any possible racemic, enantiomeric or diastereoisomeric isomer form, and also the pharmaceutically acceptable addition salts with mineral and organic acids or with mineral and organic bases of said compounds of formula (I).

The compounds can be administered parenterally, orally, perlingually, rectally or topically.

A subject of the invention is also the pharmaceutical compositions which contain, as active principle, at least one of the medicinal compounds of formula (I).

These compositions can be provided in the form of injectable solutions or suspensions, of tablets, of coated tablets, of capsules, of syrups, of suppositories, of creams, of ointments and of lotions. These pharmaceutical forms are prepared according to the usual methods. The active principle can be incorporated into excipients usually used in these compositions, such as aqueous or nonaqueous vehicles, talc, gum arabic, lactose, starch, magnesium stearate, cocoa butter, fatty substances of animal or plant origin, paraffin derivatives, glycols, various wetting agents, dispersants or emulsifiers, preserving agents.

The usual dose, which is variable according to the individual treated and the condition in question, can, for example, be from 10 mg to 500 mg per day in humans, given orally.

The present invention thus relates to the use of compounds of formula (I) as defined above, or of pharmaceutically acceptable salts of said compounds of formula (I) for preparing medicinal products intended to inhibit the activity of protein kinases, and in particular of a protein kinase.

The present invention thus relates to the use of compounds of formula (I) as defined above, or of pharmaceutically acceptable salts of said compounds of formula (I) in which the protein kinase is a tyrosine protein kinase.

The present invention thus relates to the use of compounds of formula (I) as defined above, or of pharmaceutically acceptable salts of said compounds of formula (I) in which the protein kinase is selected from the following group:

IGF1, Raf, EGF, PDGF, VEGF, Tie2, KDR, Flt1-3, FAK, Src, Abl, cKit, cdk1-9, Aurora1-2, cdc7, Akt, Pdk, S6K, Jnk, IR, FLK-1, FGFR1, FGFR2, FGFR3, FGFR4, FGFR5, PLK and Pyk2.

The present invention thus relates to the use of compounds of formula (I) as defined above, or of pharmaceutically acceptable salts of said compounds of formula (I), in which the protein kinase is more particularly selected from the following group: IGF1, cdc7, Aurora1-2, Src, Jnk, FAK, KDR, IR and Tie2.

The present invention thus relates particularly to the use of compounds of formula (I) as defined above, or of pharmaceutically acceptable salts of said compounds of formula (I), in which the protein kinase is IGF1R.

The present invention also relates to the use of compounds of formula (I) as defined above, or of pharmaceutically acceptable salts of said compounds of formula (I), in which the protein kinase is in a cell culture, and also to this use in a mammal.

The present invention thus relates to the use of compounds of formula (I) as defined above, or of pharmaceutically acceptable salts of said compounds of formula (I), for preparing a medicinal product intended to prevent or treat a disease characterized by a disturbance of the activity of a protein kinase, and in particular such a disease in a mammal.

The present invention relates to the use of compounds of formula (I) as defined above, or of pharmaceutically acceptable salts of said compounds of formula (I), for preparing a medicinal product intended to prevent or treat a disease belonging to the following group: blood vessel proliferation disorders, fibrotic disorders, mesangial cell proliferation disorders, metabolic disorders, allergies, asthma, thromboses, nervous system diseases, retinopathies, psoriasis, rheumatoid arthritis, diabetes, muscle degeneration, diseases in oncology, and cancers.

The present invention thus relates to the use of compounds of formula (I) as defined above, or of pharmaceutically acceptable salts of said compounds of formula (I), for preparing a medicinal product intended to treat diseases in oncology.

The present invention relates particularly to the use of compounds of formula (I) as defined above, or of pharmaceutically acceptable salts of said compounds of formula (I), for preparing a medicinal product intended to treat cancers.

Among these cancers, the present invention focuses most particularly on the treatment of solid tumors and on the treatment of cancers that are resistant to cytotoxic agents.

Among these cancers, the present invention relates most particularly to the treatment of breast cancer, stomach cancer, colon cancer, lung cancer, ovarian cancer, uterine cancer, brain cancer, kidney cancer, cancer of the larynx, cancer of the lymphatic system, thyroid cancer, cancer of the urogenital tract, cancer of the tract including the bladder and prostate, bone cancer, pancreatic cancer, and melanomas.

The present invention focuses even more particularly on the treatment of breast cancer, colon cancer and lung cancer.

The present invention thus relates to the use of compounds of formula (I) as defined above, or of pharmaceutically acceptable salts of said compounds of formula (I), for preparing a medicinal product intended for cancer chemotherapy.

As medicinal products according to the present invention, intended for cancer chemotherapy, the compounds of formula (I) according to the present invention can be used alone or in combination with chemotherapy or radiotherapy, or alternatively in combination with other therapeutic agents.

The present invention thus relates in particular to the pharmaceutical compositions as defined above, containing, in addition to the active principles, other medicinal products for chemotherapy against cancer.

Such therapeutic agents may be commonly used antitumor agents.

As examples of known inhibitors of protein kinases, mention may in particular be made of butyrolactone, flavopiridol, 2-(2-hydroxyethylamino)-6-benzylamino-9-methylpurine, olomucine, Glivec and Iressa.

The compounds of formula (I) according to the present invention may thus also advantageously be used in combination with antiproliferative agents; by way of examples of such antiproliferative agents, but without, however, being limited to this list, mention may be made of aromatase inhibitors, antiestrogens, topoisomerase I inhibitors, topoisomerase II inhibitors, agents that are active on microtubules, alkylating agents, histone deacetylase inhibitors, farnesyl transferase inhibitors, COX-2 inhibitors, MMP inhibitors, mTOR inhibitors, antineoplastic antimetabolites, platinum compounds, compounds which decrease protein kinase activity and also anti-angiogenic compounds, gonadorelin agonists, anti-androgens, bengamides, bisphosphonates and trastuzumab.

Mention may thus be made, by way of examples, of anti-microtubule agents such as taxoids, vinca alkaloids, alkylating agents such as cyclophosphamide, DNA-intercalating agents such as cis-platinum, agents that are interactive on topoisomerase, such as camptothecin and derivatives, anthracyclines such as adriamycin, antimetabolites such as 5-fluorouracil and derivatives, and the like.

The present invention therefore relates to compounds of formula (I) as protein kinase inhibitors, said compounds of formula (I) being in any possible racemic, enantiomeric or diastereoisomeric isomer form, and also the pharmaceutically acceptable addition salts with mineral and organic acids or with mineral and organic bases of said compounds of formula (I) and also the prodrugs thereof.

The present invention relates particularly to compounds of formula (I) as defined above, as IGF1R inhibitors.

The starting compounds for synthesizing the compounds of formula (I) according to the invention may be known, described in the documents of those skilled in the art or commercially available, or may be prepared according to usual methods known to those skilled in the art or else according to the methods described in the attached schemes.

The experimental section hereinafter gives, more particularly, an illustration of the syntheses described in the schemes of the present invention, with the preparation of examples 1 to 175 of the present application. The examples whose preparation follows, whether this involves preparations of compounds or preparations of pharmaceutical compositions, illustrate the present invention without, however, limiting it.

In the preparations which follow, the analytical methods and purification methods used to characterize the compounds are as follows:

Mass Spectrometry:

The spectra were produced by electron impact (EI) and/or by chemical desorption-ionization (CI) (reactant gas: ammonia) on a Finnigan SSQ 7000 spectrometer.

Analytical Methods: Method A

Unless explicitly otherwise indicated, the reverse-phase liquid chromatography mass spectrometry (LC/MS) analyses were carried out on a Micromass model LCT device connected to an HP 1100 device. The abundance of the compounds was measured by means of an HP G1315A diode array detector over a wavelength of 200-600 nm (DAD) and a Sedex 65 light scattering detector. Acquisition of the mass spectra was carried out over a range of 180 to 800. The data were analyzed using the Micromass MassLynx software. Separation was carried out on a Hypersil BDS C18, 3 µm (50×4.6 mm) column, elution being carried out with a linear gradient of 5 to 90% of acetonitrile containing 0.05% (v/v) of trifluoroacetic acid (TFA) in water containing 0.05% (v/v) TFA, over 3.5 min at a flow rate of 1 cm$^3$/min. The total time for analysis, including the column re-equilibration period, is 7 min.

Purification Methods: Method B

In general, the compounds obtained were purified by reverse-phase liquid chromatography mass spectrometry (LC/MS) using a Waters FractionLynx system composed of a Waters model 600 gradient pump, a Waters model 515 regeneration pump, a Waters Reagent Manager dilution pump, a Waters model 2700 autoinjector, two Rheodyne LabPro model valves, a Waters model 996 diode array detector, a Waters model ZMD mass spectrometer and a Gilson model 204 fraction collector. The system was controlled by the Waters FractionLynx software. The separation was performed alternately on two Waters Symmetry columns ($C_{18}$, 5 µm, 19×50 mm, catalogue reference 186000210), one column undergoing regeneration with a 95/5 (v/v) water/acetonitrile mixture containing 0.07% (v/v) of trifluoroacetic acid, while the other column was used for separation. The columns were eluted using a linear gradient of acetonitrile containing 0.07% (v/v) of trifluoroacetic acid in water containing 0.07% (v/v) of trifluoroacetic acid, at a flow rate of 10 cm$^3$ min. At the separation column outlet, a thousandth of the effluent was separated out using an LC Packing Accurate device, diluted with methanol at a flow rate of 0.05 cm$^3$/min and sent to the detectors, in a proportion of 75% to the diode array detector and the remaining 25% to the mass spectrometer. The rest of the effluent (999/1000) was sent to the fraction collector, where the flow was discarded as long as the mass of the expected compound was not detected by the FractionLynx software. The molecular formulae of the expected compounds are supplied to the FractionLynx software, which initiates collection of the compound when the detected mass signal corresponds to the [M+H]$^+$ and/or [M+Na]$^+$ ion. In certain cases, depending on the analytical LC/MS results, when an intense ion corresponding to (M+2H)$^{++}$ was detected, the value corresponding to half the calculated molecular mass (MW/2) is also supplied to the FractionLynx software. Under these conditions, the collection is also initiated when the mass signal for the [M+2H]++ ion and/or the [M+Na+H]++ ion is (are) detected. The compounds were collected in tared glass tubes.

The solutions having a volume greater than 0.5 cm$^3$ are purified in two stages, the others in a single stage. The fractions are collected in pre-labeled and pre-tared hemolysis tubes, and only the tubes containing the compound of expected molecular mass are used.

Unless explicitly otherwise indicated, the binary elution gradient used for these purifications is as follows:

Concentration gradient chromatographic method B

| | Time (min) | | | | |
|---|---|---|---|---|---|
| | 0 | 0.5 | 9.5 | 12 | 12.5 |
| MeCN % | 5 | 5 | 95 | 95 | 5 |

In the text, the method referred to as "method D" uses the same equipment as that described above, but with the elution gradient below.

Concentration gradient chromatographic method C

| | Time (min) | | | | |
|---|---|---|---|---|---|
| | 0 | 5 | 9 | 12 | 12.5 |
| MeCN % | 5 | 5 | 95 | 95 | 5 |

In the text, the method referred to as "method E" uses the same equipment as that described above, but with the elution gradient below.

Concentration gradient chromatographic method E

| | Time (min) | | | | | |
|---|---|---|---|---|---|---|
| | 0 | 1 | 8 | 9 | 11 | 11.5 | 12 |
| % Acetonitrile | 2 | 2 | 75 | 98 | 98 | 2 | 2 |

In the text, the method referred to as "method F" uses the same equipment as that described above, but with the elution gradient below.

Concentration gradient chromatographic method F

| | Time (min) | | | | | | |
|---|---|---|---|---|---|---|---|
| | 0 | 1 | 8 | 9 | 11 | 11.5 | 12 |
| MeCN % | 5 | 5 | 75 | 95 | 95 | 5 | 5 |

In the text, the method referred to as "method G" uses the same equipment as that described above, but with the elution gradient below.

Concentration gradient chromatographic method G

| | Time (min) | | | | | |
|---|---|---|---|---|---|---|
| | 0 | 1.5 | 8 | 10 | 12 | 12.5 |
| MeCN % | 1 | 1 | 50 | 95 | 95 | 5 |

EXAMPLE 1

2-(5,6-Dimethoxy-1-vinyl-1H-indol-3-yl)-1H-pyrrolo[2,3-b]pyridine trifluoroacetate The 2-(5,6-Dimethoxy-1-vinyl-1H-indol-3-yl)-1H-pyrrolo-[2,3-b]pyridine trifluoroacetate can be prepared in the following way:

A solution of 2-(5,6-dimethoxy-1H-indol-3-yl)-1-(toluene-4-sulfonyl)-1H-pyrrolo[2,3-b]pyridine (0.5 g; 1.117 mmol) in dimethylformamide (5 ml) is placed in a 10 ml round-bottomed flask closed with a septum, and then 1-bromo-2-chloroethane is added (0.865 g; 0.5 ml; 6.032 mmol). The reaction mixture is stirred at ambient temperature and then sodium hydride (0.1 g; 3.35 mmol) is added by means of 33 successive portions. When the reaction mixture becomes green, 1-bromo-2-chloroethane (0.865 g; 0.5 cm$^3$; 6.03 mmol) is added. The reaction is monitored by TLC (50/50 cyclohexane/ethyl acetate) until the starting compound disappears. The reaction mixture is run into a mixture of 20 ml of water and a saturated ammonium chloride solution (20 ml). Ethyl acetate (50 ml) is added, and then separation by settling out and extraction with ethyl acetate (30 ml) are performed. The combined extracts are washed with a saturated ammonium chloride solution (30 ml), dried over magnesium sulfate and evaporated under reduced pressure. The evaporation product is taken up in a 50/50 cyclohexane/ethyl acetate mixture and then left at ambient temperature for 24 hours. The solid formed is filtered off, rinsed with a 72/25 cyclohexane/ethyl acetate mixture (15 ml), and then dried under reduced pressure. The compound obtained is purified by LCMS (method B).

2-[1-(2-chloroethyl)-5,6-dimethoxy-1H-indol-3-yl]-1-(toluene-4-sulfonyl)-1H-pyrrolo[2,3-b]pyridine (0.33 g) is isolated, the characteristics of which are as follows:

$^1$H NMR spectrum (300 MHz, (CD$_3$)$_2$SO d6, δ in ppm): 2.30 (s: 3H); 3.73 (s: 3H); 3.90 (s: 3H); 4.09 (t, J=6 Hz: 2H); 4.63 (t, J=6 Hz: 2H); 6.76 (s: 1H); 6.95 (s: 1H); 7.26 (d, J=8.5 Hz: 2H); 7.27 (s: 1H); 7.32 (dd, J=8 and 5 Hz: 1H); 7.55 (s: 1H); 7.58 (d, J=8.5 Hz: 2H); 7.96 (dd, J=8 and 1.5 Hz: 1H); 8.38 (dd, J=5 and 1.5 Hz: 1H).

Mass spectrum: (EI): m/z=509 [M]$^+$; m/z=354 [M-C$_7$H$_7$NSO$_2$]+(base peak)

2-(5,6-Dimethoxy-1-vinyl-1H-indol-3-yl)-1H-pyrrolo[2,3-b]pyridine trifluoroacetate (0.042 g) is also isolated, the characteristics of which are as follows:

$^1$H NMR spectrum (300 MHz, (CD$_3$)$_2$SO d6, δ in ppm): 3.89 (s: 3H); 3.93 (s: 3H); 4.86 (broad d, J=8.5 Hz: 1H); 5.32 (broad d, J=15.5 Hz: 1H); 6.97 (d, J=2 Hz: 1H); 7.11 (dd, J=8 and 5 Hz: 1H); 7.46 (s: 1H); 7.47 (s: 1H); 7.63 (dd, J=15.5 and 8.5 Hz: 1H); 7.99 (broad d, J=8 Hz: 1H); 8.21 (dd, J=5 and 1.5 Hz: 1H); 8.34 (s: 1H); 11.96 (unresolved peak: 1H).

Mass spectrum: (EI): m/z=319 [M]$^+$ (base peak)

2-(5,6-Dimethoxy-1H-indol-3-yl)-1-(toluene-4-sulfonyl)-1H-pyrrolo[2,3-b]pyridine is obtained as described in patent WO 03/0006881A1.

EXAMPLES 2 TO 79

A) Preparation: 2-[1-(2-iodoethyl)-5,6-dimethoxy-1H-indol-3-yl]-1-(toluene-4-sulfonyl)-1H-pyrrolo[2,3-b]pyridine can be prepared in the following way:

A solution of 2-[1-(2-chloroethyl)-5,6-dimethoxy-1H-indol-3-yl]-1-(toluene-4-sulfonyl)-1H-pyrrolo[2,3-b]pyridine (0.331 g; 649 µmol), described in example 1, and sodium iodide (0.195 g; 1.298 mmol) in methyl ethyl ketone (5 ml) is placed in a 10 ml round-bottomed flask. The reaction mixture is brought to reflux for 16 hours. After evaporation, the product is taken up in a mixture of water (15 ml) and ethyl acetate (15 ml). After separation by settling out and extraction with ethyl acetate (2×15 ml), the organic extracts are combined, dried over magnesium sulfate, and then evaporated under reduced pressure. The evaporation residue is chromatographed on silica gel, elution being carried out with a mixture of cyclohexane and ethyl acetate (50/50). The fractions containing the expected compound are combined and evaporated, giving 2-[1-(2-iodoethyl)-5,6-dimethoxy-1H-indol-3-yl]-1-(toluene-4-sulfonyl)-1H-pyrrolo[2,3-b]pyridine (0.24 g; 69%), the characteristics of which are as follows:

LC/MS analysis: tr=3.9 min, m/z 601.99 [M+H]$^+$ b) Alkylation of Examples 2 to 79

The amines below, in solution in dimethylformamide at a concentration of 90 µmol per 0.5 ml of dimethylformamide, are placed in tared and labeled glass tubes (1.2×10 cm).

The compound 2-[1-(2-iodoethyl)-5,6-dimethoxy-1H-indol-3-yl]-1-(toluene-4-sulfonyl)-1H-pyrrolo[2,3-b]pyridine is dissolved in dimethylformamide at a concentration of 30 µmol per 0.5 ml of solvent.

| Ex | Name or reagent | Formula | MW (g/mol) | Weight (mg) |
|---|---|---|---|---|
| 2 | 2-(2-aminoethyl)-1-methylpyrrolidine | C7H16N2 | 128.22 | 11.540 |
| 3 | 2-(aminomethyl)-1-ethylpyrrolidine | C7H16N2 | 128.22 | 11.540 |
| 4 | n-(2-aminoethyl)pyrrolidine | C6H14N2 | 114.19 | 10.280 |
| 5 | furfurylamine | C5H7NO | 97.12 | 8.741 |
| 6 | I-methioninol | C5H13NOS | 135.23 | 12.170 |
| 7 | imidazole | C3H4N2 | 68.08 | 6.127 |
| 8 | 3-pyrroline | C4H7N | 69.11 | 6.220 |
| 9 | pyrrolidine | C4H9N | 71.12 | 6.401 |
| 10 | tetrahydrofurfurylamine | C5H11NO | 101.15 | 9.104 |
| 11 | 1-piperonylpiperazine | C12H16N2O2 | 220.27 | 19.820 |
| 12 | 3,4-methylenedioxybenzylamine | C8H9BO2 | 151.17 | 13.610 |
| 13 | 2-methylpiperazine | C3H12N2 | 100.16 | 9.014 |
| 14 | 1-phenylpiperazine | C10H14N2 | 162.24 | 14.600 |
| 15 | 1-(2-methoxyphenyl)piperazine | C11H16N2O | 192.26 | 17.300 |
| 16 | n-(3-trifluoromethylphenyl)piperazine | C11H13F3N2 | 230.23 | 20.720 |
| 17 | 1-(4-fluorophenyl)piperazine | C10H13FN2 | 180.23 | 16.220 |
| 18 | 1-ethoxycarbonylpiperazine | C7H14N2O2 | 158.2 | 14.240 |
| 19 | 1-methylpiperazine | C5H12N2 | 100.16 | 9.014 |
| 20 | 1-benzylpiperazine | C11H16N2 | 176.26 | 15.860 |
| 21 | n-(2-hydroxyethyl)piperazine | C6H14N2O | 130.19 | 11.720 |
| 22 | 2,6-dimethylmorpholine | C6H13NO | 115.18 | 10.370 |
| 23 | 1,4-dioxa-8-azaspiro[4.5]decane | C7H13NO2 | 143.19 | 12.890 |
| 24 | piperidine | C5H11N | 85.15 | 7.664 |
| 25 | 2-piperidineethanol | C7H15NO | 129.2 | 11.630 |
| 26 | 3,3-dimethylpiperidine | C7H15N | 113.2 | 10.190 |
| 27 | 3,5-dimethylpiperidine | C7H15N | 113.2 | 10.190 |
| 28 | 4-hydroxy-4-phenylpiperidine | C11H15NO | 177.25 | 15.950 |
| 29 | 4-methylpiperidine | C6H13N | 99.18 | 8.926 |
| 30 | 4-piperidineethanol | C7H15NO | 129.2 | 11.630 |
| 31 | 1-(2-pyridyl)piperazine | C9H13N3 | 163.22 | 14.690 |
| 32 | 4-piperidinopiperidine | C10H20N2 | 168.28 | 15.150 |
| 33 | 40-amino-1-benzylpiperidine | C12H18N2 | 190.29 | 17.130 |
| 34 | 1-(2-aminoethyl)piperidine | C7H16N2 | 128.22 | 11.540 |
| 35 | 2-amino-2-methyl-1-propanol | C4H11NO | 89.14 | 8.023 |
| 36 | 2-amino-5-diethylaminopentane | C9H22N2 | 158.29 | 14.250 |
| 37 | benzylamine | C7H9N | 107.16 | 9.644 |
| 38 | N,N-diethylethylenediamine | C6H16N2 | 116.21 | 10.460 |
| 39 | ethanolamine | C2H7NO | 61.08 | 5.497 |
| 40 | N,N-dimethyl-1,3-propanediamine | C5H14N2 | 102.18 | 9.196 |
| 41 | 1-(3-aminopropyl)imidazole | C6H11N3 | 125.17 | 11.270 |
| 42 | (s)-(+)-2-(methoxymethyl)pyrrolidine | C6H13NO | 115.18 | 10.370 |
| 43 | (s)-(+)-1-(2-pyrrolidinylmethyl)pyrrolidine | C9H18N2 | 154.26 | 13.880 |
| 44 | 3-hydroxypiperidine | C5H11NO | 101.15 | 9.104 |
| 45 | 1-(3-aminopropyl)-4-methylpiperazine | C8H19N3 | 157.26 | 14.150 |
| 46 | N1,N1-dimethyl-1,2-propanediamine | C5H14N2 | 102.18 | 9.196 |
| 47 | N,N-diisopropylethylenediamine | C8H20N2 | 144.26 | 12.980 |
| 48 | 3-(2-methylpiperidin-1-yl)propylamine | C9H20N2 | 156.27 | 14.06 |
| 49 | dl-2-amino-1-propanol | C3H9NO | 75.11 | 3.756 |
| 50 | tryptamine hydrochloride | C10H13ClN2 | 196.68 | 9.834 |
| 51 | (s)-(+)-2-(anilinomethyl)pyrrolidine | C11H16N2 | 176.26 | 8.813 |
| 52 | (+/−)-nornicotine | C9H12N2 | 148.21 | 7.411 |
| 53 | 2-(2-aminoethyl)pyridine | C7H10N2 | 122.17 | 6.109 |
| 54 | 4-benzyl-4-hydroxypiperidine | C12H17NO | 191.28 | 9.564 |
| 55 | N-aminopropylpiperidine | C8H18N2 | 142.25 | 7.112 |
| 56 | N-(2-aminoethyl)-n-ethyl-m-toluidine | C11H18N2 | 178.28 | 8.914 |

-continued

| Ex | Name or reagent | Formula | MW (g/mol) | Weight (mg) |
|---|---|---|---|---|
| 57 | 1-(4-methoxyphenyl)piperazine | C11H16N2O | 192.26 | 9.613 |
| 58 | 1-(2-phenylethyl)piperazine | C12H18N2 | 190.29 | 9.515 |
| 59 | 1-(4-pyridyl)piperazine | C9H13N3 | 163.22 | 8.161 |
| 60 | 1-(2-hydroxyphenyl)piperazine 2 HBr | C10H16Br2N2O | 340.06 | 17.00 |
| 61 | adenine | C5H5N5 | 135.13 | 6.757 |
| 62 | N,N-2,2-tetramethyl-1,3-propanediamine | C7H18N2 | 130.23 | 6.512 |
| 63 | 1-cyclohexylpiperazine | C10H20N2 | 168.28 | 8.414 |
| 64 | N-methylhomopiperazine | C6H14N2 | 114.19 | 5.710 |
| 65 | d-prolinol | C5H11NO | 101.15 | 5.058 |
| 66 | (s)-(+)-2-amino-1-butanol | C4H11NO | 89.14 | 4.457 |
| 67 | dimethylamine | C2H7N | 45.08 | 1.352 |
| 68 | diethylamine | C4H11N | 73.14 | 2.194 |
| 69 | 1-(3-pyrrolidinopropyl)homopiperazine | C12H25N3 | 211.35 | 6.340 |
| 70 | 2-(1H-pyrrol-1-yl)-1-ethanamine | C6H10N2 | 110.16 | 3.305 |
| 71 | 2-(1-benzyl-piperidinyl)ethylamine | C14H22N2 | 218.34 | 6.550 |
| 72 | diethanolamine | C4H11NO2 | 105.14 | 12.620 |
| 73 | 2-(2-methylaminoethyl)pyridine | C8H12N2 | 136.2 | 16.340 |
| 74 | N-ethylmethylamine | C3H9N | 59.11 | 7.093 |
| 75 | N,N,N'-trimethylethylenediamine | C5H14N2 | 102.18 | 12.260 |
| 76 | N-methylisobutylamine | C5H13N | 87.17 | 10.460 |
| 77 | 4-(ethylaminomethyl)pyridine | C8H12N2 | 136.2 | 16.340 |
| 78 | bis(2-methoxyethyl)amine | C6H15NO2 | 133.19 | 15.980 |
| 79 | 3-methylamino-1,2-propanediol | C4H11NO2 | 105.14 | 12.620 |

0.5 ml of each of the solutions prepared above is distributed into reactors suitable for parallel synthesis, along with 0.5 ml per well of the solution of 2-[1-(2-iodoethyl)-5,6-dimethoxy-1H-indol-3-yl]-1-(toluene-4-sulfonyl)-1H-pyrrolo[2,3-b]pyridine in dimethylformamide described above, and then from 0.01 to 0.015 g of potassium carbonate is added. Since the reactors are closed by means of a septum, they are placed at 80° C. for 16 hours, with orbital shaking. After returning to ambient temperature, the content of the reactors is filtered and then purified by reverse-phase liquid chromatography mass spectrometry (method B). After evaporation of the fractions, weighing and analysis of the results of preparative reverse-phase liquid chromatography mass spectrometry, the intermediate compounds are isolated and identified, and are used in the following step.

c) Detosylation of Examples 2 to 79

Each compound isolated above is dissolved in a methanolic potassium hydroxide solution at 0.1 g/ml (0.5 ml), and each tube is then stoppered and shaken at ambient temperature for 60 hours. The content of each tube is evaporated under reduced pressure, diluted with distilled water (1.5 ml) and extracted with dichloromethane (3×0.9 ml). The organic extracts are combined, dried over magnesium sulfate, filtered in tared and labeled glass tubes (1.2×10 cm), and then evaporated. The compounds isolated after evaporation are weighed and diluted with dimethyl sulfoxide (0.5 ml) and are then subjected to purification by reverse-phase liquid chromatography mass spectrometry in preparative mode (method B). The fractions containing the compounds of expected molar mass are evaporated, weighed and diluted to a concentration of 10 mM in dimethyl sulfoxide. The expected compounds are identified and characterized by reverse-phase liquid chromatography mass spectrometry analysis (method A). The results obtained are reported in the table below.

| Ex | IUPAC (Parent) | EF (parent) | MW (parent) | RT (min.) | m/z | % | TRACE |
|---|---|---|---|---|---|---|---|
| 2 | {2-[5,6-Dimethoxy-3-(1H-pyrrolo[2,3-b]pyridin-2-yl)indol-1-yl]ethyl}-[2-(1-methylpyrrolidin-2-yl)ethyl]amine | C26H33N5O2 | 447.58 | 2.51 | 448.43 | 79 | DAD |
| 3 | {2-[5,6-Dimethoxy-3-(1H-pyrrolo[2,3-b]pyridin-2-yl)indol-1-yl]ethyl}-(1-ethylpyrrolidin-2-ylmethyl)amine | C26H33N5O2 | 447.58 | 2.48 | 448.43 | 83 | DAD |
| 4 | {2-[5,6-Dimethoxy-3-(1H-pyrrolo[2,3-b]pyridin-2-yl)-3alambda7-indol-1-yl]ethyl}-(2-pyrrolidin-1-yl-ethyl)amine | C25H31N5O2 | 433.56 | 2.50 | 434.43 | 82 | DAD |
| 5 | {2-[5,6-Dimethoxy-3-(1H-pyrrolo[2,3-b]pyridin-2-yl)indol-1-yl]ethyl}furan-2-ylmethylamine | C24H24N4O3 | 416.48 | 2.71 | 417.35 | 88 | DAD |
| 6 | 2-{2-[5,6-Dimethoxy-3-(1H-pyrrolo[2,3-b]pyridin-2-yl)-indol-1-yl]ethylamino}-4-methylsulfanyl-butan-1-ol | C24H30N4O3S | 454.59 | 2.71 | 455.38 | 91 | DAD |

-continued

| Ex | IUPAC (Parent) | EF (parent) | MW (parent) | RT (min.) | m/z | % | TRACE |
|---|---|---|---|---|---|---|---|
| 7 | 2-[1-(2-Imidazol-1-yl-ethyl)-5,6-dimethoxy-1H-indol-3-yl]-1H-pyrrolo[2,3-b]pyridine | C22H21N5O2 | 387.44 | 2.54 | 388.36 | 84 | DAD |
| 8 | 2-{1-[2-(2,5-Dihydropyrrol-1-yl)-ethyl]-5,6-dimethoxy-1H-indol-3-yl}-1H-pyrrolo[2,3-b]pyridine | C23H24N4O2 | 388.47 | 2.61 | 389.37 | 96 | DAD |
| 9 | 2-[5,6-Dimethoxy-1-(2-pyrrolidin-1-ylethyl)-1H-indol-3-yl]-1H-pyrrolo[2,3-b]pyridine | C23H26N4O2 | 390.49 | 2.61 | 391.39 | 100 | DAD |
| 10 | {2-[5,6-Dimethoxy-3-(1H-pyrrolo[2,3-b]pyridin-2-yl)indol-1-yl]-ethyl}(tetrahydro-furan-2-ylmethyl)amine | C24H28N4O3 | 420.51 | 2.64 | 421.39 | 94 | DAD |
| 11 | 2-{1-[2-(4-Benzo[1,3]dioxol-5-ylmethylpiperazin-1-yl)ethyl]-5,6-dimethoxy-1H-indol-3-yl}-1H-pyrrolo[2,3-b]pyridine | C31H33N5O4 | 539.64 | 2.84 | 540.39 | 100 | DAD |
| 12 | 1,3-Benzodioxol-5-ylmethyl-{2-[5,6-dimethoxy-2-(1H-pyrrolo-[2,3-b]pyridin-3-yl)indol-1-yl]-ethyl}amine | C27H26N4O4 | 470.53 | 2.83 | 471.38 | 100 | DAD |
| 13 | 2-{5,6-Dimethoxy-1-[2-(2-methyl-piperazin-1-yl)ethyl]-1H-indol-3-yl}-1H-pyrrolo[2,3-b]pyridine | C24H29N5O2 | 419.53 | 2.58 | 420.41 | 94 | DAD |
| 14 | 2-{5,6-Dimethoxy-1-[2-(4-phenyl-piperazin-1-yl)ethyl]-1H-indol-3-yl}-1H-pyrrolo[2,3-b]pyridine | C29H31N5O2 | 481.60 | 2.95 | 482.42 | 100 | DAD |
| 15 | 2-(5,6-Dimethoxy-1-{2-[4-(2-methoxyphenyl)piperazin-1-yl]-ethyl}-1H-indol-3-yl)-1H-pyrrolo[2,3-b]pyridine | C30H33N5O3 | 511.63 | 2.94 | 512.43 | 100 | DAD |
| 16 | 2-(5,6-Dimethoxy-1-{2-[4-(3-trifluoromethylphenyl)piperazin-1-yl]}-1H-indol-3-yl}-1H-pyrrolo[2,3-b]pyridine | C30H30F3N5O2 | 549.60 | 3.22 | 550.36 | 97 | DAD |
| 17 | 2-(1-{2-[4-(4-Fluorophenyl)-piperazin-1-yl]ethyl}-5,6-dimethoxy-1H-indol-3-yl)-1H-pyrrolo[2,3-b]pyridine | C29H30FN5O2 | 499.59 | 2.99 | 500.39 | 100 | DAD |
| 18 | 4-{2-[5,6-Dimethoxy-3-(1H-pyrrolo[2,3-b]pyridin-2-yl)indol-1-yl]ethyl}piperazine-1-carboxylic acid ethyl ester | C26H31N5O4 | 477.56 | 2.69 | 478.41 | 100 | ELS |
| 19 | 2-{5,6-Dimethoxy-1-[2-(4-methyl-piperazin-1-yl)ethyl]-1H-indol-3-yl}-1H-pyrrolo[2,3-b]pyridine | C24H29N5O2 | 419.53 | 2.58 | 420.40 | 90 | DAD |
| 20 | 2-{1-[2-(4-Benzylpiperazin-1-yl)-ethyl]-5,6-dimethoxy-1H-indol-3-yl}-1H-pyrrolo[2,3-b]pyridine | C30H33N5O2 | 495.63 | 2.83 | 496.43 | 100 | DAD |
| 21 | 2-(4-{2-[5,6-Dimethoxy-3-(1H-pyrrolo[2,3-b]pyridin-2-yl)indol-1-yl]-ethyl}piperazin-1-yl)ethanol | C25H31N5O3 | 449.55 | 2.57 | 450.44 | 100 | DAD |
| 22 | 2-{1-[2-(2,6-Dimethylmorpholin-4-yl)ethyl]-5,6-dimethoxy-1H-indol-3-yl}-1H-pyrrolo[2,3-b]pyridine | C25H30N4O3 | 434.54 | 2.68 | 435.42 | 100 | DAD |
| 23 | 8-{2-[5,6-Dimethoxy-3-(1H-pyrrolo[2,3-b]pyridin-2-yl)indol-1-yl]ethyl}-1,4-dioxa-8-aza-spiro[4,5]decane | C26H30N4O4 | 462.55 | 2.68 | 463.40 | 100 | DAD |
| 24 | 2-[5,6-Dimethoxy-1-(2-piperidin-1-yl-ethyl)-1H-indol-3-yl]-1H-pyrrolo[2,3-b]pyridine | C24H28N4O2 | 404.51 | 2.64 | 405.39 | 95 | DAD |
| 25 | 2-(1-{2-[5,6-Dimethoxy-3-(1H-pyrrolo[2,3-b]pyridin-2-yl)indol-1-yl]-ethyl}piperidin-2-yl)ethanol | C26H32N4O3 | 448.57 | 2.63 | 449.44 | 100 | DAD |
| 26 | 2-{1-[2-(3,3-Dimethylpiperidin-1-yl)ethyl]-5,6-dimethoxy-1H-indol-3-yl}-1H-pyrrolo[2,3-b]pyridine | C26H32N4O2 | 432.57 | 2.81 | 433.44 | 100 | DAD |
| 27 | 2-{1-[2-(3,5-Dimethylpiperidin-1-yl)ethyl]-5,6-dimethoxy-1H-indol-3-yl}-1H-pyrrolo[2,3-b]pyridine | C26H32N4O2 | 432.57 | 2.85 | 433.44 | 100 | DAD |
| 28 | 1-{2-[5,6-Dimethoxy-3-(1H-pyrrolo[2,3-b]pyridin-2-yl)indol-1-yl]-ethyl}-4-phenylpiperidin-4-ol | C30H32N4O3 | 496.61 | 2.84 | 497.41 | 100 | DAD |

-continued

| Ex | IUPAC (Parent) | EF (parent) | MW (parent) | RT (min.) | m/z | % | TRACE |
|---|---|---|---|---|---|---|---|
| 29 | 2-{5,6-Dimethoxy-1-[2-(4-methyl-piperidin-1-yl)ethyl]-1H-indol-3-yl}-1H-pyrrolo[2,3-b]pyridine | C25H30N4O2 | 418.54 | 2.74 | 419.42 | 100 | DAD |
| 30 | 2-(1-{2-[5,6-Dimethoxy-3-(1H-pyrrolo[2,3-b]pyridin-2-yl)indol-1-yl]ethyl}piperidin-4-yl)ethanol | C26H32N4O3 | 448.57 | 2.59 | 449.43 | 95 | DAD |
| 31 | 2-{5,6-Dimethoxy-1-[2-(4-pyridin-2-ylpiperazin-1-yl)ethyl]-1H-indol-3-yl}-1H-pyrrolo[2,3-b]pyridine | C28H30N6O2 | 482.59 | 2.55 | 483.42 | 100 | DAD |
| 32 | 1'-{2-5,6-Dimethoxy-3-(1H-pyrrolo[2,3-b]pyridin-2-yl)-indol-1-yl]ethyl}-[1,4']bipiperidinyl | C29H37N5O2 | 487.65 | 2.51 | 488.46 | 100 | DAD |
| 33 | (1-Benzylpiperidin-4-yl)-{2-[5,6-dimethoxy-3-(1H-pyrrolo-[2,3-b]pyridin-2-yl)-indol-1-yl]-ethyl}-amine | C31H35N5O2 | 509.65 | 2.64 | 510.42 | 100 | DAD |
| 34 | {2-[5,6-Dimethoxy-3-(1H-pyrrolo[2,3-b]pyridin-2-yl)indol-1-yl]ethyl}-(2-piperidin-1-ylethyl)-amine | C26H33N5O2 | 447.58 | 2.54 | 448.43 | 91 | DAD |
| 35 | 2-{2-[5,6-Dimethoxy-3-(1H-pyrrolo[2,3-b]pyridin-2-yl)indol-1-yl]ethylamino}-2-methyl-propan-1-ol | C23H28N4O3 | 408.50 | 2.50 | 409.41 | 96 | DAD |
| 36 | N4-{2-[5,6-Dimethoxy-3-(1H-pyrrolo[2,3-b]pyridin-2-yl)indol-1-yl]ethyl}-N1,N1-diethylpentane-1,4-diamine | C28H39N5O2 | 477.65 | 2.53 | 478.49 | 92 | DAD |
| 37 | Benzyl-{2-[5,6-dimethoxy-3-(1H-pyrrolo[2,3-b]pyridin-2-yl)indol-1-yl]ethyl}amine | C26H26N4O2 | 426.52 | 2.82 | 427.38 | 100 | DAD |
| 38 | N'-{2-[5,6-Dimethoxy-3-(1H-pyrrolo[2,3-b]pyridin-2-yl)indol-1-yl]ethyl}-N,N-diethylethane-1,2-diamine | C25H33N5O2 | 435.57 | 2.52 | 436.45 | 92 | DAD |
| 39 | 2-{2-[5,6-Dimethoxy-3-(1H-pyrrolo[2,3-b]pyridin-2-yl)indol-1-yl]ethylamino}ethanol | C21H24N4O3 | 380.45 | 2.57 | 381.36 | 91 | DAD |
| 40 | N'-{2-[5,6-Dimethoxy-3-(1H-pyrrolo[2,3-b]pyridin-2-yl)indol-1-yl]ethyl}-N,N-dimethylpropane-1,3-diamine | C24H31N5O2 | 421.54 | 2.47 | 422.42 | 86 | DAD |
| 41 | {2-[5,6-Dimethoxy-3-(1H-pyrrolo[2,3-b]pyridin-2-yl)indol-1-yl]ethyl}-(3-imidazol-1-ylpropyl)-amine | C25H28N6O2 | 444.54 | 2.47 | 445.41 | 92 | DAD |
| 42 | 2-{5,6-Dimethoxy-1-[2-(5-methoxymethylpyrrolidin-1-yl)-ethyl]-1H-indol-3-yl}-1H-pyrrolo[2,3-b]pyridine | C25H30N4O3 | 434.54 | 2.66 | 435.42 | 95 | DAD |
| 43 | 2-{5,6-Dimethoxy-1-[2-(5-pyrrolidin-1-ylmethylpyrrolidin-1-yl)ethyl]-1H-indol-3-yl}-1H-pyrrolo[2,3-b]pyridine | C28H35N5O2 | 473.62 | 2.53 | 474.47 | 92 | DAD |
| 44 | 1-{2-[5,6-Dimethoxy-3-(1H-pyrrolo[2,3-b]pyridin-2-yl)indol-1-yl]ethyl}piperidin-3-ol | C24H28N4O3 | 420.51 | 2.57 | 421.40 | 97 | DAD |
| 45 | {2-[5,6-Dimethoxy-3-(1H-pyrrolo[2,3-b]pyridin-2-yl)indol-1-yl]ethyl}-[3-(4-methylpiperazin-1-yl)propyl]amine | C27H36N6O2 | 476.62 | 2.46 | 477.46 | 95 | DAD |
| 46 | N2-{2-[5,6-Dimethoxy-3-(1H-pyrrolo[2,3-b]pyridin-2-yl)indol-1-yl]ethyl}-N1,N1-dimethylpropane-1,2-diamine | C24H31N5O2 | 421.54 | 2.49 | 422.42 | 84 | DAD |
| 47 | N'-{2-[5,6-Dimethoxy-3-(1H-pyrrolo[2,3-b]pyridin-2-yl)indol-1-yl]ethyl}-N,N-diisopropylethane-1,2-diamine | C27H37N5O2 | 463.63 | 2.54 | 464.47 | 100 | DAD |
| 48 | {2-[5,6-Dimethoxy-3-(1H-pyrrolo[2,3-b]pyridin-2-yl)indol-1-yl]ethyl}-[3-(2-methylpiperidin-1-yl)propyl]amine | C28H37N5O2 | 475.63 | 2.53 | 476.48 | 100 | DAD |
| 49 | 2-{2-[5,6-Dimethoxy-3-(1H-pyrrolo[2,3-b]pyridin-2-yl)indol-1-yl]ethylamino}propan-1-ol | C22H26N4O3 | 394.47 | 2.54 | 395.38 | 96 | DAD |

-continued

| Ex | IUPAC (Parent) | EF (parent) | MW (parent) | RT (min.) | m/z | % | TRACE |
|---|---|---|---|---|---|---|---|
| 50 | {2-[5,6-Dimethoxy-3-(1H-pyrrolo[2,3-b]pyridin-2-yl)indol-1-yl]ethy}-[2-(1H-indol-3-yl)ethyl]-amine | C29H29N5O2 | 479.58 | 2.95 | 480.41 | 100 | DAD |
| 51 | (1-{2-[5,6-Dimethoxy-3-(1H-pyrrolo[2,3-b]pyridin-2-yl)indol-1-yl]ethyl}pyrrolidin-2-ylmethyl)-phenylamine | C30H33N5O2 | 495.63 | 2.98 | 496.44 | 100 | DAD |
| 52 | 2-{5,6-Dimethoxy-1-[2-(5-pyridin-3-yl-pyrrolidin-1-yl)ethyl]-1H-indol-3-yl}-1H-pyrrolo[2,3-b]pyridine | C28H29N5O2 | 467.57 | 2.57 | 468.41 | 97 | DAD |
| 53 | {2-[5,6-Dimethoxy-3-(1H-pyrrolo[2,3-b]pyridin-2-yl)indol-1-yl]ethyl}-(2-pyridin-2-ylethyl)-amine | C26H27N5O2 | 441.53 | 2.55 | 442.41 | 95 | DAD |
| 54 | 4-Benzyl-1-{2-[5,6-dimethoxy-3-(1H-pyrrolo[2,3-b]pyridin-2-yl)-indol-1-yl]ethyl}piperidin-4-ol | C31H34N4O3 | 510.64 | 2.89 | 511.41 | 100 | DAD |
| 55 | {2-[5,6-Dimethoxy-3-(1H-pyrrolo[2,3-b]pyridin-2-yl)indol-1-yl]ethyl}-(3-piperidin-1-yl-propyl)amine | C27H35N5O2 | 461.61 | 2.51 | 462.46 | 94 | DAD |
| 56 | N'-{2-[5,6-Dimethoxy-3-(1H-pyrrolo[2,3-b]pyridin-2-yl)indol-1-yl]ethyl}-N-ethyl-N-m-tolylethane-1,2-diamine | C30H35N5O2 | 497.64 | 3.11 | 498.43 | 100 | DAD |
| 57 | 2-(5,6-Dimethoxy-1-{2-[4-(4-methoxyphenyl)piperazin-1-yl]-ethyl}-1H-indol-3-yl)-1H-pyrrolo[2,3-b]pyridine | C30H33N5O3 | 511.63 | 2.96 | 512.43 | 100 | DAD |
| 58 | 2-{5,6-Dimethoxy-1-[2-(4-phenethylpiperazin-1-yl)ethyl]-1H-indol-3-yl}-1H-pyrrolo-[2,3-b]pyridine | C31H35N5O2 | 509.65 | 2.91 | 510.42 | 100 | DAD |
| 59 | 2-{5,6-Dimethoxy-1-[2-(4-pyridin-4-ylpiperazin-1-yl)ethyl]-1H-indol-3-yl}-1H-pyrrolo[2,3-b]pyridine | C28H30N6O2 | 482.59 | 2.48 | 483.42 | 94 | ELS |
| 60 | 2-(4-{2-[5,6-Dimethoxy-3-(1H-pyrrolo[2,3-b]pyridin-2-yl)indol-1-yl]ethyl}piperazin-1-yl)phenol | C29H31N5O3 | 497.60 | 2.85 | 498.39 | 100 | DAD |
| 61 | {2-[5,6-Dimethoxy-3-(1H-pyrrolo[2,3-b]pyridin-2-yl)indol-1-yl]ethyl}purin-6-ylamine | C24H22N8O2 | 454.49 | 2.55 | 455.36 | 100 | DAD |
| 62 | N'-{2-[5,6-Dimethoxy-3-(1H-pyrrolo[2,3-b]pyridin-2-yl)indol-1-yl]ethyl}-2,2,N,N-tetramethyl-propane-1,3-diamine | C26H35N5O2 | 449.60 | 2.49 | 450.47 | 92 | DAD |
| 63 | 2-{1-[2-(4-Cyclohexylpiperazin-1-yl)ethyl]-5,6-dimethoxy-1H-indol-3-yl}-1H-pyrrolo[2,3-b]pyridine | C29H37N5O2 | 487.65 | 2.77 | 488.45 | 100 | DAD |
| 64 | 2-{5,6-Dimethoxy-1-[2-(4-methyl-perhydro-1,4-diazepin-1-yl)ethyl]-1H-indol-3-yl}-1H-pyrrolo[2,3-b]pyridine | C25H31N5O2 | 433.56 | 2.49 | 434.43 | 94 | DAD |
| 65 | (1-{2-[5,6-Dimethoxy-3-(1H-pyrrolo[2,3-b]pyridin-2-yl)-indol-1-yl]ethyl}pyrrolidin-2-yl)methanol | C24H28N4O3 | 420.51 | 2.56 | 421.40 | 97 | DAD |
| 66 | 2-{2-[5,6-Dimethoxy-3-(1H-pyrrolo[2,3-b]pyridin-2-yl)indol-1-yl]ethylamino}butan-1-ol | C23H28N4O3 | 408.50 | 2.60 | 409.40 | 97 | DAD |
| 67 | {2-[5,6-Dimethoxy-3-(1H-pyrrolo[2,3-b]pyridin-2-yl)-indol-1-yl]ethyl}dimethylamine | C21H24N4O2 | 364.449 | 2.70 | 365.30 | 100 | DAD |
| 68 | {2-[5,6-Dimethoxy-3-(1H-pyrrolo[2,3-b]pyridin-2-yl)indol-1-yl]ethyl}diethylamine | C23H28N4O2 | 392.503 | 2.78 | 393.30 | 100 | DAD |
| 69 | 2-(5,6-Dimethoxy-1-{2-[4-(3-pyrrolidin-1-yl-propyl)perhydro-1,4-diazepin-1-yl]ethyl}-1H-indol-3-yl)-1H-pyrrolo[2,3-b]pyridine | C31H42N6O2 | 530.717 | 2.66 | 531.34 | 100 | DAD |
| 70 | {2-[5,6-Dimethoxy-3-(1H-pyrrolo[2,3-b]pyridin-2-yl)indol-1-yl]ethyl}-(2-pyrrol-1-ylethyl)amine | C25H27N5O2 | 429.524 | 2.94 | 430.26 | 100 | DAD |

-continued

| Ex | IUPAC (Parent) | EF (parent) | MW (parent) | RT (min.) | m/z | % | TRACE |
|---|---|---|---|---|---|---|---|
| 71 | [2-(1-Benzylpiperidin-4-yl)ethyl]-{2-[5,6-dimethoxy-3-(1H-pyrrolo[2,3-b]pyridin-2-yl)indol-1-yl]ethyl}amine | C33H39N5O2 | 537.708 | 2.83 | 538.29 | 100 | DAD |
| 72 | 2-[{2-[5,6-Dimethoxy-3-(1H-pyrrolo[2,3-b]pyridin-2-yl)indol-1-yl]ethyl}-(2-hydroxyethyl)amino]-ethanol | C23H28N4O4 | 424.501 | 2.54 | 425.65 | 100 | DAD |
| 73 | {2-[5,6-Dimethoxy-3-(1H-pyrrolo[2,3-b]pyridin-2-yl)indol-1-yl]ethyl}methyl-(2-pyridin-2-yl-ethyl)amine | C27H29N5O2 | 455.562 | 2.63 | 456.70 | 100 | DAD |
| 74 | {2-[5,6-Dimethoxy-3-(1H-pyrrolo[2,3-b]pyridin-2-yl)indol-1-yl]ethyl}ethylmethylamine | C22H26N4O2 | 378.476 | 2.61 | 379.59 | 100 | DAD |
| 75 | N-{2-[5,6-Dimethoxy-3-(1H-pyrrolo[2,3-b]pyridin-2-yl)indol-1-yl]-ethyl}-N,N',N'-trimethylethane-1,2-diamine | C24H31N5O2 | 421.545 | 2.53 | 422.2 | 100 | DAD |
| 76 | {2-[5,6-Dimethoxy-3-(1H-pyrrolo[2,3-b]pyridin-2-yl)indol-1-yl]ethyl}isobutylmethylamine | C24H30N4O2 | 406.53 | 2.75 | 407.21 | 96 | DAD |
| 77 | {2-[5,6-Dimethoxy-3-(1H-pyrrolo[2,3-b]pyridin-2-yl)indol-1-yl]ethyl}ethylpyridin-4-ylmethylamine | C27H29N5O2 | 455.562 | 2.62 | 456.13 | 100 | DAD |
| 78 | {2-[5,6-Dimethoxy-3-(1H-pyrrolo[2,3-b]pyridin-2-yl)indol-1-yl]ethyl}bis(2-methoxyethyl)-amine | C25H32N4O4 | 452.555 | 2.71 | 453.26 | 100 | DAD |
| 79 | 3-({2-[5,6-Dimethoxy-3-(1H-pyrrolo[2,3-b]pyridin-2-yl)indol-1-yl]ethyl}methylamino)propane-1,2-diol | C23H28N4O4 | 424.501 | 2.54 | 425.59 | 94 | DAD |

EXAMPLE 80

{2-[5,6-Dimethoxy-3-(1H-pyrrolo[2,3-b]pyridin-2-yl)indol-1-yl]ethyl}-(2-methoxyethyl)methylamine trifluoroacetate a) {2-[5,6-Dimethoxy-3-(1H-pyrrolo[2,3-b]pyridin-2-yl)indol-1-yl]ethyl}-(2-methoxyethyl)methylamine trifluoroacetate can be prepared in the following way:

(2-{5,6-Dimethoxy-3-(1-(toluene-4-sulfonyl)-1H-pyrrolo[2,3-b]-pyridin-2-yl)indol-1-yl}ethyl)-(2-methoxyethyl)methylamine trifluoroacetate (0.0152 g; 22.46 µmol) is dissolved in a methanolic potassium hydroxide solution (0.5 ml; 0.1 g of potassium hydroxide/ml methanol) and then agitated at ambient temperature for 48 hours. After evaporation, the residue is taken up, with agitation, in 0.7 ml of a dimethyl sulfoxide and 12N aqueous hydrochloric acid (50/50 v/v). After returning to ambient temperature, dimethyl sulfoxide (0.35 ml) is added and then purification is carried out by reverse-phase liquid chromatography mass spectrometry (method B). The fractions containing the expected compound are combined and evaporated.

{2-[5,6-Dimethoxy-3-(1H-pyrrolo[2,3-b]pyridin-2-yl)indol-1-yl]ethyl}-(2-methoxyethyl)methylamine trifluoroacetate (0.0094 g; 80%) is isolated, the characteristics of which are as follows:

LC/MS analysis: tr=2.4 min, m/z=409.24 [M+H]$^+$ b) (2-{5,6-Dimethoxy-3-[1-(toluene-4-sulfonyl)-1H-pyrrolo[2,3-b]pyridin-2-yl)indol-1-yl}ethyl)-(2-methoxyethyl)methylamine trifluoroacetate can be prepared in the following way:

A solution of 2-[1-(2-chloroethyl)-5,6-dimethoxy-1H-indol-3-yl]-1-(toluene-4-sulfonyl)-1H-pyrrolo[2,3-b]pyridine (0.021 g; 50 µmol) in N-methylpyrrolidine (0.5 ml) is placed in a 5 ml conical-bottomed Wheaton reactor, and then 2-methoxy-N-methylamine (0.013 g; 150 µmol) and potassium carbonate (0.021 g; 150 µmol) are added. The reaction mixture is agitated and heated at 70° C. overnight. After returning to ambient temperature, the mixture is filtered and evaporated to dryness and the residue is then taken up in dimethyl sulfoxide and purified by reverse-phase liquid chromatography mass spectrometry (method B). After treatment and evaporation of the fractions, (2-{5,6-dimethoxy-3-[1-(toluene-4-sulfonyl)-1H-pyrrolo[2,3-b]pyridin-2-yl)indol-1-yl}ethyl)-(2-methoxyethyl)methylamine trifluoroacetate (0.015 g; 45%) is isolated, the characteristics of which are as follows:

LC/MS analysis (method B): tr=5.6 min, m/z=563.35 [M+H]$^+$

EXAMPLE 81

2-[(3-{2-[5,6-Dimethoxy-3-(1H-pyrrolo[2,3-b]pyridin-2-yl)indol-1-yl]ethylamino}propyl)(2-hydroxyethyl)amino]ethanol trifluoroacetate a) 2-[(3-{2-[5,6-Dimethoxy-3-(1H-pyrrolo[2,3-b]pyridin-2-yl)indol-1-yl]ethylamino}propyl)(2-hydroxyethyl)amino]ethanol trifluoroacetate can be prepared in the following way:

(2-[[3-(2-{5,6-Dimethoxy-3-(1-[toluene-4-sulfonyl)-1H-pyrrolo[2,3-b]pyridin-2-yl]indol-1-yl)ethylamino}propyl](2-hydroxyethyl)amino]ethanol trifluoroacetate (0.013 g; 17.6 µmol) is dissolved in a methanolic potassium hydroxide solution (0.5 ml; 0.1 g of potassium hydroxide per ml methanol) and then agitated at ambient temperature for 48 hours.

After evaporation, the residue is taken up, with agitation, in 0.7 ml of a mixture of dimethyl sulfoxide and 12N aqueous hydrochloric acid (50/50 v/v). After returning to ambient temperature, 0.35 ml of dimethyl sulfoxide are added and then purification is carried out by reverse-phase liquid chromatography mass spectrometry (method B). The fractions containing the expected compound are combined and evaporated, resulting in 2-[(3-{2-[5,6-dimethoxy-3-(1H-pyrrolo[2,3-b]pyridin-2-yl)indol-1-yl]ethylamino}propyl)(2-hydroxyethyl)amino]ethanol trifluoroacetate (0.005 g; 39%), the characteristics of which are as follows:

LC/MS analysis: tr=3.1 min, m/z=482.02 [M+H]$^+$ b) 2-[[3-{5,6-Dimethoxy-3-[1-(toluene-4-sulfonyl)-1H-pyrrolo[2,3-b]pyridin-2-yl]indol-1-yl}ethylamino)propyl](2-hydroxyethyl)amino]ethanol trifluoroacetate can be prepared in the following way:

A solution of 2-[1-(2-chloroethyl)-5,6-dimethoxy-1H-indol-3-yl]-1-(toluene-4-sulfonyl)-1H-pyrrolo[2,3-b]pyridine (0.02 g; 50 µmol) in N-methylpyrrolidone (0.5 ml) is placed in a 5 ml conical-bottomed Wheaton reactor, and then N-(3-aminopropyl)diethanolamine (0.024 g; 150 µmol) and potassium carbonate (0.021 g; 150 µmol) are added. The reaction mixture is stirred and heated at 70° C. overnight. After returning to ambient temperature, the mixture is filtered and evaporated to dryness and the residue is then taken up in dimethyl sulfoxide and purified by reverse-phase liquid chromatography mass spectrometry (method B). After treatment and evaporation of the fractions, 2-[[3-(2-{5,6-dimethoxy-3-[1-(toluene-4-sulfonyl)-1H-pyrrolo[2,3-b]pyridin-2-yl]-indol-1-yl}ethylamino)propyl]-(2-hydroxyethyl)amino]ethanol trifluoroacetate is isolated (0.013 g, 35%), the characteristics of which are as follows:

LC/MS analysis (method B): tr=5 min, m/z=636.43 [M+H]$^+$

EXAMPLE 82

2-(4-{3-[5,6-Dimethoxy-3-(1H-pyrrolo[2,3-b]pyridin-2-yl)indol-1-yl]propyl}piperazin-1-yl)ethanol trifluoroacetate a) 2-(4-{3-[5,6-Dimethoxy-3-(1H-pyrrolo[2,3-b]pyridin-2-yl)indol-1-yl]propyl}piperazin-1-yl)ethanol trifluoroacetate can be prepared in the following way:

A solution of 2-[4-(3-{5,6-dimethoxy-3-[1-(toluene-4-sulfonyl)-1H-pyrrolo[2,3-b]pyridin-2-yl]indol-1-yl}propyl)piperazin-1-yl]ethanol trifluoroacetate (0.038 g; 52.2 µmol) in a methanolic potassium hydroxide solution (3 ml, 0.1 g of potassium hydroxide per ml of methanol) is placed in a hemolysis tube (1.3×10 cm) and is agitated at 20° C. for 72 hours. The solid form is filtered off and then purified by reverse-phase liquid chromatography mass spectrometry (method E). The fractions containing the expected compound are combined and then evaporated under reduced pressure, giving 2-(4-{3-[5,6-dimethoxy-3-(1H-pyrrolo[2,3-b]pyridin-2-yl)indol-1-yl]propyl}piperazin-1-yl)ethanol trifluoroacetate (0.022 g; 90%), the characteristics of which are as follows:

LC/MS analysis: tr=2.7 min., m/z=464.29 [M+H]$^+$ b) 2-[4-(3-[5,6-Dimethoxy-3-[1-(toluene-4-sulfonyl)-1H-pyrrolo[2,3-b]pyridin-2-yl]indol-1-yl]propyl)piperazin-1-yl]ethanol trifluoroacetate can be prepared in the following way:

A solution of 2-[1-(3-iodopropyl)-5,6-dimethoxy-1H-indol-3-yl]-1-(toluene-4-sulfonyl)-1H-pyrrolo[2,3-b]pyridine (0.04 g; 65 µmol) in dimethylformamide (0.5 ml) is placed in a hemolysis tube (1.3×10 cm) and then potassium carbonate (0.027 g; 195 µmol) and N-(2-hydroxyethyl)piperazine (0.025 g; 195 µmol) are successively added. The reactor is agitated at 60° C. for 16 hours. After returning to 21° C. and filtration, the solution obtained is purified by reverse-phase liquid chromatography mass spectrometry (method B). The fractions containing the expected compound are combined and then evaporated under reduced pressure, giving 2-[4-(3-{5,6-dimethoxy-3-[1-(toluene-4-sulfonyl)-1H-pyrrolo[2,3-b]pyridin-2-yl]indol-1-yl}propyl)piperazin-1-yl]ethanol trifluoroacetate (0.038 g, 69%), used as it is in the following step.

c) 2-[1-(3-Iodopropyl)-5,6-dimethoxy-1H-indol-3-yl]-1-(toluene-4-sulfonyl)-1H-pyrrolo[2,3-b]pyridine can be prepared in the following way:

2-[1-(3-Chloropropyl)-5,6-dimethoxy-1H-indol-3-yl]-1-(toluene-4-sulfonyl)—1H-pyrrolo[2,3-b]pyridine (0.395 g; 753.8 µmol) and sodium iodide (0.169 g; 1.13 mmol) in methyl ethyl ketone (10 ml) are placed in a 50 ml single-necked flask, at reflux. After 16 hours, sodium iodide (0.169 g; 1.13 mmol) is added and reflux is maintained for a further 5 hours. The reaction mixture is evaporated under reduced pressure and the residue is then dissolved in 50 ml of ethyl acetate, transferred into a separating funnel and washed with 2 times 30 ml of distilled water. The organic extract is dried over magnesium sulfate, filtered and evaporated under reduced pressure, to give the crude compound, which is purified by chromatography on silica gel (10 µg, silica 20-40 µm), elution being carried out at 10 ml/min with a mixture of cyclohexane and ethyl acetate (70/30; v/v). The fractions containing the expected compound are combined and evaporated to give 2-[1-(3-iodopropyl)-5,6-dimethoxy-1H-indol-3-yl]-1-(toluene-4-sulfonyl)-1H-pyrrolo[2,3-b]pyridine in the form of an amorphous solid (0.287 g, 62%), the characteristics of which are as follows:

Mass spectrum (EI): m/z=615 [M]$^+$; m/z=460 [M-C$_7$H$_7$NSO$_2$]$^+$; m/z=333 [460-I]$^+$ (base peak)

d) 2-[1-(3-Chloropropyl)-5,6-dimethoxy-1H-indol-3-yl]-1-(toluene-4-sulfonyl)-1H-pyrrolo[2,3-b]pyridine can be prepared in the following way:

A solution of 2-(5,6-dimethoxy-1H-indol-3-yl)-1-(toluene-4-sulfonyl)-1H-pyrrolo[2,3-b](0.447 g; 998 µmol) in solution in dimethylformamide (10 ml) is placed in 25 ml three-necked flask maintained under argon, and then sodium hydride (0.0898 g; 2.99 mmol) is added. The mixture is agitated at 21° C. for 10 minutes and then 1-bromo-3-chloropropane (0.514 g; 2.99 mmol) is added. The reaction is carried out at this temperature for 1 hour 30 min. The reaction mixture is run into 100 ml of water and then extracted three times with 50 ml of ethyl acetate. The organic extracts are combined, washed with 50 ml of a saturated ammonium chloride solution, dried over magnesium sulfate and then evaporated. An oil is isolated, which is triturated in diisopropyl ether. The solid formed is filtered off. 2-[1-(3-Chloropropyl)-5,6-dimethoxy-1H-indol-3-yl]-1-(toluene-4-sulfonyl)-1H-pyrrolo[2,3-b]pyridine is isolated in the form of a white solid (0.395 g; 75.5%), the characteristics of which are as follows:

$^1$H NMR spectrum (300 MHz, (CD$_3$)$_2$SO d6, δ in ppm): 2.30 (s: 3H); 2.31 (mt: 2H); 3.66 (t, J=6.5 Hz: 2H); 3.74 (s: 3H); 3.90 (s: 3H); 4.41 (broad t, J=6.5 Hz: 2H); 6.79 (s: 1H); 6.96 (s: 1H); 7.21 (s: 1H); 7.26 (broad d, J=8.5 Hz: 2H); 7.32 (dd, J=8 and 5 Hz: 1H); 7.51 (s: 1H); 7.58 (d, J=8.5 Hz: 2H); 7.96 (dd, J=8 and 1.5 Hz: 1H); 8.37 (dd, J=5 and 1.5 Hz: 1H).

Mass spectrum (EI): m/z=523 [M]$^+$; m/z=368 [M-C$_7$H$_7$NSO$_2$]$^+$ (base peak)

2-(5,6-Dimethoxy-1H-indol-3-yl)-1-(toluene-4-sulfonyl)-1H-pyrrolo[2,3-b]pyridine was prepared as described in patent WO 03/000688 A1.

EXAMPLE 83

2-{5,6-Dimethoxy-1-[3-(4-methylperhydro-1,4-diazepin-1-yl)propyl]-1H-indol-3-yl}-1H-pyrrolo[2,3-b]pyridine trifluoroacetate a) 2-{5,6-Dimethoxy-1-[3-(4-methylperhydro-1,4-diazepin-1-yl)propyl]-1H-indol-3-yl}-1H-pyrrolo[2,3-b]pyridine can be prepared in the same way as above (example 82a), but using 2-{5,6-dimethoxy-1-[3-(4-methylperhydro-1,4-diazepin-1-yl)propyl]-1H-indol-3-yl}-1-(toluene-4-sulfonyl)-1H-pyrrolo[2,3-b]pyridine trifluoroacetate, (0.053 g, 63.9 µmol). 2-{5,6-dimethoxy-1-[3-(4-methylperhydro-1,4-diazepin-1-yl)propyl]-1H-indol-3-yl}-1H-pyrrolo[2,3-b]pyridine trifluoroacetate (0.023 g, 45%) is thus obtained, the characteristics of which are as follows:

LC/MS analysis: tr=2.8 min. m/z=448.30 [M+H]$^+$ b) 2-{5,6-Dimethoxy-1-[3-(4-methylperhydro-1,4-diazepin-1-yl)propyl]-1H-indol-3-yl}-1-(toluene-4-sulfonyl)-1H-pyrrolo[2,3-b]pyridine trifluoroacetate can be prepared in the same way as above (example 82b), but using 2-[1-(3-iodopropyl)-5,6-dimethoxy-1H-indol-3-yl]-1-(toluene-4-sulfonyl)-1H-pyrrolo[2,3-b]pyridine (0.04 g, 65 µmol), potassium carbonate (0.027 g; 195 µmol) and 1-methylhomopiperazine (0.022 g; 195 µmol); 2-{5,6-dimethoxy-1-[3-(4-methylperhydro-1,4-diazepin-1-yl)propyl]-1H-indol 3-yl}-1-(toluene-4-sulfonyl)-1H-pyrrolo[2,3-b]pyridine trifluoroaceate (0.053 g; 98%) is obtained, which is used as it is in the following step.

c) 2-[1-(3-Iodopropyl)-5,6-dimethoxy-1H-indol-3-yl]-1-(toluene-4-sulfonyl)-1H-pyrrolo[2,3-b]pyridine is prepared according to example 82c.

EXAMPLES 84 to 87

Step 1: alkylation

The amines specified in the table below are weighed out and solubilized in dimethylformamide (concentration of 120 µmol in 0.5 ml of dimethylformamide).

| Example | Name | Empirical formula | MW (g/mol) | Weight (mg) |
|---|---|---|---|---|
| 84 | morpholine | C4H9NO | 87.12 | 10.450 |
| 85 | 4-piperidinopiperidine | C10H20N2 | 168.28 | 20.190 |
| 86 | 4-piperidineethanol | C7H15NO | 129.2 | 15.500 |
| 87 | 3-hydroxypiperidine | C5H11NO | 101.15 | 12.140 |

0.5 ml of each amine solution is distributed into reactors suitable for parallel synthesis, then potassium carbonate (0.017 g per well) is added and, finally, 40 µmol of 2-[1-(3-iodopropyl)-5,6-dimethoxy-1H-indol-3-yl]-1-(toluene-4-sulfonyl)-1H-pyrrolo[2,3-b]pyridine (example 82c) in solution in dimethylformamide (0.5 ml) is distributed per reactor. The calypso reactor is closed and then placed at 50° C. for 16 hours with orbital shaking. After returning to 20° C., the solutions obtained above are purified by reverse-phase liquid chromatography mass spectrometry (method B). After evaporation, weighing, dilution and analysis by reverse-phase liquid chromatography mass spectrometry (method A), the expected compounds are isolated, which are used in the following step.

Step 2: Deprotection

Each compound obtained above is treated with 1 ml of a methanolic potassium hydroxide solution (0.1 g of potassium hydroxide per ml of methanol) for 48 hours at 21° C. The solutions are evaporated under reduced pressure and the solids obtained are then dissolved in dimethyl sulfoxide (0.5 ml). 0.5 ml of 1M aqueous hydrochloric acid is then added to the solution thus obtained and the compounds obtained are then purified by means of two successive rounds of reverse-phase liquid chromatography mass spectrometry (method E). After treatment of the fractions and analysis by reverse-phase liquid chromatography mass spectrometry (method A), the following compounds are identified and characterized:

| Ex | NAME | EF | MW (g/mol) | RT (min) | m/z | % |
|---|---|---|---|---|---|---|
| 84 | 2-[5,6-Dimethoxy-1-(3-morpholin-4-ylpropyl)-1H-indol-3-yl]-1H-pyrrolo[2,3-b]pyridine | C24H28N4O3 | 420.51 | 2.66 | 421.69 | 100 |
| 85 | 1'-{3-[5,6-Dimethoxy-3-(1H-pyrrolo[2,3-b]-pyridin-2-yl)indol-1-yl]-propyl}-[1,4']bipiperidyl | C30H39N5O2 | 501.67 | 2.56 | 502.14 | 96 |
| 86 | 2-(1-{3-[5,6-Dimethoxy-3-(1H-pyrrolo[2,3-b]-pyridin-2-yl)indol-1-yl]propyl}piperidin-4-yl)ethanol | C27H34N4O3 | 462.59 | 2.64 | 463.08 | 100 |
| 87 | 1-{3-[5,6-Dimethoxy-3-(1H-pyrrolo[2,3-b]-pyridin-2-yl)indol-1-yl]propyl}piperidin-3-ol | C25H30N4O3 | 434.54 | 2.61 | 435.12 | 100 |

EXAMPLE 88

2-[5,6-Dimethoxy-1-(2-methoxyethyl)-1H-indol-3-yl]-1H-pyrrolo[2,3-b]pyridine a) 2-[5,6-Dimethoxy-1-(2-methoxyethyl)-1H-indol-3-yl]-1H-pyrrolo[2,3-b]pyridine is prepared in the following way:

0.080 g of 2-[5,6-dimethoxy-1-(2-methoxyethyl)-1H-indol-3-yl]-1-(toluene-4-sulfonyl)-1H-pyrrolo[2,3-b]pyridine is added, at a temperature in the region of 20° C., to a solution of 3.1 ml of methanolic potassium hydroxide (0.1 g/ml; 1.78M). The reaction medium is agitated at this same temperature for 5 hours. The reaction medium is then heated at 50° C. for 4 hours. After cooling, the solid formed is filtered off through sintered glass, washed twice with 3 ml of methanol, and then 5 times with 5 ml of water. The solid is dried in an oven (35° C.) under vacuum. 0.019 g of 2-[5,6-dimethoxy-1-(2-methoxyethyl)-1H-indol-3-yl]-1H-pyrrolo[2,3-b]pyridine is thus obtained, the characteristics of which are as follows:

$^1$H NMR spectrum (300 MHz, (CD$_3$)$_2$SO d6, δ in ppm): 3.29 (s: 3H); 3.73 (t, J=5 Hz: 2H); 3.87 (s: 3H); 3.90 (s: 3H); 4.37 (broad t, J=5 Hz: 2H); 6.79 (broad s: 1H); 7.03 (dd, J=8 and 5 Hz: 1H); 7.22 (s: 1H); 7.44 (s: 1H); 7.87 (broad d, J=8 Hz: 1H); 7.87 (s: 1H); 8.03 (dd, J=5 and 1.5 Hz: 1H); 11.79 (broad s: 1H).

Mass spectrum (EI): m/z 351 [M+H]$^+$ (base peak)

b) 2-[5,6-Dimethoxy-1-(2-methoxyethyl)-1H-indol-3-yl]-1-(toluene-4-sulfonyl)-1H-pyrrolo[2,3-b]pyridine is prepared in the following way:

0.01 g of sodium hydride (60%) is added to a solution of 0.1 g of 2-[5,6-dimethoxy-1H-indol-3-yl]-1-(toluene-4-sulfonyl)-1H-pyrrolo[2,3-b]pyridine in 2.5 ml of anhydrous dimethylformamide, under an inert argon atmosphere at a temperature in the region of 20° C. Agitation is maintained at this temperature for 30 minutes. 0.023 ml of bromoethyl methyl ether is added. The reaction medium is agitated at the same temperature for 16 hours. 3 ml of water and 3 ml of ethyl acetate are added. After separation by settling out, the organic phase is dried over sodium sulfate, filtered, and then concentrated under reduced pressure. The residue obtained is purified on a flash-pack chromatography cartridge (silica, dichloromethane as eluent). The fractions containing the product are concentrated under reduced pressure. 0.082 g of 2-[5,6-dimethoxy-1-(2-methoxyethyl)-1H-indol-3-yl]-1-(toluene-4-sulfonyl)-1H-pyrrolo[2,3-b]pyridine is thus obtained, the characteristics of which are as follows:

Mass spectrum (EI): m/z=505 [M]$^+$; m/z=350 (base peak)

The compound 2-(5,6-dimethoxy-1H-indol-3-yl]-1-(toluene-4-sulfonyl)—1H-pyrrolo[2,3-b]pyridine is prepared according to the process described in patent WO 03/000688 A1.

EXAMPLE 89

2-[5,6-Dimethoxy-3-(1H-pyrrolo[2,3-b]pyridin-2-yl)indol-1-yl]ethanol a) 2-[5,6-Dimethoxy-3-(1H-pyrrolo[2,3-b]pyridin-2-yl)indol-1-yl]ethanol is prepared in the following way:

1.65 ml of a 5N aqueous potassium hydroxide solution are added to a solution of 0.18 g of 2-{5,6-dimethoxy-3-[1-(toluene-4-sulfonyl)-1H-pyrrolo[2,3-b]pyridin-2-yl]indol-1-yl}ethanol in 10 ml of methanol, at a temperature in the region of 20° C. The reaction medium is refluxed for 4 hours. After cooling, the solid formed is filtered off through sintered glass, and washed twice with 3 ml of methanol and then five times with 5 ml of water. The solid is purified by flash-pack chromatography (silica, 95/05 by volume dichloromethane/methanol as eluents). 0.045 g of 2-[5,6-dimethoxy-3-(1H-pyrrolo[2,3-b]pyridin-2-yl)indol-1-yl]ethanol is obtained, the characteristics of which are as follows:

$^1$H NMR spectrum (300 MHz, (CD$_3$)$_2$SO d6, δ in ppm): 3.80 (unresolved peak: 2H); 3.87 (s: 3H); 3.91 (s: 3H); 4.26 (broad t, J=5.5 Hz: 2H); 5.00 (unresolved peak: 1H); 6.78 (d, J=2 Hz: 1H); 7.03 (dd, J=8 and 5 Hz: 1H); 7.19 (s: 1H); 7.45 (s: 1H); 7.87 (broad d, J=8 Hz: 1H); 7.89 (s: 1H); 8.13 (dd, J=5 and 1.5 Hz: 1H); 11.78 (broad s: 1H).

Mass spectrum (EI): m/z=337 [M]$^+$ (base peak)

b) 2-{5,6-Dimethoxy-3-[1-(toluene-4-sulfonyl)-1H-pyrrolo[2,3-b]pyridin-2-yl]indol-1-yl}ethanol is prepared in the following way:

1.52 ml of tetrabutylammonium fluoride (TBAF) are added, dropwise, to a solution of 0.46 g of 2-[5,6-dimethoxy-1-(2-tert-butyldimethylsilyloxyethyl)indol-3-yl]-1-(toluene-4-sulfonyl)-1H-pyrrolo[2,3-b]pyridine in 9.5 ml of anhydrous tetrahydrofuran, under an inert argon atmosphere at a temperature in the region of 20° C. The reaction medium is agitated at the same temperature for 6 hours. The reaction medium is concentrated under reduced pressure. The residue obtained is purified by flash chromatography (silica, 98/02 by volume dichloromethane/methanol as eluents, argon). The fractions containing the product are concentrated under reduced pressure. 0.187 g of 2-{5,6-dimethoxy-3-[1-(toluene-4-sulfonyl)-1H-pyrrolo[2,3-b]pyridin-2-yl]-indol-1-yl}ethanol, the characteristics of which are as follows:

$^1$H NMR spectrum (300 MHz, (CD$_3$)$_2$SO d6, δ in ppm): 2.30 (s: 3H); 3.74 (s: 3H); 3.83 (mt: 2H); 3.88 (s: 3H); 4.30 (t, J=6 Hz: 2H); 5.00 (unresolved peak: 1H); 6.75 (s: 1H); 6.95 (s: 1H); 7.20 (s: 1H); 7.25 (broad d, J=8 Hz: 2H); 7.31 (dd, J=8 and 5 Hz: 1H); 7.50 (s: 1H); 7.58 (d, J=8 Hz: 2H); 7.95 (dd, J=8 and 1.5 Hz: 1H); 8.37 (dd, J=5 and 1.5 Hz: 1H).

c) 2-[5,6-Dimethoxy-1-(2-tert-butyldimethylsilyloxyethyl)indol-3-yl]-1-(toluene-4-sulfonyl)-1H-pyrrolo[2,3-b]pyridine) is prepared in the following way:

0.049 g of sodium hydride (at 60%) is added to a solution of 0.5 g of 2-(5,6-dimethoxy-1H-indol-3-yl]-1-(toluene-4-sulfonyl)-1H-pyrrolo[2,3-b]pyridine in 12.5 ml of anhydrous dimethylformamide, under an inert argon atmosphere at a temperature in the region of 20° C. Agitation is maintained at this temperature for 30 minutes. 0.264 ml of 2-tert-butyldimethylsilyloxyethyl bromide is added. The reaction medium is agitated at the same temperature for 16 hours. 25 ml of water and 20 ml of ethyl acetate are added. After separation by settling out, the organic phase is dried over sodium sulfate, filtered, and then concentrated under reduced pressure. The residue obtained is purified by flash chromatography (silica, 98/02 by volume dichloromethane/methanol as eluents, argon). The fractions containing the product are concentrated under reduced pressure. 0.47 g of 2-[5,6-dimethoxy-1-(2-tert-butyldimethylsilyloxyethyl)indol-3-yl]-1-(toluene-4-sulfonyl)-1H-pyrrolo[2,3-b]pyridine is thus obtained, the characteristics of which are as follows:

Mass spectrum (EI): m/z=605 [M]$^+$; m/z=450 (base peak)

The compound 2-(5,6-dimethoxy-1H-indol-3-yl]-1-(toluene-4-sulfonyl)-1H-pyrrolo[2,3-pyridine is prepared according to the process described in patent WO 03/000688 A1.

EXAMPLE 90

3-[5,6-Dimethoxy-3-(1H-pyrrolo[2,3-b]pyridin-2-yl)indol-1-yl]propanol a) 3-[5,6-Dimethoxy-3-(1H-pyrrolo[2,3-b]pyridin-2-yl)indol-1-yl]propanol is prepared by following the procedure described in example 88a, but using 0.24 g of 3-[5,6-dimethoxy-3-(1-(toluene-4-sulfonyl)-1H-pyrrolo[2,3-b]pyridin-2-yl)indol-1-yl]propanol and a solution of 9.3 ml of methanolic potassium hydroxide (0.1 g/ml; 1.78M). After purification by flash-pack chromatography (silica, 98/02 by volume dichloromethane/methanol as eluents), 0.103 g of 3-[5,6-dimethoxy-3-(1H-pyrrolo[2,3-b]pyridin-2-yl)indol-1-yl]propanol is obtained, the characteristics of which are as follows:

¹H NMR spectrum (300 MHz, (CD₃)₂SO d6, δ in ppm): 1.99 (mt: 2H); 3.48 (mt: 2H); 3.88 (s: 3H); 3.92 (s: 3H); 4.27 (broad t, J=7 Hz: 2H); 4.66 (broad t, J=5 Hz: 1H); 6.78 (d, J=2 Hz: 1H); 7.03 (dd, J=8 and 5 Hz: 1H); 7.17 (s: 1H); 7.45 (s: 1H); 7.87 (s: 1H); 7.87 (dd, J=8 and 1.5 Hz: 1H); 8.13 (dd, J=5 and 1.5 Hz: 1H); 11.73 (unresolved peak: 1H).

Mass spectrum (EI): m/z=351 [M]⁺ (base peak)

b) 3-{5,6-Dimethoxy-3-[1-(toluene-4-sulfonyl)-1H-pyrrolo[2,3-b]pyridin-2-yl]indol-1-yl}propanol and 2-[5,6-dimethoxy-1-(3-fluoropropyl)indol-3-yl]-1-(toluene-4-sulfonyl)-1H-pyrrolo[2,3-b]pyridine are prepared by following the procedure described in example 89b, but using 0.605 g of 2-[5,6-dimethoxy-1-(3-tert-butyldimethylsilyloxypropyl)indol-3-yl]-1-(toluene-4-sulfonyl)-1H-pyrrolo[2,3-b]pyridine and 1.95 ml of tetrabutylammonium fluoride (TBAF). After purification by flash chromatography (silica, 98/02 by volume dichloromethane/methanol as eluents, argon), 0.243 g of 3-{5,6-dimethoxy-3-[1-(toluene-4-sulfonyl)-1H-pyrrolo[2,3-b]pyridin-2-yl]indol-1-yl}propanol is obtained, the characteristics of which are as follows:

Mass spectrum (EI): m/z=505 [M]⁺ (base peak) and 0.046 g of 2-[5,6-dimethoxy-1-(3-fluoropropyl)indol-3-yl]-1-(toluene-4-sulfonyl)-1H-pyrrolo[2,3-b]pyridine is obtained, the characteristics of which are as follows:

Mass spectrum (EI): m/z=507 [M]⁺ (base peak)

c) 2-[5,6-Dimethoxy-1-(3-tert-butyldimethylsilyloxypropyl)indol-3-yl]-1-(toluene-4-sulfonyl)-1H-pyrrolo[2,3-b]pyridine is prepared by following the procedure described in example 89c, but using 0.285 ml of 2-tert-butyldimethylsilyloxypropyl bromide and 0.5 g of 2-[5,6-dimethoxy-1H-indol-3-yl]-1-(toluene-4-sulfonyl)-1H-pyrrolo[2,3-b]pyridine and 0.049 g of sodium hydride (at 60%). After purification by flash chromatography (silica, 98/02 by volume dichloromethane/methanol as eluents, argon), 0.605 g of 2-[5,6-dimethoxy-1-(3-tert-butyldimethylsilyloxypropyl)indol-3-yl]-1-(toluene-4-sulfonyl)-1H-pyrrolo[2,3-b]pyridine is obtained, the characteristics of which are as follows:

Mass spectrum (EI): m/z=619 [M]⁺ (base peak)

The compound 2-(5,6-dimethoxy-1H-indol-3-yl]-1-(toluene-4-sulfonyl)-1H-pyrrolo[2,3-b]pyridine is prepared according to the process described in patent WO 03/000688 A1.

EXAMPLE 91

2-[1-(3-Fluoropropyl)-5,6-dimethoxy-1H-indol-3-yl]-1H-pyrrolo[2,3-b]pyridine

2-[1-(3-fluoropropyl)-5,6-dimethoxy-1H-indol-3-yl]-1H-pyrrolo[2,3-b]pyridine is prepared by following the procedure described in example 88a, but using 0.042 g of 2-[5,6-dimethoxy-1-(3-fluoropropyl)indol-3-yl]-1-(toluene-4-sulfonyl)-1H-pyrrolo[2,3-b]pyridine and 1.63 ml of a 5N aqueous potassium hydroxide solution. After purification by flash-pack chromatography (silica, 98/02 by volume dichloromethane/methanol as eluents), 0.008 g of 2-[1-(3-fluoropropyl)-5,6-dimethoxy-1H-indol-3-yl]-1H-pyrrolo[2,3-b]pyridine is obtained, the characteristics of which are as follows:

¹H NMR spectrum (300 MHz, (CD₃)₂SO d6, d in ppm): 2.22 (dt, J=26 and 6.5 Hz: 2H); 3.88 (s: 3H); 3.91 (s: 3H); 4.33 (t, J=6.5 Hz: 2H); 4.52 (dt, J=48 and 6.5 Hz: 2H); 6.80 (broad d, J=2 Hz: 1H); 7.04 (dd, J=8 and 5 Hz: 1H); 7.18 (s: 1H); 7.45 (s: 1H); 7.88 (broad dd, J=8 and 1.5 Hz: 1H); 7.89 (s: 1H); 8.14 (dd, J=5 and 1.5 Hz: 1H); 11.78 (broad s: 1H).

Mass spectrum (EI): m/z=353 [M]⁺ (base peak)

EXAMPLE 92

3-[5,6-Dimethoxy-3-(1H-pyrrolo[2,3-b]pyridin-2-yl) indol-1-yl]propionic acid a) 3-[5,6-Dimethoxy-3-(1H-pyrrolo[2,3-b]pyridine-2-yl) indol-1-yl]propionic acid is prepared by following the procedure described in example 88a, but using 1 g of methyl 3-[5,6-dimethoxy-3-(1-(toluene-4-sulfonyl)-1H-pyrrolo[2,3-b] pyridin-2-yl)indol-1-yl]propionate and a solution of 74 ml of methanolic potassium hydroxide (0.1 g/ml; 1.78M). 0.601 g of 3-[5,6-dimethoxy-3-(1H-pyrrolo[2,3-b]pyridin-2-yl)indol-1-yl]propionic acid is obtained, the characteristics of which are as follows:

¹H NMR spectrum (300 MHz, (CD₃)₂SO d6, d in ppm): 2.82 (t, J=6.5 Hz: 2H); 3.88 (s: 3H); 3.90 (s: 3H); 4.44 (t, J=6.5 Hz: 2H); 6.78 (broad d, J=2 Hz: 1H); 7.03 (dd, J=8 and 5 Hz: 1H); 7.22 (s: 1H); 7.44 (s: 1H); 7.86 (broad d, J=8 Hz: 1H); 7.87 (s: 1H); 8.13 (broad dd, J=5 and 1.5 Hz: 1H); 11.78 (broad s: 1H).

Mass spectrum (EI): m/z=365 [M]⁺ (base peak)

b) Methyl 3-{5,6-dimethoxy-3-[1-(toluene-4-sulfonyl)-1H-pyrrolo[2,3-b]pyridin-2-yl]indol-1-yl}propionate is prepared in the following way:

0.34 g of potassium carbonate and 0.243 ml of methyl acrylate are added, dropwise, to a solution of 1 g of 2-(5,6-dimethoxy-1H-indol-3-yl]-1-(toluene-4-sulfonyl)-1H-pyrrolo[2,3-b]pyridine in 20 ml of anhydrous dimethylformamide, under an inert argon atmosphere at a temperature in the region of 20° C. The reaction medium is agitated at the same temperature for 16 hours. 20 ml of water and 20 ml of ethyl acetate are added. After separation by settling out, the organic phase is dried over sodium sulfate, filtered, and then concentrated under reduced pressure. After purification by flash chromatography (silica, dichloromethane as eluent, argon), the fractions containing the product are concentrated under reduced pressure. 1 g of methyl 3-{5,6-dimethoxy-3-[1-(toluene-4-sulfonyl)-1H-pyrrolo[2,3-b]pyridin-2-yl]indol-1-yl}propionate is thus obtained, the characteristics of which are as follows:

Mass spectrum (EI): EI: m/z=533 [M]⁺ (base peak), m/z=378

The compound 2-[5,6-dimethoxy-1H-indol-3-yl]-1-(toluene-4-sulfonyl)-1H-pyrrolo[2,3-b]pyridine is prepared according to the process described in patent WO 03/000688 A1.

EXAMPLE 93

3-[5,6-Dimethoxy-3-(1H-pyrrolo[2,3-b]pyridin-2-yl) indol-1-yl]-1-morpholin-4-yl-propan-1-one 3-[5,6-Dimethoxy-3-(1H-pyrrolo[2,3-b]pyridin-2-yl)-indol-1-yl]-1-morpholin-4-ylpropan-1-one is prepared in the following way:

0.036 g of O-(1H-benzotriazol-1-yl)-N,N,N',N'-tetramethyluronium hexafluorophosphate is added to a solution of 0.035 g of 3-[5,6-dimethoxy-3-(1H-pyrrolo[2,3-b]pyridin-2-yl)indol-1-yl]propionic acid in 3 ml of dimethylformamide, under an inert argon atmosphere at a temperature in the region of 20° C. The reaction medium is agitated at this temperature for 1 hour. 0.01 ml of morpholine and then 0.017 ml of diisopropylethylamine are added. After agitation at the same temperature for 3 hours, 10 ml of water and 10 ml of ethyl acetate are added. After separation by settling out, the organic phase is dried over sodium sulfate, filtered, and then concentrated under reduced pressure. The residue obtained is purified by flash-pack chromatography (silica, 98/02 by volume dichloromethane/methanol as eluents). The fractions containing the product are concentrated under reduced pressure. 0.025 g of 3-[5,6-dimethoxy-3-(1H-pyrrolo[2,3-b]pyridin-2-yl)indol-1-yl]-1-morpholin-4-ylpropan-1-one is thus obtained, the characteristics of which are as follows:

$^1$H NMR spectrum (300 MHz, $(CD_3)_2SO$ d6, δ in ppm): 2.90 (t, J=6.5 Hz: 2H); from 3.30 to 3.55 (mt: 8H); 3.88 (s: 3H); 3.90 (s: 3H); 4.47 (broad t, J=6.5 Hz: 2H); 6.78 (d, J=2 Hz: 1H); 7.03 (dd, J=8 and 5 Hz: 1H); 7.19 (s: 1H); 7.44 (s: 1H); 7.86 (s: 1H); 7.87 (broad d, J=8 Hz: 1H); 8.13 (dd, J=5 and 1.5 Hz: 1H); 11.78 (broad s: 1H).

Mass spectrum (EI): m/z=434 [M]$^+$ (base peak)

EXAMPLE 94

2-[5,6-Dimethoxy-3-(1H-pyrrolo[2,3-b]pyridin-2-yl)indol-1-yl]-1-(4-hydroxypiperidin-1-yl)-ethanone a) 2-[5,6-Dimethoxy-3-(1H-pyrrolo[2,3-b]pyridin-2-yl)indol-1-yl]-1-(4-hydroxypiperidin-1-yl)ethanone is prepared by following the procedure described in example 93, but using 0.2 g of 2-[5,6-dimethoxy-3-(1H-pyrrolo[2,3-b]pyridin-2-yl)indol-1-yl]acetic acid and 0.07 g of 4-hydroxypiperidine. After purification by flash-pack chromatography (silica, 98/02 by volume dichloromethane/methanol as eluents), 0.096 g of 2-[5,6-dimethoxy-3-(1H-pyrrolo[2,3-b]pyridin-2-yl)-indol-1-yl]-1-(4-hydroxypiperidin-1-yl)ethanone is obtained, the characteristics of which are as follows:

$^1$H NMR spectrum (300 MHz, $(CD_3)_2SO$ d6, δ in ppm): from 1.20 to 1.55 (mt: 2H); from 1.70 to 1.95 (mt: 2H); 3.12 and from 3.20 to 3.45 (respectively broad t, J=11 Hz and mt: 2H in total); from 3.75 to 4.00 (mt: 2H); 3.78 (mt: 1H); 3.84 (s: 3H); 3.91 (s: 3H); 4.81 (d, J=3.5 Hz: 1H); 5.21 (limited AB, J=16.5 Hz: 2H); 6.79 (d, J=2 Hz: 1H); 7.03 (dd, J=8 and 5 Hz: 1H); 7.10 (s: 1H); 7.46 (s: 1H); 7.76 (s: 1H); 7.88 (dd, J=8 and 1.5 Hz: 1H); 8.13 (dd, J=5 and 1.5 Hz: 1H); 11.76 (broad s: 1H).

Mass spectrum (EI): m/z=434 [M]$^+$ (base peak)

b) 2-[5,6-Dimethoxy-3-(1H-pyrrolo[2,3-b]pyridin-2-yl)indol-1-yl]acetic acid is prepared by following the procedure described in example 88a, but using 1 g of tert-butyl 2-{5,6-dimethoxy-3-[1-(toluene-4-sulfonyl)-1H-pyrrolo[2,3-b]pyridin-2-yl]indol-1-yl}acetate and a solution of 73 ml of methanolic potassium hydroxide (0.1 g/ml; 1.78M). 0.701 g of 2-[5,6-dimethoxy-3-(1H-pyrrolo[2,3-b]pyridin-2-yl)indol-1-yl]acetic acid is obtained, the characteristics of which are as follows:

Mass spectrum (EI): m/z=351 [M]$^+$ (base peak)

c) tert-Butyl 2-{5,6-dimethoxy-3-[1-(toluene-4-sulfonyl)-1H-pyrrolo[2,3-b]pyridin-2-yl]indol-1-yl)-acetate is prepared by following the procedure described in example 89c, but using 1.91 g of tert-butyl bromoacetate and 4 g of 2-(5,6-dimethoxy-1H-indol-3-yl]-1-(toluene-4-sulfonyl)-1H-pyrrolo[2,3-b]pyridine. 4.5 g of tert-butyl 2-{5,6-dimethoxy-3-[1-(toluene-4-sulfonyl)-1H-pyrrolo[2,3-b]pyridin-2-yl]indol-1-yl}acetate are obtained, the characteristics of which are as follows:

Mass spectrum (CI): m/z=562 [M+H]$^+$ (base peak)

EXAMPLE 95

2-[5,6-Dimethoxy-3-(1H-pyrrolo[2,3-b]pyridin-2-yl)indol-1-yl]-1-thiazolidin-3-ylethanone 2-[5,6-Dimethoxy-3-(1H-pyrrolo[2,3-b]pyridin-2-yl)-indol-1-yl]-1-thiazolidin-3-ylethanone is prepared by following the procedure described in example 93, but using 0.2 g of 2-[5,6-dimethoxy-3-(1H-pyrrolo[2,3-b]pyridin-2-yl)indol-1-yl]acetic acid and 0.061 g of thiazolidine. 0.133 g of 2-[5,6-dimethoxy-3-(1H-pyrrolo[2,3-b]pyridin-2-yl)indol-1-yl]-1-thiazolidin-3-ylethanone is obtained, the characteristics of which are as follows:

$^1$H NMR spectrum (400 MHz, $(CD_3)_2SO$ d6, at a temperature of 373 K, δ in ppm): 3.16 (unresolved peak: 2H); from 3.85 to 3.95 (mt: 2H); 3.86 (s: 3H); 3.90 (s: 3H); 4.66 (broad s: 2H); 5.16 (s: 2H); 6.72 (d, J=1.5 Hz: 1H); 7.01 (dd, J=8 and 4.5 Hz: 1H); 7.11 (s: 1H); 7.49 (s: 1H); 7.76 (s: 1H); 7.86 (dd, J=8 and 1.5 Hz: 1H); 8.13 (dd, J=4.5 and 1.5 Hz: 1H); 11.45 (unresolved peak: 1H).

Mass spectrum (EI): m/z=422 [M]$^+$ (base peak)

EXAMPLE 96

4-{[5,6-Dimethoxy-3-(1H-pyrrolo[2,3-b]pyridin-2-yl)indol-1-yl]acetyl}-1-methylpiperazin-2-one 4-{[5,6-Dimethoxy-3-(1H-pyrrolo[2,3-b]pyridin-2-yl)-indol-1-yl]acetyl}-1-methylpiperazin-2-one is prepared by following the procedure described in example 93, but using 0.1 g of 2-[5,6-dimethoxy-3-(1H-pyrrolo[2,3-b]pyridin-2-yl)indol-1-yl]acetic acid and 0.039 g of 1-methylpiperazin-2-one. 0.088 g of 4-{[5,6-dimethoxy-3-(1H-pyrrolo[2,3-b]pyridin-2-yl)indol-1-yl]acetyl}-1-methylpiperazin-2-one is obtained, the characteristics of which are as follows:

$^1$H NMR spectrum (300 MHz, $(CD_3)_2SO$ d6, δ in ppm). At ambient temperature, a 50/50 mixture of rotamers is observed.

2.94 and 2.96 (2 s: 3H in total); 3.39 and 3.54 (2 mts: 2H in total); 3.75 and 3.91 (2 mts: 2H in total); 3.85 (s: 3H); 3.91 (s: 3H); 4.07 and 4.34 (2 broad s: 2H in total); 5.25 and 5.30 (2 broad s: 2H in total); 6.79 (d, J=1.5 Hz: 1H); 7.04 (dd, J=8 and 5 Hz: 1H); 7.13 and 7.15 (2 broad s: 1H in total); 7.46 (s: 1H); 7.71 and 7.74 (2 s: 1H in total); 7.88 (broad d, J=8 Hz: 1H); 8.14 (dd, J=5 and 1.5 Hz: 1H); 11.79 (unresolved peak: 1H).

Mass spectrum (EI): m/z=447 [M]$^+$ (base peak)

EXAMPLE 97

4-Chloro-2-(5,6-dimethoxy-1-methyl-1H-indol-3-yl)-1H-pyrrolo[2,3-b]pyridine a) 4-Chloro-2-(5,6-dimethoxy-1-methyl-1H-indol-3-yl)-1H-pyrrolo[2,3-b]pyridine is prepared by following the procedure described in example 89a, but using 2.8 g of 4-chloro-2-(5,6-dimethoxy-1-methyl-1H-indol-3-yl)-1-(toluene-4-sulfonyl)-1H-pyrrolo[2,3-b]pyridine and 25.5 ml of a 5N aqueous potassium hydroxide solution. 1.81 g of 4-chloro-2-(5,6-dimethoxy-1-methyl-1H-indol-3-yl)-1H-pyrrolo[2,3-b]pyridine are obtained, the characteristics of which are as follows:

$^1$H NMR spectrum (300 MHz, $(CD_3)_2SO$ d6, δ in ppm): 3.86 (s: 3H); 3.89 (s: 3H); 3.92 (s: 3H); 6.73 (s: 1H); 7.16 (d, J=5 Hz: 1H); 7.17 (s: 1H); 7.46 (s: 1H); 7.86 (s: 1H); 8.09 (d, J=5 Hz: 1H); 12.16 (unresolved peak: 1H).

Mass spectrum (EI): m/z=341 [M]$^+$ (base peak)

b) 4-Chloro-2-(5,6-dimethoxy-1-methyl-1H-indol-3-yl)-1-(toluene-4-sulfonyl)-1H-pyrrolo[2,3-b]pyridine is prepared by following the procedure described in example 89c, but using 7.1 g of 4-chloro-2-(5,6-dimethoxy-1H-indol-3-yl)-1-(toluene-4-sulfonyl)-1H-pyrrolo[2,3-b]pyridine and 1.10 ml of methyl iodide. After purification by flash chromatography (silica, 40/60 by volume ethyl acetate/cyclohexane as eluents, argon), 5.69 g of 4-chloro-2-(5,6-dimethoxy-1-methyl-1H-indol-3-yl)-1-(toluene-4-sulfonyl)-1H-pyrrolo[2,3-b]pyridine are obtained, the characteristics of which are as follows:

Mass spectrum (EI): m/z=495 $[M]^+$ m/z=340 (base peak)

c) 4-Chloro-2-(5,6-dimethoxy-1H-indol-3-yl)-1-(toluene-4-sulfonyl)-1H-pyrrolo[2,3-b]pyridine is prepared in the following way:

67 ml of a saturated aqueous sodium bicarbonate solution and 1.34 g of tetrakis(triphenylphosphine)palladium are added to a solution of 10 g of 1-(toluene-4-sulfonyl)-1H-2-iodo-4-chloropyrrolo[2,3-b]pyridine, 245 ml of anhydrous dimethylformamide and 7.42 g of 1-tert-butyloxycarbonyl-5,6-dimethoxyindol-3-boronic acid, under an inert argon atmosphere at a temperature in the region of 20° C. The reaction medium is heated at 130° C. for 45 minutes. After cooling, the reaction medium is concentrated under reduced pressure. The oil obtained is taken up with 300 ml of water and 300 ml of ethyl acetate. After separation by settling out, the organic phase is dried over sodium sulfate, filtered, and then concentrated under reduced pressure. The residue obtained is purified by flash chromatography (silica, 40/60 by volume ethyl acetate/cyclohexane as eluents, argon). The fractions containing the product are concentrated under reduced pressure. 7.52 g of 4-chloro-2-(5,6-dimethoxy-1H-indol-3-yl)-1-(toluene-4-sulfonyl)-1H-pyrrolo[2,3-b]pyridine are thus obtained, the characteristics of which are as follows:

Mass spectrum (EI): m/z=481 $[M]^+$; m/z=326 (base peak)

The compounds 1-(toluene-4-sulfonyl)-1H-2-iodo-4-chloropyrrolo[2,3-b]pyridine and 1-tert-butyloxy-carbonyl-5,6-dimethoxyindol-3-boronic acid are prepared according to the process described in patent WO 03000688 A1.

EXAMPLE 98

2-(5,6-dimethoxy-1-methyl-1H-indol-3-yl)-1H-pyrrolo[2,3-b]pyridine-4-carbonitrile a) 2-(5,6-Dimethoxy-1-methyl-1H-indol-3-yl)-1H-pyrrolo[2,3-b]pyridine-4-carbonitrile can be prepared in the following way:

A suspension of 0.14 g of 2-(5,6-dimethoxy-1-methyl-1H-indol-3-yl)-1-(toluene-4-sulfonyl)-1H-pyrrolo[2,3-b]pyridine-4-carbonitrile in 1.3 ml of a 5 N aqueous potassium hydroxide solution and 5 ml of methanol is brought to a temperature in the region of 60° C. for approximately 30 minutes. After returning to around 20° C., the insoluble material is filter-dried, and washed with water until a neutral pH is obtained. The insoluble material is purified by flash chromatography on a silica column [eluent: dichloromethane/methanol (98/2 by volume)]. 0.05 g of 2-(5,6-dimethoxy-1-methyl-1H-indol-3-yl)-1H-pyrrolo[2,3-b]pyridine-4-carbonitrile is obtained in the form of a solid, the characteristics of which are as follows:

Silica TLC [eluent: dichloromethane/methanol (98/2 by volume)] Rf=0.17

$^1$H NMR spectrum (300 MHz, $(CD_3)_2SO$ d6, δ in ppm): 3.87 (s: 3H); 3.89 (s: 3H); 3.92 (s: 3H); 6.87 (broad s: 1H); 7.17 (s: 1H); 7.44 (broad d, J=5 Hz: 1H); 7.49 (broad s: 1H); 7.95 (s: 1H); 8.25 (d, J=5 Hz: 1H); 12.44 (unresolved peak: 1H).

Mass spectrum (EI): m/z=332 $[M]^+$ (base peak); m/z=317 $[M-CH_3]^+$; m/z=289; $[m/z=317-CO]^+$ b) 2-(5,6-Dimethoxy-1-methyl-1H-indol-3-yl)-1-(toluene-4-sulfonyl)-1H-pyrrolo[2,3-b]pyridine-4-carbonitrile can be prepared in the following way:

0.029 g of [1,1'-bis(diphenylphosphino)ferrocene] palladium(II) is added to a suspension, degassed with argon for approximately 15 minutes, of 0.2 g of 4-chloro-2-(5,6-dimethoxy-1-methyl 1H-indol-3-yl)-1-(toluene-4-sulfonyl)-1H-pyrrolo[2,3-b]pyridine, 0.084 g of zinc cyanide and 0.013 g of zinc powder in 20 ml of N,N-dimethylacetamide. The reaction mixture is brought to a temperature in the region of 150° C. for approximately 2 hours 30 minutes. After returning to around 20° C., the reaction mixture is filtered through celite and the insoluble material is washed with 100 ml of dichloromethane. The filtrate is washed with three times 100 l of water, dried in the magnesium sulfate, filtered and concentrated to dryness under reduced pressure (13 kPa). The residue is purified by flash chromatography on a silica column [eluent: cyclohexane/ethyl acetate (50/50 by volume)]. 0.14 g of 2-(5,6-dimethoxy-1-methyl-1H-indol-3-yl)-1-(toluene-4-sulfonyl)-1H-pyrrolo[2,3-b]pyridine-4-carbonitrile is obtained in the form of a lake, the characteristics of which are as follows:

Silica TLC [eluent: cyclohexane/ethyl acetate (50/50 by volume)]=Rf 0.40

Mass spectrum (EI): m/z=486 $[M]^+$; m/z=331 $[M-C_7H_7O_2S]^+$ (base peak); m/z=316 $[331-CH_3]^+$.; m/z=155 $[C_7H_7O_2S^+]$; m/z=91 $[C_7H_7+]$ 4-Chloro-2-(5,6-dimethoxy-1-methyl-1H-indol-3-yl)-1-(toluene-4-sulfonyl)-1H-pyrrolo[2,3-b]pyridine is prepared as described in example 97b.

EXAMPLE 99

4-chloro-2-[5,6-dimethoxy-1-(2-morpholin-4-ylethyl)-1H-indol-3-yl]-1H-pyrrolo[2,3-b]pyridine a) 4-Chloro-2-[5,6-dimethoxy-1-(2-morpholin-4-ylethyl)-1H-indol-3-yl]-1H-pyrrolo[2,3-b]pyridine can be prepared in the following way:

A solution of 0.54 g of 4-chloro-2-[5,6-dimethoxy-1-(2-morpholin-4-ylethyl)-1H-indol-3-yl]-1-(toluene-4-sulfonyl)-1H-pyrrolo[2,3-b]pyridine and 1.8 g of potassium hydroxide in 18 ml of methanol is brought to around 60° C. for approximately 2 hours. After cooling to approximately 20° C., the precipitate is filter-dried, washed with two times 3 ml of methanol and three times 5 ml of water, and then dried in an oven under reduced pressure (13 kPa) at a temperature in the region of 40° C. for approximately 8 hours. 0.241 g of 4-chloro-2-[5,6-dimethoxy-1-(2-morpholin-4-ylethyl)-1H-indol-3-yl]-1H-pyrrolo[2,3-b]pyridine is obtained in the form of a solid, the characteristics of which are as follows:

Melting point: 240° C. (Köfler bench)

$^1$H NMR spectrum (300 MHz, $(CD_3)_2SO$ d6, δ in ppm): 2.48 (t, J=4.5 Hz: 4H); 2.74 (t, J=6.5 Hz: 2H); 3.49 (t, J=4.5 Hz: 4H); 3.87 (s: 3H); 3.89 (s: 3H); 4.32 (broad t, J=6.5 Hz: 2H); 6.71 (s: 1H); 7.14 (d, J=5 Hz: 1H); 7.20 (s: 1H): 7.42 (s: 1H); 7.92 (s: 1H); 8.07 (d, J=5 Hz: 1H); 12.13 (unresolved peak: 1H).

Mass spectrum (EI): m/z=440 $[M]^+$ (base peak); m/z=340 $[M-C_5H_{10}NO]^+$; m/z=100 $[C_5H_{10}NO]^+$ b) 4-Chloro-2-[5,6-dimethoxy-1-(2-morpholin-4-yl-ethyl)-1H-indol-3-yl]-1-(toluene-4-sulfonyl)-1H-pyrrolo[2,3-b]pyridine can be prepared in the following way:

A suspension of 1 g of 4-chloro-2-(5,6-dimethoxy-1H-indol-3-yl)-1-(toluene-4-sulfonyl)-1H-pyrrolo[2,3-b]pyridine, 0.655 g of 4-(2-chloroethyl)morpholine hydrochloride and 1.11 g of potassium carbonate in 10 ml of dimethylformamide is heated at around 95° C. for approximately 3 hours. After cooling to a temperature in the region of 20° C., the reaction mixture is run into 20 ml of water, and extracted with three times 100 ml of ethyl acetate. The combined organic phases are washed with 100 ml of a saturated aqueous sodium chloride solution, dried over magnesium sulfate, filtered and concentrated to dryness under reduced pressure (13 kPa). The residue is purified by flash chromatography on a silica column [eluent: cyclohexane/ethyl acetate (90/10 by volume)]. 0.54 g of 4-chloro-2-[5,6-dimethoxy-1-(2-morpholin-4-yl-ethyl)-1H-indol-3-yl]-1-(toluene-4-sulfonyl)-1H-pyrrolo[2,3-b]pyridine is obtained in the form of a solid, the characteristics of which are as follows:

Silica TLC [eluent: dichloromethane/methanol (98/2 by volume)] Rf=0.18

Mass spectrum (EI): m/z=594 $[M]^+$; m/z=481 $[M-C_6H_{11}NO]^+$; m/z=439$[M-C_7H_7O_2S]^+$; m/z=326 $[m/z=481-C_7H_7O_2S]^+$; m/z=100$[C_5H_{10}NO^+]$ (base peak)

4-Chloro-2-(5,6-dimethoxy-1H-indol-3-yl)-1-(toluene-4-sulfonyl)-1H-pyrrolo[2,3-b]pyridine is prepared as described in example 97c.

EXAMPLE 100

2-(1-{2-[3-(4-chloro-1H-pyrrolo[2,3-b]pyridin-2-yl)-5,6-dimethoxyindol-1-yl]ethyl}piperidin-4-yl)ethanol a) 2-(1-{2-[3-(4-chloro-1H-pyrrolo[2,3-b]pyridin-2-yl)-5,6-dimethoxyindol-1-yl]ethyl}piperidin-4-yl)ethanol can be prepared as in example 99a:

But using 0.160 g of 2-[1-(2-{3-[4-chloro-1-(toluene-4-sulfonyl)-1H-pyrrolo[2,3-b]pyridin-2-yl]-5,6-dimethoxyindol-1-yl}ethyl)piperidin-4-yl]ethanol and 0.58 g of potassium hydroxide in 10 ml of methanol. After flash chromatography on a silica column [eluent: dichloromethane/methanol (80/20 by volume)], 0.078 g of 2-(1-{2-[3-(4-chloro-1H-pyrrolo[2,3-b]pyridin-2-yl)-5,6-dimethoxyindol-1-yl]ethyl}piperidin-4-yl)ethanol is thus obtained in the form of a solid, the characteristics of which are as follows:

Melting point: 200° C. (Köfler bench)

$^1$H NMR spectrum (300 MHz, $(CD_3)_2SO$ d6, δ in ppm): from 1.00 to 1.25 (mt: 2H); from 1.25 to 1.40 (mt: 3H); 1.63 (very broad d, J=13 Hz: 2H); 1.99 (broad t, J=11.5 Hz: 2H); 2.70 (t, J=6.5 Hz: 2H); 2.93 (broad d, J=11.5 Hz: 2H); 3.43 (unresolved peak: 2H); 3.88 (s: 3H); 3.90 (s: 3H); 4.32 (mt: 3H); 6.71 (broad s: 1H); 7.15 (d, J=5 Hz: 1H); 7.20 (s: 1H); 7.42 (s: 1H); 7.92 (s: 1H); 8.07 (d, J=5 Hz: 1H); 12.16 (unresolved peak: 1H).

Mass spectrum (EI): m/z=482 $[M]^+$; m/z=142 $[C_8H_{16}NO]^+$ (base peak)

b) 2-[1-(2-{3-[4-Chloro-1-(toluene-4-sulfonyl)-1H-pyrrolo[2,3-b]pyridin-2-yl]-5,6-dimethoxyindol-1-yl}ethyl)piperidin-4-yl]ethanol can be prepared in the following way:

A suspension of 0.280 g of 4-chloro-2-[1-(2-iodoethyl)-5,6-dimethoxy-1H-indol-3-yl]-1-(toluene-4-sulfonyl)-1H-pyrrolo[2,3-b]pyridine, 0.061 g of potassium carbonate and 0.114 g of 2-piperidin-4-ylethanol in 30 ml of acetonitrile is brought to a temperature in the region of 60° C. After heating at this temperature for approximately 5 hours, 0.061 g of potassium carbonate and 0.114 g of 2-piperidin-4-ylethanol are again added and the mixture is agitated at this temperature for approximately 2 hours. After returning to a temperature in the region of 20° C., the mixture is concentrated to dryness under reduced pressure (13 kPa), and then taken up with 50 ml of water and extracted with three times 40 ml of dichloromethane. The combined organic phases are dried over magnesium sulfate, filtered and concentrated to dryness under reduced pressure (13 kPa). The residue is purified by flash chromatography on a silica column [eluent: dichloromethane/methanol (95/5 by volume)]. 0.16 g of 2-[1-(2-{3-[4-chloro-1-(toluene-4-sulfonyl)-1H-pyrrolo[2,3-b]pyridin-2-yl]-5,6-dimethoxyindol-1-yl}ethyl)piperidin-4-yl]ethanol is obtained in the form of an oil, the characteristics of which are as follows:

Mass spectrum (EI): m/z=636 $[M]^+$; m/z=481 $[M-C_7H_7O_2S]^+$; m/z=142 $[C_8H_{16}NO]^+$ (base peak)

c) 4-Chloro-2-[1-(2-iodoethyl)-5,6-dimethoxy-1H-indol-3-yl]-1-(toluene-4-sulfonyl)-1H-pyrrolo[2,3-b]pyridine can be prepared in the following way:

A suspension of 0.760 g of 4-chloro-2-[1-(2-chloroethyl)-5,6-dimethoxy-1H-indol-3-yl]-1-(toluene-4-sulfonyl)-1H-pyrrolo[2,3-b]pyridine and 0.315 g of sodium iodide in 70 ml of 2-butanone is brought to reflux for approximately 24 hours. The reaction mixture is evaporated to dryness under reduced pressure (13 kPa), taken up with 50 ml of water, and extracted with three times 50 ml of ethyl acetate. The combined organic phases are dried over magnesium sulfate, filtered and concentrated to dryness under reduced pressure (13 kPa). 0.98 g of 4-chloro-2-[1-(2-iodoethyl)-5,6-dimethoxy-1H-indol-3-yl]-1-(toluene-4-sulfonyl)-1H-pyrrolo[2,3-b]pyridine is obtained in the form of a yellow oil, the characteristics of which are as follows:

Silica TLC [eluent: dichloromethane/ethyl acetate (90/10 by volume)]
Rf=0.71

Mass spectrum (EI): m/z=635 $[M]^+$ (base peak); m/z=480 $[M-C_7H_7O_2S]^+$; m/z=353 $[480-I]^+$; m/z=338 $[353-CH_3]^+$; m/z=91 $[C_7H_7]^+$ d) 4-Chloro-2-[1-(2-chloroethyl)-5,6-dimethoxy-1H-indol-3-yl]-1-(toluene-4-sulfonyl)-1H-pyrrolo[2,3-b]pyridine can be prepared in the following way:

0.79 g of potassium hydroxide and 0.61 g of potassium carbonate are added to a solution of 1 g of 4-chloro-2-(5,6-dimethoxy-1H-indol-3-yl)-1-(toluene-4-sulfonyl)-1H-pyrrolo[2,3-b]pyridine and 0.013 g of tetrabutylammonium bromide in 25 ml of 1,2-dichloroethane. The suspension obtained is brought to around 50° C. for approximately 5 hours. After returning to a temperature in the region of 20° C. and agitating at this temperature for approximately 16 hours, the reaction mixture is filtered through celite; the insoluble material is washed with three times 10 ml of dichloromethane. The filtrate is washed with three times 50 ml of water, dried over magnesium sulfate, filtered, and concentrated to dryness under reduced pressure. The residue is purified; by flash chromatography on a silica column [eluent: cyclohexane/ethyl acetate (75/25 by volume)]. 0.62 g of 4-chloro-2-[1-(2-chloroethyl)-5,6-dimethoxy-1H-indol-3-yl]-1-(toluene-4-sulfonyl)-1H-pyrrolo[2,3-b]pyridine is obtained in the form of a solid, the characteristics of which are as follows:

Silica TLC [eluent: cyclohexane/ethyl acetate (50/50 by volume)]
Rf=0.41

Mass spectrum (EI): m/z=543 $[M]^+$; m/z=388 $[M-C_7H_7O_2S]^+$ (base peak); m/z=91 $[C_7H_7]^+$ 4-Chloro-2-(5,6-dimethoxy-1H-indol-3-yl)-1-(toluene-4-sulfonyl)-1H-pyrrolo[2,3-b]pyridine is prepared as described in example 97c.

EXAMPLE 101

4-chloro-2-{5,6-dimethoxy-1-[2-(4-methylpiperazin-1-yl)ethyl]-1H-indol-3-yl}-1H-pyrrolo[2,3-b]pyridine a) 4-Chloro-2-{5,6-dimethoxy-1-[2-(4-methylpiperazin-1-yl)ethyl]-1H-indol-3-yl}-1H-pyrrolo[2,3-b]pyridine can be prepared as in example 100a:

But using 0.2 g of 4-chloro-2-{5,6-dimethoxy-1-[2-(4-methylpiperazin-1-yl)ethyl]-1H-indol-3-yl}-1-(toluene-4-sulfonyl)-1H-pyrrolo[2,3-b]pyridine and 0.65 g of potassium hydroxide in 7 ml of methanol. After flash chromatography on a silica column [eluent: dichloromethane/methanol (80/20 by volume)], 0.05 g of 4-chloro-2-{5,6-dimethoxy-1-[2-(4-methylpiperazin-1-yl)ethyl]-1H-indol-3-yl}-1H-pyrrolo[2,3-b]pyridine is thus obtained in the form of a solid, the characteristics of which are as follows:

Melting point: 192° C. (Köfler bench)

$^1$H NMR spectrum (300 MHz, (CD$_3$)$_2$SO d6, δ in ppm): 2.16 (s: 3H); 2.33 (unresolved peak: 4H); from 2.40 to 2.55 (mt: 4H); 2.74 (broad t, J=6.5 Hz: 2H); 3.88 (s: 3H); 3.91 (s: 3H); 4.30 (broad t, J=6.5 Hz: 2H); 6.71 (broad s: 1H); 7.15 (d, J=5 Hz: 1H); 7.20 (s: 1H); 7.43 (s: 1H); 7.93 (s: 1H); 8.08 (d, J=5 Hz: 1H); 12.14 (unresolved peak: 1H).

Mass spectrum (EI): m/z=453 [M]$^+$; m/z=113 [C$_6$H$_{13}$N$_2$]$^+$ (base peak) m/z=70 [C$_4$H$_8$N]$^+$ b) 4-Chloro-2-{5,6-dimethoxy-1-[2-(4-methylpiperazin-1-yl)ethyl]-1H-indol-3-yl}-1-(toluene-4-sulfonyl)-1H-pyrrolo[2,3-b]pyridine can be prepared as in example 100b:

But using 0.98 g of 4-chloro-2-[1-(2-iodoethyl)-5,6-dimethoxy-1H-indol-3-yl]-1-(toluene-4-sulfonyl)-1H-pyrrolo[2,3-b]pyridine, 0.21 g of potassium carbonate and 0.31 g of 1-methylpiperazine in 100 ml of acetonitrile. After flash chromatography on a silica column [eluent: dichloro ethane/methanol (90/10 by volume)], 0.52 g of 4-chloro-2-(5,6-dimethoxy-1-[2-(4-methylpiperazin-1-yl)ethyl]-1H-indol-3-yl}-1-(toluene-4-sulfonyl)-1H-pyrrolo[2,3-b]pyridine is thus obtained in the form of an oil, the characteristics of which are as follows:

Mass spectrum (EI): m/z=607 [M]$^+$; m/z=452 [M-C$_7$H$_7$O$_2$S]$^+$; m/z=113 [C$_6$H$_{13}$N$_2$]$^+$ (base peak); m/z=70 [C$_4$H$_8$N]$^+$

EXAMPLE 102

2-{5,6-dimethoxy-1-[2-(4-methylpiperazin-1-yl)ethyl]-1H-indol-3-yl}-1H-pyrrolo[2,3-b]pyridine-4-carbonitrile 2-{5,6-Dimethoxy-1-[2-(4-methylpiperazin-1-yl)ethyl]-1H-indol-3-yl}-1H-pyrrolo[2,3-b]pyridine-4-carbonitrile can be prepared in the following way:

0.036 g of [1,1'-bis(diphenylphosphino)ferrocene]palladium(II) is added to a suspension, degassed with argon for approximately 15 minutes, 0.3 g of 4-chloro-2-(5,6-dimethoxy-1-methyl-1H-indol-3-yl)-1-(toluene-4-sulfonyl)-1H-pyrrolo[2,3-b]pyridine, 0.104 g of zinc cyanide and 0.016 g of zinc powder in 20 ml of N,N-dimethylacetamide. The reaction mixture is brought to a temperature in the region of 150° C. for approximately 1 hour. After returning to around 20° C. and agitation of the mixture for 18 hours, the reaction mixture is filtered through celite and the insoluble material is washed with 100 ml of dichloromethane. The filtrate is washed twice with 100 ml of water and then with 100 ml of a saturated aqueous sodium chloride solution, dried over magnesium sulfate, filtered, and concentrated to dryness under reduced pressure (13 kPa). The residue is purified by flash chromatography on a silica column [eluent: dichloromethane/methanol (90/10 by volume)]. 0.08 g of 2-{5,6-dimethoxy-1-[2-(4-methylpiperazin-1-yl)ethyl]-1H-indol-3-yl}-1H-pyrrolo[2,3-b]pyridine-4-carbonitrile is obtained in the form of a solid, the characteristics of which are as follows:

Melting point: 196° C. (Köfler bench)

$^1$H NMR spectrum (300 MHz, (CD$_3$)$_2$SO d6, δ in ppm): 2.17 (s: 3H); 2.34 (unresolved peak: 4H); from 2.40 to 2.55 (mt: 4H); 2.75 (t, J=6.5 Hz: 2H); 3.89 (s: 3H); 3.92 (s: 3H); 4.33 (broad t, J=6.5 Hz: 2H); 6.98 (d, J=1.5 Hz: 1H); 7.23 (s: 1H); 7.45 (d, J=5 Hz: 1H); 7.49 (s: 1H); 8.03 (s: 1H); 8.26 (d, J=5 Hz: 1H); 12.43 (broad s: 1H).

Mass spectrum (EI): m/z=444 [M]$^+$; m/z=113 [C$_6$H$_{13}$N$_2$]$^+$ (base peak); m/z=70 [C$_4$H$_8$N]$^+$

EXAMPLE 103

5-chloro-2-(5,6-dimethoxy-1-methyl-1H-indol-3-yl)-1H-pyrrolo[2,3-b]pyridine a) 5-Chloro-2-(5,6-dimethoxy-1-methyl-1H-indol-3-yl)-1H-pyrrolo[2,3-b]pyridine can be prepared in the following way:

A suspension of 0.44 g of 5-chloro-3-(5,6-dimethoxy-1-methyl-1H-indol-3-ylethynyl)pyridin-2-ylamine and 0.58 g of potassium tert-butoxide in 25 ml of 1-methylpyrrolidin-2-one is heated at a temperature in the region of 70° C. for approximately 4 hours 30 minutes. The mixture is concentrated to dryness under reduced pressure (13 kPa). The residue is taken up with 40 ml of water and the pH of the suspension obtained is brought to approximately 4-5 by adding glacial acetic acid. After agitation for approximately 10 minutes, the solid is filter-dried, washed with three times 5 ml of water and then air-dried. After recrystallization from 160 ml of propan-1-ol, 0.28 g of 5-chloro-2-(5,6-dimethoxy-1-methyl-1H-indol-3-yl)-1H-pyrrolo[2,3-b]pyridine is obtained in the form of a beige solid, the characteristics of which are as follows:

Melting point: 282° C. (Büchi capillary)

$^1$H NMR spectrum (300 MHz, (CD$_3$)$_2$SO d6, δ in ppm): 3.84 (s: 3H); 3.88 (s: 3H); 3.89 (s: 3H); 6.76 (broad s: 1H); 7.14 (s: 1H); 7.42 (s: 1H); 7.81 (s: 1H); 7.91 (d, J=3 Hz: 1H); 8.09 (d, J=3 Hz: 1H); 11.99 (unresolved peak: 1H).

Mass spectrum (EI): m/z=341 [M]$^+$ (base peak); m/z=326 [M-CH$_3$]$^+$ b) 5-Chloro-3-(5,6-dimethoxy-1-methyl-1H-indol-3-ylethynyl)pyridin-2-ylamine can be prepared in the following way:

A suspension of 0.43 g of 5-chloro-3-ethynylpyridin-2-ylamine, 0.6 g of 3-iodo-5,6-dimethoxy-1-methyl-1H-indole (example 103-f), and 0.072 g of copper iodide, in a mixture of 60 ml of triethylamine and 30 ml of dimethylformamide, is degassed with argon for 15 minutes. 0.066 g of bis(triphenylphosphine) palladium(II) chloride is added to the above suspension. The mixture is agitated at around 20° C. for approximately 6 hours; 0.075 g of 5-chloro-3-ethynylpyridin-2-ylamine is added and the mixture is agitated at this same temperature for 2 days. The mixture is concentrated to dryness under reduced pressure (13 kPa). The residue is taken up with 100 ml of water and extracted with three times 100 ml of dichloromethane. The organic phases are combined, dried over magnesium sulfate, filtered, and concentrated under reduced pressure (13 kPa). The residue is purified by flash chromatography on a silica column [eluent: cyclohexane/ethyl acetate (50/50 by volume)]. 0.44 g of 5-chloro-3-(5,6-dimethoxy-1-methyl-1H-indol-3-ylethynyl)pyridin-2-ylamine is thus obtained in the form of a solid, the characteristics of which are as follows:

Melting point: 192° C. (Köfler bench)

Mass spectrum (EI): m/z=341 [M]$^+$ (base peak); m/z=326 [M-CH$_3$]$^+$ c) 5-Chloro-3-ethynylpyridin-2-ylamine can be prepared in the following way:

A suspension of 1.6 g of 5-chloro-3-trimethylsilanylethynylpyridin-2-ylamine and 1.24 g of potassium fluoride in 80 ml of methanol is brought to reflux for approximately 3 hours 30 minutes. After returning to a temperature in the region of 20° C., the mixture is filtered through celite, and the insoluble material is washed three times with 50 ml of methanol. The filtrate is concentrated to dryness under reduced pressure (13 kPa). The residue is taken up with 100 ml of dichloromethane. The solution obtained is washed with three times 60 ml of water, dried over magnesium sulfate, filtered, and concentrated to dryness under reduced pressure (13 kPa). 0.97 g of 5-chloro-3-ethynylpyridin-2-ylamine is thus obtained in the form of a solid, the characteristics of which are as follows:

Silica TLC [eluent: cyclohexane/ethyl acetate (50/50 by volume)]
Rf=0.72

Mass spectrum (CI): m/z=153 [M+H]$^+$ (base peak)

d) 5-Chloro-3-trimethylsilanylethynylpyridin-2-ylamine can be prepared in the following way:

A suspension of 2.54 g of 5-chloro-3-iodopyridin-2-ylamine, 2.12 ml of ethynyltrimethylsilane, 0.38 g of copper iodide and 0.47 g of lithium chloride in 7 ml of triethylamine and 75 ml of dimethylformamide is degassed under argon for approximately 15 minutes. 0.408 g of [1,1'-bis(diphenylphosphino)ferrocene] palladium(II) chloride is added to the above suspension. The mixture is heated at around 40° C. for approximately 19 hours and then concentrated to dryness under reduced pressure (13 kPa). The residue is taken up with 50 ml of water, and extracted with three times 100 ml of ethyl acetate. The combined organic phases are dried over magnesium sulfate, filtered, and concentrated to dryness under reduced pressure (13 kPa). The residue is purified by flash chromatography on a silica column [eluent: cyclohexane/ethyl acetate (70/30 by volume)]. 1.63 g of 5-chloro-3-trimethylsilanylethynylpyridin-2-ylamine are obtained in the form of a solid, the characteristics of which are as follows:

Melting point: 108° C. (Köfler bench)

Mass spectrum (CI): m/z=225 [M+H]$^+$ (base peak)

e) 5-Chloro-3-iodopyridin-2-ylamine can be prepared in the following way:

A mixture of 6.43 g of 5-chloropyridin-2-ylamine and 12.38 g of N-iodosuccinimide in 300 ml of glacial acetic acid is heated at around 55° C. for 6 hours. After returning to a temperature of approximately 20° C., the mixture is agitated for approximately 18 hours and then concentrated to dryness under reduced pressure (13 kPa). The residue is taken up with 400 ml of water; the pH of the suspension obtained is brought back to approximately 8 by adding a saturated aqueous sodium hydrogen carbonate solution. The precipitate is filter-dried, washed with water, and dried at 40° C. under reduced pressure (13 kPa) for approximately 3 hours. 12.35 g of 5-chloro-3-iodopyridin-2-ylamine are obtained in the form of a solid, the characteristics of which are as follows:

Silica TLC [eluent: cyclohexane/ethyl acetate (50/50 by volume)]
Rf 0.68

Mass spectrum (EI): m/z=254 [M]$^+$ (base peak); m/z=127 [M-I]$^+$; m/z=100 [127-HCN]$^+$; m/z=92 [127-Cl]$^+$ f) 3-Iodo-5,6-dimethoxy-1-methyl-1H-indole can be prepared in the following way:

0.465 g of powdered potassium hydroxide is added to a solution of 0.5 g of 5,6-dimethoxy-1H-indole in 15 ml of dimethylformamide. A solution of 0.725 g of bisublimated iodine in 15 ml of dimethylformamide is added dropwise to the above mixture. After agitation of the reaction medium for approximately 3 hours at a temperature in the region of 20° C., 0.21 ml of iodomethane is added dropwise, maintaining the mixture at this same temperature by cooling using a water bath. After agitation at around 20° C. for 1 hour 30 minutes, the mixture is run into a solution of 1.5 g of sodium thiosulfate in 150 ml of water cooled to around 5° C., and agitated for approximately 10 minutes. The precipitate is filter-dried, washed with five times 5 ml of water cooled to around 5° C., and then dried under vacuum (13 kPa) over phosphorus pentaoxide. 0.78 g of 3-iodo-5,6-dimethoxy-1-methyl-1H-indole is obtained in the form of a solid, the characteristics of which are as follows:

Melting point: 80-90° C. with decomposition (Köfler bench)

Mass spectrum (EI): m/z=317 [M]$^+$ (base peak); m/z=302 [M-CH$_3$]$^+$; m/z=190 [M-I]

EXAMPLE 104

2-(5,6-dimethoxy-1-methyl-1H-indol-3-yl)-5-fluoro-1H-pyrrolo[2,3-b]pyridine a) 2-(5,6-Dimethoxy-1-methyl-1H-indol-3-yl)-5-fluoro-1H-pyrrolo[2,3-b]pyridine can be prepared as in example 103a:

But using 0.19 g of 3-(5,6-dimethoxy-1-methyl-1H-indol-3-ylethynyl)-5-fluoropyridin-2-ylamine and 0.263 g of potassium tert-butoxide in 15 ml of 1-methylpyrrolidin-2-one. After flash chromatography on a silica column [eluent: dichloromethane/ethyl acetate (90/10 by volume)], 0.046 g of 2-(5,6-dimethoxy-1-methyl-1H-indol-3-yl)-5-fluoro-1H-pyrrolo[2,3-b]pyridine is thus obtained in the form of a solid, the characteristics of which are as follows:

Melting point: 283° C. (Büchi capillary)

$^1$H NMR spectrum (300 MHz, (CD$_3$)$_2$SO d6, δ in ppm): 3.83 (s: 3H); 3.87 (s: 3H); 3.89 (s: 3H); 6.76 (broad s: 1H); 7.13 (s: 1H); 7.41 (s: 1H); 7.70 (dd, J=9.5 and 3 Hz: 1H); 7.80 (s: 1H); 8.06 (dd, J=3 and 2.5 Hz: 1H); 11.87 (unresolved peak: 1H).

Mass spectrum (EI): m/z=325 [M]$^+$ (base peak); m/z=310 [M-CH$_3$]$^+$; m/z=282 [M-CO]$^+$ b) 3-(5,6-Dimethoxy-1-methyl-1H-indol-3-ylethynyl)-5-fluoropyridin-2-ylamine can be prepared in the following way:

0.049 g of bis(triphenylphosphine) palladium(II) chloride is added to a suspension, degassed with argon for approximately 15 minutes, of 0.57 g of 3-ethynyl-5,6-dimethoxy-1-methyl-1H-indole, 0.316 g of 5-fluoro-3-iodopyridin-2-ylamine and 0.06 g of copper iodide in 39.5 ml of triethylamine and 20 ml of dimethylformamide, and the mixture is agitated at a temperature in the region of 20° C. for 18 hours and then concentrated to dryness under reduced pressure (13 kPa). The residue is taken up with 150 ml of dichloromethane. The organic solution is washed with five times 50 ml of water, dried on magnesium sulfate, filtered, and concentrated to dryness under reduced pressure (13 kPa). The residue is purified by flash chromatography on a silica column [eluent: cyclohexane/ethyl acetate (50/50 by volume)].

0.14 g of 3-(5,6-dimethoxy-1-methyl-1H-indol-3-ylethynyl)-5-fluoropyridin-2-ylamine is obtained in the form of a solid, the characteristics of which are as follows:

Silica TLC [eluent: dichloromethane/methanol (98/2 by volume)] Rf=0.28

Mass spectrum (CI): m/z=326 [M+H]$^+$ (base peak)

c) 5-Fluoro-3-iodopyridin-2-ylamine can be prepared as in example 103e:

But using 5 g of 5-fluoropyridin-2-ylamine and 11.04 g of N-iodosuccinimide in 250 ml of glacial acetic acid. 6.1 g of 5-fluoro-3-iodopyridin-2-ylamine are thus obtained in the form of a solid, the characteristics of which are as follows:

Melting point: 70° C. (Köfler bench)

Mass spectrum (CI): m/z=239 [M+H]$^+$ (base peak)

d) 3-Ethynyl-5,6-dimethoxy-1-methyl-1H-indole can be prepared as in example 103c:

But using 1.71 g of 5,6-dimethoxy-1-methyl-3-trimethylsilanylethynyl-1H-indole and 1.04 g of potassium fluoride in 70 ml of methanol. 1 g of 3-ethynyl-5,6-dimethoxy-1-methyl-1H-indole is thus obtained in the form of a solid, the characteristics of which are as follows:

Silica TLC (eluent: dichloromethane) Rf=0.49

Mass spectrum (EI): m/z=215 [M]$^+$ (base peak); m/z=200 [M-CH$_3$]$^+$ m/z=172 [M-CO]$^+$ e) 5,6-Dimethoxy-1-methyl-3-trimethylsilanylethynyl-1H-indole can be prepared in the following way:

0.421 g of bis(triphenylphosphine) palladium(II) chloride is added to a suspension of 3.81 g of 3-iodo-5,6-dimethoxy-1-methyl-1H-indole, 2.36 g of ethynyltrimethylsilane and 0.457 g of copper iodide in 150 ml of triethylamine, degassed under argon for 15 minutes. The mixture is agitated at a temperature in the region of 20° C. for approximately 18 hours and then heated at around 50° C. for approximately 24 hours. After returning to a temperature in the region of 20° C., the mixture is diluted with 100 ml of ethyl acetate, and washed with 150 ml of water. The aqueous phase is re-extracted with two times 150 ml of ethyl acetate; the combined organic phases are washed with 200 ml of a saturated aqueous sodium chloride solution, dried over magnesium sulfate, filtered, and concentrated to dryness under reduced pressure (13 kPa). After filtration through silica and elution with dichloromethane, 1.71 g of 5,6-dimethoxy-1-methyl-3-trimethylsilanylethynyl-1H-indole are obtained in the form of a solid, the characteristics of which are as follows:

Melting point: 124° C. (Köfler bench)

Mass spectrum (EI): m/z=287 [M]$^+$ (base peak); m/z=272 [M-CH$_3$]$^+$ m/z=214 [M-SiMe$_3$]$^+$ 3-Iodo-5,6-dimethoxy-1-methyl-1H-indole is described in example 103f.

EXAMPLE 105

2-[5,6-dimethoxy-1-(2-morpholin-4-ylethyl)-1H-indol-3-yl]-5-fluoro-1H-pyrrolo[2,3-b]pyridine a) 2-[5,6-Dimethoxy-1-(2-morpholin-4-ylethyl)-1H-indol-3-yl]-5-fluoro-1H-pyrrolo[2,3-b]pyridine can be prepared in the following way:

A solution of 2.08 g of potassium hydroxide in 7 ml of water is added to a solution of 0.83 g of 2-[5,6-dimethoxy-1-(2-morpholin-4-ylethyl)-1H-indol-3-yl]-5-fluoro-1-(toluene-4-sulfonyl)—1H-pyrrolo[2,3-b]pyridine in 100 ml of methanol brought to reflux. The mixture is agitated at reflux for 3 hours 30 minutes. After returning to around 20° C. the mixture is concentrated to dryness under reduced pressure (13 kPa). The residue is taken up with 50 ml of water and extracted with three times 80 ml of dichloromethane. The combined organic phases are dried over magnesium sulfate, filtered, and concentrated to dryness under reduced pressure (13 kPa). The residue is purified by flash chromatography on a silica column [eluent: ethyl acetate/methanol (90/10 by volume)]. 0.37 g of 2-[5,6-dimethoxy-1-(2-morpholin-4-ylethyl)-1H-indol-3-yl]-5-fluoro-1H-pyrrolo[2,3-b] pyridine is obtained in the form of a solid, the characteristics of which are as follows:

Melting point: 205-210° C. (Köfler bench)

$^1$H NMR spectrum (300 MHz, (CD$_3$)$_2$SO d6, δ in ppm): 2.49 (broad t, J=4.5 Hz: 4H); 2.73 (t, J=6.5 Hz: 2H); 3.61 (broad t, J=4.5 Hz: 4H); 3.87 (s: 3H); 3.89 (s: 3H); 4.32 (broad t, J=6.5 Hz: 2H); 6.78 (broad s: 1H); 7.20 (s: 1H); 7.41 (s: 1H); 7.70 (dd, J=9.5 and 3 Hz: 1H); 7.89 (s: 1H); 8.07 (dd, J=3 and 2.5 Hz: 1H); 11.88 (unresolved peak: 1H).

Mass spectrum (EI): m/z=424 [M]$^+$; m/z=100 [C$_5$H$_{10}$NO]$^+$ (base peak)

b) 2-[5,6-Dimethoxy-1-(2-morpholin-4-ylethyl)-1H-indol-3-yl]-5-fluoro-1-(toluene-4-sulfonyl)-1H-pyrrolo[2,3-b] pyridine can be prepared as in example 10b:

But using 1 g of 5-fluoro-2-[1-(2-iodoethyl)-5,6-dimethoxy-1H-indol-3-yl]-1-(toluene-4-sulfonyl)-1H-pyrrolo[2,3-b]pyridine, 0.223 g of potassium carbonate and 0.28 ml of morpholine in 100 ml of acetonitrile. 0.83 g of 2-[5,6-dimethoxy-1-(2-morpholin-4-ylethyl)-1H-indol-3-yl]-5-fluoro-1-(toluene-4-sulfonyl)-1H-pyrrolo[2,3-b]pyridine is thus obtained in the form of a solid, the characteristics of which are as follows:

Melting point: 182° C. (Köfler bench)

Mass spectrum (CI): m/z=620 [M'+H]$^+$; m/z=579[M+H]$^+$ (base peak)

c) 5-Fluoro-2-[1-(2-iodoethyl)-5,6-dimethoxy-1H-indol-3-yl]-1-(toluene-4-sulfonyl)-1H-pyrrolo[2,3-b]pyridine can be prepared as in example 100c:

But using 2 g of 5-fluoro-2-[1-(2-chloroethyl)-5,6-dimethoxy-1H-indol-3-yl]-1-(toluene-4-sulfonyl)-1H-pyrrolo[2,3-b]pyridine, 0.85 g of sodium iodide in 100 ml of 2-butanone. 2.2 g of 5-fluoro-2-[1-(2-iodoethyl)-5,6-dimethoxy-1H-indol-3-yl]-1-(toluene-4-sulfonyl)-1H-pyrrolo[2,3-b]pyridine are thus obtained in the form of a solid, the characteristics of which are as follows:

Melting point: 176° C. (Köfler bench)

Mass spectrum (EI): m/z=619 [M]$^+$; m/z=492 [M-I]$^+$; m/z=464 [M-C$_7$H$_7$O$_2$S]$^+$ (base peak); m/z=337 [464-I]$^+$ d) 5-Fluoro-2-[1-(2-chloroethyl)-5,6-dimethoxy-1H-indol-3-yl]-1-(toluene-4-sulfonyl)-1H-pyrrolo[2,3-b]pyridine can be prepared as in example 100d:

But using 2 g of 2-(5,6-dimethoxy-1H-indol-3-yl)-5-fluoro-1-(toluene-4-sulfonyl)-1H-pyrrolo[2,3-b]pyridine, 0.028 g of tetrabutylammonium bromide, 1.89 g of potassium hydroxide and 1.38 g of potassium carbonate in 50 ml of 1,2-dichloroethane. After flash chromatography on a silica column [eluent: dichloromethane/methanol (98.5/1.5 by volume)], 2.05 g of 5-fluoro-2-[1-(2-chloroethyl)-5,6-dimethoxy-1H-indol-3-yl]-1-(toluene-4-sulfonyl)-1H-pyrrolo[2,3-b]pyridine are thus obtained in the form of a solid, the characteristics of which are as follows:

Melting point: 150° C. (Köfler bench)

Mass spectrum (EI): m/z=527 [M]$^+$; m/z=372 [M-C$_7$H$_7$O$_2$S]$^+$(base peak)

e) 2-(5,6-Dimethoxy-1H-indol-3-yl)-5-fluoro-1-(toluene-4-sulfonyl)-1H-pyrrolo[2,3-b]pyridine can be prepared in the following way:

A mixture of 3.1 g of 5-fluoro-2-iodo-1-(toluene-4-sulfonyl)-1H-pyrrolo[2,3-b]pyridine, 2.4 g of 1-tert-butyloxycarbonyl-5,6-dimethoxy-1H-indole-3-boronic acid and 20.3 ml of a saturated aqueous sodium hydrogen carbonate solution in 100 ml of dimethylformamide is degassed with argon for approximately 15 minutes and then 0.43 g of tetrakis(triphenylphosphine)palladium is added. The mixture is heated at around 110° C. for approximately 2 hours and then concentrated to dryness under reduced pressure (13 kPa). The residue is taken up with 500 ml of water, and extracted with three times 250 ml of ethyl acetate. The combined organic phases are dried over magnesium sulfate, filtered, and concentrated to dryness under reduced pressure. The residue is taken up with 100 ml of diisopropyl ether, filter-dried, washed with three times 20 ml of diisopropyl ether, and dried under reduced pressure (13 kPa) in the presence of potassium hydroxide chips at a temperature in the region of 20° C. 2.66 g of 2-(5,6-dimethoxy-1H-indol-3-yl)-5-fluoro-1-(toluene-4-sulfonyl)-1H-pyrrolo[2,3-b]pyridine are obtained in the form of a solid, the characteristics of which are as follows:

Melting point: 218° C. (Köfler bench)

Mass spectrum (EI): m/z=465 [M]$^+$; m/z=310 [M-C$_7$H$_7$O$_2$S]$^+$(base peak)

1-Tert-butyloxycarbonyl-5,6-dimethoxy-1H-indole-3-boronic acid is prepared as described in patent WO 03000688A1.

f) 5-Fluoro-2-iodo-1-(toluene-4-sulfonyl)-1H-pyrrolo[2,3-b]pyridine can be prepared in the following way:

7.54 ml of a solution of N-butyllithium at 1.6 N in hexane is added, dropwise, maintaining the temperature of the medium in the region of −75° C., to a solution, cooled to approximately −78° C., of 3.5 g of 5-fluoro-1-(toluene-4-sulfonyl)-1H-pyrrolo[2,3-b]pyridine in 100 ml of tetrahydrofuran. After agitation for approximately one hour at the same temperature, a solution of 6.12 g of bisublimated iodine in 50 ml of tetrahydrofuran is run in dropwise. After the temperature has returned to around 20° C., the reaction mixture is diluted with 600 ml of ethyl acetate, washed three times with 100 ml of a 5% aqueous sodium thiosulfate solution, dried over magnesium sulfate, treated with vegetable black, filtered, and concentrated to dryness under reduced pressure (13 kPa). The residue is taken up with 30 ml of diisopropyl ether, filter-dried, washed with three times 5 ml of diisopropyl ether, and dried under reduced pressure (13 kPa). 3.6 g of 5-fluoro-2-iodo-1-(toluene-4-sulfonyl)-1H-pyrrolo[2,3-b]pyridine are obtained in the form of a solid, the characteristics of which are as follows:

Melting point: 158° C. (Köfler bench)

Mass spectrum (EI): m/z=416 [M]$^+$; m/z=352 [M-SO2]$^+$; m/z=155 [C$_7$H$_7$O$_2$S]+; m/z=91 [C$_7$H$_7$]$^+$ (base peak)

g) 5-Fluoro-1-(toluene-4-sulfonyl)-1H-pyrrolo[2,3-b]pyridine can be prepared in the following way:

A mixture of 2.3 g of 5-fluoro-1H-pyrrolo[2,3-b]pyridine, 3.54 g of 4-methylbenzenesulfonyl chloride, 7.56 g of sodium hydroxide dissolved in 55 ml of water, and 0.115 g of tetrabutylammonium hydrogen sulfate in 125 ml of toluene is agitated at around 20° C. for approximately 24 hours. The mixture is diluted with 500 ml of ethyl acetate; the organic phase is washed with three times 200 ml of water, dried over magnesium sulfate, filtered, and concentrated to dryness under reduced pressure (13 kPa). The residue is purified by flash chromatography on a silica column [eluent: dichloromethane]. 3.85 g of 5-fluoro-1-(toluene-4-sulfonyl)-1H-pyrrolo[2,3-b]pyridine are obtained in the form of a solid, the characteristics of which are as follows:

Melting point: 160° C. (Köfler bench)

Mass spectrum (EI): m/z=290 [M]$^+$; m/z=226 [M-SO$_2$]$^+$.; m/z=155 [C$_7$H$_7$O$_2$S]$^+$; m/z=91 [C$_7$H$_7$]$^+$ (base peak)

h) 5-Fluoro-1H-pyrrolo[2,3-b]pyridine can be prepared in the following way:

A mixture of 3.8 g of 5-fluoro-3-trimethylsilanylethynylpyridin-2-ylamine and 3.4 g of potassium tert-butoxide in 100 ml of 1-methylpyrrolidin-2-one is brought to around 130° C. for approximately 4 hours. After returning to a temperature in the region of 20° C., the mixture is run into 1000 ml of a saturated aqueous sodium chloride solution and extracted with five times 250 ml of diethyl ether. The organic phases are combined, washed with five times 100 ml of a saturated aqueous sodium chloride solution, dried over magnesium sulfate, filtered, and concentrated to dryness under reduced pressure (13 kPa). 2.35 g of 5-fluoro-1H-pyrrolo[2,3-b]pyridine are obtained in the form of a solid, the characteristics of which are as follows:

Melting point: 110° C. (Köfler bench)

Mass spectrum (EI): m/z=136 [M]$^+$ (base peak); m/z=109 [M-HCN]$^+$ i) 5-Fluoro-3-trimethylsilanylethynylpyridin-2-ylamine can be prepared as described in example 103d:

But using 14 g of 5-fluoro-3-iodopyridin-2-ylamine, 12.47 ml of ethynyltrimethylsilane, 2.24 g of copper iodide, 2.74 g of lithium chloride, 41.33 ml of triethylamine and 2.15 g of [1,1'-bis(diphenylphosphino)ferrocene] palladium(II) chloride in 441 ml of dimethylformamide. After flash chromatography on a silica column (eluent: dichloromethane), 7.91 g of 5-fluoro-3-trimethylsilanylethynylpyridin-2-ylamine are thus obtained in the form of a solid, the characteristics of which are as follows:

Melting point: 65° C. (Köfler bench)

Mass spectrum (EI): m/z=208 [M]$^+$; m/z=193 [M-CH$_3$]$^+$ (base peak)

5-Fluoro-3-iodopyridin-2-ylamine is described in example 104c.

EXAMPLE 106

2-{5,6-Dimethoxy-1-[2-(4-methylpiperazin-1-yl)ethyl]-1H-indol-3-yl}-5-fluoro-1H-pyrrolo[2,3-b]pyridine a) 2-{5,6-Dimethoxy-1-[2-(4-methylpiperazin-1-yl)ethyl]-1H-indol-3-yl}-5-fluoro-1H-pyrrolo[2,3-b]pyridine can be prepared as in example 105a:

But using 0.82 g of 2-[5,6-dimethoxy-1-[2-(4-methylpiperazin-1-yl)ethyl]-1H-indol-3-yl]-5-fluoro-1-(toluene-4-sulfonyl)-1H-pyrrolo[2,3-b]pyridine dissolved in 100 ml of methanol and 2 g of potassium hydroxide dissolved in 7 ml of water. After flash chromatography on a silica column [eluent: dichloromethane/methanol (70/30 by volume)], 0.37 g of 2-{5,6-dimethoxy-1-[2-(4-methyl-piperazin-1-yl)ethyl]-1H-indol-3-yl}-5-fluoro-1H-pyrrolo[2,3-b]pyridine is thus obtained in the form of a solid, the characteristics of which are as follows:

Melting point: 210° C. (Köfler bench)

$^1$H NMR spectrum (300 MHz, (CD$_3$)$_2$SO d6, δ in ppm): 2.16 (s: 3H); 2.32 (unresolved peak: 4H); from 2.40 to 2.55 (mt: 4H); 2.73 (broad t, J=6.5 Hz: 2H); 3.87 (s: 3H); 3.89 (s: 3H); 4.30 (broad t, J=6.5 Hz: 2H); 6.76 (broad s: 1H); 7.18 (s: 1H); 7.42 (s: 1H); 7.71 (dd, J=9.5 and 3 Hz: 1H); 7.88 (s: 1H); 8.07 (mt: 1H); 11.87 (unresolved peak: 1H).

Mass spectrum (EI): m/z=437 [M]$^+$; m/z=113 [C$_6$H$_{13}$N$_2$]$^+$ (base peak); m/z=70 [C$_4$H$_8$N]$^+$ b) 2-[5,6-Dimethoxy-1-[2-(4-methylpiperazin-1-yl)ethyl]-1H-indol-3-yl]-5-fluoro-1-(toluene-4-sulfonyl)-1H-pyrrolo[2,3-b]pyridine can be prepared as described in example 100b:

But using 1 g of 5-fluoro-2-[1-(2-iodoethyl)-5,6-dimethoxy-1H-indol-3-yl]-1-(toluene-4-sulfonyl)-1H-pyrrolo[2,3-b]pyridine, 0.223 g of potassium carbonate and 0.323 g of 1-methylpiperazine in 100 ml of acetonitrile. 0.83 g of 2-[5,6-dimethoxy-1-[2-(4-methylpiperazin-1-yl)ethyl]-1H-indol-3-yl]-5-fluoro-1-(toluene-4-sulfonyl)-1H-pyrrolo[2,3-b]pyridine is thus obtained in the form of a solid, the characteristics of which are as follows:

Melting point: 188° C. (Köfler bench)

Mass spectrum (EI): m/z=591 [M]$^+$; m/z=491 [M-C$_4$H$_8$N]$^+$; m/z=436 [M-C$_7$H$_7$O$_2$S]$^+$; m/z=113 [C$_6$H$_{13}$N$_2$]$^+$ (base peak); m/z=70 [C$_4$H$_8$N]$^+$

EXAMPLE 107

[1-Carboxymethyl-5-methoxy-3-(1H-pyrrolo[2,3-b]pyridin-2-yl)-1H-indol-6-yloxy]acetic acid a) [1-carboxymethyl-5-methoxy-3-(1H-pyrrolo[2,3-b]pyridin-2-yl)-1H-indol-6-yloxy]acetic acid is prepared in the following way:

0.3 ml of a methanolic potassium hydroxide solution (0.1 g/ml) is placed in a hemolysis tube containing {5-methoxy-1-methoxycarbonylmethyl-3-[1-(toluene-4-sulfonyl)-1H-pyrrolo[2,3-b]pyridin-2-yl]-1H-indol-6-yloxy}acetic acetate (0.056 g; 97.1 μmol), then the mixture is agitated at 20° C. for 16 hours. Reverse-phase liquid chromatography mass spectrometry analysis shows that the expected product forms but is not in the majority. Purification attempts carried out at this stage of the reaction are fruitless and the compounds obtained, all containing mixtures of starting compound and of expected product, are evaporated and re-reacted with 2 ml of methanolic potassium hydroxide (0.1 g/ml) for 20 hours. The reaction mixture becomes milky in color. The mixture is evaporated to dryness and taken up with a mixture of 1 ml of dimethyl sulfoxide and 1 ml of a 6M aqueous hydrochloric acid solution. The solution thus obtained is purified by reverse-phase liquid chromatography mass spectrometry (method C), after filtering-off the white precipitate which is formed. After evaporation of the fractions, the tubes containing the expected compound are combined so as to obtain [1-carboxymethyl-5-methoxy-3-(1H-pyrrolo[2,3-b]pyridin-2-yl)-1H-indol-6-yloxy]acetic acid (0.015 g; 31%) the characteristics of which are as follows:

LC/MS analysis: tr=2.9 min [M+H]$^+$; m/z=396.17 [M+H]$^+$ b) The methyl ester of {5-methoxy-1-methoxycarbonylmethyl-3-[1-(toluene-4-sulfonyl)-1H-pyrrolo[2,3-b]pyridin-2-yl]-1H-indol-6-yloxy}acetic acid is prepared in the following way:

A solution of 5-methoxy-3-[1-(toluene-4-sulfonyl)-1H-pyrrolo[2,3-b]pyridin-2-yl]-1H-indol-6-ol (0.043 g; 100 μmol), in solution in dimethylformamide (10 ml), is placed in a 1.3×10 cm hemolysis tube, then potassium carbonate (0.027 g; 200 μmol) is added and the mixture is agitated at ambient temperature for 5 minutes. Methyl bromoacetate (0.028 ml; 300 μmol) is added and the mixture is then heated at 50° C. for 4 hours, the TLC control (eluent: 50/50 v/v cyclohexane/ethyl acetate) showing that the reaction has come to an end. The reaction mixture is run into 5 ml of distilled water and the reaction mixture is then extracted with ethyl acetate (15 ml). The combined extracts are washed with water (20 ml), dried over magnesium sulfate, filtered, and evaporated to give a crude compound which is purified by chromatography on silica gel, elution being carried out with a mixture of cyclohexane and ethyl acetate (60/40 v/v). The fractions containing the expected compound are combined and evaporated to give the methyl ester of {5-methoxy-1-methoxycarbonylmethyl-3-[1-(toluene-4-sulfonyl)-1H-pyrrolo[2,3-b]pyridin-2-yl]-1H-indol-6-yloxy}acetic acid (0.056 g; 97%), the characteristics of which are as follows:

LC/MS analysis: tr=4.1, m/z=578.1 [M+H]$^+$ c) 5-Methoxy-3-[1-(toluene-4-sulfonyl)-1H-pyrrolo[2,3-b]pyridin-2-yl]-1H-indol-6-ol is prepared in the following way:

A solution of 2-(6-benzyloxy-5-methoxy-1H-indol-3-yl)-1-(toluene-4-sulfonyl)-1H-pyrrolo[2,3-b]pyridine (0.52 g; 993 μmol), in acetonitrile (40 ml) is treated with trimethyl silyl iodide (0.353 ml; 2.483 mmol; 2.5 eq.) at 50° C. for 2 hours and then at 20° C. for 16 hours, in a 100 ml three-necked flask. After evaporation, the reaction mixture is taken up in a mixture of dichloromethane (50 ml) and water (50 ml) and is then separated by settling out. The aqueous phase is extracted with dichloromethane (250 ml); the extracts are combined, dried over magnesium sulfate, and evaporated to give a compound which is purified by chromatography on silica gel (10 g, 35 μm silica), elution being carried out with a mixture of cyclohexane and ethyl acetate (60/40 vol/vol). The fractions containing the expected compound are combined and evaporated, resulting in a solid which is triturated in diisopropyl ether so as to obtain 5-methoxy-3-[1-(toluene-4-sulfonyl)-1H-pyrrolo[2,3-b]pyridin-2-yl]-1H-indol-6-ol, (0.215 g; 50%), the characteristics of which are as follows:

$^1$H NMR spectrum (300 MHz, (CD$_3$)$_2$SO d6, δ in ppm): 2.30 (s: 3H); 3.75 (s: 3H); 6.75 (s: 1H); 6.90 (s: 1H); 6.93 (broad s: 1H); 7.26 (broad d, J=8.5 Hz: 2H); 7.304 (dd, J=8 and 5 Hz: 1H); 7.42 (d, J=2.5 Hz: 1H); 7.57 (broad d, J=8.5 Hz: 2H); 7.94 (dd, J=8 and 1.5 Hz: 1H); 8.34 (dd, J=5 and 1.5 Hz: 1H); 8.71 (broad s: 1H); 11.08 (broad s: 1H).

EXAMPLE 108

{5-Methoxy-1-methyl-3-[1-(toluene-4-sulfonyl)-1H-pyrrolo[2,3-b]pyridin-2-yl]-1H-indol-6-yloxy}acetic acid a) (5-Methoxy-1-methyl-3-[1-(toluene-4-sulfonyl)-1H-pyrrolo[2,3-b]pyridin-2-yl]-1H-indol-6-yloxy}acetic acid is prepared in the following way:

A solution of methyl {5-methoxy-1-methyl-3-[1-(toluene-4-sulfonyl)-1H-pyrrolo[2,3-b]pyridin-2-yl]-1H-indol-6-yloxy}acetate, (0.91 g; 1.751 mmol) in methanolic potassium hydroxide (74 ml at 1 g/ml) is placed in a 100 ml round-bottomed flask, at 20° C. for 16 hours with agitation. After reaction, the precipitate formed is filtered off, and rinsed with methanol (20 ml). A suspension of the above solid in water (30 ml) is placed in a 250 ml Erlenmeyer flask and the pH is then adjusted to 4 with 2N aqueous hydrochloric acid. The yellow solid formed is triturated in the reaction mixture and is then filtered, rinsed with water and dried under reduced pressure. {5-Methoxy-1-methyl-3-[1-(toluene-4-sulfonyl)-1H-pyrrolo[2,3-b]pyridin-2-yl]-1H-indol-6-yloxy}acetic acid (0.666 g; 98%) is isolated, the characteristics of which are as follows:

Mass spectrum (IC): m/z=352 [M+H]$^+$ (base peak)

b) The methyl ester of {5-methoxy-1-methyl-3-[1-(toluene-4-sulfonyl)-1H-pyrrolo[2,3-b]pyridin-2-yl]-1H-indol-6-yloxy}acetic acid is prepared in the following way:

A solution of 5-methoxy-1-methyl-3-[1-(toluene-4-sulfonyl)-1H-pyrrolo[2,3-b]pyridin-2-yl]-1H-indol-6-ol, (0.558 g; 1.247 mmol) dissolved in dimethylformamide (10 ml) is placed in a 25 ml three-necked flask, under argon, then sodium hydride (0.045 g; 1.49 mmol) is added, and the mixture is agitated at ambient temperature for 10 minutes. As soon as there is no more gas being given off, methyl bromoacetate (0.142 ml; 1.496 mmol) is added dropwise, and the mixture is left at ambient temperature for 3 hours with agitation. The reaction mixture is run into 100 ml of distilled water and the solid formed is then filtered off and washed with water (30 ml). The solid is dissolved in dichloromethane (150 ml), and the solution thus obtained is then washed with distilled water (50 ml), dried over magnesium sulfate and then evaporated under reduced pressure, resulting in methyl {5-methoxy-1-methyl-3-[1-(toluene-4-sulfonyl)-1H-pyrrolo[2,3-b]pyridin-2-yl]-1H-indol-6-yloxy}acetate, in the form of a brown-colored oil (0.5 g; 77%), the characteristics of which are as follows:

LC/MS analysis: tr=4.1 min; m/z=520.13 [M+H$^+$)

c) 5-Methoxy-1-methyl-3-[1-(toluene-4-sulfonyl)-1H-pyrrolo[2,3-b]pyridin-2-yl]-1H-indol-6-ol is prepared in the following way:

A solution of 2-(6-benzyloxy-5-methoxy-1-methyl-1H-indol-3-yl)-1-(toluene-4-sulfonyl)-1H-pyrrolo[2,3-b]pyridine (1.5 g; 2.79 mmol) in acetonitrile (120 ml) is placed in a 250 ml three-necked flask at 20° C., and then trimethylsilyl iodide (0.956 ml; 6.97 mmol) is added dropwise. The reaction mixture is heated at 50° C. for 4 hours and is then evaporated to dryness under reduced pressure. The evaporation residue is taken up in dichloromethane (200 ml) and then washed with distilled water (1×200 ml). The extracts are combined, washed with distilled water, dried over magnesium sulfate and evaporated under reduced pressure, to produce the crude compound which is purified by chromatography on a silica cartridge (AIT FlashSmart Pack, BP-0610300-093, 50 g silica), elution being carried out at 15 ml/min with a dichloromethane/ethyl acetate (95/5 v/v) mixture. The fractions containing the expected product are combined and evaporated to give 5-methoxy-1-methyl-3-[1-(toluene-4-sulfonyl)-1H-pyrrolo[2,3-b]pyridin-2-yl]-1H-indol-6-ol (0.87 g; 70%) in the form of an ochre foam, which is used as it is for the following step.

d) 2-(6-Benzyloxy-5-methoxy-1-methyl-1H-indol-3-yl)-1-(toluene-4-sulfonyl)-1H-pyrrolo[2,3-b]pyridine is prepared in the following way:

A solution of 2-(6-benzyloxy-5-methoxy-1H-indol-3-yl)-1-(toluene-4-sulfonyl)-1H-pyrrolo[2,3-b]pyridine (1 g, 1.9 mmol) in dimethylformamide (10 ml) is placed in a 25 ml three-necked flask placed under argon, then sodium hydride (0.063 g; 2.101 mmol) is added and the mixture is left to agitate for 15 minutes. When there is no longer any gas being given off, methyl iodide (0.131 ml, 2.101 mmol) is added dropwise and the mixture is left to react at 21° C. for 2 hours. The reaction medium is run into 100 ml of distilled water, and then extracted with 2 times 100 ml of dichloromethane. The organic extracts are combined, dried over magnesium sulfate, filtered, and evaporated to dryness under reduced pressure. The evaporation compound is triturated in diisopropyl ether. The pulverulent solid compound thus obtained is filtered off and rinsed. 2-(6-Benzyloxy-5-methoxy-1-methyl-1H-indol-3-yl)-1-(toluene-4-sulfonyl)-1H-pyrrolo[2,3-b]pyridine (0.888 g; 86%) is isolated in the form of a beige-colored solid, the characteristics of which are as follows:

$^1$H NMR spectrum (300 MHz, (CD$_3$)$_2$SO d6, δ in ppm): 2.30 (s: 3H); 3.77 (s: 3H); 3.87 (s: 3H); 5.21 (s: 2H); 6.76 (s: 1H); 7.00 (s: 1H); 7.27 (broad d, J=8.5 Hz: 2H); 7.29 (s: 1H); 7.31 (dd, J=8 and 5 Hz: 1H); 7.39 (broad t, J=7.5 Hz: 1H); 7.47 (broad t, J=7.5 Hz: 2H); 7.51 (s: 1H); from 7.55 to 7.65 (mt: 4H); 7.95 (dd, J=8 and 1.5 Hz: 1H); 8.36 (dd, J=5 and 1.5 Hz: 1H).

2-(6-Benzyloxy-5-methoxy-1H-indol-3-yl)-1-(toluene-4-sulfonyl)-1H-pyrrolo[2,3-b]pyridine was prepared as described in patent WO 03000688 A1.

EXAMPLES 109 TO 146

Preparation of the Reagents:

A solution of [5-methoxy-1-methyl-3-(1H-pyrrolo[2,3-b]pyridin-2-yl)-1H-indol-6-yloxy]acetic acid, (prepared as in example 108), (0.228 g; 0.585 mmol) in dimethylformamide (3.25 ml; Solution A) and also a solution of N,N'-dicyclohexylcarbodiimide (0.465 g, 2.25 mmol) in dimethylformamide (3.75 ml; Solution C) and a mixture of 1-hydroxybenzotriazole (0.206 g; 1.52 mmol) and dimethylaminopyridine (0.015 g; 0.12 mmol) in dimethylformamide (3.75 ml; Solution D) are prepared and placed in receptacles. Each amine in the table below can be weighed and diluted in dimethylformamide.

TABLE 1

Reagents used

| Ex. | Entry | Name | Formula | Molecular weight (g/mol) | Equivalent | Weight (mg) |
|---|---|---|---|---|---|---|
| 109 | 1 | morpholine | C4H9NO | 87.12 | 3.000 | 13.069 |
| 110 | 2 | n-(2-hydroxyethyl)piperazine | C6H14N2O | 130.19 | 3.000 | 19.530 |
| 111 | 3 | n,n-dimethylethylenediamine | C4H12N2 | 88.15 | 3.000 | 13.220 |
| 112 | 4 | diethylamine | C4H11N | 73.14 | 3.000 | 10.970 |
| 113 | 5 | 3-hydroxypiperidine | C5H11NO | 101.15 | 3.000 | 15.170 |
| 114 | 6 | n,n,n'-trimethylethylenediamine | C5H14N2 | 102.18 | 3.000 | 15.330 |
| 115 | 7 | 1-cyclohexylpiperazine | C10H20N2 | 168.28 | 3.000 | 25.240 |
| 116 | 8 | 1-methylhomopiperazine | C6H14N2 | 114.19 | 3.000 | 17.130 |
| 117 | 9 | 4-(4-methylpiperazino)aniline | C11H17N3 | 191.28 | 3.000 | 28.690 |
| 118 | 10 | cis-perhydropyrrolo[3,4-c]-pyrrole-1,3-dione | C6H8N2O2 | 140.14 | 3.000 | 21.020 |
| 119 | 11 | 2-(2-methylaminoethyl)pyridine | C8H12N2 | 136.2 | 3.000 | 20.430 |
| 120 | 12 | 1-methylpiperazine | C5H12N2 | 100.16 | 3.000 | 15.020 |
| 121 | 13 | 1-(2-furoyl)piperazine | C9H12N2O2 | 180.21 | 3.000 | 27.030 |
| 122 | 14 | 3-(n-acetyl-n-methylamino)-pyrrolidine | C7H14N2O | 142.2 | 3.000 | 21.330 |
| 123 | 15 | 1-hydroxyethylethoxypiperazine | C8H18N2O2 | 174.24 | 3.000 | 26.140 |
| 124 | 16 | 4-piperidineethanol | C7H15NO | 129.2 | 3.000 | 19.380 |
| 125 | 17 | 3-(aminomethyl)pyridine | C6H8N2 | 108.14 | 3.000 | 16.220 |
| 126 | 18 | 3-methylamino-1,2-propanediol | C4H11NO2 | 105.14 | 3.000 | 15.770 |

TABLE 1-continued

Reagents used

| Ex. | Entry | Name | Formula | Molecular weight (g/mol) | Equivalent | Weight (mg) |
|---|---|---|---|---|---|---|
| 127 | 19 | 2-methoxy-n-methylethylamine | C4H11NO | 89.14 | 3.000 | 13.370 |
| 128 | 20 | cis-perhydropyrrolo[3,4-c]-pyrrol-1-one | C6H10N2O | 126.16 | 3.000 | 18.920 |
| 129 | 21 | 2-(methylamino)ethanol | C3H9NO | 75.11 | 3.000 | 11.270 |
| 130 | 22 | diethanolamine | C4H11NO2 | 105.14 | 3.000 | 15.770 |
| 131 | 23 | n,n-dimethyl-n'-ethylethylene-diamine | C6H16N2 | 116.21 | 3.000 | 17.430 |
| 132 | 24 | 4-benzyl-4-hydroxypiperidine | C12H17NO | 191.28 | 3.000 | 28.690 |
| 133 | 25 | 4-(ethylaminomethyl)pyridine | C8H12N2 | 136.2 | 3.000 | 20.430 |
| 134 | 26 | bis(2-methoxyethyl)amine | C6H15NO2 | 133.19 | 3.000 | 19.980 |
| 135 | 27 | 1,1,7,7-tetraethyldiethylene-triamine | C12H29N3 | 215.39 | 3.000 | 32.310 |
| 136 | 28 | methyl-4-(aminomethyl)benzoate hydrochloride | C9H12ClNO2 | 201.65 | 3.000 | 30.250 |
| 137 | 29 | (3aR,6aS)-2-phenyltetrahydro-pyrrolo[3,4-c]pyrrole-1,3-dione hydrochloride | C12H13ClN2O2 | 252.7 | 3.000 | 37.910 |
| 138 | 30 | (3aR,6aS)-2-benzyltetrahydro-pyrrolo[3,4-c]pyrrole-1,3-dione hydrochloride | C13H15ClN2O2 | 266.73 | 3.000 | 40.010 |
| 139 | 31 | 4-Amino-1-benzopyran-8-carboxylic acid methyl ester hydrochloride | C12H17NO3 | 223.27 | 3.000 | 33.490 |
| 140 | 32 | 2-aminopyridine | C5H6N2 | 94.12 | 3.000 | 14.120 |
| 141 | 33 | 4-aminopyridine | C5H6N2 | 94.12 | 3.000 | 14.120 |
| 142 | 34 | 4-piperidinoaniline | C11H16N2 | 176.26 | 3.000 | 26.440 |
| 143 | 35 | methyl-4-(aminomethyl)benzoate hydrochloride | C9H12ClNO2 | 201.65 | 3.0 | 45.050 |
| 144 | 36 | 2-amino-3-hydroxypyridine | C5H6N2O | 110.12 | 3.000 | 37.66 |
| 145 | 37 | 2-amino-3-methylpyridine | C6H8N2 | 108.14 | 3.000 | 37.00 |
| 146 | 38 | m-anisidine | C7H9NO | 123.16 | 3.000 | 42.12 |

Preparation of the Non-Commercial Amines Used

Preparation of cis-perhydropyrrolo[3,4-c]pyrrole-1,3-dione (example 118)

a) Cis-perhydropyrrolo[3,4-c]pyrrole-1,3-dione is prepared in the following way:

A solution 5-benzyl-tetrahydropyrrolo[3,4-c]pyrrole-1,3-dione, (11.5 g; 49.9 mmol) in ethanol (200 ml) is placed in a 1000 ml autoclave and palladium-on-charcoal (5%; 2 g; 0.9 mmol) is then added. After having purged the reactor with nitrogen, the autoclave is placed under 58 bars of hydrogen at 70° C. for 16 hours. After returning to 20° C., filtration and washing of the catalyst, evaporation is carried out under reduced pressure and the solid obtained is then recrystallized from methanol (100 ml) and drying is carried out under reduced pressure at constant weight. Perhydropyrrolo[3,4-c]pyrrole-1,3-dione, (3.6 g) is isolated, the characteristics of which are as follows:

Melting point: 222° C. (Köfler bench)

b) 5-Benzyl-tetrahydro-pyrrolo[3,4-c]pyrrole-1,3-dione is prepared in the following way:

A suspension of 2-acetyl-5-benzyltetrahydropyrrolo[3,4-c]pyrrole-1,3-dione, (107.7 g; 395 mmol) in ethanol is placed in a 1000 ml round-bottomed flask and the suspension is warmed while at the same time adding a 4N aqueous sodium hydroxide solution (200 ml). The reaction mixture is agitated for 30 minutes and then evaporated under reduced pressure. The evaporation residue is taken up in a mixture of water (100 ml) and ethyl acetate (300 ml), which is acidified to pH 4 by adding 4N aqueous hydrochloric acid (100 ml). After separation by settling out and extraction with ethyl acetate (2×200 ml), the organic extracts are combined, washed with brine (100 ml), dried over magnesium sulfate, filtered, and evaporated under reduced pressure. The evaporation residue is crystallized from ethanol (100 ml) and then 7.5 g of the solid obtained are recrystallized from acetonitrile (25 ml). The solid obtained is filtered off, washed with acetonitrile (5 ml) and then dried under reduced pressure at constant weight. 5-Benzyltetrahydropyrrolo[3,4-c]pyrrole-1,3-dione (5.8 g) is isolated, the characteristics of which are as follows:

Melting point: 158° C. (Köfler bench).

c) 2-Acetyl-5-benzyltetrahydropyrrolo[3,4-c]pyrrole-1,3-dione is prepared in the following way:

A mixture of N-acetylmaleimide (64 g; 460 mmol) and n-butoxymethyl-n-trimethylsilylmethylbenzylamine (128 g; 460 mmol) in dichloromethane (1000 ml) is placed in a 2000 ml three-necked flask and the reaction mixture is then cooled to 10° C. Trifluoroacetic acid (0.5 cm$^3$) is run in while maintaining effective agitation. The temperature of the reaction mixture increases to 38° C. over 15 minutes. Potassium carbonate (100 g) is added and the reaction mixture is agitated at 20° C. for 48 hours. The solid is removed by filtration and the filtrate is then evaporated under reduced pressure. The oil obtained is purified by chromatography on silica gel (silica, 40-63 µm, eluent: 65/35 v/v cyclohexane/ethyl acetate). The fractions containing the expected compound are combined and then evaporated under reduced pressure, giving 2-acetyl-5-benzyltetrahydropyrrolo[3,4-c]pyrrole-1,3-dione, (107.7 g; 86%), in the form of a brown oil which is used directly in the following step.

d) N-acetyl maleimide is prepared in the following way:

A solution of maleimide (68 g; 700 mmol) in acetic anhydride (500 ml) is placed in a 1000 ml three-necked flask and the reaction mixture is then brought to reflux for 3 hours. After returning to 20° C., the reaction mixture is evaporated under reduced pressure, resulting in an oil, which is crystallized from ethyl acetate (100 ml). After filtering-off the solid and washing with ethyl acetate (25 ml) and diisopropyl ether (100 ml), and drying under reduced pressure at constant weight, N-acetylmaleimide (64.1 g; 65.8%) is isolated, the characteristics of which are as follows:

Melting point: 58° C. (Köfler bench)

Preparation of cis-perhydropyrrolo[3,4-c]pyrrole-1-one (example 128)

a) Hexahydropyrrolo[3,4-c]pyrrole-1-one is prepared in the following way:

A solution of 5-benzylhexahydropyrrolo[3,4-c]pyrrole-1-one, (7.2 g; 33 mmol) in absolute ethanol (100 ml) is placed in a 250 ml autoclave and palladium-on-charcoal at 5% (1.5 g) is then added. After having purged with nitrogen, the autoclave is placed under 5-6 bar of hydrogen at 70° C. for 16 hours. After returning to 20° C., the catalyst is filtered off and the filtrate is evaporated under reduced pressure. The compound obtained is taken up in acetonitrile (15 ml) at reflux, filtered, under hot conditions, through paper and then crystallized. After crystallization, the solid obtained is filtered off, washed with acetonitrile (3 ml) and then with diethyl ether (20 ml) and, finally, dried under reduced pressure at constant weight. Hexahydropyrrolo[3,4-c]pyrrole-1-one, (1.3 g; 31%) is isolated, the characteristics of which are as follows:

Melting point: 145° C. (Köfler bench)

b) 5-Benzylhexahydropyrrolo[3,4-c]pyrrole-1-one is prepared in the following way:

5-Benzyl-3-hydroxyhexahydropyrrolo[3,4-c]pyrrole-1-one, (7 g; 30 mmol) in suspension in dichloromethane (50 ml) is placed in a 1000 ml three-necked flask and is then cooled in an ice bath. Trimethylsilane (7.1 g; 60 mmol) is run in slowly at 3° C. The reaction mixture is homogeneous and is left to react at 25° C. for 10 minutes, and is then cooled to 3° C. in order to run in trifluoro-acetic acid (50 ml). The reaction mixture is agitated at 20° C. for 16 hours and then evaporated under reduced pressure. The residue is taken up in a mixture of ethyl acetate (100 ml) and 4 N aqueous sodium peroxide (50 ml), separated by settling out and washed with water (100 ml). After drying over magnesium sulfate and evaporation under reduced pressure, a yellow-colored oil is isolated, which is purified by chromatography on silica gel (silica: 40-63 µm eluent: 90/10 ethyl acetate/methanol). The fractions containing the expected compound are combined and then evaporated under reduced pressure, giving 5-benzyl-hexahydropyrrolo[3,4-c]pyrrole-1-one, (7.2 g) which is used directly in the following step.

c) 5-Benzyl-3-hydroxyhexahydropyrrolo[3,4-c]pyrrole-1-one is prepared in the following way:

A solution of 5-benzyltetrahydropyrrolo[3,4-c]pyrrole-1,3-dione, (12.7 g; 55 mmol) {preparation described for the preparation of cis-perhydropyrrolo[3,4-c]pyrrole-1,3-dione (b)} is added to a suspension of lithium aluminum tetrahydride (2 g; 55 mmol) in tetrahydrofuran, cooled to 3° C. in an ice bath, in a 500 ml three-necked flask. The reaction mixture is agitated at this temperature for 25 minutes and then water (2 ml), 4 N aqueous sodium hydroxide (2 ml) and water (6 ml) are successively added. The solid thus formed is removed by filtration; the filtrate is dried over magnesium sulfate and then evaporated under reduced pressure, resulting in a white solid which is triturated in diisopropyl ether (50 ml). The solid formed is filtered off, washed with diisopropyl ether (25 ml), and then dried under reduced pressure at constant weight. 5-Benzyl-3-hydroxyhexahydropyrrolo[3,4-c]pyrrol-1-one (7 g; 55%) is isolated, the characteristics of which are as follows:

Melting point: 138° C. (Köfler bench).

EXAMPLE 137

Preparation (3aR,6aS)-2-phenyltetrahydropyrrolo[3,4-c]pyrrole-1,3-dione hydrochloride a) (3aR,6aS)-2-phenyltetrahydropyrrolo[3,4-c]pyrrole-1,3-dione hydrochloride is prepared in the following way:

A suspension of 2-phenyltetrahydropyrrolo[3,4-c]pyrrole-1,3-dione (8 g; 37 mmol) in ethanol (80 ml) is placed in a 250 ml three-necked flask and the reaction mixture is then brought to 70° C. The solution thus obtained is treated under hot conditions with 4.9 N hydrochloric ethanol (37 mmol) and then left to return to 20° C. The solid formed is filtered off, washed with ethanol (10 ml) and then with diethyl ether (25 ml), and dried under reduced pressure at constant weight. 2-Phenyltetrahydropyrrolo[3,4-c]pyrrole-1,3-dione hydrochloride (6.85 g; 73.1%) is isolated, the characteristics of which are as follows:

Melting point: 250° C. (Köfler bench)

b) 2-Phenyltetrahydropyrrolo[3,4-c]pyrrole-1,3-dione is prepared in the following way:

A solution of 5-benzyl-2-phenyltetrahydropyrrolo[3,4-c]pyrrole-1,3-dione, freed of its hydrochloride beforehand by treatment with 4 N sodium hydroxide (93.2 g; 304 mmol), in absolute ethanol (1200 ml) is placed in a 5000 ml autoclave and palladium-on-charcoal at 5% (11 g) is then added. After having purged with nitrogen, the autoclave is placed under 64 bar of hydrogen at 70° C. for 12 hours. After returning to 20° C., the catalyst is filtered off and the filtrate is evaporated under reduced pressure. The compound obtained is triturated in diisopropyl ether (500 ml) and the solid obtained is filtered off, washed with diisopropyl ether and, finally, dried under reduced pressure at constant weight. 2-Phenyltetrahydropyrrolo[3,4-c]pyrrole-1,3-dione, (6.6 g; 92%) is isolated, the characteristics of which are as follows:

Melting point: 128° C. (Köfler bench)

c) 5-benzyl-2-phenyltetrahydropyrrolo[3,4-c]pyrrole-1,3-dione is prepared in the following way:

A mixture of phenylmaleimide (77.85 g; 450 mmol) and n-(buthoxymethyl)-n-(trimethylsilylmethyl)benzylamine (180 g; 450 mmol) in dichloromethane (1000 ml) is placed in a 2000 ml three-necked flask and then trifluoroacetic acid (0.1 ml) is run in while maintaining effective agitation. The temperature of the reaction mixture increases to 36° C. during the 2 hours of reaction, and then potassium carbonate (100 g) is added and the reaction mixture is agitated for 15 minutes at 20° C. The solid is removed by filtration and the filtrate is then evaporated under reduced pressure. The oil obtained is dissolved in acetone (2000 ml) and then treated with 4.9 N hydrochloric ethanol (490 mmol) and agitated at 20° C. for 16 hours. The solid formed is filtered off, washed with acetone (150 ml) and with diethyl ether (250 ml), and dried under reduced pressure at constant weight. 5-Benzyl-2-phenyltetrahydropyrrolo[3,4-c]pyrrole-1,3-dione hydrochloride (129 g) is isolated and is used directly in the following step.

EXAMPLE 138

Preparation of (3aR,6aS)-2-benzyltetrahydropyrrolo [3,4-c]pyrrole-1,3-dione hydrochloride a) (3aR,6aS)-2-Benzyltetrahydropyrrolo[3,4-c]pyrrole-1, 3-dione hydrochloride is prepared in the following way:

A solution of 2,5-dibenzyltetrahydropyrrolo[3,4-c]pyrrole-1,3-dione (253 g; 790 mmol) in ethanol (2000 ml) is placed in a 5000 ml autoclave and palladium-on-activated charcoal at 5% (2 g; 0.9 mmol) is then added. After having purged the reactor with nitrogen, the autoclave is placed under 59 bar of hydrogen at 70° C. for 16 hours. After returning to 20° C., and filtering off and washing the catalyst, the reaction mixture is concentrated down to 2000 ml, under reduced pressure, and 9.6 N hydrochloric ethanol (90 ml) is then added. The crystallized solid obtained is filtered off, then washed with ethanol (100 ml) and with diethyl ether (250 ml) and, finally, dried under reduced pressure at constant weight. 2-Benzyltetrahydropyrrolo[3,4-c]pyrrole-1,3-dione hydrochloride (3.6 g) is isolated, the characteristics of which are as follows:

Melting point: 240° C. (Köfler bench)

b) 2,5-Dibenzyltetrahydropyrrolo[3,4-c]pyrrole-1,3-dione is prepared in the following way:

A mixture of benzyl maleimide (70.4 g; 376 mmol) and n-(butoxymethyl)-n-(trimethylsilylmethyl)benzylamine (105 g; 376 mmol) in dichloromethane (1000 ml) is placed in a 2000 ml three-necked flask, and trifluoroacetic acid (1 ml) is then run in while maintaining effective agitation. The temperature of the reaction mixture increases to 33° C. over one hour of reaction, then potassium carbonate (50 g) is added and the reaction mixture is agitated for 10 minutes at 20° C. The solid is removed by filtration, and the filtrate is then evaporated under reduced pressure. The oil obtained is taken up in diisopropyl ether (500 ml) and then triturated until crystallization occurs. The solid formed is filtered off, washed with diisopropyl ether (50 ml) and dried under reduced pressure at constant weight. 2,5-Dibenzyltetrahydropyrrolo[3,4-c]pyrrole-1,3-dione (70 g; 58%) is isolated, the characteristics of which are as follows:

Melting point: 100° C. (Köfler bench)

0.25 ml of solution A (50 µmol per reactor), 0.25 ml of solution B, each amine solution in the table above, 0.25 ml of solution C and 0.035 ml of triethylamine are successively distributed into a set of reactors suitable for parallel synthesis. The reactors are closed and then agitated and heated at 88° C. for 4 hours 30 minutes. After returning to ambient temperature, the reactors are agitated for 48 hours. The content of each reactor is filtered and then each filtrate is adsorbed onto a solid-phase extraction cartridge (2 g of SCX phase per cartridge at 0.8 mmol/g, prior wetting with methanol: 5 volumes; first elution: 5 volumes methanol) and then desorbed with a second elution of 5 volumes of methanol/ammonia, 2M. After evaporation of the ammoniacal methanol, the compounds are diluted in 1 ml of dimethyl sulfoxide and purified by reverse-phase liquid chromatography mass spectrometry (method C). The fractions containing the expected compounds are evaporated, weighed, diluted to 10 mM in dimethyl sulfoxide and analyzed by reverse-phase liquid chromatography mass spectrometry.

1. The compounds thus purified are characterized by virtue of their retention time and their molecular peak. (Table below).
2. The compounds derived from the coupling of [5-methoxy-1-methyl-3-(1H-pyrrolo[2,3-b]pyridin-2-yl)-1H-indol-6-yloxy]acetic acid (prepared as in example 88) and the precursors mentioned in lines 16, 17, 18 and 19 of the table above are subjected to a further cycle of purification by reverse-phase liquid chromatography mass spectrometry (method D). The fractions containing the expected compounds are evaporated, weighed, diluted to 10 mM in dimethyl sulfoxide and then analyzed by reverse-phase liquid chromatography mass spectrometry. The purified compounds are characterized by virtue of their retention time and their molecular peak (table below).
3. The compounds derived from the coupling of [5-methoxy-1-methyl-3-(1H-pyrrolo[2,3-b]pyridin-2-yl)-1H-indol-6-yloxy]acetic acid and the precursors mentioned on lines 21, 22, 23, 24, 25, 26, 27, 28, 29, 30, 31 and 35 are subjected to a further cycle of purification by reverse-phase liquid chromatography mass spectrometry (method D). The fractions containing the expected compounds are evaporated, weighed, diluted to 10 mM and analyzed by reverse-phase liquid chromatography mass spectrometry. The purified compounds are characterized by virtue of their retention time and their molecular peak (table below).
4. The compounds derived from the coupling of [5-methoxy-1-methyl-3-(1H-pyrrolo[2,3-b]pyridin-2-yl)-1H-indol-6-yloxy]acetic acid and the precursors mentioned in lines 29 and 30 are subjected to a further cycle of purification by reverse-phase liquid chromatography mass spectrometry (method D). The fractions containing the expected compounds are evaporated, weighed, diluted to 10 mM and analyzed by reverse-phase liquid chromatography mass spectrometry. The purified compounds are characterized by virtue of their retention time and their molecular peak (table below).

EXAMPLE 139

4-{2-[5-Methoxy-1-methyl-3-(1H-pyrrolo[2,3-b] pyridin-2-yl)-1H-indol-6-yloxy]acetylamino}-1-benzopyran-8-carboxylic acid The methyl ester of 4-{2-[5-methoxy-1-methyl-3-(1H-pyrrolo[2,3-b]pyridin-2-yl)-1H-indol-6-yloxy]-acetylamino}-1-benzopyran-8-carboxylic acid derived from the coupling of [5-methoxy-1-methyl-3-(1H-pyrrolo[2,3-b]pyridin-2-yl)-1H-indol-6-yloxy]acetic acid (obtained as described in example 88) with the precursor mentioned in line 31 of the table above is dissolved in 1 ml of a methanolic potassium hydroxide solution (0.1 g of potassium per ml of methanol) and then agitated at ambient temperature for 16 hours. After evaporation, the compound is diluted in a mixture of dimethyl sulfoxide (0.75 ml) and 12N aqueous hydrochloric acid (0.25 ml). The solution obtained is filtered and purified by reverse-phase liquid chromatography mass spectrometry (method F). 4-{2-[5-Methoxy-1-methyl-3-(1H-pyrrolo[2,3-b]pyridin-2-yl)-1H-indol-6-yloxy]acetylamino}-1-benzopyran-8-carboxylic acid (0.0016 g, 30%) is isolated, the characteristics of which are as follows:

LC/MS analysis: tr=3.5 min, m/z=526.88 [M+H$^+$)

| Example | Name (parent) | EF | MW (g/mol) | RT (min) | m/z | % | trace |
|---|---|---|---|---|---|---|---|
| 109 | 2-[5-Methoxy-1-methyl-3-(1H-pyrrolo[2,3-b]pyridin-2-yl)-1H-indol-6-yloxy]-1-morpholin-4-ylethanone | C23H24N4O4 | 420.47 | 2.50 | 421.74 | 80 | DAD |
| 110 | 1-[4-(2-Hydroxyethyl-piperazin-1-yl]-2-[5-methoxy-1-methyl-3-(1H-pyrrolo[2,3-b]pyridin-2-yl)-1H-indol-6-yloxy]ethanone | C25H29N5O4 | 463.54 | 2.31 | 464.34 | 63 | DAD |
| 111 | N-(2-Dimethylaminoethyl)-2-[5-methoxy-1-methyl-3-(1H-4lambda-4-pyrrolo[2,3-b]pyridin-2-yl)-1H-indol-6-yloxy]acetamide | C23H27N5O3 | 421.50 | 2.69 | 422.32 | 100 | DAD |
| 112 | N,N-Diethyl-2-[5-methoxy-1-methyl-3-(1H-pyrrolo[2,3-b]pyridin-2-yl)-1H-indol-6-yloxy]acetamide | C23H26N4O3 | 406.49 | 3.01 | 407.31 | 100 | DAD |
| 113 | 1-(3-Hydroxy-piperidin-1-yl)-2-[5-methoxy-1-methyl-3-(1H-pyrrolo-[2,3-b]pyridin-2-yl)-1H-indol-6-yl-oxy]ethanone | C24H26N4O4 | 434.50 | 2.58 | 435.30 | 84 | DAD |
| 114 | N-(2-Dimethylaminoethyl)-2-[5-methoxy-1-methyl-3-(1H-pyrrolo-[2,3-b]pyridin-2-yl)-1H-indol-6-yl-oxy]-N-methylacetamide | C24H29N5O3 | 435.53 | 2.24 | 436.35 | 97 | DAD |
| 115 | 1-(4-Cyclohexylpiperazin-1-yl)-2-[5-methoxy-1-methyl-3-(1H-pyrrolo-[2,3-b]pyridin-2-yl)-1H-indol-6-yl-oxy]ethanone | C29H35N5O3 | 501.63 | 2.43 | 502.39 | 98 | DAD |
| 116 | 2-[5-Methoxy-1-methyl-3-(1H-pyrrolo[2,3-b]pyridin-2-yl)-1H-indol-6-yloxy]-1-(4-methyl-[1,4]diazepan-1-yl)ethanone | C25H29N5O3 | 447.54 | 2.33 | 448.35 | 97 | DAD |
| 117 | 2-[5-Methoxy-1-methyl-3-(1H-pyrrolo[2,3-b]pyridin-2-yl)-1H-indol-6-yloxy]-N-[4-(4-methylpiperazin-1-yl)-phenyl]acetamide | C30H32N6O3 | 524.62 | 2.94 | 525.38 | 100 | DAD |
| 118 | 5-{2-[5-Methoxy-1-methyl-3-(1H-pyrrolo[2,3-b]pyridin-2-yl)-1H-indol-6-yloxy]acetyl}tetrahydro-pyrrolo-[3,4-c]pyrrole-1,3-dione | C25H23N5O5 | 473.49 | 2.58 | 474.29 | 98 | DAD |
| 119 | 2-[5-Methoxy-1-methyl-3-(1H-pyrrolo[2,3-b]pyridin-2-yl)-1H-indol-6-yloxy]-N-methyl-N-(2-pyridin-2-yl-ethyl)acetamide | C27H27N5O3 | 469.54 | 2.53 | 470.45 | 84 | DAD |
| 120 | 2-[5-Methoxy-1-methyl-3-(1H-pyrrolo[2,3-b]pyridin-2-yl)-1H-indol-6-yloxy]-1-(4-methylpiperazin-1-yl)-ethanone | C24H27N5O3 | 433.51 | 2.46 | 435.42 | 97 | DAD |
| 121 | 1-[4-(Furan-2-carbonyl)piperazin-1-yl]-2-[5-methoxy-1-methyl-3-(1H-pyrrolo[2,3-b]pyridin-2-yl)-1H-indol-6-yloxy]ethanone | C28H27N5O5 | 513.55 | 2.89 | 514.41 | 87 | DAD |
| 122 | N-(1-{2-[5-Methoxy-1-methyl-3-(1H-pyrrolo[2,3-b]pyridin-2-yl)-1H-indol-6-yloxy]acetyl}pyrrolidin-3-yl)-N-methylacetamide | C26H29N5O4 | 475.55 | 2.67 | 476.44 | 78 | DAD |
| 123 | 1-{4-[2-(2-Hydroxyethoxy)ethyl]-piperazin-1-yl}-2-[5-methoxy-1-methyl-3-(1H-pyrrolo[2,3-b]pyridin-2-yl)-1H-indol-6-yloxy]ethanone | C27H33N5O5 | 507.59 | 2.45 | 508.46 | 96 | DAD |
| 124 | 1-[4-(2-Hydroxyethyl)piperidin-1-yl]-2-[5-methoxy-1-methyl-3-(1H-pyrrolo[2,3-b]pyridin-2-yl)-1H-indol-6-yloxy]ethanone | C26H30N4O4 | 462.55 | 2.76 | 463.45 | 100 | DAD |
| 125 | 2-[5-Methoxy-1-methyl-3-(1H-pyrrolo[2,3-b]pyridin-2-yl)-1H-indol-6-yloxy]-N-pyridin-3-ylmethylacetamide | C25H23N5O3 | 441.49 | 2.50 | 442.41 | 100 | DAD |
| 126 | N-(2,3-Dihydroxypropyl)-2-[5-methoxy-1-methyl-3-(1H-pyrrolo[2,3-b]pyridin-2-yl)-1H-indol-6-yloxy]-N-methylacetamide | C23H26N4O5 | 438.48 | 2.53 | 439.41 | 100 | DAD |
| 127 | N-(2-Methoxyethyl)-2-[5-methoxy-1-methyl-3-(1H-pyrrolo[2,3-b]pyridin-2-yl)-1H-indol-6-yloxy]-N-methylacetamide | C23H26N4O4 | 422.48 | 2.83 | 423.42 | 100 | DAD |
| 128 | (3aS,6aS)-5-{2-[5-Methoxy-1-methyl-3-(1H-pyrrolo[2,3-b]pyridin-2-yl)-1H-indol-6-yloxy]acetyl}hexa- | C25H25N5O4 | 459.19 | 2.55 | 460.08 | 90 | DAD |

| Example | Name (parent) | EF | MW (g/mol) | RT (min) | m/z | % | trace |
|---|---|---|---|---|---|---|---|
| | hydropyrrolo[3,4-c]pyrrol-1-one trifluoroacetate | | | | | | |
| 129 | N-(2-Hydroxyethyl)-2-[5-methoxy-1-methyl-3-(1H-pyrrolo[2,3-b]pyridin-2-yl)-1H-indol-6-yloxy]-N-methylacetamide trifluoroacetate | C22H24N4O4 | 408.18 | 2.59 | 409.06 | 89 | DAD |
| 130 | N,N-Bis-(2-hydroxyethyl)-2-[5-methoxy-1-methyl-3-(1H-pyrrolo-[2,3-b]pyridin-2-yl)-1H-indol-6-yl-oxy]acetamide trifluoroacetate | C23H26N4O5 | 438.19 | 2.50 | 439.21 | 87 | DAD |
| 131 | N-(2-Dimethylaminoethyl)-N-ethyl-2-[5-methoxy-1-methyl-3-(1H-pyrrolo[2,3-b]pyridin-2-yl)-1H-indol-6-yloxy]acetamide trifluoroacetate | C25H31N5O3 | 449.24 | 2.54 | 450.08 | 98 | DAD |
| 132 | 1-(4-Benzyl-4-hydroxypiperidin-1-yl)-2-[5-methoxy-1-methyl-3-(1H-pyrrolo[2,3-b]pyridin-2-yl)-1H-indol-6-yloxy]ethanone trifluoroacetate | C31H32N4O4 | 524.24 | 3.14 | 525.83 | 100 | DAD |
| 133 | N-Ethyl-2-[5-methoxy-1-methyl-3-(1H-pyrrolo[2,3-b]pyridin-2-yl)-1H-indol-6-yloxy]-N-pyridin-4-ylmethylacetamide trifluoroacetate | C27H27N5O3 | 469.21 | 2.56 | 470.07 | 100 | DAD |
| 134 | N,N-Bis-(2-methoxyethyl)-2-[5-methoxy-1-methyl-3-(1H-pyrrolo-[2,3-b]pyridin-2-yl)-1H-indol-6-yl-oxy]acetamide trifluoroacetate | C25H30N4O5 | 466.22 | 2.93 | 467.39 | 100 | DAD |
| 135 | N,N-Bis-(2-diethylaminoethyl)-2-[5-methoxy-1-methyl-3-(1H-pyrrolo-[2,3-b]pyridin-2-yl)-1H-indol-6-yl-oxy]acetamide trifluoroacetate | C31H44N6O3 | 548.35 | 2.43 | 549.02 | 90 | DAD |
| 136 | 4-({2-[5-Methoxy-1-methyl-3-(1H-pyrrolo[2,3-b]pyridin-2-yl)-1H-indol-6-yloxy]acetylamino}methyl)-benzoic acid methyl ester | C28H26N4O5 | 498.54 | 3.80 | 499.74 | 89 | DAD |
| 137 | (3aR,6aS)-5-{2-[5-Methoxy-1-methyl-3-(1H-pyrrolo[2,3-b]pyridin-2-yl)-1H-indol-6-yloxy-acetyl}-2-phenyltetrahydropyrrolo[3,4-c]-pyrrole-1,3-dione | C31H27N5O5 | 549.58 | 3.70 | 550.81 | 100 | DAD |
| 138 | (3aR,6aS)-2-Benzyl-5-{2-[5-methoxy-1-methyl-3-(1H-pyrrolo-[2,3-b]pyridin-2-yl)-1H-indol-6-yl-oxy]acetyl}tetrahydropyrrolo[3,4-c]-pyrrole-1,3-dione | C32H29N5O5 | 563.61 | 3.80 | 564.85 | 100 | DAD |
| 139 | 4-{2-[5-Methoxy-1-methyl-3-(1H-pyrrolo[2,3-b]pyridin-2-yl)-1H-indol-6-yloxy]acetylamino}-1-benzopyran-8-carboxylic acid | C29H26N4O6 | 526.18 | 3.50 | 526.88 | 100 | DAD |
| 140 | 2-[5-Methoxy-1-methyl-3-(1H-pyrrolo[2,3-b]pyridin-2-yl)-1H-indol-6-yloxy]-N-pyridin-2-ylacetamide | C24H21N5O3 | 427.20 | 2.87 | 428.13 | 86 | DAD |
| 141 | 2-[5-Methoxy-1-methyl-3-(1H-pyrrolo[2,3-b]pyridin-2-yl)-1H-indol-6-yloxy]-N-pyridin-4-ylacetamide | C24H21N5O3 | 427.50 | 2.52 | 428.63 | 100 | DAD |
| 142 | 2-[5-Methoxy-1-methyl-3-(1H-pyrrolo[2,3-b]pyridin-2-yl)-1H-indol-6-yloxy]-N-(4-piperidin-1-yl-phenyl)-acetamide | C30H31N5O3 | 509.61 | 2.68 | 510.75 | 100 | DAD |
| 143 | 4-({2-[5-Methoxy-1-methyl-3-(1H-pyrrolo[2,3-b]pyridin-2-yl)-1H-indol-6-yloxy]acetylamino}methyl)-benzoic acid | C27H24N4O5 | 484.51 | 3.8 | 485.34 | 85 | DAD |
| 144 | N-(3-Hydroxypyridin-2-yl)-2-[5-methoxy-1-methyl-3-(1H-pyrrolo-[2,3-b]pyridin-2-yl)-1H-indol-6-yl-oxy]acetamide | C24H21N5O4 | 443.46 | 2.68 | 444.59 | 83 | DAD |
| 145 | 2-[5-Methoxy-1-methyl-3-(1H-pyrrolo[2,3-b]pyridin-2-yl)-1H-indol-6-yloxy]-N-(3-methylpyridin-2-yl)-acetamide | C25H23N5O3 | 441.49 | 2.67 | 442.34 | 85 | DAD |
| 146 | 2-[5-Methoxy-1-methyl-3-(1H-pyrrolo[2,3-b]pyridin-2-yl)-1H-indol-6-yloxy]-N-(3-methoxyphenyl)-acetamide | C26H24N4O4 | 456.50 | 3.31 | 457.30 | 84 | DAD |

EXAMPLE 147

2-[1-Methyl-5-methoxy-6-(2-morpholin-4-yl-ethoxy)-1H-indol-3-yl]-1H-pyrrolo[2,3-b]pyridine a) 2-[1-Methyl-5-methoxy-6-(2-morpholin-4-yl-ethoxy)-1H-indol-3-yl]-1H-pyrrolo[2,3-b]pyridine is prepared by following the procedure described in example 89a, but using 0.24 g of 2-[1-methyl-5-methoxy-6-(2-morpholin-4-ylethoxy)-1H-indol-3-yl]-1-(toluene-4-sulfonyl)-1H-pyrrolo[2,3-b]pyridine and 1.93 ml of a 5N aqueous potassium hydroxide solution. 0.116 g of 2-[1-methyl-5-methoxy-6-(2-morpholin-4-ylethoxy)-1H-indol-3-yl]-1H-pyrrolo[2,3-b]pyridine is obtained, the characteristics of which are as follows:

$^1$H NMR spectrum (300 MHz, (CD$_3$)$_2$SO d6, δ in ppm): from 2.50 to 2.65 (mt: 4H); 2.76 (t, J=6 Hz: 2H); 3.60 (broad t, J=5 Hz: 4H); 3.79 (s: 3H); 3.87 (s: 3H); 4.16 (t, J=6 Hz: 2H); 6.73 (d, J=1.5 Hz: 1H); 6.99 (dd, J=8 and 5 Hz: 1H); 7.16 (s: 1H); 7.42 (s: 1H); 7.77 (s: 1H); 7.82 (broad d, J=8 Hz: 1H); 8.09 (dd, J=5 and 1.5 Hz: 1H); 11.71 (broad s: 1H).

Mass spectrum (EI): m/z=407 [M]$^+$ (base peak)

b) 2-[1-Methyl-5-methoxy-6-(2-morpholin-4-ylethoxy)-1H-indol-3-yl]-1-(toluene-4-sulfonyl)-1H-pyrrolo[2,3-b]pyridine is prepared in the following way:

0.11 g of potassium carbonate and 0.14 ml of morpholine are added to a solution of 0.24 g of 2-[1-methyl-5-methoxy-6-(2-iodoethoxy)-1H-indol-3-yl]-1-(toluene-4-sulfonyl)-1H-pyrrolo[2,3-b]pyridine in 24 ml of acetonitrile, under an inert argon atmosphere at a temperature in the region of 20° C. The reaction medium is heated at 60° C. for 24 hours. After cooling, the reaction medium is concentrated under reduced pressure. The oil obtained is taken up with 10 ml of water and 10 ml of ethyl acetate. After separation by settling out, the organic phase is dried over magnesium sulfate, filtered and then concentrated under reduced pressure. The residue obtained is purified by flash-pack chromatography (silica, 30/70 by volume ethyl acetate/cyclohexane as eluents). The fractions containing the product are concentrated under reduced pressure. 0.24 g of 2-[1-methyl-5-methoxy-6-(2-morpholin-4-ylethoxy)-1H-indol-3-yl]-1-(toluene-4-sulfonyl)-1H-pyrrolo[2,3-b]pyridine is thus obtained, the characteristics of which are as follows:

Mass spectrum (CI): m/z=561 [M+H]$^+$ (base peak)

c) 2-[1-Methyl-5-methoxy-6-(2-iodoethoxy)-1H-indol-3-yl]-1-(toluene-4-sulfonyl)-1H-pyrrolo[2,3-b]pyridine is prepared in the following way:

0.260 g of sodium iodide is added to a solution of 0.59 g of 2-[1-methyl-5-methoxy-6-(2-chloroethoxy)-1H-indol-3-yl]-1-(toluene-4-sulfonyl)-1H-pyrrolo[2,3-b]pyridine in 42 ml of 2-butanone, under an inert argon atmosphere at a temperature in the region of 20° C. The reaction medium is refluxed for 24 hours. After cooling, the reaction medium is concentrated under reduced pressure. The residue obtained is purified by flash-pack chromatography (silica, dichloromethane as eluent). The fractions containing the product are concentrated under reduced pressure. 0.565 g of 2-[1-methyl-5-methoxy-6-(2-iodoethoxy)-1H-indol-3-yl]-1-(toluene-4-sulfonyl)-1H-pyrrolo[2,3-b]pyridine is thus obtained, the characteristics of which are as follows:

Mass spectrum (EI): m/z=601 [M]$^+$, m/z=446 (base peak)

d) 2-[1-Methyl-5-methoxy-6-(2-chloroethoxy)-1H-indol-3-yl]-1-(toluene-4-sulfonyl)-1H-pyrrolo[2,3-b]pyridine is prepared in the following manner:

0.101 g of sodium hydride (at 60% in oil) is added to a solution of 0.94 g of 2-[1-methyl-5-methoxy-6-hydroxy)-1H-indol-3-yl]-1-(toluene-4-sulfonyl)-1H-pyrrolo[2,3-b]pyridine in 22 ml of dimethylformamide, under an inert argon atmosphere at a temperature in the region of 20° C. The reaction medium is agitated at this temperature for 15 minutes. 0.525 ml of 1-chloro-2-bromoethane is subsequently added. After agitating for 2 hours at the same temperature, 0.1 g of sodium hydride (at 60% in oil) and 0.525 ml of 1-chloro-2-bromoethane are again added. The reaction medium is maintained at this temperature for 20 hours, with agitation. 20 ml of water and 20 ml of ethyl acetate are added; after separation by settling out, the organic phase is dried over magnesium sulfate, filtered, and then concentrated under reduced pressure. The residue obtained is purified by flash-pack chromatography (silica, 35/65 by volume ethyl acetate/cyclohexane as eluents). The fractions containing the product are concentrated under reduced pressure. 0.596 g of 2-[1-methyl-5-methoxy-6-(2-chloroethoxy)-1H-indol-3-yl]-1-(toluene 4-sulfonyl)-1H-pyrrolo[2,3-b]pyridine is thus obtained, the characteristics of which are as follows:

Mass spectrum (EI): m/z=509 [M]$^+$, m/z=354 (base peak)

e) 2-[1-Methyl-5-methoxy-6-hydroxy)-1H-indol-3-yl]-1-(toluene-4-sulfonyl)-1H-pyrrolo[2,3-b]pyridine is prepared in the following way:

0.798 ml of iodotrimethylsilane is added to a solution of 1.2 g of 2-[1-methyl-5-methoxy-6-benzyloxy)-1H-indol-3-yl]-1-(toluene-4-sulfonyl)-1H-pyrrolo[2,3-b]pyridine in 90 ml of acetonitrile, under an inert argon atmosphere at a temperature in the region of 20° C. The reaction medium is heated at 50° C. for 4 hours. After cooling, 60 ml of water and 60 ml of ethyl acetate are added; after separation by settling out, the organic phase is dried over magnesium sulfate, filtered, and then concentrated under reduced pressure. The residue obtained is purified by flash chromatography (silica, 40/60 by volumes ethyl acetate/cyclohexane as eluents, argon). The fractions containing the product are concentrated under reduced pressure. 0.825 g of 2-[1-methyl-5-methoxy-6-hydroxy)-1H-indol-3-yl]-1-(toluene-4-sulfonyl)-1H-pyrrolo[2,3-b]pyridine is thus obtained, the characteristics of which are as follows:

Mass spectrum (EI): m/z=447 [M]$^+$, m/z=292 (base peak)

The compound 2-[1-methyl-5-methoxy-6-benzyloxy)-1H-indol-3-yl]-1-(toluene-4-sulfonyl)-1H-pyrrolo[2,3-b]pyridine is prepared according to the process described in patent WO 03000688 A1.

EXAMPLE 148

2-{1-Methyl-5-methoxy-6-[2-(4-methyl-piperazin-1-yl)ethoxy]-1H-indol-3-yl}-1H-pyrrolo[2,3-b]pyridine a) 2-{1-Methyl-5-methoxy-6-[2-(4-methylpiperazin-1-yl)-ethoxy]-1H-indol-3-yl}-1H-pyrrolo[2,3-b]pyridine is prepared by following the procedure described in example 89a, but using 0.195 g of 2-[1-methyl-5-methoxy-6-(2-(4-methylpiperazin-4-ylethoxy)-1H-indol-3-yl]-1-(toluene-4-sulfonyl)-1H-pyrrolo[2,3-b]pyridine and 1.53 ml of a 5N aqueous potassium hydroxide solution. After purification by flash-pack chromatography (silica, 90/10 by volume dichloromethane/methanol as eluents, argon), 0.086 g of 2-[1-methyl-5-methoxy-6-[2-(4-methylpiperazin-1-yl)-ethoxy]-1H-indol-3-yl]-1H-pyrrolo[2,3-b]pyridine is obtained, the characteristics of which are as follows:

$^1$H NMR spectrum (300 MHz, (CD$_3$)$_2$SO d6, δ in ppm): 2.18 (s: 3H); 2.37 (unresolved peak: 4H) from 2.50 to 2.65 (mt: 4H); 2.78 (t, J=6 Hz: 2H); 3.83 (s: 3H); 3.90 (s: 3H); 4.17 (t, J=6 Hz: 2H); 6.77 (d, J=2 Hz: 1H); 7.03 (dd, J=8 and 5 Hz:

1H); 7.20 (s: 1H); 7.46 (s: 1H); 7.80 (s: 1H); 7.86 (broad dd, J=8 and 1.5 Hz: 1H); 8.13 (dd, J=5 and 1.5 Hz: 1H); 11.75 (broad s: 1H).

Mass spectrum (EI): m/z=419 [M]$^+$, m/z=127 (base peak)

b) 2-[1-Methyl-5-methoxy-6-(2-(4-methylpiperazin-4-yl-ethoxy)-1H-indol-3-yl]-1-(toluene-4-sulfonyl)-1H-pyrrolo [2,3-b]pyridine is prepared by following the procedure described in example 147b but using 0.1 ml of N-methylpiperazine and 0.27 g of 2-[1-methyl-5-methoxy-6-(2-iodoethoxy)-1H-indol-3-yl]-1-(toluene-4-sulfonyl)-1H-pyrrolo[2, 3-b]pyridine. After purification by flash-pack chromatography (silica, 90/10 by volume dichloromethane/methanol as eluents, argon), 0.197 g of 2-[1-methyl-5 methoxy-6-(2-(4-methylpiperazin-4-yl-ethoxy)-1H-indol-3-yl]-1-(toluene-4-sulfonyl)-1H-pyrrolo[2,3-b]pyridine is obtained, the characteristics of which are as follows:

Mass spectrum (EI): m/z=573 [M]$^+$, m/z=127 (base peak)

EXAMPLE 149

1-{2-[1-Methyl-5-methoxy-3-(1H-pyrrolo[2,3-b] pyridin-2-yl)-1H-indol-6-yloxy]ethyl}piperidin-4-ol a) 1-{2-[1-Methyl-5-methoxy-3-(1H-pyrrolo[2,3-b]pyridin-2-yl)-1H-indol 6-yloxy]ethyl}piperidin-4-ol is prepared by following the procedure described in example 89a, but using 0.23 g of 1-{2-[1-methyl-5-methoxy-3-(1-(toluene-4-sulfonyl)-1H-pyrrolo[2,3-b]pyridin-2-yl)-1H-indol-6-yloxy]ethyl}piperidin-4-ol and 1.8 ml of a 5N aqueous potassium hydroxide solution. After purification by flash-pack chromatography (silica, 90/10 by volume dichloromethane/methanol as eluents, argon), 0.017 g of 1-{2-[5-1-methyl-methoxy-3-(1H-pyrrolo[2,3-b]pyridin-2-yl)-1H-indol-6-yloxy]ethyl}piperidin-4-ol is obtained, the characteristics of which are as follows:

$^1$H NMR spectrum (300 MHz, (CD$_3$)$_2$SO d6, δ in ppm): 1.41 (mt: 2H); 1.72 (very broad d, J=12 Hz: 2H); 2.16 (broad t, J=11 Hz: 2H); 2.73 (t, J=6 Hz: 2H); 2.84 (mt: 2H); 3.45 (mt: 1H); 3.81 (s: 3H); 3.88 (s: 3H); 4.13 (t, J=6 Hz: 2H); 4.55 (d, J=4 Hz: 1H); 6.75 (broad d, J=2 Hz: 1H); 7.00 (dd, J=8 and 5 Hz: 1H); 7.16 (s: 1H); 7.42 (s: 1H); 7.77 (s: 1H); 7.84 (broad d, J=8 Hz: 1H); 8.12 (broad dd, J=5 and 1.5 Hz: 1H); 11.73 (broad s: 1H).

Mass spectrum (EI): m/z=420 [M]$^+$, m/z=128 (base peak)

b) 1-{2-[1-methyl-5-methoxy-3-(1-(toluene-4-sulfonyl)-1H-pyrrolo[2,3-b]pyridin-2-yl)-1H-indol-6-yloxy]
ethyl}piperidin-4-ol is prepared by following the procedure described in example 147b, but using 0.089 g of 4-hydroxypiperidine and 0.265 g of 2-[1-methyl-5-methoxy-6-(2-iodoethoxy)-1H-indol-3-yl]-1-(toluene-4-sulfonyl)-1H-pyrrolo[2,3-b]pyridine. After purification by flash-pack chromatography (silica, 90/10 by volume dichloromethane/methanol as eluents, argon), 0.234 g of 1-{2-[1-methyl-5 methoxy-3-(1-(toluene-4-sulfonyl)-1H-pyrrolo[2,3-b]pyridin-2-yl)-1H-indol-6-yloxy]ethyl}piperidin-4-ol is obtained, the characteristics of which are as follows:

Mass Spectrum (CI): m/z=575 [M+H]$^+$ (base peak).

EXAMPLES 150 TO 159 a) 2-[6-(2-Iodoethoxy)-5-methoxy-1-methyl-1H-indol-3-yl]-1-(toluene-4-sulfonyl)-1H-pyrrolo[2,3-b]pyridine is prepared in the following way:

A solution of 2-[6-(2-chloroethoxy)-5-methoxy-1-methyl-1H-indol-3-yl]-1-(toluene-4-sulfonyl)-1H-pyrrolo[2,3-b]pyridine (0.660 g, 1,294 μmol) in methyl ethyl ketone (10 ml) is placed in a 50 ml single-necked flask and sodium iodide (0.29 g; 1.941 mmol) is then added. The reaction mixture is refluxed for 16 hours. Analysis by thin layer chromatography (50/50 cyclohexane/ethyl acetate) shows that the reaction has come to an end. After returning to 20° C., the reaction mixture is evaporated under reduced pressure and the residue is taken up in a mixture of water (50 ml) and dichloromethane (50 ml), which is separated by settling out; the organic extract is washed with water (30 ml) and dried over magnesium sulfate. After evaporation, the compound obtained is purified by chromatography on silica gel (cartridge FC-10-Si-BP-Sup, 10 g of silica with a particle size of 15-35 μm, elution being carried out with a 70/30 mixture of cyclohexane/ethyl acetate). The fractions containing the expected: compound are combined and then evaporated under reduced pressure, giving 2-[6-(2-iodoethoxy)-5-methoxy-1-methyl-1H-indol-3-yl]-1-(toluene-4-sulfonyl)-1H-pyrrolo[2,3-b]pyridine (0.695 g; 89%) the characteristics of which are as follows:

LC/MS analysis: tr=4.0, m/z=601.96 [M+H]$^+$ b) 2-[6-(2-Chloroethoxy)-5-methoxy-1-methyl-1H-indol-3-yl]-1-(toluene-4-sulfonyl)-1H-pyrrolo[2,3-b]pyridine is prepared in the following way:

A solution of 5-methoxy-1-methyl-3-[1-(toluene-4-sulfonyl)-1H-pyrrolo[2,3-b]pyridin-2-yl]-1H-indol-6-ol (0.8 g; 1.788 mmol) in solution in dimethylformamide (5 ml) is placed in a 50 ml round-bottomed flask rendered inert with argon, and sodium hydride (0.064 g; 2.146 mmol) is then added. The reaction mixture becomes brown in color and 1-bromo-2-chloroethane (0.308 g; 2.146 mmol) is added. The reaction mixture is agitated for 1 hour 30 minutes at 20° C. and then sodium hydride (0.064 g; 2.146 mmol) and 1-bromo-2-chloroethane (2×0.5 ml) are again added. Analysis by thin layer chromatography (50/50 cyclohexane/ethyl acetate) shows that the reaction has come to an end. The reaction mixture is diluted with water (150 ml) and ethyl acetate (50 ml), and extracted with ethyl acetate (2×50 ml). The organic extracts are combined, dried over magnesium sulfate, filtered, and evaporated under reduced pressure, resulting in the crude compound, which is purified by chromatography on silica gel (AIT cartridge FC 25 Si-BP-Sup, eluent: 65/35 cyclohexane/ethyl acetate at 10 ml/min). The fractions containing the expected compound are combined and then evaporated under reduced pressure, giving the expected 2-[6-(2-chloroethoxy)-5-methoxy-1-methyl-1H-indol-3-yl]-1-(toluene-4-sulfonyl)-1H-pyrrolo[2,3-b]pyridine (0.66 g; 72%) in the form of a powder, the characteristics of which are as follows:

$^1$H NMR spectrum (300 MHz, (CD$_3$)$_2$SO d6, δ in ppm): 2.30 (s: 3H); 3.75 (s: 3H); 3.87 (s: 3H); 4.04 (broad t, J=5 Hz: 2H); 4.36 (broad t, J=5 Hz: 2H); 6.75 (s: 1H); 6.99 (s: 1H); 7.20 (s: 1H); 7.26 (broad d, J=9 Hz: 2H); 7.30 (dd, J=8 and 5 Hz: 1H); 7.54 (d, J=9 Hz: 2H); 7.59 (broad s: 1H); 7.94 (dd, J=8 and 1.5 Hz: 1H); 8.35 (dd, J=5 and 1.5 Hz: 1H).

c) Alkylation of Examples 150 to 159

Each amine in the table below is weighed and solubilized in dimethylformamide (0.5 ml), in 10 glass reactors (1.3×10 cm). 2-[6-(2-Iodoethoxy)-5-methoxy-1-methyl-1H-indol-3-yl]-1-(toluene-4-sulfonyl)-1H-pyrrolo[2,3-b]pyridine (0.05 g/reactor, 83 μmol/reactor) in dimethylformamide (0.5 ml/reactor), followed by potassium carbonate (0.035 g/reactor, 249 μmol/reactor), are added to this solution. The reactors are closed and then placed in an oil bath at 60° C. for 4 hours 30 minutes. The content of each reactor is filtered and then transferred onto a solid-phase extraction cartridge (Varian Mega BondElut-SCX, ref: 12256011, 1gr, 6 ml, Batch 1728002, UNRESOLVED PEAKG code 3102) pre-conditioned with methanol (12 ml). The solid-phase extraction cartridges are eluted with methanol (2×6 ml) and then with methanol/2M ammonia (2×6 ml). The ammonia-containing elution fractions are combined and evaporated to give the crude compounds. The crude compounds are purified by chromatography on silica gel (24 ml cartridge containing 10 g of 40-60 μm silica gel with dichloromethane), elution being carried out with a mixture of dichloromethane/methanol in varying proportions, but adapted to each case (from 97/3 to 80/20). The fractions containing the expected compounds are combined and evaporated, resulting in the corresponding intermediate compounds, which are used in the detosylation step.

After a first elution with methanol (6 ml), the cartridges are eluted with 2N ammoniacal methanol (5 ml); the ammonia-containing eluate is evaporated to dryness. The compounds thus obtained are finally purified by chromatography on silica gel (cartridges of 2 g of 40-60 μm silica gel, dichloromethane), elution being carried out with a mixture of dichloromethane and 2M ammoniacal methanol (95/5) at 5 ml/min. The fractions containing the expected compound are combined and then evaporated under reduced pressure, giving the expected compounds. Each of the compounds is solubilized in dimethylformamide (0.6 ml) and then eluted on

|  | Name | Formula | MW (g/mol) | Eq. | Weight (mg) |
|---|---|---|---|---|---|
| 150 | n-(2-hydroxyethyl)piperazine | C6H14N2O | 130.19 | 3.000 | 32.470 |
| 151 | 3-hydroxypiperidine | C5H11NO | 101.15 | 3.000 | 25.230 |
| 152 | n,n,n'-trimethylethylenediamine | C5H14N2 | 102.18 | 3.000 | 25.480 |
| 153 | 1-(2-furoyl)piperazine | C9H12N2O2 | 180.21 | 3.000 | 44.940 |
| 154 | 3-(n-acetyl-n-methylamino)pyrrolidine | C7H14N2O | 142.2 | 3.000 | 35.460 |
| 155 | 1-methylhomopiperazine | C6H14N2 | 114.19 | 3.000 | 28.480 |
| 156 | 1-hydroxyethylethoxypiperazine | C8H18N2O2 | 174.24 | 3.000 | 43.460 |
| 157 | 3-methylamino-1,2-propanediol | C4H11NO2 | 105.14 | 3.000 | 26.220 |
| 158 | 2-methoxy-n-methylethylamine | C4H11NO | 89.14 | 3.000 | 22.230 |
| 159 | 4-(4-methylpiperazino)aniline | C11H17N3 | 191.28 | 3.000 | 47.710 | d) Deprotection of Examples 150 to 159 A methanolic potassium hydroxide solution (1.5 ml per tube, 0.1 g of potassium hydroxide/ml of methanol) is added to 10 hemolysis tubes (1.3×10 cm) containing the compounds derived from the reaction described above, and the tubes are then agitated at 20° C. for 16 hours. After evaporation under reduced pressure, the residues are taken up in dimethylformamide (0.6 ml) and the solutions thus obtained are then eluted on solid-phase extraction cartridges (Varian, Mega Bond Elut, SCX, 2 g, 6 ml, Ref. 19102), pre-conditioned with methanol (2×6 ml).

solid-phase extraction cartridges (Varian, Mega Bond Elut, SCX, 0.5 g, 3 ml) pre-conditioned with methanol (2×3 ml). After a first elution with methanol (4.8 ml), the cartridges are eluted with 2N ammoniacal methanol (4.8 ml); the ammonia-containing eluate is evaporated to dryness, giving the expected compounds, which are characterized by reverse-phase liquid chromatography mass spectrometry (method A). The retention times and molecular ions are reported in the table below.

| ex | Name (parent) | EF | MW (g/mol) | RT (min) | M + H$^+$ | % | Trace |
|---|---|---|---|---|---|---|---|
| 150 | 2-(4-{2-[5-Methoxy-1-methyl-3-(1H-pyrrolo[2,3-b]pyridin-2-yl)-1H-indol-6-yloxy]ethyl}piperazin-1-yl)ethanol | C25H31N5O3 | 449.55 | 2.28 | 450.32 | 85.00 | DAD |
| 151 | 1-{2-[5-N-Methoxy-1-methyl-3-(1H-pyrrolo[2,3-b]pyridin-2-yl)-1H-indol-6-yloxy]ethyl}piperidin-3-ol | C24H28N4O3 | 420.51 | 2.40 | 421.29 | 100.00 | DAD |
| 152 | N-{2-[5-Methoxy-1-methyl-3-(1H-pyrrolo[2,3-b]pyridin-2-yl)-1H-indol-6-yloxy]ethyl}-N,N',N'-trimethylethane-1,2-diamine | C24H31N5O2 | 421.54 | 2.26 | 422.32 | 94.00 | DAD |
| 153 | Furan-2-yl-(4-{2-[5-methoxy-1-methyl-3-(1H-pyrrolo[2,3-b]-pyridin-2-yl)-1H-indol-6-yloxy]-ethyl}piperazin-1-yl)methanone | C28H29N5O4 | 499.57 | 2.56 | 500.29 | 74.00 | DAD |
| 154 | N-(1-{2-[5-Methoxy-1-methyl-3-(1H-pyrrolo[2,3-b]pyridin-2-yl)-1H-indol-6-yloxy]ethyl}-pyrrolidin-3-yl)-N-methylacetamide | C26H31N5O3 | 461.57 | 2.45 | 462.32 | 96.00 | DAD |
| 155 | 2-{5-Methoxy-1-methyl-6-[2-(4-methylperhydro-1,4-diazepin-1-yl)ethoxy]-1H-indol-3-yl}-1H pyrrolo[2,3-b]pyridine | C25H31N5O2 | 433.56 | 2.26 | 434.31 | 100.00 | DAD |
| 156 | 2-[2-(4-{2-[5-Methoxy-1-methyl-3-(1H-pyrrolo[2,3-b]pyridin-2-yl)-1H-indol-6-yloxy]-ethyl}piperazin-1-yl)ethoxy]ethanol | C27H35N5O4 | 493.61 | 2.28 | 494.33 | 97.00 | DAD |
| 157 | 3-({2-[5-Methoxy-1-methyl-3-(1H-pyrrolo[2,3-b]pyridin-2-yl)-1H- | C23H28N4O4 | 424.50 | 2.32 | 425.28 | 84.00 | DAD |

| ex | Name (parent) | EF | MW (g/mol) | RT (min) | M + H⁺ | % | Trace |
|---|---|---|---|---|---|---|---|
| | indol-6-yloxy]ethyl}methyl-amino)propane-1,2-diol | | | | | | |
| 158 | (2-Methoxyethyl)-{2-[5-methoxy-1-methyl-3-(1H-pyrrolo[2,3-b]pyridin-2-yl)-1H-indol-6-yloxy]-ethyl}methylamine | C23H28N4O3 | 408.50 | 2.47 | 409.28 | 100.00 | DAD |
| 159 | {2-[5-Methoxy-1-methyl-3-(1H-pyrrolo[2,3-b]pyridin-2-yl)-1H-indol-6-yloxy]ethyl}-[4-(4-methyl-piperazin-1-yl)phenyl]amine | C30H34N6O2 | 510.64 | 2.39 | 511.32 | 100.00 | DAD |

EXAMPLES 160 TO 164 a) 2-[6-(3-Iodopropoxy)-5-methoxy-1-methyl-1H-indol-3-yl]-1-(toluene-4-sulfonyl)-1H-pyrrolo[2,3-b]pyridine is prepared in the following way:

A solution of 2-[6-(3-chloropropoxy)-5-methoxy-1-methyl-1H-indol-3-yl]-1-(toluene-4-sulfonyl)-1H-pyrrolo[2,3-b]pyridine (0.415 g; 792 µmol) in methyl ethyl ketone (10 ml) is placed in a 50 ml single-necked flask and sodium iodide (0.178 g; 1.18 mmol) is then added. The reaction mixture is refluxed for 16 hours. Analysis by thin layer chromatography (50/50 cyclohexane/ethyl acetate) shows that the starting compound is still present. Additional sodium iodide (0.178 g; 1.18 mmol) is introduced and the reflux is maintained for 3 hours. After returning to 20° C., the precipitate is dissolved in dichloromethane (200 ml) and then washing with water (50 ml) and drying over magnesium sulfate are carried out. After evaporation, the residue is taken up in ethyl acetate (20 ml); the insoluble material is removed and the filtrate is then evaporated under reduced pressure. 2-[6-(3-Iodopropoxy)-5-methoxy-1-methyl-1H-indol-3-yl]-1-(toluene-4-sulfonyl)-1H-pyrrolo[2,3-b]pyridine (0.367 g; 75%) is isolated, the characteristics of which are as follows:

LC/MS analysis: tr=4.32 min; m/z=615.96 [M+H]⁺ b) 2-[6-(3-Chloropropoxy)-5-methoxy-1-methyl-1H-indol-3-yl]-1-(toluene-4-sulfonyl)-1H-pyrrolo[2,3-b]pyridine is prepared in the following way:

A solution of 5-methoxy-1-methyl-3-[1-(toluene-4-sulfonyl)-1H-pyrrolo[2,3-b]pyridin-2-yl]-1H-indol-6-ol (0.45 g; 1.006 mmol) in solution in dimethylformamide (5 ml) is placed in a 50 ml round-bottomed flask rendered inert with argon, and sodium hydride (0.06 g; 2.01 mmol) is then added. The reaction mixture becomes dark in color and 1-bromo-3-chloropropane (0.199 ml, 2.01 mmol) is added. The reaction mixture is agitated for 30 minutes at 20° C. The reaction mixture is diluted with dichloromethane (50 ml) and water (100 ml), separated by settling out, and extracted with dichloromethane (2×50 ml). The organic extracts are combined, dried over magnesium sulfate, filtered and evaporated under reduced pressure, resulting in an oil. The oil is taken up in diisopropyl ether (10 ml) and then triturated, discarding crystals. After filtration, washing with diisopropyl ether and drying under reduced pressure, 2-[6-(3-chloropropoxy)-5-methoxy-1-methyl-1H-indol-3-yl]-1-(toluene-4-sulfonyl)-1H-pyrrolo[2,3-b]pyridine is isolated in the form of ochre-colored crystals (0.415 g; 79%), the characteristics of which are as follows:

¹H NMR spectrum (300 MHz, (CD₃)₂SO d6, δ in ppm): 2.27 (mt: 2H); 2.30 (s: 3H); 3.75 (s: 3H); 3.87 (s: 3H); 3.89 (t, J=6.5 Hz: 2H); 4.20 (t, J=6.5 Hz: 2H); 6.74 (s: 1H); 6.97 (s: 1H); 7.19 (s: 1H); 7.26 (broad d, J=8.5 Hz: 2H); 7.29 (dd, J=8 and 5 Hz: 1H); 7.50 (s: 1H); 7.57 (d, J=8.5 Hz: 2H); 7.93 (dd, J=8 and 1.5 Hz: 1H); 8.34 (dd, J=5 and 11.5 Hz: 1H).

c) Alkylation of Examples 160 to 164

The 5 amines described in the table below are weighed and are solubilized in dimethyl formamide (0.5 ml), in five 1.2×10 cm hemolysis tubes. A solution of 2-[6-(3-iodopropoxy)-5-methoxy-1-methyl-1H-indol-3-yl]-1-(toluene-4-sulfonyl)-1H-pyrrolo[2,3-b]pyridine (81.2 µmol/tube) in dimethylformamide (0.5 ml/tube) is placed in 5 hemolysis tubes (1.2×10 cm), and the solutions of amines described below are added to said solution. Potassium carbonate (0.035 g/tube) is added using a spatula. The reactors are closed and then heated at 65° C. for 3 hours with agitation. After returning to ambient temperature, the contents of each reactor is filtered and the filtrates are purified by reverse-phase liquid chromatography mass spectrometery (2 injections per sample, method B). The fractions containing the expected compounds are combined and then evaporated under reduced pressure, giving the compounds which are used in the following step.

| ex | Name | Formula | MW | Equivalent | Weight mg |
|---|---|---|---|---|---|
| 160 | morpholine | C4H9NO | 87.12 | 3,010 | 21.300 |
| 161 | 1-methylpiperazine | C5H12N2 | 100.16 | 3,000 | 24.410 |
| 162 | 4-(4-methyl-piperazino)-aniline | C11H17N3 | 191.28 | 3,000 | 46.610 |
| 163 | 1-methyl-homopiperazine | C6H14N2 | 114.19 | 3,000 | 27.830 |
| 164 | 1-hydroxyethylethoxy-piperazine | C8H18N2O2 | 174.24 | 3,000 | 42.460 | d) Detosylation of Examples 160 to 164

A methanolic potassium hydroxide solution (1.6 ml per tube, solution at 0.1 g of potassium hydroxide per ml of methanol) is added to 5 hemolysis tubes (1.2×10 cm) containing the compounds obtained above, and the mixture is then agitated at 20° C. for 16 hours before being evaporated to dryness. The evaporation residues are taken up in a mixture of dimethylformamide (0.8 ml) and acetic acid (0.2 ml), and then purified by reverse-phase liquid chromatography mass spectrometry (method B, 2 injections per sample). The fractions containing the expected compounds are combined and then eluted on solid-phase extraction cartridges (Varian Mega BondElut-SCX cartridges, 1 gr, 6 ml) pre-conditioned with methanol (2×6 ml). After elution with methanol (2×6 ml) and then elution with 2M ammoniacal methanol (2×6 ml), the ammonia-containing eluates are combined and evaporated under reduced pressure. The dry extracts are taken up in a mixture of dichloromethane and methanol (90/10), and then filtered through silica cartridges (Thermoquest, Hypersep Silica, 0.1 g, #60300-494). The eluates are evaporated under reduced pressure, resulting in the expected compounds, which are characterized by virtue of their retention time and molecular peak.

| ex | NAME | EF | MW (g/mol) | RT (min) | M + H⁺ | Trace | % |
|---|---|---|---|---|---|---|---|
| 160 | 2-[5-Methoxy-1-methyl-6-(3-morpholin-4-yl-propoxy)-1H-indol-3-yl]-1H-pyrrolo[2,3-b]-pyridine | C24H28N4O3 | 420.51 | 2.47 | 421.32 | DAD | 96 |
| 161 | 2-{5-Methoxy-1-methyl-6-[3-(4-methylpiperazin-1-yl)-propoxy]-1H-indol-3-yl}-1H-pyrrolo[2,3-b]-pyridine | C25H31N5O2 | 433.56 | 2.32 | 434.34 | DAD | 100 |
| 162 | {3-[5-Methoxy-1-methyl-3-(1H-pyrrolo[2,3-b]-pyridin-2-yl)-1H-indol-6-yloxy]propyl}-[4-(4-methylpiperazin-1-yl)-phenyl]amine | C31H36N6O2 | 524.67 | 2.41 | 525.38 | DAD | 100 |
| 163 | 2-{5-Methoxy-1-methyl-6-[3-(4-methylperhydro-1,4-diazepin-1-yl)-propoxy]-1H-indol-3-yl}-1H-pyrrolo[2,3-b]-pyridine | C26H33N5O2 | 447.58 | 2.31 | 448.36 | DAD | 100 |
| 164 | 2-[2-(4-{3-[5-Methoxy-1-methyl-3-(1H-pyrrolo[2,3-b]pyridin-2-yl)-1H-indol-6-yloxy]-propyl}-piperazin-1-yl)ethoxy]-ethanol | C28H37N5O4 | 507.63 | 2.33 | 508.37 | DAD | 100 |

EXAMPLES 165 TO 167 a) 2-{6-[2-(2-Chloroethoxy)ethoxy]-5-methoxy-1-methyl-1H-indol-3-yl}-1-(toluene-4-sulfonyl)-1H-pyrrolo[2,3-b]pyridine is prepared in the following way:

A solution 2-{6-[2-(2-chloroethoxy)ethoxy]-5-methoxy-1-methyl-1H-indol-3-yl}-1-(toluene-4-sulfonyl)-1H-pyrrolo[2,3-b]pyridine (0.145 g, 261.7 µmol) in methyl ethyl ketone (3 ml) is placed in a 50 ml single-necked flask and sodium iodide (0.118 g; 785 µmol) is then added. The reaction mixture is refluxed for 16 hours. Analysis by thin layer chromatography (50/50 cyclohexane/ethyl acetate) shows that the starting compound is still present. Additional sodium iodide (0.178 g; 1.18 mmol) is introduced and the reflux is maintained for 3 hours. After returning to 20° C., the precipitate is dissolved in dichloromethane (30 ml), then washing with water (10 ml) and drying over magnesium sulfate are carried out. After evaporation, the residue is taken up in diisopropyl ether (10 ml); the solid formed is removed and the filtrate is then evaporated under reduced pressure. 2-{6-[2-(2-Chloroethoxy)ethoxy]-5-methoxy-1-methyl-1H-indol-3-yl}-1-(toluene-4-sulfonyl)-1H-pyrrolo[2,3-b]pyridine (0.137 g; 81%) is isolated, which is used as it is.

b) 2-{6-[2-(2-Chloroethoxy)ethoxy]-5-methoxy-1-methyl-1H-indol-3-yl}-1-(toluene-4-sulfonyl)-1H-pyrrolo[2,3-b]pyridine is prepared in the following way:

A solution of 5-methoxy-1-methyl-3-[1-(toluene-4-sulfonyl)-1H-pyrrolo[2,3-b]pyridin-2-yl]-1H-indol-6-ol (2.998 g; 670 µmol) in dimethylformamide (3 ml) is placed in a 10 ml round-bottomed flask, sodium hydride (0.603 g; 2.01 mmol) is then added and the mixture is agitated for 5 minutes. The reaction mixture becomes green in color, and bis(2-chloroethyl) ether (0.235 ml; 2.01 mmol) is then added. The reaction mixture is then agitated for 1 hour 30 minutes at 20° C. Analysis by thin layer chromatography (50/50 cyclohexane/ethyl acetate) shows that the starting compound has been used up. The reaction mixture is run into water (30 ml) and then extracted with dichloromethane (20 ml). The organic extracts are combined, dried over magnesium sulfate, filtered and evaporated under reduced pressure, to give the crude compound, which is purified by chromatography on silica gel (AIT cartridge, Flash Silica column, 20-40 µm, 25 g, ref: FC-25SI-BP-SUP, 10 ml/min, 70/30 to 50/50 cyclohexane/ethyl acetate). The fractions containing the expected compound are combined and then evaporated under reduced pressure, giving 2-{6-[2-(2-chloroethoxy)ethoxy]-5-methoxy-1-methyl-1H-indol-3-yl}-1-(toluene-4-sulfonyl)-1H-pyrrolo[2,3-b]pyridine (0.145 g; 39%), which is used as it is for the following step.

c) Alkylation of Examples 165 to 167

The amines described in the table below are placed in 3 hemolysis tubes (1.2×10 cm) and solubilized in dimethylformamide (1 ml per tube). A solution of 2-{6-[2-(2-chloroethoxy)ethoxy]-5-methoxy-1-methyl-1H-indol-3-yl}-1-(toluene-4-sulfonyl)-1H-pyrrolo[2,3-b]pyridine (0.032 g per tube, 50 µmol per reactor) is placed in 4 hemolysis tubes) 1.2×10 cm), and then each solution of amine described above, and also potassium carbonate (0.021 g; 150 µmol per tube), are then added. The reactors are closed and then heated at 65° C. for 6 hours with agitation. After returning to 20° C., the content of each tube is filtered and then diluted with acetic acid (0.2 ml). The solutions thus obtained are eluted on solid-phase extraction cartridges (Varian, Mega Bond Elut, SCX, 2 g, 6 ml, #19102) pre-conditioned with methanol (2×6 ml). After a first elution with methanol (6 ml), the cartridges are eluted with 2N ammoniacal methanol (5 ml); the ammonia-containing eluate is evaporated to dryness, so as to give the expected compounds, which are used in the following step.

| Name | Formula | Mol weight | Equivalent | Weight mg |
|---|---|---|---|---|
| 165 1-methylpiperazine | C5H12N2 | 100.16 | 3.000 | 15.020 |
| 166 4-piperidinopiperidine | C10H20N2 | 168.28 | 3.000 | 25.240 |
| 167 1-methyl-homopiperazine | C6H14N2 | 114.19 | 3.000 | 17.130 | d) Detosylation of Examples 165 to 167

A methanolic potassium hydroxide solution (1.5 ml, solution at 0.1 g of potassium hydroxide per ml of methanol) is added to 3 hemolysis tubes (1.2×10 cm) containing the compounds obtained above, and each reaction mixture is then agitated at 20° C. for 16 hours. The content of each tube is diluted with acetic acid (0.2 ml) and then loaded onto an extraction cartridge (Varian, Mega Bond Elut, SCX, 2 g, 6 ml, Ref. 19102, Batch 1706002) pre-conditioned with methanol (2×6 ml). After a first elution with methanol (6 ml), the cartridges are eluted with 2N ammoniacal methanol (2×5 ml); the ammonia-containing eluate is evaporated to dryness and each sample is then diluted in dimethyl sulfoxide (0.5 ml) and purified by reverse-phase liquid chromatography mass spectrometry (method G). The fractions containing the expected compound are combined and then evaporated under reduced pressure, giving the expected compounds. The fractions are loaded onto SCX cartridges (Varian Mega BondElut-SCX cartridges, ref: 12256011, 1 g, 6 ml, Batch 1728002, UNRESOLVED PEAKG code 3102) pre-conditioned with methanol (2×6 ml). After elution with methanol (2×6 ml), the cartridges are eluted with 2N ammoniacal methanol (2×6 ml) and the ammonia-containing eluates are evaporated under reduced pressure to give the expected compounds, characterized by their retention time and peak (table below)

2-[5-methoxy-6-(2-methoxyethoxy)-1-methyl-1H-indol-3-yl]-1H-pyrrolo[2,3-b]pyridine is obtained, the characteristics of which are as follows:

$^1$H NMR spectrum (300 MHz, (CD$_3$)$_2$SO d6, δ in ppm): 3.39 (s: 3H); 3.76 (mt: 2H); 3.83 (s: 3H); 3.91 (s: 3H); 4.21 (mt: 2H); 6.78 (d, J=2 Hz: 1H); 7.04 (dd, J=8 and 5 Hz: 1H); 7.17 (s: 1H); 7.46 (s: 1H); 7.80 (s: 1H); 7.88 (dd, J=8 and 1.5 Hz: 1H); 8.13 (dd, J=5 and 1.5 Hz: 1H); 11.75 (broad s: 1H).

Mass spectrum (EI): m/z=351 [M]$^+$ (base peak)

b) 2-[5-Methoxy-6-(2-methoxyethoxy)-1-methyl-1H-indol-3-yl]-1-(toluene-4-sulfonyl)-1H-pyrrolo[2,3-b]pyridine is prepared by following the procedure described in example 147d, but using 0.195 g of 1-bromo-2-methoxyethane instead of 1-chloro-2-bromoethane used in example 147d, and 0.224 g of 2-[1-methyl-5-methoxy-6-hydroxyl-1H-indol-3-yl]-1-(toluene-4-sulfonyl)-1H-pyrrolo[2,3-b]pyridine. After purification by flash-pack chromatography (silica, 80/20 by volume ethyl acetate/cyclohexane as eluents, argon), 0.121 g of 2-[5-methoxy-6-(2-methoxyethoxy)-1-methyl-1H-indol-3-yl]-1H-pyrrolo[2,3-b]pyridine is obtained, the characteristics of which are as follows:

Mass spectrum (EI): m/z=505 [M]$^+$ (base peak)

EXAMPLE 169

2-[5-Methoxy-6-(2-hydroxyethoxy)-1-methyl-1H-indol-3-yl]-1H-pyrrolo[2,3-b]pyridine a) 2-[5-Methoxy-6-(2-hydroxyethoxy)-1-methyl-1H-indol-3-yl]-1H-pyrrolo[2,3-b]pyridine is prepared by following the procedure as described in example 89a, but using 0.5 g of 2-[5-methoxy-6-(2-acetyloxyethoxy)-1-methyl-1H-indol-3-yl]-1-(toluene-4-sulfonyl)-1H-pyrrolo[2,3-b]pyridine and 8.43 ml of a 5N aqueous potassium hydroxide solution. After purification by flash-pack chromatography (silica, 95/05 by volume dichloromethane/methanol as eluents,

| Ex | Name (parent) | Formula (parent) | MW | Rt | M + H$^+$ | % | trace |
|---|---|---|---|---|---|---|---|
| 165 | 2-(5-Methoxy-1-methyl-6-{2-[2-(4-methyl-piperazin-1-yl)ethoxy]ethoxy}-1H-indol-3-yl)-1H-pyrrolo[2,3-b]pyridine | C26H33N5O3 | 463.58 | 2.37 | 464 | 100 | DAD |
| 166 | 1'-(2-{2-[5-Methoxy-1-methyl-3-(1H-pyrrolo[2,3-b]pyridin-2-yl)-1H-indol-6-yloxy]ethoxy}ethyl)-[1,4']bipiperidinyl | C31H41N5O3 | 531.70 | 2.4 | 532 | 100 | DAD |
| 167 | 2-(5-Methoxy-1-methyl-6-{2-[2-(4-methyl-perhydro-1,4-diazepin-1-yl)ethoxy]-ethoxy}-1H-indol-3-yl)-1H-pyrrolo[2,3-b]pyridine | C27H35N5O3 | 477.61 | 2.36 | 478 | 100 | DAD |

EXAMPLE 168

2-[5-Methoxy-6-(2-methoxyethoxy)-1-methyl-1H-indol-3-yl]-1H-pyrrolo[2,3-b]pyridine a) 2-[5-Methoxy-6-(2-methoxyethoxy)-1-methyl-1H-indol-3-yl]-1H-pyrrolo[2,3-b]pyridine is prepared by following the procedure described in example 89a, but using 0.102 g of 2-[5-methoxy-6-(2-methoxyethoxy)-1-methyl-1H-indol-3-yl]-1-(toluene-4-sulfonyl)-1H-pyrrolo[2,3-b]pyridine and 0.80 ml of 5N potassium hydroxide. After purification by flash-pack chromatography (silica, 92.5/7.5 by volume dichloromethane/methanol as eluents, argon), 0.033 g of argon), 0.103 g of 2-[5-methoxy-6-(2-hydroxyethoxy)-1-methyl-1H-indol-3-yl]-1H-pyrrolo[2,3-b]pyridine is obtained, the characteristics of which are as follows:

$^1$H NMR spectrum (300 MHz, (CD$_3$)$_2$SO d6, δ in ppm): from 3.75 to 3.85 (mt: 2H); 3.82 (s: 3H); 3.90 (s: 3H); 4.09 (t, J=5.5 Hz: 2H); 4.88 (broad t, J=5 Hz: 1H); 6.76 (d, J=2 Hz: 1H); 7.02 (dd, J=8 and 5 Hz: 1H); 7.15 (s: 1H); 7.44 (s: 1H); 7.79 (s: 1H); 7.86 (broad dd, J=8 and 1.5 Hz: 1H); 8.12 (dd, J=5 and 1.5 Hz: 1H); 12.24 (unresolved peak: 1H).

Mass spectrum (EI): m/z=337 [M]$^+$ (base peak)

b) 2-[5-Methoxy-6-(2-acetyloxyethoxy)-1-methyl-1H-indol-3-yl]-1-(toluene-4-sulfonyl)-1H-pyrrolo[2,3-b]pyridine is prepared by following the procedure described in example 147d, but using 0.246 ml of 2-bromoethyl acetate and 0.5 g of 2-[1-methyl-5-methoxy-6-hydroxyl-1H-indol-3-yl]-1-(toluene-4-sulfonyl)-1H-pyrrolo[2,3-b]pyridine. After purification by flash-pack chromatography (silica, 40/60 by volume ethyl acetate/cyclohexane as eluents), 0.506 g of 2-[5-methoxy-6-(2-acetyloxyethoxy)-1-methyl-1H-indol-3-yl]-1-(toluene-4-sulfonyl)-1H-pyrrolo[2,3-b]pyridine is obtained, the characteristics of which are as follows:

Mass spectrum (EI): m/z=533 [M]$^+$, m/z=292 (base peak)

EXAMPLE 170

2-(5-Methoxy-1,6-dimethyl-1H-indol-3-yl)-1H-pyrrolo [2,3-b]pyridine a) 2-(5-Methoxy-1,6-dimethyl-1H-indol-3-yl)-1H-pyrrolo[2,3-b]-pyridine is prepared by following the procedure described in example 189a, but using 0.028 g of 2-(5-methoxy-1,6-dimethyl-1H-indol-3-yl)-1-(toluene-4-sulfonyl)-1H-pyrrolo[2,3-b]pyridine and 0.283 ml of a 5N aqueous potassium hydroxide solution. 0.01 g of 2-(5-methoxy-1,6-dimethyl-1H-indol-3-yl)-1H-pyrrolo[2,3-b]-pyridine is obtained, the characteristics of which are as follows:

$^1$H NMR spectrum (300 MHz, (CD$_3$)$_2$SO d6, δ in ppm): 2.33 (s: 3H); 3.83 (s: 3H); 3.94 (s: 3H); 6.78 (d, J=2 Hz: 1H); 7.03 (dd, J=8 and 5 Hz: 1H); 7.35 (broad s: 1H); 7.40 (broad s: 1H); 7.84 (s: 1H); 7.87 (broad dd, J=8 and 1.5 Hz: 1H); 8.12 (dd, J=5 and 1.5 Hz: 1H); 11.78 (broad s: 1H).

Mass spectrum (ES$^+$): m/z=292 [M+H]$^+$ (base peak)

b) 2-(5-Methoxy-1,6-dimethyl-1H-indol-3-yl)-1-(toluene-4-sulfonyl)-1H-pyrrolo[2,3-b]pyridine is prepared in the following way:

0.012 g of methylboronic acid, 0.0715 g of potassium carbonate and 0.020 g of tetrakis(triphenylphosphine)palladium are added to a solution of 0.1 g of 2-[1-methyl-5-methoxy-6-(trifluorosulfonyloxy)-1H-indol-3-yl]-1-(toluene-4-sulfonyl)-1H-pyrrolo[2,3-b]pyridine in 3 ml of anhydrous dioxane, under an inert argon atmosphere at a temperature in the region of 20° C. The reaction medium is heated at 120° C. for 24 hours. After cooling, 5 ml of water and 5 ml of ethyl acetate are added. After separation by settling out, the organic phase is dried over sodium sulfate, filtered, and then concentrated under reduced pressure. The residue obtained is purified by flash-pack chromatography (silica, 30/70 by volume ethyl acetate/cyclohexane as eluents). The fractions containing the products are concentrated under reduced pressure. 0.03 g of 2-(5-methoxy-1,6-dimethyl-1H-indol-3-yl)-1-(toluene-4-sulfonyl)-1H-pyrrolo[2,3-b]pyridine is thus obtained, the characteristics of which are as follows:

Mass spectrum (EI): m/z=445 [M]$^+$, m/z=290 (base peak)

c) 2-[1-Methyl-5-methoxy-6-(trifluorosulfonyloxy)-1H-indol-3-yl]-1-(toluene-4-sulfonyl)-1H-pyrrolo[2,3-b]pyridine is prepared in the following way:

0.451 ml of triflic anhydride and 1.35 ml of pyridine are added to a solution of 1 g of 2-[1-methyl-5-methoxy-6-hydroxy-1H-indol-3-yl]-1-(toluene-4-sulfonyl)-1H-pyrrolo[2,3-b]pyridine in 30 ml of dichloromethane, under an inert argon atmosphere at a temperature in the region of 0° C. The reaction medium is agitated at this temperature for 3 hours. The ice bath is removed. After returning to a temperature in the region of 20° C., 15 ml of water are added. After separation by settling out, the organic phase is dried over sodium sulfate, filtered, and then concentrated under reduced pressure. The residue obtained is purified by flash-pack chromatography (silica, dichloromethane as eluent). The fractions containing the product are concentrated under reduced pressure. 1.12 g of 2-[1-methyl-5-methoxy-6-(trifluorosulfonyloxy)-1-H-indol-3-yl]-1-(toluene-4-sulfonyl)-1H-pyrrolo[2,3-b]pyridine are thus obtained, the characteristics of which are as follows:

Mass spectrum (CI): m/z=580 [M+H]$^+$ (base peak)

The compound 2-[1-methyl-5-methoxy-6-hydroxy-1H-indol-3-yl]-1-(toluene-4-sulfonyl)-1H-pyrrolo[2,3-b]pyridine is prepared according to the process described in example 147e.

EXAMPLE 171

4-Chloro-2-{1-methyl-5-methoxy-6-[2-(4-methylpiperazin-1-yl)ethoxy]-1H-indol-3-yl}-1H-pyrrolo [2,3-b]-pyridine a) 4-Chloro-2-{1-methyl-5-methoxy-6-[2-(4-methylpiperazin-1-yl)ethoxy]-1H-indol-3-yl}-1H-pyrrolo[2,3-b]pyridine is prepared by following the procedure described in example 89a, but using 0.300 g of 4-chloro-2-[1-methyl-5-methoxy-6-(2-(4-methylpiperazin-4-yl-ethoxy)-1H-indol-3-yl]-1-(toluene-4-sulfonyl)-1H-pyrrolo[2,3-b]pyridine and 2.22 ml of a 5N aqueous potassium hydroxide solution. 0.169 g of 4-chloro-2-[1-methyl-5-methoxy-6-[2-(4-methylpiperazin-1-yl)ethoxy]-1H-indol-3-yl)-1H-pyrrolo[2,3-b]pyridine is obtained, the characteristics of which are as follows:

$^1$H NMR spectrum (300 MHz, (CD$_3$)$_2$SO d6, δ in ppm): 2.17 (s: 3H); 2.36 (unresolved peak: 4H); from 2.45 to 2.60 (mt: 4H); 2.77 (t, J=6.5 Hz: 2H); 3.84 (s: 3H); 3.90 (s: 3H); 4.16 (t, J=6.5 Hz: 2H); 6.71 (broad s: 1H); 7.14 (d, J=5 Hz: 1H); 7.21 (s: 1H); 7.44 (s: 1H); 7.85 (s: 1H); 8.08 (d, J=5 Hz: 1H); 12.16 (unresolved peak: 1H).

Mass spectrum (EI): m/z=453 [M]$^+$, m/z=127 (base peak)

b) 4-Chloro-2-[1-methyl-5-methoxy-6-(2-methoxyethoxy)-1H-indol-3-yl]-1-(toluene-4-sulfonyl)-1H-pyrrolo[2,3-b]pyridine is prepared by following the procedure described in example 147b, but using 0.087 ml of N-methylpiperazine and 0.25 g of 4-chloro-2-[1-methyl-5-methoxy-6-(2-iodoethoxy)-1H-indol-3-yl]-1-(toluene-4-sulfonyl)-1H-pyrrolo[2,3-b]pyridine. 0.303 g of 4-chloro-2-[1-methyl-5-methoxy-6-(2-(4-methylpiperazin-4-yl-ethoxy)-1H-indol-3-yl]-1-(toluene-4-sulfonyl)-1H-pyrrolo[2,3-b]pyridine is obtained, the characteristics of which are as follows:

Mass spectrum (EI): m/z=607 [M]$^+$, m/z=127 (base peak)

c) 4-Chloro-2-[1-methyl-5-methoxy-6-(2-iodoethoxy)-1H-indol-3-yl]-1-(toluene-4-sulfonyl)-1H-pyrrolo[2,3-b]pyridine is prepared by following the procedure described in example 147c, but using 1.15 g of 4-chloro-2-[1-methyl-5-methoxy-6-(2-chloroethoxy)-1H-indol-3-yl]-1-(toluene-4-sulfonyl)-1H-pyrrolo[2,3-b]pyridine and 0.950 g of sodium iodide. After purification by flash chromatography (silica, 40/60 by volume ethyl acetate/cyclohexane as eluents, argon), 1.21 g of 4-chloro-2-[1-methyl-5-methoxy-6-(2-iodoethoxy)-1H-indol-3-yl]-1-(toluene-4-sulfonyl)-1H-pyrrolo[2,3-b]pyridine are obtained, the characteristics of which are as follows:

Mass spectrum (EI): m/z=635 [M]$^+$, m/z=480 (base peak)

d) 4-Chloro-2-[1-methyl-5-methoxy-6-(2-chloroethoxy)-1H-indol-3-yl]-1-(toluene-4-sulfonyl)-1H-pyrrolo[2,3-b]pyridine is prepared by following the procedure described in example 147d, but using 1.3 g of 4-chloro-2-[1-methyl-5-methoxy-6-hydroxy-1H-indol-3-yl]-1-(toluene-4-sulfonyl)-1H-pyrrolo[2,3-b]pyridine and 0.675 cm$^3$ of 1-bromo-2-chloroethane. After purification by flash chromatography (silica, 40/60 by volume ethyl acetate/cyclohexane as eluents, argon), 1.16 g of 4-chloro-2-[1-methyl-5-methoxy-6-(2- chloroethoxy)-1H-indol-3-yl]-1-(toluene-4-sulfonyl)-1H-pyrrolo[2,3-b]pyridine are obtained, the characteristics of which are as follows:

Mass spectrum (CI): m/z=544 [M+H]$^+$ (base peak)

e) 4-chloro-2-[1-methyl-5-methoxy-6-hydroxy)-1H-indol-3-yl]-1-(toluene-4-sulfonyl)-1H-pyrrolo[2,3-b]pyridine is prepared by following the procedure described in example 147e, but using 1.8 g of 4-chloro-2-[1-methyl-5-methoxy-6-benzyloxy)-1H-indol-3-yl]-1-(toluene-4-sulfonyl)-1H-pyrrolo[2,3-b]pyridine and 1.124 ml of iodotrimethylsilane. After purification by flash chromatography (silica, 40/60 by volume ethyl acetate/cyclohexane as eluents, argon), 1.3 g of 4-chloro-2-[1-methyl-5-methoxy-6-hydroxy)-1H-indol-3-yl]-1-(toluene-4-sulfonyl)-1H-pyrrolo[2,3-b]pyridine are obtained, the characteristics of which are as follows:

Mass spectrum (CI): m/z=482 [M+H]$^+$ (base peak)

f) 4-Chloro-2-[1-methyl-5-methoxy-6-benzyloxy)-1H-indol-3-yl]-1-(toluene-4-sulfonyl)-1H-pyrrolo[2,3-b]pyridine is prepared by following the procedure described in example 89c, but using 2.5 g of 4-chloro-2-(5-methoxy-6-benzyloxy-1H-indol-3-yl)-1-(toluene-4-sulfonyl)-1H-pyrrolo[2,3-b]pyridine and 0.335 ml of methyl iodide. After purification by flash chromatography (silica, 40/60 by volume ethyl acetate/cyclohexane as eluents, argon), 2.1 g of 4-chloro-2-(1-methyl-5-methoxy-6-benzyloxy-1H-indol-3-yl)-1-(toluene-4-sulfonyl)-1H-pyrrolo[2,3-b]pyridine are obtained, the characteristics of which are as follows:

Mass spectrum (CI): m/z=571 [M]$^+$, m/z=480 (base peak)

g) 4-Chloro-2-(5-methoxy-6-benzyloxy-1H-indol-3-yl)-1-(toluene-4-sulfonyl)-1H-pyrrolo[2,3-b]pyridine is prepared by following the procedure described in example 97c, but using 2.75 g of 1-tert-butyloxycarbonyl-5-methoxy-6-benzyloxy-indol-3-boronic acid and 3 g of 1-(toluene-4-sulfonyl)-1H-2-iodo-4-chloro-pyrrolo-[2,3-b]pyridine. After purification by flash chromatography (silica, 40/60 by volume ethyl acetate/cyclohexane as eluents, argon), 2.53 g of 4-chloro-2-(5-methoxy-6-benzyloxy-1H-indol-3-yl)-1-(toluene-4-sulfonyl)-1H-pyrrolo[2,3-b]pyridine are obtained, the characteristics of which are as follows:

Mass spectrum (EI): m/z=557 [M]$^+$, m/z=466 (base peak)

The compounds 1-(toluene-4-sulfonyl)-1H-2-iodo-4-chloropyrrolo[2,3-b]pyridine and 1-tert-butyloxy-carbonyl-5-methoxy-6-benzyloxyindol-3-boronic acid are prepared according to the process described in patent WO 03000688 A1.

EXAMPLE 172

4-Chloro-2-{1-methyl-5-methoxy-6-[2-(4-piperidylpiperidin-1-yl)ethoxy]-1H-indol-3-yl}-1H-pyrrolo[2,3-b]pyridine a) 4-Chloro-2-{1-methyl-5-methoxy-6-[2-(4-piperidylpiperidin-1-yl)ethoxy]-1H-indol-3-yl}-1H-pyrrolo[2,3-b]pyridine is prepared by following the procedure described in example 89a, but using 0.41 g of 4-chloro-2-[1-methyl-5-methoxy-6-(2-(4-piperidylpiperidin-1-yl)ethoxy)-1H-indol-3-yl]-1-(toluene-4-sulfonyl)-1H-pyrrolo[2,3-b]pyridine and 2.73 ml of a 5N aqueous potassium hydroxide solution. 0.272 g of 4-chloro-2-{5-methoxy-1-methyl-6-[2-(4-piperidylpiperidin-1-yl)ethoxy]-1H-indol-3-yl}-1H-pyrrolo[2,3-b]pyridine is obtained, the characteristics of which are as follows:

$^1$H NMR spectrum (300 MHz, (CD$_3$)$_2$SO d6, δ in ppm): from 1.30 to 1.60 (mt: 8H); 1.70 (broad d, J=12 Hz: 2H); 2.05 (broad t, J=11 Hz: 2H); 2.18 (broad tt, J=12 and 3.5 Hz: 1H); 2.46 (mt: 4H); 2.75 (t, J=6 Hz: 2H); 3.04 (broad d, J=11 Hz: 2H); 3.83 (s: 3H); 3.90 (s: 3H); 4.15 (t, J=6 Hz: 2H); 6.71 (broad s: 1H); 7.15 (dd, J=5.5 Hz: 1H); 7.20 (s: 1H); 7.44 (s: 1H); 7.85 (s: 1H); 8.19 (d, J=5.5 Hz: 1H); 12.14 (broad s: 1H).

Mass spectrum (EI): m/z=521 [M]$^+$, m/z=195 (base peak)

b) 4-Chloro-2-[1-methyl-5-methoxy-6-(2-(4-piperidylpiperidin-1-yl)ethoxy)-1H-indol-3-yl]-1-(toluene-4-sulfonyl)-1H-pyrrolo[2,3-b]pyridine is prepared by following the procedure described in example 147b, but using 0.212 g of 4-piperidinopiperidine and 0.400 g of 4-chloro-2-[1-methyl-5-methoxy-6-(2-iodoethoxy)-1H-indol-3-yl]-1-(toluene-4-sulfonyl)-1H-pyrrolo[2,3-b]pyridine. 0.415 g of 4-chloro-2-[1-methyl-5-methoxy-6-(2-(4-piperidylpiperidin-1-yl)ethoxy)-1H-indol-3-yl]-1-(toluene-4-sulfonyl)-1H-pyrrolo[2,3-b]pyridine is obtained, the characteristics of which are as follows:

Mass spectrum (CI): m/z=676 [M+H]$^+$

EXAMPLE 173

4-Chloro-2-{5-methoxy-1-methyl-6-[2-(2-pyrrolidinethylamino)ethoxy]-1H-indol-3-yl}-1H-pyrrolo[2,3-b]-pyridine a) 4-Chloro-2-{5-methoxy-1-methyl-6-[2-(2-pyrrolidinethylamino)ethoxy]-1H-indol-3-yl}-1H-pyrrolo[2,3-b]pyridine is prepared by following the procedure described in example 89a, but using 0.22 g of 4-chloro-2-{1-methyl-5-methoxy-6-(2-(2-pyrrolidinethylamino)ethoxy]-1H-indol-3-yl}-1-(toluene-4-sulfonyl)-1H-pyrrolo[2,3-b]pyridine and 1.6 ml of a 5N aqueous potassium hydroxide solution. After purification by flash-pack chromatography (silica, 12/3/0.5 by volume chloroform/methanol/aqueous ammonia (28%) as eluents), 0.095 g of 4-chloro-2-{5-methoxy-1-methyl-6-[2-(2-pyrrolidinethylamino)ethoxy]-1H-indol-3-yl}-1H-pyrrolo[2,3-b]pyridine is obtained, the characteristics of which are as follows:

$^1$H NMR spectrum (300 MHz, (CD$_3$)$_2$SO d6, δ in ppm): 1.70 (mt: 4H); from 1.70 to 2.10 (very broad unresolved peak: 1H); 2.45 (mt: 4H); from 2.45 to 2.55 (mt: 2H); 2.73 (t, J=6.5 Hz: 2H); 2.97 (t, J=6 Hz: 2H); 3.84 (s: 3H); 3.91 (s: 3H); 4.13 (t, J=6 Hz: 2H); 6.72 (s large: 1H); 7.15 (d, J=5.5 Hz: 1H); 7.18 (s: 1H); 7.45 (s: 1H); 7.85 (s: 1H); 8.08 (d, J=5.5 Hz: 1H); 12.14 (broad s: 1H).

Mass spectrum (CI): m/z=468 [M+H]$^+$ b) 4-Chloro-2-{1-methyl-5-methoxy-6-[2-(2-pyrrolidinethylamino)ethoxy]-1H-indol-3-yl}-1-(toluene-4-sulfonyl)-1H-pyrrolo[2,3-b]pyridine is prepared by following the procedure described in example 147b, but using 0.100 ml of N-(2-aminoethyl)pyrrolidine and 0.3 g of 4-chloro-2-[1-methyl-5-methoxy-6-(2-iodoethoxy)-1H-indol-3-yl]-1-(toluene-4-sulfonyl)-1H-pyrrolo[2,3-b]pyridine. 0.229 g of 4-chloro-2-{5-methoxy-1-methyl-6-[2-(2-pyrrolidinethylamino)ethoxy]-1H-indol-3-yl}-1-(toluene-4-sulfonyl)-1H-pyrrolo[2,3-b]pyridine is obtained, the characteristics of which are as follows:

Mass, spectrum (CI): m/z=622 [M+H]$^+$ (base peak)

EXAMPLE 174

4-Chloro-2-{1-methyl-5-methoxy-6-[2-(2-piperidinethylamino)ethoxy]-1H-indol-3-yl}-1H-pyrrolo[2,3-b]-pyridine a) 4-Chloro-2-{1-methyl-5-methoxy-6-[2-(2-piperidinethylamino)ethoxy]-1H-indol-3-yl}-1H-pyrrolo[2,3-b]pyridine is prepared by following the procedure described in example 89a but using 10.240 g of 4-chloro-2-{1-methyl-5-methoxy-6-[2-(2-piperidinethylamino)ethoxy]-1H-indol-3- yl}-1-(toluene-4-sulfonyl)-1H-pyrrolo[2,3-b]pyridine and 1.7 ml of a 5N aqueous potassium hydroxide solution. After purification by flash-pack chromatography (silica, 40/5/0.5 by volume dichloromethane/methanol/aqueous ammonia (28%) as eluents), 0.092 g of 4-chloro-2-{1-methyl-5-methoxy-6-[2-(2-pyrrolidinethylamino)ethoxy]-1H-indol-3-yl}-1H-pyrrolo[2,3-b]pyridine is obtained, the characteristics of which are as follows:

$^1$H NMR spectrum (300 MHz, (CD$_3$)$_2$SO d6, δ in ppm): 1.40 (mt: 2H); 1.51 (mt: 4H); 1.88 (broad unresolved peak: 1H); 2.35 (mt: 4H); 2.39 (t, J=6.5 Hz: 2H); 2.71 (t, J=6.5 Hz: 2H); 2.96 (t, J=5.5 Hz: 2H); 3.83 (s: 3H); 3.91 (s: 3H); 4.13 (t, J=5.5 Hz: 2H); 6.71 (broad s: 1H); 7.15 (dd, J=5.5 Hz: 1H); 7.17 (s: 1H); 7.45 (s: 1H); 7.85 (s: 1H); 8.08 (d, J=5.5 Hz: 1H); 12.14 (broad s: 1H).

Mass spectrum (CI): m/z=482 [M+H]$^+$ (base peak)

b) 4-Chloro-2-{1-methyl-5-methoxy-6-[2-(2-piperidinethylamino)ethoxy]-1H-indol-3-yl}-1-(toluene-4-sulfonyl)-1H-pyrrolo[2,3-b]pyridine is prepared by following the procedure described in example 147b, but using 0.135 ml of N-(2-aminoethyl)piperidine and 0.3 g of 4-chloro-2-[1-methyl-5-methoxy-6-(2-iodoethoxy)-1H-indol-3-yl]-1-(toluene-4-sulfonyl)-1H-pyrrolo[2,3-b]pyridine. 0.246 g of 4-chloro-2-{1-methyl-5-methoxy-6-[2-(2-piperidinethylamino)ethoxy]-1H-indol-3-yl}-1-(toluene-4-sulfonyl)-1H-pyrrolo[2,3-b]-pyridine is obtained, the characteristics of which are as follows:

Mass spectrum (CI): m/z=636 [M+H]$^+$ (base peak)

EXAMPLE 175

2-(5,7-Dimethoxy-1-methyl-1H-indol-3-yl)-1H-pyrrolo [2,3-b]pyridine a) 2-(5,7-Dimethoxy-1-methyl-1H-indol-3-yl)-1H-pyrrolo[2,3-b]pyridine can be prepared in the following way:

3.3 ml of a 5N aqueous potassium hydroxide solution are added to a solution of 0.31 g of 2-(5,7-dimethoxy-1-methyl-1H-indol-3-yl)-1-(toluene-4-sulfonyl)-1H-pyrrolo[2,3-b]pyridine in 20 ml of methanol. The mixture is heated at around 80° C. for approximately 18 hours. The reaction medium is run into a mixture of 100 ml of ice plus, water, and extracted with three times 75 ml of ethyl acetate. The combined organic phases are washed with 100 ml of water and then with 100 ml of a saturated aqueous sodium chloride solution, dried over magnesium sulfate, filtered and concentrated to dryness under reduced pressure (13 kPa). The residue is purified by flash chromatography on a silica column [eluent: dichloromethane]. 0.073 g of 2-(5,7-dimethoxy-1-methyl-1H-indol-3-yl)-1H-pyrrolo[2,3-b]pyridine is obtained in the form of a solid, the characteristics of which are as follows:

Melting point: 220° C. (Köfler bench)

$^1$H NMR spectrum (300 MHz, (CD$_3$)$_2$SO d6, δ in ppm): 3.86 (s: 3H); 3.90 (s: 3H); 4.01 (s: 3H); 6.43 (d, J=2 Hz: 1H); 6.71 (d, J=2 Hz: 1H); 6.99 (d, J=1.5 Hz: 1H); 7.01 (dd, J=8 and 5 Hz: 1H); 7.76 (s: 1H); 7.85 (broad d, J=8 Hz: 1H); 8.11 (dd, J=5 and 1.5 Hz: 1H); 11.74 (unresolved peak: 1H).

Mass spectrum (EI): m/z=307 [M]$^+$ (base peak); m/z=292 [M-CH$_3$]$^+$ b) 2-(5,7-Dimethoxy-1-methyl-1H-indol-3-yl)-1-(toluene-4-sulfonyl)-1H-pyrrolo[2,3-b]pyridine can be prepared in the following way:

0.028 g of sodium hydride at 60% in oil is added, in small portions, to solution of 0.26 g of 2-(5,7-dimethoxy-1H-indol-3-yl)-1-(toluene-4-sulfonyl)-1H-pyrrolo[2,3-b]pyridine in 11.5 ml of dimethylformamide. The suspension is agitated for approximately 1 hour at around 20° C. and then 0.04 ml of iodomethane is added. After agitation for approximately 18 hours at around 20° C., the mixture is run into 100 ml of a mixture of ice plus water, and extracted with three times 75 ml of ethyl acetate. The combined organic phases are dried over magnesium sulfate, filtered and concentrated to dryness under reduced pressure. 0.3 g of 2-(5,7-dimethoxy-1-methyl-1H-indol-3-yl)-1-(toluene-4-sulfonyl)-1H-pyrrolo[2,3-b]pyridine is obtained in the form of a foam, the characteristics of which are as follows:

Mass spectrum (EI): m/z=461 [M]$^+$ (base peak); m/z 306 [M-C$_7$H$_7$O$_2$S]$^+$ c) 2-(5,7-Dimethoxy-1H-indol-3-yl)-1-(toluene-4-sulfonyl)-1H-pyrrolo[2,3-b]pyridine can be prepared as described in example 105e:

But using 2.9 g of 2-iodo-1-(toluene-4-sulfonyl)-1H-pyrrolo[2,3-b]pyridine, 2.34 g of 1-tert-butyloxycarbonyl-5,7-dimethoxy-1H-indole-3 boronic acid and 19 ml of a saturated aqueous solution of sodium hydrogen carbonate in 63 ml of dimethylformamide, and 0.42 g of tetrakis(triphenylphosphine)palladium is added. After flash chromatography on a silica column [eluent: cyclohexane/ethyl acetate (70/30 by volume)], 0.26 g of 2-(5,7-dimethoxy-1H-indol-3-yl)-1-(toluene-4-sulfonyl)-1H-pyrrolo[2,3-b]pyridine is thus obtained in the form of a solid, the characteristics of which are as follows:

silica TLC [eluent: cyclohexane/ethyl acetate (70/30 by volume)]
Rf=0.51

Mass spectrum (EI): m/z=447 [M]$^+$ (base peak); m/z=292 [M-C$_7$H$_7$O$_2$S]$^+$ The preparation of 2-iodo-1-(toluene-4-sulfonyl)-1H-pyrrolo[2,3-b]pyridine is described in patent WO 2003000688 A1.

d) 1-tert-Butyloxycarbonyl-5,7-dimethoxy-1H-indole-3-boronic acid can be prepared in the following way:

9.82 ml of a 2.5N solution of n-butyllithium in hexane are added, dropwise, while maintaining the temperature at around −100° C., to a solution of 2.2 g of tert-butyl ester of 3-iodo-5,7-dimethoxyindole-1-carboxylic acid and 1.8 ml of tributyl borate in 33 ml of tetrahydrofuran cooled to −100° C. The cooling bath is removed and, when the temperature of the reaction medium reaches approximately −5° C., 2 g of ice are added. After agitation for one hour at a temperature in the region of 20° C., the mixture is concentrated to dryness under reduced pressure (13 kPa). The residue is extracted with 200 ml of ethyl acetate, and washed with 100 ml of a saturated aqueous sodium chloride solution The organic phase is dried over magnesium sulfate, filtered and concentrated to dryness under reduced pressure (13 kPa). 2.34 g of 1-tert-butyloxycarbonyl-5,7-dimethoxy-1H-indole-3-boronic acid are thus obtained in the form of a solid, which is used as it is for the following step.

e) The tert-butyl ester of 3-iodo-5,7-dimethoxy-indole-1-carboxylic acid can be prepared in the following way:

0.94 g of powdered potassium hydroxide is added to a solution of 1.18 g of 5,7-dimethoxy-1H-indole in 34 ml of dimethylformamide. A solution of 1.71 g of bisublimated iodine in 34 ml of dimethylformamide is added dropwise to the above mixture. After agitation of the mixture for 3 hours at a temperature in the region of 20° C., 0.062 g of 4-dimethylaminopyridine is added, followed by a solution of 1.82 g of di-tert-butyl dicarbonate in 10 ml of dimethylformamide. After agitation for approximately 18 hours at around 20° C., the mixture is run into 89 ml of a 0.2% aqueous sodium thiosulfate solution. The mixture is extracted with three times 200 ml of ethyl acetate. The organic phases are combined, dried over magnesium sulfate, filtered and concentrated to dryness under reduced pressure (13 kPa). The residue is purified by flash chromatography on a silica column [eluent: cyclohexane/ethyl acetate (90/10 by volume)]. 2.2 g of tert-butyl ester of 3-iodo-5,7-dimethoxyindole-1-carboxylic acid are obtained in the form of a solid, the characteristics of which are as follows:

silica TLC [eluent: cyclohexane/ethyl acetate (70/30 by volume)] Rf=0.67

Mass spectrum (EI): m/z=403 [M]$^+$; m/z=303 [M-CO$_2$tBu]$^+$. (base peak)

5,7-Dimethoxy-1H-indole was prepared according to the method described by P. J. Milligan and S La Berge, Journal of Medicinal Chemistry, 1970, Vol. 13, No. 6, 1248-1

EXAMPLE 176

4-chloro-5-fluoro-2-[5,6-dimethoxy-1-(2-morpholin-4-ylethyl)-1H-indol-3-yl]-1H-pyrrolo[2,3-b]pyridine (A003364503 (P-32416-147-2))

a) 4-Chloro-5-fluoro-2-[5,6-dimethoxy-1-(2-morpholin-4-ylethyl)-1H-indol-3-yl]-1H-pyrrolo[2,3-b]pyridine may be prepared by following the procedure described in Example 100a, but starting with 0.260 g of 4-chloro-5-fluoro-2-[1-(2-morpholin-4-ylethyl)-5,6-dimethoxy-1H-indol-3-yl]-1-(toluene-4-sulfonyl)-1H-pyrrolo[2,3-b]pyridine and 0.62 g of 85% potassium hydroxide. After purification by crystallization from 11 cm$^3$ of acetonitrile, 0.115 g of 4-chloro-5-fluoro-2-[5,6-dimethoxy-1-(2-morpholin-4-ylethyl)-1H-indol-3-yl]-1H-pyrrolo[2,3-b]pyridine is obtained, the characteristics of which are as follows:

$^1$H NMR spectrum (300 MHz, (CD$_3$)$_2$SO d6, δ in ppm): 2.47 (partially masked m, 4H); 2.71 (broad t, J=6.5 Hz, 2H); 3.57 (m, 4H); 3.86 (s, 3H); 3.89 (s, 3H); 4.31 (broad t, J=6.5 Hz, 2H); 6.74 (d, J=2.0 Hz, 1H); 7.19 (s, 1H); 7.42 (s, 1H); 7.93 (s, 1H); 8.19 (d, J=2.0 Hz, 1H); 12.2 (broad s, 1H).

Mass spectrum (EI): m/z=458 (M)$^+$ (base peak)

b) 4-Chloro-5-fluoro-2-[1-(2-morpholin-4-ylethyl)-5,6-dimethoxy-1H-indol-3-yl]-1-(toluene-4-sulfonyl)-1H-pyrrolo[2,3-b]pyridine may be prepared by following the procedure described in Example 100b, but starting with 0.280 g of 4-chloro-5-fluoro-2-[1-(2-iodoethyl)-5,6-dimethoxy-1H-indol-3-yl]-1-(toluene-4-sulfonyl)-1H-pyrrolo[2,3-b]pyridine, 0.065 g of potassium carbonate and 0.075 g of morpholine. 0.270 g of 4-chloro-5-fluoro-2-[1-(2-morpholin-4-ylethyl)-5,6-dimethoxy-1H-indol-3-yl]-1-(toluene-4-sulfonyl)-1H-pyrrolo[2,3-b]pyridine is thus obtained in the form of an orange-colored resin, the characteristics of which are as follows:

Rf TLC, silica [eluent: cyclohexane/methanol (95/5 by volume)]=0.52

$^1$H NMR spectrum (300 MHz, (CD$_3$)$_2$SO d6, δ in ppm): 2.27 (s, 3H); from 2.45 to 2.55 (masked m, 4H); 2.77 (t, J=6.5 Hz, 2H); 3.58 (m, 4H); 3.70 (s, 3H); 3.87 (s, 3H); 4.35 (t, J=6.5 Hz, 2H); 6.77 (s, 1H); 6.84 (s, 1H); 7.17 (s, 1H); 7.20 (broad d, J=8.5 Hz, 2H); 7.49 (broad d, J=8.5 Hz, 2H); 7.60 (s, 1H); 8.48 (d, J=2.0 Hz, 1H)

c) 4-Chloro-5-fluoro-2-[1-(2-iodoethyl)-5,6-dimethoxy-1H-indol-3-yl]-1-(toluene-4-sulfonyl)-1H-pyrrolo[2,3-b]pyridine may be prepared by following the procedure described in Example 100c, but starting with 0.260 g of 4-chloro-5-fluoro-2-[1-(2-chloroethyl)-5,6-dimethoxy-1H-indol-3-yl]-1-(toluene-4-sulfonyl)-1H-pyrrolo[2,3-b]pyridine and 0.104 g of sodium iodide. 0.283 g of 4-chloro-5-fluoro-2-[1-(2-iodoethyl)-5,6-dimethoxy-1H-indol-3-yl]-1-(toluene-4-sulfonyl)-1H-pyrrolo[2,3-b]pyridine is thus obtained in the form of an orange-colored resin, the characteristics of which are as follows:

Rf TLC, silica [eluent: dichloromethane/ethyl acetate (95/5 by volume)]=0.72

Mass spectrum (EI): m/z 653 (M)$^+$ base peak d) 4-Chloro-5-fluoro-2-[1-(2-chloroethyl)-5,6-dimethoxy-1H-indol-3-yl]-1-(toluene-4-sulfonyl)-1H-pyrrolo[2,3-b]pyridine may be prepared by following the procedure described in Example 100d, but starting with 0.390 g of 4-chloro-5-fluoro-2-(5,6-dimethoxy-1H-indol-3-yl)-1-(toluene-4-sulfonyl)-1H-pyrrolo[2,3-b]pyridine and 0.005 g of tetrabutylammonium bromide in 30 cm$^3$ of 1,2-dichloroethane, 0.343 g of potassium hydroxide and 0.251 g of potassium carbonate. 0.260 g of 4-chloro-5-fluoro-2-[1-(2-chloroethyl)-5,6-dimethoxy-1H-indol-3-yl]-1-(toluene-4-sulfonyl)-1H-pyrrolo[2,3-b]pyridine is obtained in the form of an orange-colored resins the characteristics of which are as follows:

TLC, silica [eluent: dichloromethane/ethyl acetate (95/5 by volume)] Rf=0.56

Mass spectrum (EI): m/z=562 (M)$^+$ e) 4-Chloro-5-fluoro-2-(5,6-dimethoxy-1H-indol-3-yl)-1-(toluene-4-sulfonyl)-1H-pyrrolo[2,3-b]pyridine may be prepared by following the procedure described in Example 97c, but starting with 0.750 g of 1-(toluene-4-sulfonyl)-1H-2-iodo-4-chloro-5-fluoropyrrolo[2,3-b]pyridine, 0.534 g of 1-tert-butyloxycarbonyl-5,6-dimethoxyindol-3-boronic acid and 0.096 g of tetrakis(triphenylphosphine)palladium. 0.390 g of 4-chloro-2-(5,6-dimethoxy-1H-indol-3-yl)-1-(toluene-4-sulfonyl)-1H-pyrrolo[2,3-b]pyridine is thus obtained, the characteristics of which are as follows:

$^1$H NMR spectrum (300 MHz, (CD$_3$)$_2$SO d6, δ in ppm): 2.29 (s, 3H); 3.70 (s, 3H); 3.82 (s, 3H); 6.79 (s, 1H); 6.92 (s, 1H); 7.00 (s, 1H); 7.26 (broad d, J=8.5 Hz, 2H); 7.52 (broad d, J=8.5 Hz, 2H); 7.53 (s, 1H); 8.47 (d, J=2.0 Hz, 1H); 11.3 (broad s, 1H).

Mass spectrum (EI): m/z=499 (M)$^+$ 1-tert-Butyloxycarbonyl-5,6-dimethoxyindol-3-boronic acid is prepared according to the process described in patent WO 03/000688 A1.

f) 1-(Toluene-4-sulfonyl)-1H-2-iodo-4-chloro-5-fluoropyrrolo[2,3-b]pyridine may be prepared in the following manner:

1.18 cm$^3$ of tert-BuLi are added dropwise to a solution of 0.650 g of 1-(toluene-4-sulfonyl)-1H-4-chloro-5-fluoropyrrolo[2,3-b]pyridine in 15 cm$^3$ of tetrahydrofuran at about −78° C. After stirring the reaction medium for 30 minutes at about, −78° C., a solution of 1.01 g of iodine in 6 cm$^3$ of tetrahydrofuran is added dropwise, and the temperature is maintained at −78° C. for 2 h. The temperature is allowed to return to about 0° C. After addition of 5 cm$^3$ of saturated aqueous ammonium chloride solution, the reaction mixture is extracted with 80 cm$^3$ of ethyl acetate, the organic phase is then washed with 3 times 20 cm$^3$ of water, and then dried over magnesium sulfate and concentrated under reduced pressure (13 kPa). 0.750 g of 1-(toluene-4-sulfonyl)-1H-2-iodo-4-chloro-5-fluoropyrrolo[2,3-b]pyridine is thus obtained in the form of a cream-colored solid, the characteristics of which are as follows:

TLC, silica [eluent: dichloromethane] Rf=0.59

Mass spectrum (EI): m/z=451 (M)$^+$ g) 1-(Toluene-4-sulfonyl)-1H-4-chloro-5-fluoropyrrolo[2,3-b]pyridine may be prepared in the following manner:

A mixture of 1.30 g of 4-chloro-5-fluoro-1H-pyrrolo[2,3-b]pyridine, 1.6 g of 4-methylbenzenesulfonyl chloride, 3.40 g of sodium hydroxide dissolved in 16 cm$^3$ of water, and 0.052 g of tetrabutylammonium hydrogen sulfate in 200 cm³ of toluene is stirred for about 24 hours in the region of 20° C. The mixture is diluted with 500 cm³ of ethyl acetate; the organic phase is washed with three times 200 cm³ of water, dried over magnesium sulfate, filtered and concentrated to dryness under reduced pressure (13 kPa). The residue is purified by flash chromatography on a column of silica [eluent: dichloromethane]. 1.90 µg of 4-chloro-5-fluoro-1-(toluene-4-sulfonyl)-1H-pyrrolo[2,3-b]pyridine are thus obtained in the form of a powder, the characteristics of which are as follows:

Melting point: melting at 125° C. (Köfler block)

¹H NMR spectrum (300 MHz, (CD₃)₂SO d6, δ in ppm) 2.36 (s, 3H); 6.93 (d, J=3.0 Hz, 1H); 7.44 (broad d, J=8.0 Hz, 2H); 7.99 (broad d, J=8.0 Hz, 2H); 8.12 (d, J=3.0 Hz, 1H); 8.52 (d, J=2.5 Hz, 1H)

Mass spectrum (EI): m/z=324 (M)⁺ h) 4-chloro-5-fluoro-1H-pyrrolo[2,3-b]pyridine may be prepared in the following manner:

A solution of 1.7 g of 5-fluoro-1H-pyrrolo[2,3-b]pyridine-7-oxide in 10 cm³ of phosphorus oxychloride is maintained at the reflux point of the POCl₃ for 8 hours. After distilling off the POCl₃ under vacuum, the residue is treated with 50 g of ice, and the pH of the solution obtained is brought in the region of 8-9 by addition of sodium hydrogen carbonate. The aqueous phase is extracted with five times 80 cm³ of ethyl acetate. The combined organic phases are then dried over magnesium sulfate, filtered and concentrated to dryness under reduced pressure (13 kPa). 1.3 g of 4-chloro-5-fluoro-1H-pyrrolo[2,3-b]pyridine are thus obtained in the form of a solid, the characteristics of which are as follows:

Rf TLC, silica (eluent: dichloromethane/methanol (98/2 by volume)]=0.19

¹H NMR spectrum (400 MHz, (CD₃)₂SO d6, δ in ppm): 6.56 (m, 1H); 7.70 (m, 1H); 8.35 (d, J=2.5 Hz, 1H); 12.15 (broad m, 1H)

Mass spectrum (EI): m/z=170 (M)⁺ i) 5-Fluoro-1H-pyrrolo[2,3-b]pyridine 7-oxide may be prepared in the following manner:

6.22 g of 3-chloroperbenzoic acid are added to a solution of 2.7 g of 5-fluoro-1H-pyrrolo[2,3-b]pyridine in 70 cm³ of dimethoxyethane. The reaction medium is stirred in the region of 20° C. for 1 hour 30 minutes. After addition of a solution of 2 g of potassium hydroxide in 20 cm³ of methanol, the mixture is extracted with 5 times 100 cm³ of ethyl acetate. The organic phases are then washed with twice 15 cm³ of saturated ammonium chloride solution and then dried over magnesium sulfate, filtered and concentrated to dryness under reduced pressure (13 kPa) The residue is purified by flash chromatography on a column of silica [eluent: dichloromethane/methanol (95/5 by volume)], and 3.6 g of a solid are obtained, which is washed with 25 cm³ of diethyl oxide and then dewatered and dried. The residue is purified by flash chromatography on a column of silica [eluent: cyclohexane/ethyl acetate (50/50 by volume)], and 1.70 g of 5-fluoro-1H-pyrrolo[2,3-b]pyridine 7-oxide are obtained in the form of a powder, the characteristics of which are as follows:

Melting point: melting at 178° C. (Köfler block)

IR spectrum: KBr 3128; 3085; 2919; 2863; 2734; 2629; 2406; 1588; 1507; 1349; 1256; 1206; 1129; 1077; 990; 804; 723; 670 and 466 cm⁻¹ j) 5-Fluoro-1H-pyrrolo[2,3-b]pyridine may be prepared in the following manner:

A mixture of 3.80 g of 5-fluoro-3-trimethylsilanylethynylpyrid-2-ylamine and 3.40 g of potassium tert-butoxide in 100 cm³ of 1-methylpyrrolidin-2-one is maintained in the region of 130° C. for about 4 hours. After cooling to a temperature in the region of 20° C., the mixture is poured into 1000 cm³ of saturated aqueous sodium chloride solution and extracted with 5 times 250 cm³ of diethyl oxide. The organic phases are combined, washed with 5 times 100 cm³ of saturated aqueous sodium chloride solution, dried over magnesium sulfate, filtered and concentrated to dryness under reduced pressure (13 kPa). 2.35 g of 5-fluoro-1H-pyrrolo[2,3-b]pyridine are obtained in the form of a solid, the characteristics of which are as follows:

Melting point: melting at 110° C. (Köfler block)

Mass spectrum (EI): m/z=136 (M)⁺ base peak m/z=109 (M-HCN)⁺ k) 5-Fluoro-3-trimethylsilanylethynylpyrid-2-ylamine may be prepared in the following manner:

12.47 cm³ of ethynyltrimethylsilane, 2.24 g of copper iodide, 2.74 g of lithium chloride, 41.33 cm³ of triethylamine and 2.15 g of [1,1'-bis(diphenylphosphino)ferrocene]palladium(II) chloride are added to a solution of 14 g of 5-fluoro-3-iodo-pyrid-2-ylamine in 440 cm³ of dimethylformamide, degassed with argon. The solution obtained is maintained at a temperature in the region of 55° C. for about 5 hours. After cooling to a temperature in the region of 20° C., the mixture is concentrated under reduced pressure (13 kPa); the residue is taken up in 300 cm³ of water and extracted with three times 100 cm³ of ethyl acetate. The combined organic phases are washed with three times 100 cm³ of water, dried over magnesium sulfate, filtered and concentrated under reduced pressure (13 kPa). 7.91 g of 5-fluoro-3-trimethylsilanylethynylpyrid-2-ylamine are thus obtained, after flash chromatography on a column of silica (eluent; dichloromethane), in the form of a solid, the characteristics of which are as follows:

Melting point: melting at 65° C. (Köfler block)

Mass spectrum (EI): m/z=208 (M)⁺ ᵐ/ᶻ=193 (M-CH₃)⁺ base peak l) 5-Fluoro-3-iodo-pyrid-2-ylamine may be prepared in the following manner:

A mixture of 9.9 g of 5-fluoropyrid-3-ylamine and 21.85 g of N-iodosuccinimide in 400 cm³ of acetic acid is stirred for about 6 hours at a temperature in the region of 70° C. After concentrating to dryness under reduced pressure (13 kPa), the residue is taken up in 250 cm³ of water; the pH is brought to about 8 by addition of sodium hydrogen carbonate. The aqueous phase is extracted with 5 times 150 cm³ of dichloromethane. The combined organic phases are washed with three times 100 cm³ of water and then with 5 times 50 cm³ of aqueous 10% sodium thiosulfate solution, dried over sodium sulfate, filtered and concentrated to dryness under reduced pressure (13 kPa). 11 g of 5-fluoro-3-iodo-pyrid-2-ylamine are thus obtained, after flash chromatography on a column of silica (eluent: dichloromethane), in the form of a solid, the characteristics of which are as follows:

Melting point: melting at 76° C. (Köfler block)

1H NMR spectrum (300 MHz, (CD₃)₂SO d6, δ in ppm): 5.98 (broad s, 2H); from 7.93 to 7.98 (m, 2H).

Mass spectrum (EI): m/z=238 (M)⁺

EXAMPLE 177

2-(5,6-dimethoxy-1-methyl-1H-indol-3-yl)-1H-pyrrolo[2,3-b]pyrid-4-ylamine (A003346712 (P-32441-067-1))

a) 2-(5,6-Dimethoxy-1-methyl-1H-indol-3-yl)-1H-pyrrolo[2,3-b]pyrid-4-ylamine may be prepared in the following manner:

1.05 cm³ of tetrabutylammonium fluoride are added to a solution of 0.1 g of 2-(1-methyl)-5,6-dimethoxy-1H-indol-3- yl)-1-(toluene-4-sulfonyl)-1H-pyrrolo[2,3-b]pyrid-4-ylamine in 10 cm³ of tetrahydrofuran, degassed with argon. The solution obtained is refluxed for about 24 hours. After cooling to a temperature in the region of 20° C., the mixture is concentrated under reduced pressure (13 kPa); the residue is taken up in 50 cm³ of saturated sodium hydrogen carbonate solution, extracted with three times 50 cm³ of ethyl acetate and then with three times 100 cm³ of dichloromethane. The combined organic phases are washed with three times 100 cm³ of water, dried over magnesium sulfate, filtered and concentrated under reduced pressure (13 kPa). 0.015 g of 2-(5,6-dimethoxy-1-methyl-1H-indol-3-yl)-1H-pyrrolo[2,3-b]pyrid-4-ylamine are thus obtained, after flash chromatography on a column of silica [eluent: dichloromethane/methanol (90/10 by volume)], in the form of a white solid, the characteristics of which are as follows:

1H NMR spectrum (400 MHz, $(CD_3)_2SO$ d6, δ in ppm): 3.79 (s, 3H); 3.87 (s, 3H); 3.89 (s, 3H); 6.07 (broad s, 2H); 6.13 (d, J=5.0 Hz, 1H); 6.82 (broad s, 1H); 7.09 (s, 1H); 7.43 (s, 1H); 7.63 (s, 1H); 7.67 (d, J=5.0 Hz, 1H); 11.2 (broad s, 1H).

Mass spectrum (EI): m/z=322 (M)⁺ b) 2-(5,6-Dimethoxy-1-methyl-1H-indol-3-yl)-1-(toluene-4-sulfonyl)-1H-pyrrolo[2,3-b]pyrid-4-ylamine may be prepared in the following manner:

5.5 cm³ of aqueous 2N hydrochloric acid solution are added to a solution of 0.7 g of benzhydrylidene-[2-(1-methyl)-5,6-dimethoxy-1H-indol-3-yl)-1-(toluene-4-sulfonyl)-1H-pyrrolo[2,3-b]pyrid-4-yl]amine in 20 cm³ of tetrahydrofuran. The solution obtained is stirred in the region of 20° C. for about 3 hours. The mixture is concentrated under reduced pressure (13 kPa); the residue is taken up in 50 cm³ of saturated sodium hydrogen carbonate solution and extracted with three times 50 cm³ of ethyl acetate and then with three times 25 cm³ of dichloromethane. The combined organic phases are washed with three times 50 cm³ of water, dried over magnesium sulfate, filtered and concentrated under reduced pressure (13 kPa). 0.31 g of 2-(5,6-dimethoxy-1-methyl-1H-indol-3-yl)-1-(toluene-4-sulfonyl)-1H-pyrrolo[2,3-b]pyrid-4-ylamine are thus obtained, after flash chromatography on a column of silica [eluent: dichloromethane/methanol (98/2 by volume)], in the form of a pale pink solid, the characteristics of which are as follows:

TLC, silica [eluent: dichloromethane/methanol (98/2 by volume)] Rf=0.125

Mass spectrum (EI): m/z=476 (M)⁺ c) benzhydrylidene-[2-(1-methyl)-5,6-dimethoxy-1H-indol-3-yl)-1-(toluene-4-sulfonyl)-1H-pyrrolo[2,3-b]pyrid-4-yl]amine may be prepared in the following manner:

1.7 g of cesium carbonate, 0.4 g of (R)-(+)-2,2-bis(diphenylphosphino)-1,1'-binaphthyl and 0.377 g of benzophenoneimine are added to a solution of 0.8 g of 4-chloro-2-(5,6-dimethoxy-1H-indol-3-yl)-1-(toluene-4-sulfonyl)-1H-pyrrolo[2,3-b]pyridine in 80 cm³ of toluene, degassed with argon. The solution obtained is stirred in the region of 20° C. for about 15 minutes, and 0.144 g of palladium acetate is then added. The mixture is refluxed for 4 hours and, after cooling to about 20° C., is then filtered through a sinter funnel packed with Celite. The cake is washed with three times 20 cm³ of dichloromethane, and the filtrate is then concentrated under reduced pressure (13 kPa). 1.3 g of benzhydrylidene-[2-(1-methyl)-5,6-dimethoxy-1H-indol-3-yl)-1-(toluene-4-sulfonyl)-1H-pyrrolo[2,3-b]pyrid-4-yl]amine are thus obtained, after flash chromatography on a column of silica [eluent: cyclohexane/ethyl acetate (50/50 by volume)], in the form of a yellow solid, the characteristics of which are as follows:

1H NMR spectrum (400 MHz, $(CD_3)_2SO$ d6, δ in ppm): 2.31 (s, 3H); 3.72 (s, 3H); 3.82 (s, 3H); 3.86 (s, 3H); 6.49 (s, 1H); 6.61 (d, J=5.0 Hz, 1H); 6.88 (s, 1H); 7.08 (s, 1H); 7.20 (broad d, 8.5 Hz, 2H); 7.39 (broad d, J=8.5 Hz, 2H); 7.41 (s, 1H); from 7.05 to 7.75 (very broad m, 10H); 8.02 (d, J=5.0 Hz, 1H).

Mass spectrum (IC): m/z=641 (M+H)⁺

4-Chloro-2-(5,6-dimethoxy-1H-indol-3-yl)-1-(toluene-4-sulfonyl)-1H-pyrrolo[2,3-b]pyridine is obtained as described in Example 97b.

EXAMPLE 178

Cyclohexyl[2-(5,6-dimethoxy-1-methyl-1H-indol-3-yl)-1H-pyrrolo[2,3-b]pyrid-4-ylmethyl]amine (A003341949 (P-31916-162-1))

a) Cyclohexyl[2-(5,6-dimethoxy-1-methyl-1H-indol-3-yl)-1H-pyrrolo[2,3-b]pyrid-4-ylmethyl]amine may be prepared in the following manner:

1 cm³ of a 1M solution of tetrabutylammonium fluoride (TBAF) in tetrahydrofuran is added, at a temperature in the region of 20° C., to a solution of 0.14 g of cyclohexyl[2-(5,6-dimethoxy-1-methyl-1H-indol-3-yl)-1-(toluene-4-sulfonyl)-1H-pyrrolo[2,3-b]pyrid-4-ylmethyl]amine in 10 cm³ of tetrahydrofuran. The reaction medium is stirred at this same temperature for 15 hours, and then refluxed for 24 hours. After cooling, the reaction medium is evaporated to dryness under reduced pressure. 4 cm³ of water are added. The solid formed is filtered off on a sinter funnel, and washed with water and then with ethyl ether. The solid obtained is taken up in water and the medium is basified to pH 10 with 0.1N sodium hydroxide. The product is extracted five times with dichloromethane. The organic phases are combined, dried over magnesium sulfate, filtered and then concentrated under reduced pressure. 0.029 g of cyclohexyl[2-(5,6-dimethoxy-1-methyl-1H-indol-3-yl)-1H-pyrrolo[2,3-b]pyrid-4-ylmethyl]amine is thus obtained, the characteristics of which are as follows:

¹H NMR spectrum (300 MHz, $(CD_3)_2SO$ d6, δ in ppm): 1.05 to 1.28 (m, 5H); from 1.48 to 1.76 (m, 3H); from 1.85 to 2.03 (m, 2H); from 3.17 to 3.42 (masked m, 1H); 3.80 (s, 3H); 3.85 (s, 3H); 3.88 (s, 3H); 4.05 (broad s, 2H); 6.82 (d, J=2.0 Hz, 1H); 7.02 (d, J=5.0 Hz, 1H); 7.11 (s, 1H); 7.45 (s, 1H); 7.75 (s, 1H); 8.03 (d, J=5.0 Hz, 1H); 11.65 (broad s, 1H).

Mass spectrum (EI): m/z=418 (M)⁺; m/z=321 $(M-C_6H_{11}N)^+$ base peak b) Cyclohexyl[2-(5,6-dimethoxy-1-methyl-1H-indol-3-yl)-1-(toluene-4-sulfonyl)-1H-pyrrolo[2,3-b]pyrid-4-ylmethyl]amine may be prepared in the following manner:

0.16 g of 2-(5,6-dimethoxy-1-methyl-1H-indol-3-yl)-1-(toluene-4-sulfonyl)-1H-pyrrolo[2,3-b]pyrid-4-carboxaldehyde and 0.4 g of sodium sulfate are added to a solution of 0.24 g of cyclohexylamine in 5 cm³ of dichloromethane, under an inert atmosphere of argon, at a temperature in the region of 20° C. Stirring is maintained for 48 hours at room temperature. 5 cm³ of methanol and 0.023 g of sodium borohydride are added. The reaction medium is stirred at the same temperature for 6 hours. The reaction medium is concentrated under reduced pressure. The residue obtained is taken up in 10 cm³ of dichloromethane. The precipitate formed is filtered off and the filtrate is concentrated under reduced pressure and then purified by column flash chromatography (SiO2, dichloromethane/methanol, 98/02 by volume as eluent). The fractions containing the product are combined and concentrated to dryness under reduced pressure to give 0.143 g of cyclohexyl[2-(5,6-dimethoxy-1-methyl-1H-indol-3-yl)-1-(toluene-4-sulfonyl)pyrrolo[2,3-b]pyrid-4-ylmethyl]amine.

Mass spectrum (EI): m/z=572 (M)$^+$; m/z=417 (M-C$_7$H$_7$SO$_2$)$^+$ base peak; m/z=320 (m/z=417-C$_6$H$_{11}$N)$^+$ c) 2-(5,6-Dimethoxy-1-methyl-1H-indol-3-yl)-1-(toluene-4-sulfonyl)-1H-pyrrolo[2,3-b]pyrid-4-carboxaldehyde may be prepared in the following manner:

16.5 cm$^3$ of 5N hydrochloric acid are added, at a temperature in the region of 20° C., to a solution of 4.4 g of 2-(5,6-dimethoxy-1-methyl-1H-indol-3-yl)-4-(1,3-dioxolan)-2-yl-1-(toluene-4-sulfonyl)-1H-pyrrolo[2,3-b]pyridine in 100 cm$^3$ of tetrahydrofuran. The reaction medium is stirred at this same temperature for 24 hours. 30 cm$^3$ of water and 30 cm$^3$ of dichloromethane are added. After separation of the phases by settling, the organic phase is dried over magnesium sulfate, filtered, concentrated under reduced pressure and then purified on a column of silica, eluting with a 50/50 by volume mixture of cyclohexane and ethyl acetate. The fractions containing the product are combined and concentrated to dryness under reduced pressure to give 2.6 g of 2-(5,6-dimethoxy-1-methyl-1H-indol-3-yl)-1-(toluene-4-sulfonyl)-1H-pyrrolo[2,3-b]pyrid-4-carboxaldehyde, the characteristics of which are as follows:

Mass spectrum (EI): m/z=489 (M)$^+$; m/z=334 (M-C$_7$H$_7$SO$_2$)$^+$ base peak d) 2-(5,6-Dimethoxy-1-methyl-1H-indol-3-yl)-4-(1,3-dioxolan)-2-yl-1-(toluene-4-sulfonyl)-1H-pyrrolo[2,3-b]pyridine may be pre pared in the following manner:

0.462 g of a 60% suspension of sodium hydride in oil is added to a solution of 5 g of 2-(5,6-dimethoxy-1H-indol-3-yl)-4-(1,3-dioxolan)-2-yl-1-(toluene-4-sulfonyl)-1H-pyrrolo[2,3-b]pyridine in 185 cm$^3$ of anhydrous dimethylformamide (DMF), under an inert atmosphere of argon at a temperature in the region of 20° C. The reaction medium is stirred at the same temperature for 45 minutes. 0.719 cm$^3$ of methyl iodide is added dropwise. The reaction medium is stirred at this same temperature for 20 hours. 200 cm$^3$ of water and 100 cm$^3$ of ethyl acetate are added. After separation of the phases by settling, the organic phase is dried over magnesium sulfate, filtered, concentrated under reduced pressure and then purified on a column of silica, eluting with a 98/02 by volume mixture of dichloromethane and methanol. The fractions containing the product are combined and concentrated to dryness under reduced pressure to give 4.42 g of 2-(5,6-dimethoxy-1-methyl-1H-indol-3-yl)-4-(1,3-dioxolan)-2-yl-1-(toluene-4-sulfonyl)-1H-pyrrolo[2,3-b]pyridine, the characteristics of which are as follows:

Mass spectrum (EI): m/z =533 (M)$^+$; m/z=378 (M-C$_7$H$_7$SO$_2$)$^+$ base peak e) 2-(5,6-Dimethoxy-1H-indol-3-yl)-4-(1,3-dioxolan)-2-yl-1-(toluene-4-sulfonyl)-1H-pyrrolo[2,3-b]pyridine may be prepared in the following manner:

41 cm$^3$ of saturated sodium bicarbonate solution and 0.611 g of tetrakis(triphenylphosphine)palladium are added to a solution of 6.2 g of 4-(1,3-dioxolan)-2-yl-2-iodo-1-(toluene-4-sulfonyl)-1H-pyrrolo[2,3-b]pyridine, 135 cm$^3$ of anhydrous DMF and 7.42 g of 1-t-butyloxycarbonyl-5,6-dimethoxyindol-3-boronic acid, under an inert atmosphere of argon at a temperature in the region of 20° C. The reaction medium is heated at 130° C. for 3 hours. After cooling, the reaction medium is concentrated under reduced pressure. The oil obtained is taken up in 80 cm$^3$ of water and 100 cm$^3$ of ethyl acetate. After separation of the phases by settling, the organic phase is dried over sodium sulfate, filtered and then concentrated under reduced pressure. The residue obtained is purified by flash chromatography (SiO2, ethyl acetate/cyclohexane 50/50 by volume as eluent, argon). The fractions containing the product are concentrated under reduced pressure. 5 g of 2-(5,6-dimethoxy-1H-indol-3-yl)-4-(1,3-dioxolan)-2-yl-1-(toluene-4-sulfonyl)-1H-pyrrolo[2,3-b]pyridine are thus obtained, the characteristics of which are as follows:

Mass spectrum (EI): m/z=519 (M)$^+$; m/z=364 (M-C$_7$H$_7$SO$_2$)$^+$ base peak 1-t-Butyloxycarbonyl-5,6-dimethoxyindol-3-boronic acid is prepared according to the process described in patent WO 03/000688 A1.

f) 4-(1,3-Dioxolan)-2-yl-2-iodo-1-(toluene-4-sulfonyl)-1H-pyrrolo[2,3-b]pyridine may be prepared in the following manner:

5.81 cm$^3$ of n-BuLi (2.5M in hexane) are added dropwise to a solution of 5 g of 4-(1,3-dioxolan)-2-yl-1-(toluene-4-sulfonyl)-1H-pyrrolo[2,3-b]pyridine in 100 cm$^3$ of anhydrous tetrahydrofuran, under an inert atmosphere of argon at a temperature in the region of −78° C. The reaction medium is stirred at this same temperature for 25 minutes, and a solution of 7.37 g of iodine in 50 cm$^3$ of tetrahydrofuran are then added dropwise. The reaction medium is stirred at −78° C. for 15 minutes. The cooling bath is removed. The temperature rises to room temperature after stirring for 2 hours. The reaction medium is stirred at room temperature for 20 hours. 15 cm$^3$ of water and 15 cm$^3$ of ethyl acetate are added. After separation of the phases by settling, the organic phase is dried over sodium sulfate, filtered and then concentrated under reduced pressure. The residue obtained is purified by flash chromatography (SiO2, dichloromethane as eluent, argon). The fractions containing the product are concentrated under reduced pressure. 6.28 g of 4-(1,3-dioxolan)-2-yl-2-iodo-1-(toluene-4-sulfonyl)-1H-pyrrolo[2,3-b]pyridine are thus obtained, the characteristics of which are as follows:

Mass spectrum (ES): m/z=471 (M+H)$^+$ base peak g) 4-(1,3-Dioxolan)-2-yl-1-(toluene-4-sulfonyl)-1H-pyrrolo[2,3-b]pyridine may be prepared in the following manner:

2.15 cm$^3$ of ethylene glycol and 0.735 g of para-toluenesulfonic acid are added to a solution of 5.8 g of 1-(toluene-4-sulfonyl)-1H-pyrrolo[2,3-b]pyridine-4-carboxaldehyde in 250 cm$^3$ of toluene, under an inert atmosphere of argon. The reaction medium is heated at 120° C. for three hours. After cooling, 50 cm$^3$ of water and 50 cm$^3$ of ethyl acetate are added. After separation of the phases by settling, the organic phase is dried over sodium sulfate, filtered and then concentrated under reduced pressure. The residue obtained is triturated in ethyl ether. The solid obtained is filtered off and then washed with 20 cm$^3$ of ethyl ether. 5.3 g of 4-(1,3-dioxolan)-2-yl-1-(toluene-4-sulfonyl)-1H-pyrrolo[2,3-b]pyridine are thus obtained, the characteristics of which are as follows:

Mass spectrum (EI): m/z=344 (M)$^+$; m/z=237 (M-C$_7$H$_7$SO$_2$)$^+$ base peak; m/z=91 (C$_7$H$_7$)$^+$ h) 1-(Toluene-4-sulfonyl)-1H-pyrrolo[2,3-b]pyridine-4-carboxaldehyde may be prepared in the following manner:

50.5 cm$^3$ of diisobutylaluminum hydride (DIBAH) as a 20% by weight solution in toluene (1M) are added dropwise to a solution of 10 g of 1-(toluene-4-sulfonyl)-1H-pyrrolo[2,3-b]pyridine-4-carbonitrile in 400 cm$^3$ of toluene, under an inert atmosphere of argon at a temperature in the region of −30° C. After stirring for 40 minutes at this same temperature, the cooling bath is removed. The temperature is allowed to rise to 20° C. The reaction medium is stirred at a temperature in the region of 20° C. for 1 hour. The reaction medium is cooled to 4° C. 1N hydrochloric acid is added dropwise to pH 6. The precipitate formed is filtered off and then washed with 50 cm$^3$ of water and 280 cm$^3$ of ethyl acetate. After separating out the filtrate by settling, the organic phase is dried over sodium sulfate, filtered, concentrated under reduced pressure and then purified by column flash chromatography (SiO2, dichloromethane as eluent, Ar). The fractions containing the product are concentrated under reduced pressure. 4.3 g of 1-(toluene-4-sulfonyl)-1H-pyrrolo[2,3-b]pyridine-4-carboxaldehyde are thus obtained, the characteristics of which are as follows:

Mass spectrum (EI): m/z=300 (M)$^+$; m/z=236 (M-SO$_2$)$^+$; m/z=91; (C$_7$H$_7^+$) base peak i) 1-(Toluene-4-sulfonyl)-1H-pyrrolo[2,3-b]pyridine-4-carbonitrile may be prepared in the following manner:

6.9 g of zinc cyanide and 1.07 g of zinc powder are added to a solution of 10 g of 4-chloro-1-(toluene-4-sulfonyl)-1H-pyrrolo[2,3-b]pyridine in 200 cm$^3$ of N,N-dimethylacetamide, under an inert atmosphere of argon. After stirring for 45 minutes at a temperature in the region of 20° C., 2.4 g of [1,1'-bis(diphenylphosphino)ferrocene]palladium(II) (PdCl2, dppf) are added. The reaction medium is heated at a temperature in the region of 140° C. for 90 minutes. After cooling, the reaction medium is filtered through Celite and then rinsed with dichloromethane. 150 cm$^3$ of water are added to the filtrate. After separation of the phases by settling, the organic phase is dried over sodium sulfate, filtered and then concentrated under reduced pressure. After purification by column flash chromatography (SiO2, cyclohexane/ethyl acetate 75/25 by volume as eluent, Ar), 8.57 g of 1-(toluene-4-sulfonyl)-1H-pyrrolo[2,3-b]pyridine-4-carbonitrile are obtained, the characteristics of which are as follows:

Mass spectrum (EI): m/z=297 (M)$^+$; m/z=233 (M-SO$_2$)$^+$.; m/z=91 (C$_7$H$_7$)$^+$ base peak The compound 4-chloro-1-(toluene-4-sulfonyl)-1H-pyrrolo[2,3-b]pyridine is prepared according to the process described in patent WO 03/000688 A1.

EXAMPLE 179

[2-(5,6-Dimethoxy-1-methyl-1H-indol-3-yl)-1H-pyrrolo[2,3-b]pyrid-4-ylmethyl](4-trifluoromethylsulfanylbenzyl)amine (A003364149 (P-32520-098-1))

a) [2-(5,6-Dimethoxy-1-methyl-1H-indol-3-yl)-1H-pyrrolo[2,3-b]pyrid-4-ylmethyl](4-trifluoromethylsulfanylbenzyl)amine may be prepared in the following manner:

0.265 cm$^3$ of 5N potassium hydroxide is added to a solution of 0.04 g of [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine in 2 cm$^3$ of methanol, at a temperature in the region of 20° C. The reaction medium is refluxed for 6 hours. After cooling, the reaction medium is concentrated under reduced pressure. The residue obtained is taken up in 4 cm$^3$ of water. The solid formed is filtered off on a sinter funnel, washed twice with 3 cm$^3$ of water and then dried under vacuum to give 0.030 g of [2-(5,6-dimethoxy-1-methyl-1H-indol-3-yl)-1H-pyrrolo[2,3-b]pyrid-4-ylmethyl](4-trifluoromethylsulfanylbenzyl)amine, the characteristics of which are as follows:

$^1$H NMR spectrum (300 MHz, (CD$_3$)$_2$SO d6, δ in ppm): from 2.85 to 3.00 (broad m, 1H); 3.80 (s, 3H); 3.85 (s, 3H); 3.87 (s, 3H); from 3.78 to 3.90 (masked m, 2H); 4.06 (broad s, 2H); 6.79 (broad s, 1H); 7.07 (d, J=5.0 Hz, 1H); 7.11 (s, 1H); 7.45 (s, 1H); 7.58 (broad d, J=8.5 Hz, 2H); 7.68 (broad d, J=8.5 Hz, 2H); 7.76 (s, 1H); 8.07 (d, J=5.0 Hz, 1H); 11.7 (broad s, 1H).

Mass spectrum (EI): m/z=526 (M)$^+$; m/z=321 (M-C$_8$H$_6$SNF$_3$)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine may be prepared as described in Example 178b, starting with 0.065 g of 2-(5,6-dimethoxy-1-methyl-1H-indol-3-yl)-1-(toluene-4-sulfonyl)-1H-pyrrolo[2,3-b]pyrid-4-carboxaldehyde and 0.08 cm$^3$ of 4-trifluoromethylsulfanylbenzylamine instead of the cyclohexylamine used in Example 178b. After purification by flash-pack chromatography (SiO2, dichloromethane/methanol 98/02 by volume as eluent), 0.044 g of [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine is obtained, the characteristics of which are as follows:

Mass spectrum (EI): m/z=680 (M)$^+$; m/z=525 (M-C$_7$H$_7$SO$_2$)$^+$; m/z=320 (m/z=525 C$_8$H$_6$SNF$_3$)$^+$ base peak

EXAMPLE 180

Phenyl[2-(5,6-dimethoxy-1-methyl-1H-indol-3-yl)-1H-pyrrolo[2,3-b]pyrid-4-ylmethyl]amine (A003390480 (P-32520-140-4))

a) Phenyl[2-(5,6-dimethoxy-1-methyl-1H-indol-3-yl)-1H-pyrrolo[2,3-b]pyrid-4-ylmethyl]amine is prepared as described in Example 179a and, starting with 0.120 g of phenyl[2-(5,6-dimethoxy-1-methyl-1H-indol-3-yl)-1-(toluene-4-sulfonyl)-1H-pyrrolo[2,3-b]pyrid-4-ylmethyl]amine instead of the [2-(5,6-dimethoxy-1-methyl-1H-indol-3-yl)-1-(toluene-4-sulfonyl)-1H-pyrrolo[2,33-b]pyrid-4-ylmethyl](4-trifluoromethylsulfanylbenzyl)amine used in Example 179a, and 0.95 cm$^3$ of 5N potassium hydroxide. 0.010 g of phenyl[2-(5,6-dimethoxy-1-methyl-1H-indol-3-yl)-1H-pyrrolo[2,3-b]pyrid-4-ylmethyl]amine is obtained, the characteristics of which are as follows:

$^1$H NMR spectrum (300 MHz, (CD$_3$)$_2$SO d6, δ in ppm): 3.81 (s, 3H); 3.87 (s, 3H); 3.89 (s, 3H); 4.61 (d, J=6.0 Hz, 2H); 6.43 (t, J=6.0 Hz, 1H); 6.49 (broad t, J=7.5 Hz, 1H); 6.61 (broad d, J=7.5 Hz, 2H); 6.91 (d, J=2.0 Hz, 1H); from 6.96 to 7.05 (m, 3H); 7.11 (s, 1H); 7.47 (s, 1H); 7.76 (s, 1H); 8.02 (d, J=5.0 Hz, 1H); 11.7 (broad s, 1H).

Mass spectrum: (ES); m/z=413; (M+H)$^+$ base peak b) Phenyl[2-(5,6-dimethoxy-1-methyl-1H-indol-3-yl)-1-(toluene-4-sulfonyl)-1H-pyrrolo[2,3-b]pyrid-4-ylmethyl]amine is prepared as described in Example 178b starting with 0.1 g of 2-(5,6-dimethoxy-1-methyl-1H-indol-3-yl)-1-(toluene-4-sulfonyl)-1H-pyrrolo[2,3-b]pyrid-4-carboxaldehyde and 0.037 cm$^3$ of aniline instead of the cyclohexylamine used in Example 178b. After purification by flash-pack chromatography (SiO2, dichloromethane/methanol 98/02 by volume as eluent), 0.122 g of phenyl[2-(5,6-dimethoxy-1-methyl-1H-indol-3-yl)-1-(toluene-4-sulfonyl)-1H-pyrrolo[2,3-b]pyrid-4-ylmethyl]amine is obtained, the characteristics of which are as follows:

Mass spectrum (ES): m/z 567 (M+H)$^+$

EXAMPLE 181

Benzyl[2-(5,6-dimethoxy-1-methyl-1H-indol-3-yl)-1H-pyrrolo[2,3-b]pyrid-4-ylmethyl]amine (A003389983 (P-32520-141-1))

a) Benzyl[2-(5,6-dimethoxy-1-methyl-1H-indol-3-yl)-1H-pyrrolo[2,3-b]pyrid-4-ylmethyl]amine is prepared as described in Example 179a starting with 0.070 g of benzyl[2-(5,6-dimethoxy-1-methyl-1H-indol-3-yl)-1-(toluene-4-sulfonyl)-1H-pyrrolo[2,3-b]pyrid-4-ylmethyl]amine instead of the [2-(5,6-dimethoxy-1-methyl-1H-indol-3-yl)-1-(toluene-4-sulfonyl)-1H-pyrrolo[2,3-b]-pyrid-4-ylmethyl](4-trifluoromethylsulfanylbenzyl)amine used in Example 179a and 0.54 cm³ of 5N potassium hydroxide. 0.038 g of benzyl[2-(5,6-dimethoxy-1-methyl-1H-indol-3-yl)-1H-pyrrolo[2,3-b]pyrid-4-ylmethyl]amine is obtained, the characteristics of which are as follows:

$^1$H NMR spectrum (300 MHz, (CD$_3$)$_2$SO d6, δ in ppm): from 2.60 to 2.80 (broad m, 1H); 3.78 (broad s, 2H); 3.81 (s, 3H); 3.85 (s, 3H); 3.87 (s, 3H); 4.03 (broad s, 2H); 6.79 (d, J=2.0 Hz, 1H); 7.06 (d, J=5.0 Hz, 1H); 7.11 (s, 1H); 7.23 (broad t, J=7.5 Hz, 1H); 7.31 (broad t, J=7.5 Hz, 2H); 7.41 (broad d, J=7.5 Hz, 2H); 7.43 (s, 1H); 7.75 (s, 1H); 8.06 (d, J=5.0 Hz, 1H); 11.65 (broad s, 1H).

Mass spectrum (EI): m/z=426 (M)$^+$; m/z=321 (M-C$_8$H$_6$SNF$_3$)$^+$ base peak b) Benzyl[2-(5,6-dimethoxy-1-methyl-1H-indol-3-yl)-1-(toluene-4-sulfonyl)-1H-pyrrolo[2,3-b]pyrid-4-ylmethyl]amine is prepared as described in Example 178b starting with 0.1 g of 2-(5,6-dimethoxy-1-methyl-1H-indol-3-yl)-1-(toluene-4-sulfonyl)-1H-pyrrolo[2,3-b]pyrid-4-carboxaldehyde and 0.045 cm³ of benzylamine instead of the cyclohexylamine used in Example 178b. After purification by flash-pack chromatography (SiO2, dichloromethane/methanol 98/02 by volume as eluent), 0.071 g of benzyl[2-(5,6-dimethoxy-1-methyl-1H-indol-3-yl)-1-(toluene-4-sulfonyl)-1H-pyrrolo[2,3-b]pyrid-4-ylmethyl]amine is obtained, the characteristics of which are as follows:

Mass spectrum (ES): m/z=581 (M+H)$^+$; m/z=474 (M+H—C$_7$H$_9$N)$^+$ base peak

EXAMPLE 182

[2-(5,6-dimethoxy-1-methyl-1H-indol-3-yl)-1H-pyrrolo[2,3-b]pyrid-4-ylmethyl]phenylethylamine (A003391552 (P-32520-158-1))

a) [2-(5,6-Dimethoxy-1-methyl-1H-indol-3-yl)-1H-pyrrolo-[2,3-b]pyrid-4-ylmethyl]phenylethylamine is prepared as described in Example 179a starting with 0.16 g of [2-(5,6-dimethoxy-1-methyl-1H-indol-3-yl)-1-(toluene-4-sulfonyl)-1H-pyrrolo[2,3-b]pyrid-4-ylmethyl]phenylethylamine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1.2 cm³ of 5N potassium hydroxide. 0.038 g of [2-(5,6-dimethoxy-1-methyl-1H-indol-3-yl)-1H-pyrrolo[2,3-b]pyrid-4-ylmethyl]-phenylethylamine is obtained, the characteristics of which are as follows:

$^1$H NMR spectrum (300 MHz, (CD$_3$)$_2$SO d6, δ in ppm): from 2.10 to 2.25 (broad m, 1H); 2.75 to 2.86 (m, 4H); 3.81 (s, 3H); 3.87 (s, 6H); 4.07 (broad s, 2H); 6.80 (broad d, J=2.0 Hz, 1H); 6.99 (d, J=5.0 Hz, 1H); 7.11 (s, 1H); from 7.12 to 7.30 (m, 5H); 7.46 (s, 1H); 7.74 (s, 1H); 8.03 (d, J=5.0 Hz, 1H); 11.65 (broad s, 1H).

Mass spectrum (EI): m/z=440 (M)$^+$; m/z=320 (M-C$_8$H$_{10}$N)$^+$ base peak b) [2-(5,6-dimethoxy-1-methyl-1H-indol-3-yl)-1-(toluene-4-sulfonyl)-1H-pyrrolo[2,3-b]pyrid-4-ylmethyl]phenylethylamine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.192 cm³ of phenylethylamine instead of the cyclohexylamine used in Example 178b. After purification by flash-pack chromatography (SiO2, dichloromethane/methanol 99/01 and then dichloromethane/methanol 98.5/1.5 by volume as eluent), 0.17 g of [2-(5,6-dimethoxy-1-methyl-1H-indol-3-yl)-1-(toluene-4-sulfonyl)-1H-pyrrolo[2,3-b]pyrid-4-ylmethyl]phenylethylamine is obtained, the characteristics of which are as follows:

Mass spectrum (ES): m/z 595 (M+H)$^+$ base peak; m/z=474 (M+H—C$_8$H$_{11}$N)$^+$

EXAMPLE 183

[2-(5,6-dimethoxy-1-methyl-1H-indol-3-yl)-1H-pyrrolo[2,3-b]pyrid-4-ylmethyl]phenylpropylamine (A003390226 (P-32520-144-1))

a) [2-(5,6-dimethoxy-1-methyl-1H-indol-3-yl)-1H-pyrrolo[2,3-b]pyrid-4-ylmethyl]phenylpropylamine is prepared as described in Example 179a starting with 0.115 g of [2-(5,6-dimethoxy-1-methyl-1H-indol-3-yl)-1-(toluene-4-sulfonyl)-1H-pyrrolo[2,3-b]pyrid-4-ylmethyl]phenylpropylamine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.85 cm³ of 5N potassium hydroxide. 0.072 g of [2-(5,6-dimethoxy-1-methyl-1H-indol-3-yl)-1H-pyrrolo[2,3-b]pyrid-4-ylmethyl]-phenylpropylamine is obtained, the characteristics of which are as follows:

$^1$H NMR spectrum (300 MHz, (CD$_3$)$_2$SO d6, δ in ppm): 1.78 (m, 2H); from 2.15 to 2.40 (broad m, 1H); 2.58 (broad t, J=6.5 Hz, 2H); 2.64 (broad t, J=7.5 Hz, 2H); 3.78 (s, 3H); 3.81 (s, 3H); 3.86 (s, 3H); 4.02 (broad s, 2H); 6.82 (broad s, 1H); 7.00 (d, J=5.0 Hz, 1H); 7.09 (s, 1H); from 7.06 to 7.28 (m, 5H); 7.45 (s, 1H); 7.75 (s, 1H); 8.03 (d, J=5.0 Hz, 1H); 11.65 (broad s, 1H).

Mass spectrum (ES): m/z=455 (M+H)$^+$; m/z=320 (M+H—C$_9$H$_{13}$N)$^+$ base peak b) [2-(5,6-dimethoxy-1-methyl-1H-indol-3-yl)-1-(toluene-4-sulfonyl)-1H-pyrrolo[2,3-b]pyrid-4-ylmethyl]phenylpropylamine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.218 cm³ of phenylpropylamine instead of the cyclohexylamine used in Example 178b. After purification by flash-pack chromatography (SiO2, dichloromethane/methanol 98/02 by volume as eluent), 0.120 g of [2-(5,6-dimethoxy-1-methyl-1H-indol-3-yl)-1-(toluene-4-sulfonyl)-1H-pyrrolo[2,3-b]pyrid-4-ylmethyl]phenylpropylamine is obtained, the characteristics of which are as follows:

Mass spectrum (EI): m/z=608 (M)$^+$; m/z=453 (M-C$_7$H$_7$SO$_2$)$^+$; m/z=320 (m/z=453-C$_9$H$_{11}$N)$^+$ base peak

EXAMPLE 184

[2-(5,6-dimethoxy-1-methyl-1H-indol-3-yl)-1H-pyrrolo[2,3-b]pyrid-4-ylmethyl]thiophen-2-ylmethylamine (A003391639 (P-32520-162-1))

a) [2-(5,6-dimethoxy-1-methyl-1H-indol-3-yl)-1H-pyrrolo[2,3-b]pyrid-4-ylmethyl]thiophen-2-ylmethylamine is prepared as described in Example 179a starting with 0.11 g of [2-(5,6-dimethoxy-1-methyl-1H-indol-3-yl)-1-(toluene-4-sulfonyl)-1H-pyrrolo[2,3-b]pyrid-4-ylmethyl]thiophen-2-ylmethylamine instead of the [2-(5,6-dimethoxy-1-methyl-1H-indol-3-yl)-1-(toluene-4-sulfonyl)-1H-pyrrolo[2,3-b]pyrid-4-ylmethyl] (4-trifluoromethylsulfanylbenzyl)amine used in Example 179a and 0.85 cm³ of 5N potassium hydroxide. 0.056 g of [2-(5,6-dimethoxy-1-methyl-1H-indol-3-yl)-

1H-pyrrolo[2,3-b]pyrid-4-ylmethyl]thiophen-2-ylmethylamine is obtained, the characteristics of which are as follows:

$^1$H NMR spectrum (300 MHz, (CD$_3$)$_2$SO d6, δ in ppm): 2.87 (broad m, 1H); 3.81 (s, 3H); 3.87 (s, 6H); 3.95 (m, 2H); 4.04 (m, 2H); 6.81 (d, J=2.0 Hz, 1H); from 6.95 to 7.01 (m, 2H); 7.03 (d, J=5.0 Hz, 1H); 7.11 (s, 1H); 7.39 (dd, J=2.0 and 5.0 Hz, 1H); 7.47 (s, 1H); 7.77 (s, 1H); 8.07 (d, J=5.0 Hz, 1H); 11.7 (broad s, 1H).

Mass spectrum (ES): m/z=433 (M+H)$^+$; m/z=337 (M+H—C$_5$H$_4$S)$^+$ base peak; m/z=320 (M+H—C$_5$H$_7$NS)$^+$ b) [2-(5,6-dimethoxy-1-methyl-1H-indol-3-yl)-1-(toluene-4-sulfonyl)-1H-pyrrolo[2,3-b]pyrid-4-ylmethyl]thiophen-2-ylmethylamine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.158 cm$^3$ of thiophen-2-methylamine instead of the cyclohexylamine used in Example 178b. After purification by flash-pack chromatography (SiO2, dichloromethane/methanol 99/01 and then dichloromethane/methanol 98.5/1.5 by volume as eluent), 0.11 g of [2-(5,6-dimethoxy-1-methyl-1H-indol-3-yl)-1-(toluene-4-sulfonyl)-1H-pyrrolo[2,3-b]pyrid-4-ylmethyl]thiophen-2-ylmethylamine is obtained, the characteristics of which are as follows:

Mass spectrum (ES): m/z=587 (M+H)$^+$ base peak; m/z=474 (M+H—C$_5$H$_7$NS)$^+$

EXAMPLE 185

[2-(5,6-dimethoxy-1-methyl-1H-indol-3-yl)-1H-pyrrolo[2,3-b]pyrid-4-ylmethyl]thiophen-2-ylethylamine (A003391615 (P-32520-160-1))

a) [2-(5,6-dimethoxy-1-methyl-1H-indol-3-yl)-1H-pyrrolo[2,3-b]pyrid-4-ylmethyl]thiophen-2-ylethylamine is prepared as described in Example 179a starting with 0.15 g of [2-(5,6-dimethoxy-1-methyl-1H-indol-3-yl)-1-(toluene-4-sulfonyl)-1H-pyrrolo[2,3-b]pyrid-4-ylmethyl]thiophen-2-ylethylamine instead of the [2-(5,6-dimethoxy-1-methyl-1H-indol-3-yl)-1-(toluene-4-sulfonyl)-1H-pyrrolo[2,3-b]pyrid-4-ylmethyl] (4-trifluoromethylsulfanylbenzyl)amine used in Example 179a and 1.12 cm$^3$ of 5N potassium hydroxide. 0.082 g of [2-(5,6-dimethoxy-1-methyl-1H-indol-3-yl)-1H-pyrrolo[2,3-b]pyrid-4-ylmethyl]thiophen-2-ylethylamine is obtained, the characteristics of which are as follows:

$^1$H NMR spectrum (300 MHz, (CD$_3$)$_2$SO d6, δ in ppm): from 2.25 to 2.38 (broad m, 1H); 2.86 (broad t, J=6.5 Hz, 2H); 3.00 (t, J=6.5 Hz, 2H); 3.80 (s, 3H); 3.86 (s, 6H); 4.07 (broad s, 2H); 6.80 (broad d, J=2.0 Hz, 1H); 6.87 (broad d, J=3.5 Hz, 1H); 6.91 (dd, J=3.5 and 5.0 Hz, 1H); 7.01 (d, J=5.0 Hz, 1H); 7.10 (s, 1H); 7.27 (broad d, J=5.0 Hz, 1H); 7.47 (s, 1H); 7.76 (s, 1H); 8.04 (d, J=5.0 Hz, 1H); 11.65 (broad s, 1H).

Mass spectrum (ES): m/z=447 (M+H)$^+$; m/z=320 (M+H—C$_6$H$_9$NS)$^+$ base peak b) [2-(5,6-dimethoxy-1-methyl-1H-indol-3-yl)-1-(toluene-4-sulfonyl)-1H-pyrrolo[2,3-b]pyrid-4-ylmethyl]thiophen-2-ylethylamine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.179 cm$^3$ of thiophen-2-ethylamine instead of the cyclohexylamine used in Example 178b. After purification by flash-pack chromatography (SiO2, dichloromethane/methanol 99/01 and then dichloromethane/methanol 98.5/1.5 by volume as eluent), 0.15 g of [2-(5,6-dimethoxy-1-methyl-1H-indol-3-yl)-1-(toluene-4-sulfonyl)-1H-pyrrolo[2,3-b]pyrid-4-ylmethyl]thiophen-2-ylethylamine is obtained, the characteristics of which are as follows:

Mass spectrum (ES): m/z=60.1 (M+H)$^+$; m/z=474 (MH—C$_6$H$_9$NS)$^+$ base peak

EXAMPLE 186

[2-(5,6-dimethoxy-1-methyl-1H-indol-3-yl)-1H-pyrrolo[2,3-b]pyrid-4-ylmethyl](2-methoxyethyl)amine (A003391652 (P-32520-163-1))

a) [2-(5,6-Dimethoxy-1-methyl-1H-indol-3-yl)-1H-pyrrolo[2,3-b]pyrid-4-ylmethyl](2-methoxyethyl)amine is prepared as described in Example 179a starting with 0.12 g of [2-(5,6-dimethoxy-1-methyl-1H-indol-3-yl)-1-(toluene-4-sulfonyl)-1H-pyrrolo[2,3-b]pyrid-4-ylmethyl](2-methoxyethyl)amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.99 cm$^3$ of 5N potassium hydroxide. 0.081 g of [2-(5,6-dimethoxy-1-methyl-1H-indol-3-yl)-1H-pyrrolo[2,3-b]pyrid-4-ylmethyl](2-methoxyethyl)amine is obtained, the characteristics of which are as follows:

$^1$H NMR spectrum (300 MHz, (CD$_3$)$_2$SO d6, δ in ppm): from 2.13 to 2.29 (broad m, 1H); 2.73 (broad t, J=6.5 Hz, 2H); 3.25 (s, 3H); 3.45 (t, J=6.5 Hz, 2H); 3.81 (s, 3H); 3.87 (s, 3H); 3.89 (s, 3H); 4.04 (broad s, 2H); 6.81 (broad d, J=2.0 Hz, 1H); 7.01 (d, J=5.0 Hz, 1H); 7.11 (s, 1H); 7.47 (s, 1H); 7.74 (s, 1H); 8.04 (d, J=5.0 Hz, 1H); 11.65 (broad s, 1H).

Mass spectrum (ES): m/z=395 (M+H)$^+$; m/z=320 (M+H—C$_3$H$_9$NO)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl](2-ethoxyethyl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.134 cm$^3$ of 2-methoxyethylamine instead of the cyclohexylamine used in Example 178b. After purification by flash-pack chromatography (SiO2, dichloromethane/methanol 99/01 and then dichloromethane/methanol 98.5/1.5 by volume as eluent), 0.11 g of [2-(5,6-dimethoxy-1-methyl-1H-indol-3-yl)-1-(toluene-4-sulfonyl)-1H-pyrrolo[2,3-b]pyrid-4-ylmethyl](2-methoxyethyl)amine is obtained, the characteristics of which are as follows:

Mass spectrum (ES): m/z 549 (M+H)$^+$ base peak; m/z=474 (M+H—C$_3$H$_9$NO)$^+$

EXAMPLE 187

4-({[2-(5,6-dimethoxy-1-methyl-1H-indol-3-yl)-1H-pyrrolo[2,3-b]pyrid-4-ylmethyl]amino}methyl)phenylamine (A003393788 (P-33047-027-1))

4-({[2-(5,6-Dimethoxy-1-methyl-1H-indol-3-yl)-1H-pyrrolo[2,3-b]pyrid-4-ylmethyl]amino}methyl)phenylamine may be prepared in the following manner:

1.6 cm$^3$ of hydrochloric acid (4N in dioxane) are added to a solution of 0.07 g of 4-[({[2-(5,6-dimethoxy-1-methyl-1H-indol-3-yl)-1H-pyrrolo[2,3-b]pyrid-4-ylmethyl]amino}methyl)phenyl]carbamic acid tert-butyl ester in 1.5 cm$^3$ of dioxane and 0.5 cm$^3$ of DMF, at a temperature in the region of 20° C. The reaction medium is stirred at room temperature for 24 hours. The reaction medium is concentrated under reduced pressure. The residue obtained is taken up in 4 cm$^3$ of water and is then neutralized with triethylamine. 4 cm³ of dichloromethane are added. After separation of the phases by settling, the organic phase is dried over magnesium sulfate, filtered and then concentrated under reduced pressure. The residue obtained is taken up in 5 cm³ of water. The solid formed is filtered off on a sinter funnel, washed twice with 3 cm³ of water and then dried under vacuum to give 0.036 g of 4-({[2-(5,6-dimethoxy-1-methyl-1H-indol-3-yl)-1H-pyrrolo[2,3-b]pyrid-4-ylmethyl]amino}methyl)phenylamine, the characteristics of which are as follows:

$^1$H NMR spectrum (300 MHz, (CD$_3$)$_2$SO d6, δ in ppm): from 3.60 to 3.78 (broad m, 2H); 3.81 (s, 3H); 3.87 (s, 6H); from 4.02 to 4.13 (broad m, 2H); from 4.85 to 5.02 (broad m, 2H); 6.53 (broad d, J=8.5 Hz, 2H); 6.80 (broad s, 1H); from 7.01 to 7.10 (m, 3H); 7.12 (s, 1H); 7.45 (s, 1H); 7.77 (s, 1H); 8.09 (d, J=5.0 Hz, 1H); 11.7 (broad m, 1H).

Mass spectrum (EI): m/z=441 (M)$^+$; m/z 321 (M-C$_7$H$_8$N$_2$)$^+$ base peak

EXAMPLE 188

4-[({[2-(5,6-dimethoxy-1-methyl-1H-indol-3-yl)-1H-pyrrolo[2,3-b]pyrid-4-ylmethyl]amino}methyl)phenyl]carbamic acid tert-butyl ester (A003393158 (P-33047-016-1))

a) 4-[({[2-(5,6-Dimethoxy-1-methyl-1H-indol-3-yl)-1H-pyrrolo[2,3-b]pyrid-4-ylmethyl]amino}methyl)phenyl]carbamic acid tert-butyl ester is prepared as described in Example 179a starting with 0.16 g of 4-[({[2-(5,6-dimethoxy-1-methyl-1H-indol-3-yl)-1-(toluene-4-sulfonyl)-1H-pyrrolo[2,3-b]pyrid-4-ylmethyl]amino}methyl)phenyl]carbamic acid tert-butyl ester instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1.04 cm³ of 5N potassium hydroxide. 0.093 g of 4-[({[2-(5,6-dimethoxy-1-methyl-1H-indol-3-yl)-1H-pyrrolo[2,3-b]pyrid-4-ylmethyl]amino}methyl)phenyl]carbamic acid tert-butyl ester is obtained, the characteristics of which are as follows:

$^1$H NMR spectrum (300 MHz, (CD$_3$)$_2$SO d6, δ in ppm): 1.48 (s, 9H); 2.60 (broad m, 1H); 3.69 (m, 2H); 3.81 (s, 3H); 3.86 (s, 3H); 3.87 (s, 3H); 4.00 (m, 2H); 6.78 (broad d, J=2.0 Hz, 1H); 7.05 (d, J=5.0 Hz, 1H); 7.11 (s, 1H); 7.25 (broad d, J=8.5 Hz, 2H); 7.40 (broad d, J=8.5 Hz, 2H); 7.42 (s, 1H); 7.74 (s, 1H); 8.06 (d, J=5.0 Hz, 1H); 9.22 (broad s, 1H); 11.65 (broad s, 1H).

Mass spectrum (ES): m/z=542 (M+H)$^+$ base peak; m/z=337 (M+H—C$_{12}$H$_{15}$NO$_2$)$^+$ b) 4-[({[2-(5,6-Dimethoxy-1-methyl-1H-indol-3-yl)-1-(toluene-4-sulfonyl)-1H-pyrrolo[2,3-b]pyrid-4-ylmethyl]amino}methyl)phenyl]carbamic acid tert-butyl ester is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.340 cm³ of (4-(aminomethyl)phenyl)carbamic acid tert-butyl ester instead of the cyclohexylamine used in Example 178b. After purification by flash-pack chromatography (SiO2, dichloromethane/methanol 99/01 and then dichloromethane/methanol 98.5/1.5 by volume as eluent), 0.16 g of 4-[({[2-(5,6-dimethoxy-1-methyl-1H-indol-3-yl)-1-(toluene-4-sulfonyl)-1H-pyrrolo[2,3-b]pyrid-4-ylmethyl]amino}methyl)phenyl]carbamic acid tert-butyl ester is obtained, the characteristics of which are as follows:

Mass spectrum (ES): m/z=696 (M+H)$^+$; m/z=337 (M+H—C$_{12}$H$_{15}$NO$_2$)$^+$ base peak

EXAMPLE 189

[2-(5,6-dimethoxy-1-methyl-1H-indol-3-yl)-1H pyrrolo[2,3-b]pyrid-4-ylmethyl](4-trifluoromethylsulfanylphenyl)amine (A003403451 (P-33047-052-1))

a) [2-(5,6-Dimethoxy-1-methyl-1H-indol-3-yl)-1H-pyrrolo[2,3-b]pyrid-4-ylmethyl](4-trifluoromethylsulfanylphenyl)amine is prepared as described in Example 179a starting with 0.08 g of [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylphenyl)amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.53 cm³ of 5N potassium hydroxide. 0.068 g of phenyl [2-(5,6-dimethoxy-1-methyl-1H-indol-3-yl)-1H-pyrrolo[2,3-b]pyrid-4-ylmethyl] (4-trifluoromethylsulfanylphenyl)amine is obtained, the characteristics of which are as follows:

$^1$H NMR spectrum (300 MHz, (CD$_3$)$_2$SO d6, δ in ppm): 3.80 (s, 3H); 3.86 (s, 3H); 3.88 (s, 3H); 4.67 (d, J=6.0 Hz, 2H); 6.70 (broad d, J=8.5 Hz, 2H); 6.90 (broad s, 1H); 6.97 (d, J=5.0 Hz, 1H); 7.10 (s, 1H); 7.23 (broad t, J=6.0 Hz, 1H); 7.32 (broad d, J=8.5 Hz, 2H); 7.47 (s, 1H); 7.77 (s, 1H); 8.04 (d, J=5.0 Hz, 1H); 11.75 (broad m, 1H).

Mass spectrum (EI): m/z=512 (M)$^+$; m/z=320 (M-C$_7$H$_5$SNF$_3$) base peak b) [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylphenyl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.219 cm³ of 4-(trifluoromethylsulfanyl)aniline instead of the cyclohexylamine used in Example 178b. After purification by flash-pack chromatography (SiO2, dichloromethane/methanol 98/02 by volume as eluent), 0.084 g of [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylphenyl)amine is obtained, the characteristics of which are as follows:

Mass spectrum (ES): m/z=667 (M+H)$^+$ base peak

EXAMPLE 190

Cyclopropyl[2-(5,6-dimethoxy-1-methyl-1H-indol-3-yl)-1H-pyrrolo[2,3-b]pyrid-4-ylmethyl]amine (A003403453 (P-33047-058-1))

a) Cyclopropyl[2-(5,6-dimethoxy-1-methyl-1H-indol-3-yl)-1H-pyrrolo[2,3-b]pyrid-4-ylmethyl]amine is prepared as described in Example 179a starting with 0.06 g of cyclopropyl[2-(5,6-dimethoxy-1-methyl-1H-indol-3-yl)-1-(toluene-4-sulfonyl)-1H-pyrrolo[2,3-b]pyrid-4-ylmethyl]amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.5 cm³ of 5N potassium hydroxide. 0.034 g of cyclopropyl[2-(5,6-dimethoxy-1-methyl-1H-indol-3-yl)-1H-pyrrolo[2,3-b]pyrid-4-ylmethyl]amine is obtained, the characteristics of which are as follows:

$^1$H NMR spectrum (300 MHz, (CD$_3$)$_2$SO d6, δ in ppm): from 0.30 to 0.42 (m, 4H); 2.13 (m, 1H); from 2.72 to 2.86 (broad m, 1H); 3.80 (s, 3H); 3.86 (s, 3H); 3.88 (s, 3H); 4.06 (broad s, 2H); 6.81 (d, J=2.0 Hz, 1H); 7.00 (d, J=5.0 Hz, 1H); 7.11 (s, 1H); 7.47 (s, 1H); 7.75 (s, 1H); 8.04 (d, J=5.0 Hz, 1H); 11.65 (broad m, 1H).

Mass spectrum (EI): m/z=376 (M)$^+$; m/z=320 (M-C$_3$H$_6$N)$^+$ base peak b) Cyclopropyl[2-(5,6-dimethoxy-1-methyl-1H-indol-3-yl)-1-(toluene-4-sulfonyl)-1H-pyrrolo[2,3-b]pyrid-4-ylmethyl]amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.107 cm$^3$ of cyclopropylamine instead of the cyclohexylamine used in Example 178b. After purification by flash-pack chromatography (SiO2, dichloromethane/methanol 98/02 by volume as eluent), 0.075 g of cyclopropyl[2-(5,6-dimethoxy-1-methyl-1H-indol-3-yl)-1-(toluene-4-sulfonyl)-1H-pyrrolo[2,3-b]pyrid-4-ylmethyl]amine is obtained, the characteristics of which are as follows:

Mass spectrum (EI): m/z=530 (M)$^+$; m/z=375 (M-C$_7$H$_7$SO$_2$) base peak; m/z=320 (m/z=375-C$_3$H$_5$N)$^+$

EXAMPLE 191

[2-(5,6-dimethoxy-1-methyl-1H-indol-3-yl)-1H-pyrrolo[2,3-b]pyrid-4-ylmethyl](4-morpholin-4-ylphenyl)amine (A003403814 (P-33047-056-2))

a) [2-(5,6-Dimethoxy-1-methyl-1H-indol-3-yl)-1H-pyrrolo[2,3-b]pyrid-4-ylmethyl](4-morpholin-4-ylphenyl)amine is prepared as described in Example 179a starting with 0.16 g of [2-(5,6-dimethoxy-1-methyl-1H-indol-3-yl)-1-(toluene-4-sulfonyl)-1H-pyrrolo[2,3-b]pyrid-4-ylmethyl](4-morpholin-4-ylphenyl)amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1.08 cm$^3$ of 5N potassium hydroxide. 0.068 g of [2-(5,6-dimethoxy-1-methyl-1H-indol-3-yl)-1H-pyrrolo[2,3-b]pyrid-4-ylmethyl](4-morpholin-4-ylphenyl)amine is obtained, the characteristics of which are as follows:

$^1$H NMR spectrum (300 MHz, (CD$_3$)$_2$SO d6, δ in ppm): 2.83 (m, 4H); 3.67 (m, 4H); 3.80 (s, 3H); 3.85 (s, 3H); 3.89 (s, 3H); 4.58 (d, J=6.0 Hz, 2H); 6.02 (t, J=6.0 Hz, 1H); 6.56 (broad d, J=8.5 Hz, 2H); 6.70 (broad d, J=8.5 Hz, 2H); 6.91 (d, J=2.0 Hz, 1H); 6.98 (d, J=5.0 Hz, 1H); 7.10 (s, 1H); 7.48 (s, 1H); 7.75 (s, 1H); 8.01 (d, J=5.0 Hz, 1H); 11.7 (broad m, 1H).

Mass spectrum (EI): m/z=497 (M)$^+$; m/z=320 (M-C$_{10}$H$_{13}$N$_2$O)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl](4-morpholin-4-ylphenyl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.273 g of 4-morpholin-4-ylphenylamine instead of the cyclohexylamine used in Example 178b. After purification by flash-pack chromatography (SiO2, dichloromethane/methanol 98/02 by volume as eluent), 0.164 g of [2-(5,6-dimethoxy-1-methyl-1H-indol-3-yl)-1-(toluene-4-sulfonyl)-1H-pyrrolo[2,3-b]pyrid-4-ylmethyl] (4-morpholin-4-ylphenyl)amine is obtained, the characteristics of which are as follows:

Mass spectrum (EI): m/z=651 (M)$^+$; m/z=496 (M-C$_7$H$_7$SO$_2$)$^+$; m/z=177 (C$_{10}$H$_{13}$N$_2$O)$^+$ base peak

EXAMPLE 192

[2-(5,6-dimethoxy-1-methyl-1H-indol-3-yl)-1H-pyrrolo[2,3-b]pyrid-4-ylmethyl](2-methyl-2H-pyrazol-3-yl)amine (A003405576 (P-33047-062-1))

a) [2-(5,6-dimethoxy-1-methyl-1H-indol-3-yl)-1H-pyrrolo[2,3-b]pyrid-4-ylmethyl](2-methyl-2H-pyrazol-3-yl)amine is prepared as described in Example 179a starting with 0.08 g of [2-(5,6-dimethoxy-1-methyl-1H-indol-3-yl)-1-(toluene-4-sulfonyl)-1H-pyrrolo[2,3-b]pyrid-4-ylmethyl](2-methyl-2H-pyrazol-3-yl)amine trifluoroacetate instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.62 cm$^3$ of 5N potassium hydroxide. After purification by flash-pack chromatography (SiO2, dichloromethane/methanol 98/02 by volume as eluent), 0.024 g of [2-(5,6-dimethoxy-1-methyl-1H-indol-3-yl)-1H-pyrrolo[2,3-b]pyrid-4-ylmethyl](2-methyl-2H-pyrazol-3-yl)amine is obtained, the characteristics of which are as follows:

$^1$H NMR spectrum (300 MHz, (CD$_3$)$_2$SO d6, δ in ppm): 3.60 (s, 3H); 3.81 (s, 3H); 3.86 (s, 3H); 3.88 (s, 3H); 4.53 (d, J=6.0 Hz, 2H); 5.28 (d, J=2.0 Hz, 1H); 6.24 (broad t, J=6.0 Hz, 1H); 6.90 (d, J=2.0 Hz, 1H); 7.00 (d, J=2.0 Hz, 1H); 7.02 (d, J=5.0 Hz, 1H); 7.11 (s, 1H); 7.47 (s, 1H); 7.77 (s, 1H); 8.04 (d, J=5.0 Hz, 1H); 11.7 (broad s, 1H).

Mass spectrum (EI): m/z=416 (M)$^+$; m/z=320 (M-C$_4$H$_6$N$_3$)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl](2-methyl-2H-pyrazol-3-yl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.149 g of 1-methyl-1H-pyrazol-5-ylamine instead of the cyclohexylamine used in Example 178b. After purification by flash-pack chromatography (SiO2, dichloromethane/methanol 98/02 by volume as eluent), followed by chromatography on a column of Kromasil C8 10 μm, eluents: water/acetonitrile/TFA 70/30/0.1 by volume, 0.08 g of [2-(5,6-dimethoxy-1-methyl-1H-indol-3-yl)-1-(toluene-4-sulfonyl)-1H-pyrrolo[2,3-b]pyrid-4-ylmethyl](2-methyl-2H-pyrazol-3-yl)amine trifluoroacetate is obtained, the characteristics of which are as follows:

Mass spectrum (EI): m/z=570 (M)$^+$; m/z=415 (M-C$_7$H$_7$SO$_2$)$^+$ base peak; m/z=320 (m/z=415-C$_4$H$_5$N$_3$)$^+$

EXAMPLE 193

[2-(5,6-dimethoxy-1-methyl-1H-indol-3-yl)-1H-pyrrolo[2,3-b]pyrid-4-ylmethyl](1-methylpiperid-4-yl)amine (A003440113 (P-33047-137-1))

a) [2-(5,6-Dimethoxy-1-methyl-1H-indol-3-yl)-1H-pyrrolo[2,3-b]pyrid-4-ylmethyl](1-methylpiperid-4-yl)amine is prepared as described in Example 179a starting with 0.07 g of [2-(5,6-dimethoxy-1-methyl-1H-indol-3-yl)-1-(toluene-4-sulfonyl)-1H-pyrrolo[2,3-b]pyrid-4-ylmethyl](1-methylpiperid-4-yl)amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.48 cm$^3$ of 5N potassium hydroxide. 0.042 g of [2-(5,6-dimethoxy-1-methyl-1H-indol-3-yl)-1H-pyrrolo[2,3-b]pyrid-4-ylmethyl](1-methylpiperid-4-yl)amine is obtained, the characteristics of which are as follows:

¹H NMR spectrum (300 MHz, (CD₃)₂SO d6, δ in ppm):
1.34 (m, 2H); 1.85 (m, 4H); 2.11 (s, 3H); 2.42 (m, 1H); 2.69 (m, 2H); 3.81 (s, 3H); 3.87 (s, 3H); 3.88 (s, 3H); 4.05 (s, 2H); 6.81 (d, J=2.0 Hz, 1H); 7.02 (d, J=5.0 Hz, 1H); 7.11 (s, 1H); 7.44 (s, 1H); 7.75 (s, 1H); 8.03 (d, J=5.0 Hz, 1H); 11.65 (broad s, 1H).

Mass spectrum (ES): m/z=434 (M+H)⁺; m/z=218 (M+2H)²⁺/2; base peak b) [2-(5,6-Dimethoxy-methyl-1H-indol-3-yl)-1-(toluene-4-sulfonyl)-1H-pyrrolo[2,3-b]pyrid-4-ylmethyl](1-methylpiperid-4-yl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.175 g of 1-methyl-4-aminopiperidine instead of the cyclohexylamine used in Example 178b. After purification by flash-pack chromatography (SiO2, dichloromethane/methanol 90/10 by volume as eluent), 0.070 g of [2-(5,6-dimethoxy-1-methyl-1H-indol-3-yl)-1-(toluene-4-sulfonyl)-1H-pyrrolo[2,3-b]pyrid-4-ylmethyl](1-methylpiperid-4-yl)amine is obtained, the characteristics of which are as follows:

Mass spectrum (IC): m/z=588 (M+H)⁺ base peak

EXAMPLE 194

(2,4-dimethoxybenzyl) [2-(5,6-dimethoxy-1-methyl-1H-indol-3-yl)-1H-pyrrolo[2,3-b]pyrid-4-ylmethyl]amine (A003408775 (P-32989-041-1))

a) (2,4-Dimethoxybenzyl)[2-(5,6-dimethoxy-1-methyl-1H-indol-3-yl)-1H-pyrrolo[2,3-b]pyrid-4-ylmethyl]amine is prepared as described in Example 179a starting with 0.05 g of (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.36 cm³ of 5N potassium hydroxide. 0.03 g of (2,4-dimethoxybenzyl)[2-(5,6-dimethoxy-1-methyl-1H-indol-3-yl)-1H-pyrrolo[2,3-b]pyrid-4-ylmethyl]amine is obtained, the characteristics of which are as follows:

¹H NMR spectrum (300 MHz, (CD₃)₂SO d6, δ in ppm):
3.67 (broad s, 2H); 3.72 (s, 3H); 3.73 (s, 3H); 3.81 (s, 3H); 3.85 (s, 3H); 3.87 (s, 3H); 4.04 (broad s, 2H); 6.49 (dd, J=2.5 and 8.5 Hz, 1H); 6.52 (d, J=2.5 Hz, 1H); 6.76 (d, J=2.0 Hz, 1H); 7.06 (d, J=5.0 Hz, 1H); 7.11 (s, 1H); 7.28 (d, J=8.5 Hz, 1H); 7.42 (s, 1H); 7.75 (s, 1H); 8.06 (d, J=5.0 Hz, 1H); 11.65 (broad s, 1H).

Mass spectrum (ES): m/z=487 (M+H)⁺ base peak b) (2,4-Dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine is prepared as described in Example 178b starting with 2 g of 2-(5,6-dimethoxy-1-methyl-1H-indol-3-yl)-1-(toluene-4-sulfonyl)-1H-pyrrolo[2,3-b]pyrid-4-carboxaldehyde and 3.39 g of 2,4-dimethoxybenzylamine instead of the cyclohexylamine used in Example 178b. After purification by flash-pack chromatography (SiO2, dichloromethane/methanol 98/02 by volume as eluent), 1.2 g of (2,4-dimethoxybenzyl) [2-(5,6-dimethoxy-1-methyl-1H-indol-3-yl)-1-(toluene-4-sulfonyl)-1H-pyrrolo[2,3-b]pyrid-4-ylmethyl]amine are obtained, the characteristics of which are as follows:

Mass spectrum (ES): m/z=641 (M+H)⁺; m/z=486 (M+H—C₇H₇SO₂)⁺

EXAMPLE 195

[2-(5,6-dimethoxy-1-methyl-1H-indol-3-yl)-1H-pyrrolo[2,3-b]pyrid-4-ylmethyl](4-piperid-1-ylphenyl)amine (A003425429 (P-333047-107-1))

a) [2-(5,6-Dimethoxy-1-methyl-1H-indol-3-yl)-1H-pyrrolo[2,33-b]pyrid-4-ylmethyl](4-piperid-1-ylphenyl)amine is prepared as described in Example 179a starting with 0.09 g of [2-(5,6-dimethoxy-1-methyl-1H-indol-3-yl)-1-(toluene-4-sulfonyl)-1H-pyrrolo[2,3-b]pyrid-4-ylmethyl](4-piperid-1-ylphenyl)amine instead of the [2-(5,6-dimethoxy-1-methyl-1H-indol-3-yl)-1-(toluene-4-sulfonyl)-1H-pyrrolo[2,3-b]pyrid-4-ylmethyl] (4-trifluoromethylsulfanylbenzyl)amine used in Example 179a and 0.55 cm³ of 5N potassium hydroxide. 0.016 g of [2-(5,6-dimethoxy-1-methyl-1H-indol-3-yl)-1H-pyrrolo[2,3-b]pyrid-4-ylmethyl](4-piperid-1-ylphenyl)amine is obtained, the characteristics of which are as follows:

¹H NMR spectrum (300 MHz, (CD₃)₂SO d6, δ in ppm):
1.45 (m, 2H); 1.59 (m, 4H); 2.83 (m, 4H); 3.82 (s, 3H); 3.88 (s, 3H); 3.90 (s, 3H); 4.57 (broad m, 2H); 6.00 (broad m, 1H); 6.55 (broad d, J=8.5 Hz, 2H); 6.70 (broad d, J=8.5 Hz, 2H); 6.92 (broad s, 1H); 7.00 (broad d, J=5.0 Hz, 1H); 7.11 (broad s, 1H); 7.49 (broad s, 1H); 7.78 (broad s, 1H); 8.02 (broad d, J=5.0 Hz, 1H); 11.7 (broad s, H).

Mass spectrum (EI): m/z=495 (M)⁺; m/z=320 (M-C₁₁H₁₅N₂)⁺; m/z=175 (C₁₁H₁₅N₂⁺) base peak b) [2-(5,6-Dimethoxy-1-methyl-1H-indol-3-yl)-1-(toluene-4-sulfonyl)-1H-pyrrolo[2,3-b]pyrid-4-ylmethyl](4-piperid-1-ylphenyl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.27 g of (4-piperid-1-ylphenyl)amine instead of the cyclohexylamine used in Example 178b. After purification by flash-pack chromatography (SiO2, dichloromethane/methanol 99/01 by volume as eluent), 0.12 g of [2-(5,6-dimethoxy-1-methyl-1H-indol-3-yl)-1-(toluene-4-sulfonyl)-1H-pyrrolo[2,3-b]pyrid-4-ylmethyl](4-piperid-1-ylphenyl)amine is obtained as a mixture (60/40) with [2-(5,6-dimethoxy-1-methyl-1H-indol-3-yl)-1-(toluene-4-sulfonyl)-1H-pyrrolo[2,3-b]pyrid-4-ylmethyl](4-piperid-1-ylphenyl)imine.

This mixture is dissolved in 7 cm³ of ethanol, at a temperature in the region of 20° C. 0.016 g of sodium borohydride is added. The reaction medium is stirred at room temperature for 24 hours. The reaction medium is concentrated under reduced pressure. The residue obtained is taken up in 3 cm³ of water and 4 cm³ of dichloromethane. After separation of the phases by settling, the organic phase is dried over magnesium sulfate, filtered and then concentrated under reduced pressure. After purification by flash-pack chromatography (SiO2, dichloromethane/methanol 99.5/0.5 by volume as eluent), 0.095 g of [2-(5,6-dimethoxy-1-methyl-1H-indol-3-yl)-1-(toluene-4-sulfonyl)-1H-pyrrolo[2,3-b]pyrid-4-ylmethyl](4-piperid-1-ylphenyl)amine is obtained, the characteristics of which are as follows:

Mass spectrum (EI): m/z=649 (M)⁺; m/z=175 (C₁₁H₁₅N₂) base peak

EXAMPLE 196

[2-(5,6-dimethoxy-1-methyl-1H-indol-3-yl)-1H-pyrrolo[2,3-b]pyrid-4-ylmethyl][4-(2,6-dimethylmorpholin-4-ylphenyl)amine (A003425496 (P-333047-113-1))

a) [2-(5,6-Dimethoxy-1-methyl-1H-indol-3-yl)-1H-pyrrolo[2,3-b]pyrid-4-ylmethyl][4-(2,6-dimethylmorpholin-4-ylphenyl)amine is prepared as described in Example 179a starting with 0.08 g of [2-(5,6-dimethoxy-1-methyl-1H-indol-3-yl)-1-(toluene-4-sulfonyl)-1H-pyrrolo[2,3-b]pyrid-4-ylmethyl][4-(2,6-dimethylmorpholin-4-ylphenyl)amine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1 cm$^3$ of 5N potassium hydroxide. 0.017 g of [2-(5,6-dimethoxy-1-methyl-1H-indol-3-yl)-1H-pyrrolo[2,3-b]pyrid-4-ylmethyl][4-(2,6-dimethylmorpholin-4-ylphenyl)amine is obtained, the characteristics of which are as follows:

$^1$H NMR spectrum (300 MHz, (CD$_3$)$_2$SO d6, δ in ppm): 1.09 (d, J=7.0 Hz, 6H); 2.08 (m, 2H); 3.21 (m, 2H); 3.63 (m, 2H); 3.80 (s, 3H); 3.87 (s, 3H); 3.89 (s, 3H); 4.56 (broad d, J=6.0 Hz, 2H); 6.00 (broad t, J=6.0 Hz, 1H); 6.55 (broad d, J=8.5 Hz, 2H); 6.69 (broad d, J=8.5 Hz, 2H); 6.91 (broad s, 1H); 6.98 (d, J=5.0 Hz, 1H); 7.11 (s, 1H); 7.47 (s, 1H); 7.75 (s, 1H); 8.01 (d, J=5.0 Hz, 1H); 11.65 (broad s, 1H).

Mass spectrum (EI): m/z=525 (M)$^+$; m/z=320 (M-C$_{12}$H$_{17}$N$_2$O) base peak; m/z=206 (C$_{12}$H$_{18}$N$_2$O)$^+$ b) [2-(5,6-Dimethoxy-1-methyl-1H-indol-3-yl)-1-(toluene-4-sulfonyl)-1H-pyrrolo[2,3-b]pyrid-4-ylmethyl][4-(2,6-dimethylmorpholin-4-ylphenyl)amine is prepared as described in Example 178b starting with 0.15 g of 2-(5,6-dimethoxy-1-methyl-1H-indol-3-yl)-1-(toluene-4-sulfonyl)-1H-pyrrolo[2,3-b]pyrid-4-carboxaldehyde and 0.316 g of 4-(2,6-dimethylmorpholin-4-ylphenyl)amine instead of the cyclohexylamine used in Example 178b. After purification by flash-pack chromatography (SiO2, dichloromethane/methanol 99/01 by volume as eluent), 0.1 g of [2-(5,6-dimethoxy-1-methyl-1H-indol-3-yl)-1-(toluene-4-sulfonyl)-1H-pyrrolo[2,3-b]pyrid-4-ylmethyl][4-(2,6-dimethylmorpholin-4-ylphenyl)amine is obtained as a mixture (50/50) with [2-(5,6-dimethoxy-1-methyl-1H-indol-3-yl)-1-(toluene-4-sulfonyl)-1H-pyrrolo[2,3-b]pyrid-4-ylmethyl][4-(2,6-dimethylmorpholin-4-ylphenyl)imine.

This mixture is dissolved in 7 cm$^3$ of ethanol, at a temperature in the region of 20° C. 0.016 g of sodium borohydride is added. The reaction medium is stirred at room temperature for 24 hours. The reaction medium is concentrated under reduced pressure. The residue obtained is taken up in 3 cm$^3$ of water and 4 cm$^3$ of dichloromethane. After separation of the phases by settling, the organic phase is dried over magnesium sulfate, filtered and then concentrated under reduced pressure. After purification by flash-pack chromatography (SiO2, dichloromethane/dethanol 99/01 by volume as eluent), 0.08 g of [2-(5,6-dimethoxy-1-methyl-1H-indol-3-yl)-1-(toluene-4-sulfonyl)-1H-pyrrolo[2,3-b]pyrid-4-ylmethyl][4-(2,6-dimethylmorpholin-4-ylphenyl)amine is obtained, the characteristics of which are as follows:

Mass spectrum (EI): m/z=679 (M)$^+$; m/z=206 (C$_{12}$H$_{18}$N$_2$O$^+$); m/z=120 (C$_7$H$_8$N$_2$$^+$) base peak

EXAMPLE 197

[2-(5,6-dimethoxy-1-methyl-1H-indol-3-yl)-1H-pyrrolo[2,3-b]pyrid-4-yl]methanol (A003377259 (P-32520-113-1))

a) [2-(5,6-Dimethoxy-1-methyl-1H-indol-3-yl)-1H-pyrrolo[2,3-b]pyrid-4-yl]methanol is prepared as described in Example 179a starting with 0.08 g of [2-(5,6-dimethoxy-1-methyl-1H-indol-3-yl)-1-(toluene-4-sulfonyl)-1H-pyrrolo[2,3-b]pyrid-4-yl]methanol instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.55 cm$^3$ of 5N potassium hydroxide. 0.036 g of [2-(5,6-dimethoxy-1-methyl-1H-indol-3-yl)-1H-pyrrolo[2,3-b]pyrid-4-yl]methanol is obtained, the characteristics of which are as follows:

$^1$H NMR spectrum (300 MHz, (CD$_3$)$_2$SO d6, δ in ppm): from 3.72 to 3.97 (broad m, 9H); 4.85 (broad s, 2H); 5.32 (broad s, 1H); 6.75 (broad s, 1H); 7.03 (broad s, 1H); 7.11 (broad s, 1H); 7.45 (broad s, 1H); 7.75 (broad s, 1H); 8.08 (broad s, 1H); 11.65 (broad s, 1H).

Mass spectrum (EI): m/z=337 (M)$^+$ base peak b) [2-(5,6-Dimethoxy-1-methyl-1H-indol-3-yl)-1-(toluene-4-sulfonyl)-1H-pyrrolo[2,3-b]pyrid-4-yl]methanol may be prepared in the following manner:

0.054 mg of sodium borohydride is added to a solution of 0.47 g of 2-(5,6-dimethoxy-1-methyl-1H-indol-3-yl)-1-(toluene-4-sulfonyl)-1H-pyrrolo[2,3-b]pyrid-4-carboxaldehyde in 10 cm$^3$ of methanol, at a temperature in the region of 20° C. The reaction medium is stirred at room temperature for 4 hours. The reaction medium is concentrated under reduced pressure. The residue obtained is taken up in 10 cm$^3$ of water and 20 cm$^3$ of ethyl acetate. After separation of the phases by settling, the organic phase is dried over magnesium sulfate, filtered and then concentrated under reduced pressure. After purification by flash-pack chromatography (SiO2, dichloromethane/methanol 98/02 by volume as eluent), 0.45 g of [2-(5,6-dimethoxy-1-methyl-1H-indol-3-yl)-1-(toluene-4-sulfonyl)-1H-pyrrolo[2,3-b]pyrid-4-yl]methanol is obtained, the characteristics of which are as follows:

Mass spectrum (ES): m/z=492 (M+H)$^+$ base peak

EXAMPLE 198

1'-[2-(5,6-dimethoxy-1-methyl-1H-indol-3-yl)-1H-pyrrolo[2,3-b]pyrid-4-ylmethyl][1,4']bipiperidyl: (A003408597 (P-33047-074-1))

a) 1-[2-(5,6-Dimethoxy-1-methyl-1H-indol-3-yl)-1H-pyrrolo[2,3-b]pyrid-4-ylmethyl][1,4']bipiperidyl is prepared as described in Example 179a starting with 0.025 g of 1'-[2-(5,6-dimethoxy-1-methyl-1H-indol-3-yl)-1-(toluene-4-sulfonyl)-1H-pyrrolo[2,3-b]pyrid-4-ylmethyl][1,4']bipiperidyl instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.17 cm$^3$ of 5N potassium hydroxide. 0.01 g of 1'-[2-(5,6-dimethoxy-1-methyl-1H-indol-3-yl)-1H-pyrrolo[2,3-b]pyrid-4-ylmethyl][1,4']bipiperidyl is obtained, the characteristics of which are as follows:

$^1$H NMR spectrum (300 MHz, (CD$_3$)$_2$SO d6, δ in ppm): from 1.30 to 1.56 (m, 8H); 1.71 (m, 2H); 2.01 (m, 2H); 2.17 (m, 1H); 2.42 (m, 4H); 2.94 (m, 2H); 3.78 (s, 2H); 3.80 (s, 3H); 3.86 (s, 3H); 3.88 (s, 3H); 6.87 (d, J=2.0 Hz, 1H); 6.93 (d, J=5.0 Hz, 1H); 7.11 (s, 1H); 7.41 (s, 1H); 7.76 (s, 1H); 8.04 (d, J=5.0 Hz, 1H); 11.70 (broad s, 1H).
Mass spectrum (EI): m/z=487 (M)$^+$; m/z=320 (M-C$_{10}$H$_{19}$N$_2$)$^+$ base peak b) 1'-[2-(5,6-Dimethoxy-1-methyl-1H-indol-3-yl)-1-(toluene-4-sulfonyl)-1H-pyrrolo[2,3-b]pyrid-4-ylmethyl][1,4']bipiperidyl may be prepared in the following manner:

0.003 g of sodium hydride is added to a solution of 0.008 g of 4-piperidinopiperidine in 0.5 cm$^3$ of THF, at a temperature in the region of 20° C. The reaction medium is stirred at room temperature for 20 minutes. 0.04 g of methanesulfonic acid 2-(5,6-dimethoxy-1-methyl-1H-indol-3-yl)-1-(toluene-4-sulfonyl)-1H-pyrrolo[2,3-b]pyrid-4-ylmethyl ester is added. The reaction medium is heated at 60° C. for 3 hours. After cooling, the reaction medium is concentrated under reduced pressure. The residue obtained is taken up in 2 cm$^3$ of water and 3 cm$^3$ of ethyl acetate. After separation of the phases by settling, the organic phase is dried over magnesium sulfate, filtered and then concentrated under reduced pressure. After purification by flash-pack chromatography (SiO2, dichloromethane/methanol 90/10 by volume as eluent), 0.026 g of 1'-[2-(5,6-dimethoxy-1-methyl-1H-indol-3-yl)-1-(toluene-4-sulfonyl)-1H-pyrrolo[2,3-b]pyrid-4-ylmethyl][1,4']bipiperidyl is obtained, the characteristics of which are as follows:
Mass spectrum (ES): m/z=642 (M+H)$^+$; m/z=244 (M+H—C$_7$H$_7$SO$_2$+H)$^{2+}$/2 base peak c) Methanesulfonic acid 2-(5,6-dimethoxy-1-methyl-1H-indol-3-yl)-1-(toluene-4-sulfonyl)-1H-pyrrolo[2,3-b]pyrid-4-ylmethyl ester may be prepared in the following manner:

0.064 g of pyridine and 0.092 g of methanesulfonic anhydride are added to a solution of 0.13 g of [2-(5,6-dimethoxy-1-methyl-1H-indol-3-yl)-1-(toluene-4-sulfonyl)-1H-pyrrolo[2,3-b]pyrid-4-yl]methanol in 5 cm$^3$ of dichloromethane, at a temperature in the region of −10° C. The reaction medium is stirred at this same temperature for one hour, and then at room temperature for 24 hours. Ice and 15 cm$^3$ of dichloromethane are added. After separation of the phases by settling, the organic phase is dried over magnesium sulfate, filtered and then concentrated under reduced pressure. After purification by flash-pack chromatography (SiO2, dichloromethane/methanol 98/02 by volume as eluent), 0.044 g of methanesulfonic acid 2-(5,6-dimethoxy-1-methyl-1H-indol-3-yl)-1-(toluene-4-sulfonyl)-1H-pyrrolo[2,3-b]pyrid-4-ylmethyl ester is obtained, the characteristics of which are as follows:
Mass spectrum (ES): m/z=570 (M+H)$^+$ base peak

EXAMPLE 199

[2-(5,6-dimethoxy-1-methyl-1H-indol-3-yl)-1H-pyrrolo[2,3-b]pyrid-4-ylmethyl]diethylamine (A003416358 (P-33047-091-1))

a) [2-(5,6-Dimethoxy-1-methyl-1H-indol-3-yl)-1H-pyrrolo[2,3-b]pyrid-4-ylmethyl]diethylamine is prepared as described in Example 179a starting with 0.060 g of [2-(5,6-dimethoxy-1-methyl-1H-indol-3-yl)-1-(toluene-4-sulfonyl)-1H-pyrrolo[2,3-b]pyrid-4-ylmethyl]diethylamine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.44 cm$^3$ of 5N potassium hydroxide. 0.034 g of [2-(5,6-dimethoxy-1-methyl-1H-indol-3-yl)-1H-pyrrolo[2,3-b]pyrid-4-ylmethyl]diethylamine is obtained, the characteristics of which are as follows:
$^1$H NMR spectrum (300 MHz, (CD$_3$)$_2$SO d6, δ in ppm): 1.06 (t, J=7.0 Hz, 6H); 2.53 (partially masked m, 4H); 3.81 (s, 3H); 3.83 (s, 2H); 3.87 (s, 6H); 6.86 (d, J=2.0 Hz, 1H); 6.99 (d, J=5.0 Hz, 1H); 7.11 (s, 1H); 7.41 (s, 1H); 7.74 (s, 1H); 8.03 (d, J=5.0 Hz, 1H); 11.65 (broad s, 1H).
Mass spectrum (EI): m/z=392 M$^+$; m/z=321 (M-C$_4$H$_9$N)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl]diethylamine may be prepared in the following manner:

0.022 cm$^3$ of thionyl chloride is added to a solution of 0.15 g of [2-(5,6-dimethoxy-1-methyl-1H-indol-3-yl)-1-(toluene-4-sulfonyl)-1H-pyrrolo[2,3-b]pyrid-4-yl]methanol in 3 cm$^3$ of dichloromethane, at a temperature in the region of 20° C., followed by addition of two drops of DMF. The reaction medium is stirred at this same temperature for 4 hours.

Next, 8 cm$^3$ of acetonitrile, 0.160 cm$^3$ of diethylamine, 0.211 g of potassium carbonate and 0.1 g of sodium iodide are added. The reaction medium is heated at 50° C. for 24 hours. After cooling, the reaction medium is filtered through a sinter funnel and the filtrate is concentrated under reduced pressure. The residue obtained is taken up in 3 cm$^3$ of water and 4 cm$^3$ of ethyl acetate. After separation of the phases by settling, the organic phase is dried over magnesium sulfate, filtered and then concentrated under reduced pressure. After purification by flash-pack chromatography (SiO2, dichloromethane/ethyl acetate 80/20 by volume as eluent), 0.036 g of [2-(5,6-dimethoxy-1-methyl-1H-indol-3-yl)-1-(toluene-4-sulfonyl)-1H-pyrrolo[2,3-b]pyrid-4-ylmethyl]diethylamine is obtained, the characteristics of which are as follows:
Mass spectrum (ES): m/z=547 (M+H)$^+$ base peak; m/z=474 ((M+H)—C$_4$H$_{11}$N)$^+$

EXAMPLE 200

[2-(5,6-dimethoxy-1-methyl-1H-indol-3-yl)-1H-pyrrolo[2,3-b]pyrid-4-ylmethyl]piperid-4-ol (A003435835 (P-33047-129-1))

a) [2-(5,6-Dimethoxy-1-methyl-1H-indol-3-yl)-1H-pyrrolo[2,3-b]pyrid-4-ylmethyl]piperid-4-ol is prepared as described in Example 179a starting with 0.045 g of [2-(5,6-dimethoxy-1-methyl-1H-indol-3-yl)-1-(toluene-4-sulfonyl)-1H-pyrrolo[2,3-b]pyrid-4-ylmethyl]piperid-4-ol instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.44 cm$^3$ of 5N potassium hydroxide. 0.031 g of [2-(5,6-dimethoxy-1-methyl-1H-indol-3-yl)-1H-pyrrolo[2,3-b]pyrid-4-ylmethyl]piperid-4-ol is obtained, the characteristics of which are as follows:
$^1$H NMR spectrum (300 MHz, (CD$_3$)$_2$SO d6, δ in ppm): 1.46 (m, 2H); 1.74 (m, 2H); 2.13 (m, 2H); 2.78 (m, 2H); 3.48 (m, 1H); 3.78 (s, 2H); 3.81 (s, 3H); 3.87 (s, 3H); 3.89 (s, 3H); 4.56 (broad m, 1H); 6.89 (broad s, 1H); 6.93 (d, J=5.0 Hz, 1H); 7.12 (s, 1H); 7.42 (s, 1H); 7.76 (s, 1H); 8.03 (d, J=5.0 Hz, 1H); 11.7 (broad s, 1H). Mass spectrum (EI): m/z=420 M$^+$; m/z=321 (M-C$_5$H$_9$NO)$^+$ base peak b) [2-(5,6-Dimethoxy-1-methyl-1H-indol-3-yl)-1-(toluene-4-sulfonyl)-1H-pyrrolo[2,3-b]pyrid-4-ylmethyl]piperid-4-ol may be prepared in the following manner:

0.027 g of piperid-4-ol, 0.075 g of potassium carbonate and 0.016 g of sodium iodide are added to a solution of 0.055 g of 4-chloromethyl-2-(5,6-dimethoxy-1-methyl-1H-indol-3-yl)-1-(toluene-4-sulfonyl)-1H-pyrrolo[2,3-b]pyridine in 3 cm$^3$ of acetonitrile, at a temperature in the region of 20° C. The reaction medium is heated at 80° C. for one hour. After cooling, the reaction medium is filtered through a sinter funnel and the filtrate is concentrated under reduced pressure. The residue obtained is taken up in 3 cm³ of water and 4 cm³ of ethyl acetate. After separation of the phases by settling, the organic phase is dried over magnesium sulfate, filtered and then concentrated under reduced pressure. 0.049 g of [2-(5,6-dimethoxy-1-methyl-1H-indol-3-yl)-1-(toluene-4-sulfonyl)-1H-pyrrolo[2,3-b]pyrid-4-ylmethyl]piperid-4-ol is obtained, the characteristics of which are as follows:

Mass spectrum (ES): m/z=575 (M+H)⁺ base peak c) 4-Chloromethyl-2-(5,6-dimethoxy-1-methyl-1H-indol-3-yl)-1-(toluene-4-sulfonyl)-1H-pyrrolo[2,3-b]pyridine may be prepared in the following manner:

0.089 cm³ of thionyl chloride and five drops of DMF are added to a solution of 0.4 g of [2-(5,6-dimethoxy-1-methyl-1H-indol-3-yl)-1-(toluene-4-sulfonyl)-1H-pyrrolo[2,3-b]pyrid-4-yl]methanol in 4 cm³ of dichloromethane, at a temperature in the region of 20° C. The reaction medium is stirred at this same temperature for 4 hours. Ice is added and the reaction medium is then neutralized with saturated sodium hydrogen carbonate solution. After separation of the phases by settling, the organic phase is dried over magnesium sulfate, filtered and then concentrated under reduced pressure. After purification by flash-pack chromatography (SiO2, dichloromethane/ethyl acetate 97.5/2.5 by volume as eluent), 0.234 g of 4-chloromethyl-2-(5,6-dimethoxy-1-methyl-1H-indol-3-yl)-1-(toluene-4-sulfonyl)-1H-pyrrolo[2,3-b]pyridine is obtained, the characteristics of which are as follows:

Mass spectrum (EI): m/z=509 M⁺; m/z=354 M-C₇H₇SO₂)⁺ base peak

EXAMPLE 201

1-[2-(5,6-dimethoxy-1-methyl-1H-indol-3-yl)-1H-pyrrolo[2,3-b]pyrid-4-ylmethyl]azetidin-3-ylamine (A003453957 (P-33047-148-1))

1-[2-(5,6-Dimethoxy-1-methyl-1H-indol-3-yl)-1H-pyrrolo[2,3-b]pyrid-4-ylmethyl]azetidin-3-ylamine may be prepared in the following manner:

0.27 cm³ of hydrochloric acid (4N in dioxane) is added to a solution of 0.051 g of {1-[2-(5,6-dimethoxy-1-methyl-1H-indol-3-yl)-1H-pyrrolo[2,3-b]pyrid-4-ylmethyl]azetidin-3-yl}carbamic acid tert-butyl ester in 3 cm³ of methanol and 0.5 cm³ of dichloromethane, at a temperature in the region of 20° C. The reaction medium is stirred at room temperature for 24 hours. The reaction medium is concentrated under reduced pressure. The residue obtained is taken up in 4 cm³ of water and is then neutralized with 1N sodium hydroxide to pH 10. 12 cm³ of dichloromethane are added. After separation of the phases by settling, the organic phase is dried over magnesium sulfate, filtered and then concentrated under reduced pressure. 0.008 g of 1-[2-(5,6-dimethoxy-1-methyl-1H-indol-3-yl)-1H-pyrrolo[2,3-b]pyrid-4-ylmethyl]azetidin-3-ylamine is obtained, the characteristics of which are as follows:

¹H NMR spectrum (300 MHz, (CD₃)₂SO d6, δ in ppm): 2.73 (m, 2H); 3.44 (m, 1H); 3.59 (m, 2H); 3.81 (s, 3H); 3.87 (s, 5H); 3.89 (s, 3H); 6.73 (d, J=2.0 Hz, 1H); 6.92 (d, J=5.0 Hz, 1H); 7.11 (s, 1H); 7.44 (s, 1H); 7.73 (s, 1H); 8.03 (d, J=5.0 Hz, 1H); 11.65 (broad s, 1H).

Mass spectrum (ES): m/z=392 (M+H)⁺

EXAMPLE 202

{1-[2-(5,6-dimethoxy-1-methyl-1H-indol-3-yl)-1H-pyrrolo[2,3-b]pyrid-4-ylmethyl]azetidin-3-yl}carbamic acid tert-butyl ester (A003452988 (P-33047-143-1))

a) {1-[2-(5,6-Dimethoxy-1-methyl-1H-indol-3-yl)-1H-pyrrolo[2,3-b]pyrid-4-ylmethyl]azetidin-3-yl}carbamic acid tert-butyl ester is prepared as described in Example 179a starting with 0.13 g of {1-[2-(5,6-dimethoxy-1-methyl-1H-indol-3-yl)-1-(toluene-4-sulfonyl)-1H-pyrrolo[2,3-b]pyrid-4-ylmethyl]azetidin-3-yl}carbamic acid tert-butyl ester instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.805 cm³ of 5N potassium hydroxide. 0.07 g of {1-[2-(5,6-dimethoxy-1-methyl-1H-indol-3-yl)-1H-pyrrolo[2,3-b]pyrid-4-ylmethyl]azetidin-3-yl}carbamic acid tert-butyl ester is obtained, the characteristics of which are as follows:

¹H NMR spectrum (300 MHz, (CD₃)₂SO d6, δ in ppm): 1.37 (s, 9H); 2.97 (t, J=7.0 Hz, 2H); 3.58 (t, J=7.0 Hz, 2H); 3.81 (s, 3H); 3.88 (s, 3H); 3.90 (s, 5H); 4.10 (m, 1H); 6.73 (d, J=2.0 Hz, 1H); 6.91 (d, J=5.0 Hz, 1H); 7.11 (s, 1H); 7.31 (broad d, J=7.0 Hz, 1H); 7.44 (s, 1H); 7.74 (s, 1H); 8.03 (d, J=5.0 Hz, 1H); 11.7 (broad s, 1H).

Mass spectrum (ES): m/z=492 (M+H)⁺ base peak; m/z=436 (MH—C₄H₈)⁺ b) {1-[2-(5,6-Dimethoxy-1-methyl-1H-indol-3-yl)-1-(toluene-4-sulfonyl)-1H-pyrrolo[2,3-b]pyrid-4-ylmethyl]azetidin-3-yl}carbamic acid tert-butyl ester is prepared as described in Example 200b starting with 0.14 g of 4-chloromethyl-2-(5,6-dimethoxy-1-methyl-1H-indol-3-yl)-1-(toluene-4-sulfonyl)-1H-pyrrolo[2,3-b]pyridine and 0.118 g of azetidin-3-ylcarbamic acid tert-butyl ester instead of the piperid-4-ol used in Example 200b. After purification by flash-pack chromatography (SiO2, dichloromethane/methanol 95/5 by volume as eluent), 0.135 g of {1-[2-(5,6-dimethoxy-1-methyl-1H-indol-3-yl)-1H-pyrrolo[2,3-b]pyrid-4-ylmethyl]azetidin-3-yl}carbamic acid tert-butyl ester is obtained, the characteristics of which are as follows:

Mass spectrum (ES): m/z=646 (M+H)⁺ base peak; m/z=590 (MH—C₄H₈)⁺

EXAMPLE 203

{1-[2-(5,6-dimethoxy-1-methyl-1H-indol-3-yl)-1H-pyrrolo[2,3-b]pyrid-4-ylmethyl]azetidin-3-yl}methylamine dihydrochloride (A003453945A (P-33047-150-1))

a) {1-[2-(5,6-Dimethoxy-1-methyl-1H-indol-3-yl)-1H-pyrrolo[2,3-b]pyrid-4-ylmethyl]azetidin-3-yl}methylamine dihydrochloride is prepared as described in Example 201 starting with 0.027 g of {1-[2-(5,6-dimethoxy-1-methyl-1H-indol-3-yl)-1-(toluene-4-sulfonyl)-1H-pyrrolo[2,3-b]pyrid-4-ylmethyl]azetidin-3-ylmethyl}carbamic acid tert-butyl ester instead of the {1-[2-(5,6-dimethoxy-1-methyl-1H-indol-3-yl)-1H-pyrrolo[2,3-b]pyrid-4-ylmethyl]azetidin-3-yl}carbamic acid tert-butyl ester used in Example 201 and 1.35 cm³ of hydrochloric acid (4N in dioxane). 0.005 g of {1-[2-(5,6-dimethoxy-1-methyl-1H-indol-3-yl)-1H-pyrrolo[2,3-b]pyrid-4-ylmethyl]azetidin-3-yl}methylamine dihydrochloride is obtained, the characteristics of which are as follows:

¹H NMR spectrum (300 MHz, (CD$_3$)$_2$SO d6, δ in ppm): 3.83 (s, 3H); 3.88 (s, 3H); 3.92 (broad s, 3H); from 2.90 to 4.35 (partially masked very broad m, 7H in total); 4.75 (m, 2H); from 7.05 to 7.10 (m, 3H); 7.60 (s, 1H); 7.81 (s, 1H); from 7.85 to 8.03 (broad m, 3H); 8.17 (broad d, J=5.0 Hz, 1H); from 140.7 to 11.2 (very broad m, 1H); 12.0 (broad m, 1H)

Mass spectrum (ES): m/z=406 (M+H)$^+$ base peak

EXAMPLE 204

{1-[2-(5,6-dimethoxy-1-methyl-1H-indol-3-yl)-1H-pyrrolo[2,3-b]pyrid-4-ylmethyl]azetidin-3-ylmethyl}carbamic acid tert-butyl ester (A003453144 (P-33047-145-1))

a) {1-[2-(5,6-Dimethoxy-1-methyl-1H-indol-3-yl)-1H-pyrrolo[2,3-b]pyrid-4-ylmethyl]azetidin-3-ylmethyl}carbamic acid tert-butyl ester is prepared as described in Example 179a starting With 0.15 g of {1-[2-(5,6-dimethoxy-1-methyl-1H-indol-3-yl)-1-(toluene-4-sulfonyl)-1H-pyrrolo[2,3-b]pyrid-4-ylmethyl]azetidin-3-ylmethyl}carbamic acid tert-butyl ester instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.909 cm$^3$ of 5N potassium hydroxide. After purification by flash-pack chromatography (SiO2, dichloromethane/methanol 95/5 by volume as eluent), 0.037 g of {1-[2-(5,6-dimethoxy-1-methyl-1H-indol-3-yl)-1-(toluene-4-sulfonyl)-1H-pyrrolo[2,3-b]pyrid-4-ylmethyl]azetidin-3-ylmethyl}carbamic acid tert-butyl ester is obtained, the characteristics of which are as follows:

¹H NMR spectrum (300 MHz, (CD$_3$)$_2$SO d6, δ in ppm): 1.36 (s, 9H); 2.97 (t, J=7.0 Hz, 2H); 3.14 (m, 3H); from 3.19 to 3.35 (masked m, 2H); 3.81 (s, 3H); 3.87 (s, 5H); 3.89 (s, 3H); 6.75 (d, J=2.0 Hz, 1H); 6.90 (broad m, 1H); 6.92 (d, J=5.0 Hz, 1H); 7.11 (s, 1H); 7.44 (s, 1H); 7.74 (s, 1H); 8.02 (d, J=5.0 Hz, 1H); 11.65 (broad s, 1H). Mass spectrum (EI): m/z=505 M$^+$; m/z=321 (M-C$_9$H$_{16}$N$_2$O$_2$)$^+$ base peak b) {1-[2-(5,6-Dimethoxy-1-methyl-1H-indol-3-yl)-1-(toluene-4-sulfonyl)-1H-pyrrolo[2,3-b]pyrid-4-ylmethyl]azetidin-3-ylmethyl}carbamic acid tert-butyl ester is prepared as described in Example 200b starting with 0.14 g of 4-chloromethyl-2-(5,6-dimethoxy-1-methyl-1H-indol-3-yl)-1-(toluene-4-sulfonyl)-1H-pyrrolo[2,3-b]pyridine and 0.123 g of azetidin-3-ylmethylcarbamic acid tert-butyl ester instead of the piperid-4-ol used in Example 200b. After purification by flash-pack chromatography (SiO2, dichloromethane/methanol 95/5 by volume as eluent), 0.154 g of {1-[2-(5,6-dimethoxy-1-methyl-1H-indol-3-yl)-1H-pyrrolo[2,3-b]pyrid-4-ylmethyl]azetidin-3-ylmethyl}carbamic acid tert-butyl ester is obtained, the characteristics of which are as follows:

Mass spectrum (EI): m/z=659 M$^+$; m/z=505 (M-C$_7$H$_6$SO$_2$)$^+$; m/z=320 (m/z=505-C$_9$H$_{17}$N$_2$O$_2$)$^+$ base peak

EXAMPLE 205

[2-(5,6-dimethoxy-1-methyl-1H-indol-3-yl)-4-(4-methylpiperazin-1-ylmethyl)-1H-pyrrolo[2,3-b]pyridine (A003438870 (P-33047-131-2))

a) [2-(5,6-Dimethoxy-1-methyl-1H-indol-3-yl)-4-(4-methylpiperazin-1-ylmethyl)-1H-pyrrolo[2,3-b]pyridine is prepared as described in Example 179a starting with 0.040 g of [2-(5,6-dimethoxy-1-methyl-1H-indol-3-yl)-1-(toluene-4-sulfonyl)-4-(4-methylpiperazin-1-ylmethyl)-1H-pyrrolo[2,3-b]pyridine instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.28 cm$^3$ of 5N potassium hydroxide. 0.014 g of [2-(5,6-dimethoxy-1-methyl-1H-indol-3-yl)-4-(4-methylpiperazin-1-ylmethyl)-1H-pyrrolo[2,3-b]pyridine is obtained, the characteristics of which are as follows:

¹H NMR spectrum (300 MHz, (CD$_3$)$_2$SO d6, δ in ppm): 2.15 (s, 3H); from 2.30 to 2.54 (partially masked m, 8H); 3.79 (s, 2H); 3.81 (s, 3H); 3.87 (s, 3H); 3.89 (s, 3H); 6.89 (d, J=2.0 Hz, 1H); 6.93 (d, J=5.0 Hz, 1H); 7.11 (s, 1H); 7.42 (s, 1H); 7.75 (s, 1H); 8.03 (d, J=5.0 Hz, 1H); 11.7 (broad s, 1H).

Mass spectrum (EI): m/z=419 M$^+$; m/z=320 (M-C$_5$H$_{11}$N$_2$)$^+$ base peak b) [2-(5,6-Dimethoxy-1-methyl-1H-indol-3-yl)-1-(toluene-4-sulfonyl)-4-(4-methylpiperazin-1-ylmethyl)-1H-pyrrolo[2,3-b]pyridine is prepared as described in Example 200b starting with 0.055 g of 4-chloromethyl-2-(5,6-dimethoxy-1-methyl-1H-indol-3-yl)-1-(toluene-4-sulfonyl)-1H-pyrrolo[2,3-b]pyridine and 0.03 cm$^3$ of 1-methylpiperazine instead of the piperid-4-ol used in Example 200b. 0.043 g of [2-(5,6-dimethoxy-1-methyl-1H-indol-3-yl)-1-(toluene-4-sulfonyl)-4-(4-methylpiperazin-1-ylmethyl)-1H-pyrrolo[2,3-b]pyridine is obtained, the characteristics of which are as follows:

Mass spectrum (ES): m/z=574 (M+H)$^+$; m/z=308 (M+acetonitrile+2H)$^{2+}$/2; m/z=231 (MH+acetonitrile-C$_7$H$_7$SO$_2$+H)$^{2+}$/2 base peak

EXAMPLE 206

[2-(5,6-dimethoxy-1-methyl-1H-indol-3-yl)-1H-pyrrolo[2,3-b]pyrid-4-yl]phenylmethanol (A003403794 (P-32989-031-1))

a) [2-(5,6-Dimethoxy-1-methyl-1H-indol-3-yl)-1H-pyrrolo[2,3-b]pyrid-4-yl]phenylmethanol is prepared as described in Example 179a starting with 0.105 g of [2-(5,6-dimethoxy-1-methyl-1H-indol-3-yl)-1-(toluene-4-sulfonyl)-1H-pyrrolo[2,3-b]pyrid-4-yl]phenylmethanol instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.85 cm$^3$ of 5N potassium hydroxide. 0.070 g Of [2-(5,6-dimethoxy-1-methyl-1H-indol-3-yl)-1H-pyrrolo[2,3-b]pyrid-4-yl]phenylmethanol is obtained, the characteristics of which are as follows:

¹H NMR spectrum (300 MHz, (CD$_3$)$_2$SO d6, δ in ppm): 3.80 (s, 3H); 3.86 (s, 3H); 3.89 (s, 3H); 6.11 (s, 1H); 6.69 (broad s, 1H); 7.10 (s, 1H); from 7.15 to 7.24 (m, 2H); from 7.26 to 7.33 (m, 3H); 7.53 (broad d, J=7.5 Hz, 2H); 7.70 (s, 1H); 8.09 (d, J=5.0 Hz, 1H); 11.65 (broad m, 1H).

Mass spectrum (EI) (IC): m/z=413 M$^+$ base peak b) [2-(5,6-Dimethoxy-1-methyl-1H-indol-3-yl)-1-(toluene-4-sulfonyl)-1H-pyrrolo[2,3-b]pyrid-4-yl]phenylmethanol may be prepared in the following manner:

0.45 cm$^3$ of phenylmagnesium bromide, 1M in THF, is added to a solution of 0.1 g of [2-(5,6-dimethoxy-1-methyl-1H-indol-3-yl)-1-(toluene-4-sulfonyl)-1H-pyrrolo[2,3-b]pyrid-4-ylmethyl]-4-carboxaldehyde in 5 cm$^3$ of THF, at a temperature in the region of 6° C. The reaction medium is stirred at this same temperature for 30 minutes and then for 24 hours at room temperature. 5 cm$^3$ of saturated ammonium chloride solution and 10 cm³ of dichloromethane are added. After separation of the phases by settling, the organic phase is dried over magnesium sulfate, filtered and then concentrated under reduced pressure. 0.105 g of [2-(5,6-dimethoxy-1-methyl-1H-indol-3-yl)-1-(toluene-4-sulfonyl)-1H-pyrrolo[2,3-b]pyrid-4-yl]phenylmethanol is obtained, the characteristics of which are as follows:

Mass spectrum (EI): m/z=567 M⁺; m/z=412 (M-C₇H₇SO₂)⁺ base peak

EXAMPLE 207

[2-(5,6-dimethoxy-1-methyl-1H-indol-3-yl)-1H-pyrrolo[2,3-b]pyrid-4-yl]propan-1-ol (A003408773 (P-32989-039-1))

a) [2-(5,6-Dimethoxy-1-methyl-1H-indol-3-yl)-1H-pyrrolo[2,3-b]pyrid-4-yl]propan-1-ol is prepared as described in Example 179a starting with 0.090 g of [2-(5,6-dimethoxy-1-methyl-1H-indol-3-yl)-1-(toluene-4-sulfonyl)-1H-pyrrolo[2,3-b]pyrid-4-yl]propan-1-ol instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.80 cm³ of 5N potassium hydroxide. 0.060 g of [2-(5,6-dimethoxy-1-methyl-1H-indol-3-yl)-1H-pyrrolo[2,3-b]-pyrid-4-yl]propan-1-ol is obtained, the characteristics of which are as follows:

¹H NMR spectrum (300 MHz, (CD₃)₂SO d6, δ in ppm): 0.90 (t, J=7.0 Hz, 3H); 1.80 (m, 2H); 3.81 (s, 3H); 3.87 (s, 3H); 3.88 (s, 3H); 4.96 (m, 1H); 5.25 (d, J=5.0 Hz, 1H); 6.75 (d, J=2.0 Hz, 1H); 7.01 (d, J=5.0 Hz, 1H); 7.11 (s, 1H); 7.44 (s, 1H); 7.74 (s, 1H); 8.07 (d, J=5.0 Hz, 1H); 11.65 (broad s, 1H).

Mass spectrum (ES): m/z 366 (M+H)⁺ base peak b) [2-(5,6-Dimethoxy-1-methyl-1H-indol-3-yl)-1-(toluene-4-sulfonyl)-1H-pyrrolo[2,3-b]pyrid-4-yl]propan-1-ol may be prepared in the following manner:

0.45 cm³ of ethylmagnesium bromide, 1M in THF, is added to a solution of 0.1 g of [2-(5,6-dimethoxy-1-methyl-1H-indol-3-yl)-1-(toluene-4-sulfonyl)-1H-pyrrolo[2,3-b]pyrid-4-ylmethyl]-4-carboxaldehyde in 5 cm³ of THF, at a temperature in the region of 6° C. The reaction medium is stirred at this same temperature for 30 minutes and then for 24 hours at room temperature. 5 cm³ of saturated ammonium chloride solution and 10 cm³ of dichloromethane are added. After separation of the phases by settling, the organic phase is dried over magnesium sulfate, filtered and then concentrated under reduced pressure. After purification by flash-pack chromatography (SiO2, dichloromethane/ethyl acetate 80/20 by volume as eluent), 0.154 g of [2-(5,6-dimethoxy-1-methyl-1H-indol-3-yl)-1-(toluene-4-sulfonyl)-1H-pyrrolo[2,3-b]pyrid-4-yl]propan-1-ol is obtained, the characteristics of which are as follows:

Mass spectrum (EI): m/z=519 M⁺; m/z=364 (M-C₇H₇SO₂)⁺ base peak

EXAMPLE 208

[2-(5,6-dimethoxy-1-methyl-1H-indol-3-yl)-1H-pyrrolo[2,3-b]pyrid-4-yl]methylamine (A003435888 (P-32989-101-2))

a) [2-(5,6-Dimethoxy-1-methyl-1H-indol-3-yl)-1H-pyrrolo[2,3-b]pyrid-4-yl]methylamine is prepared as described in Example 179a starting with 0.080 g of [2-(5,6-dimethoxy-1-methyl-1H-indol-3-yl)-1-(toluene-4-sulfonyl)-1H-pyrrolo[2,3-b]pyrid-4-yl]methylamine instead of the [2-(5,6-dimethoxy-1-methyl-1H-indol-3-yl)-1-(toluene-4-sulfonyl)-1H-pyrrolo[2,3-b]pyrid-4 ylmethyl](4-trifluoromethylsulfanylbenzyl)amine used in Example 179a and 0.80 cm³ of 5N potassium hydroxide. After purification by flash-pack chromatography (SiO2, dichloromethane/methanol 95/05 by volume as eluent), 0.015 g of [2-(5,6-dimethoxy-1-methyl-1H-indol-3-yl)-1H-pyrrolo[2,3-b]pyrid-4-yl]methylamine is obtained, the characteristics of which are as follows:

¹H NMR spectrum (300 MHz, (CD₃)₂SO d6, δ in ppm): 3.80 (s, 3H); 3.86 (s, 3H); 3.88 (s, 3H); 4.04 (s, 2H); 6.79 (d, J=2.0 Hz, 1H); 7.07 (d, J=5.0 Hz, 1H); 7.11 (s, 1H); 7.48 (s, 1H); 7.75 (s, 1H); 8.06 (d, J=5.0 Hz, 1H); 11.65 (broad s, 1H).

Mass spectrum (EI): m/z=336 M⁺ base peak b) [2-(5,6-Dimethoxy-1-methyl-1H-indol-3-yl)-1-(toluene-4-sulfonyl)-1H-pyrrolo[2,3-b]pyrid-4-yl]methylamine may be prepared in the following manner:

0.040 g of zinc and 2 cm³ of concentrated formic acid are added to a solution of 0.1 g of [2-(5,6-dimethoxy-1-methyl-1H-indol-3-yl)-1-(toluene-4-sulfonyl)-1H-pyrrolo[2,3-b]pyrid-4-carbaldehyde oxime in 6 cm³ of ethanol and 5 cm³ of water, at a temperature in the region of 20° C. The reaction medium is stirred at this same temperature for 24 hours at room temperature. The reaction medium is filtered through Celite and the filtrate is concentrated under reduced pressure. 5 cm³ of water and 10 cm³ of dichloromethane are added. The reaction medium is basified to pH 10 with 1N sodium hydroxide. After separation of the phases by settling, the organic phase is dried over magnesium sulfate, filtered and then concentrated under reduced pressure. 0.06 g of [2-(5,6-dimethoxy-1-methyl-1H-indol-3-yl)-1-(toluene-4-sulfonyl)-1H-pyrrolo[2,3-b]pyrid-4-yl]methylamine is obtained, the characteristics of which are as follows:

Mass spectrum (EI): m/z 490 M⁺; m/z=335 (M-C₇H₇SO₂)⁺ base peak c) [2-(5,6-Dimethoxy-1-methyl-1H-indol-3-yl)-1-(toluene-4-sulfonyl)-1H-pyrrolo[2,3-b]pyrid-4-carbaldehyde oxime may be prepared in the following manner:

0.2107 g of hydroxylamine hydrochloride is added to a solution of 0.5 g of [2-(5,6-dimethoxy-1-methyl-1H-indol-3-yl)-1-(toluene-4-sulfonyl)-1H-pyrrolo[2,3-b]pyrid-4-carboxaldehyde in 25 cm³ of pyridine, at a temperature in the region of 20° C. The reaction medium is heated at 50° C. for 24 hours. The reaction medium is concentrated under reduced pressure. The residue obtained is taken up in 10 cm³ of water and 10 cm³ of dichloromethane. After separation of the phases by settling, the organic phase is dried over magnesium sulfate, filtered and then concentrated under reduced pressure. 0.510 g of 2-(5,6-dimethoxy-1-methyl-1H-indol-3-yl)-1-(toluene-4-sulfonyl)-1H-pyrrolo[2,3-b]pyrid-4-carbaldehyde oxime is obtained, the characteristics of which are as follows:

Mass spectrum (EI): m/z=350 M⁺ base peak; m/z=332 (M-H₂O)⁺; m/z=306 (M-CH₂NO)⁺

EXAMPLE 209

[2-(5,6-dimethoxy-1-methyl-1H-indol-3-yl)-1H-pyrrolo[2,3-b]pyrid-4-carbaldehyde oxime (A003425653 (P-32989-091-2))

[2 (5,6-Dimethoxy-1-methyl-1H-indol-3-yl)-1H-pyrrolo[2,3-b]pyrid-4-carbaldehyde oxime is prepared as described in Example 179a starting with 0.060 g of 2-(5,6-dimethoxy-1-methyl-1H-indol-3-yl)-1-(toluene-4-sulfonyl)-1H-pyrrolo

[2,3-b]pyrid-4-carbaldehyde oxime instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.60 cm³ of 5N potassium hydroxide. After purification by flash-pack chromatography (SiO2, dichloromethane/methanol 98/02 by volume as eluent), 0.010 g of [2-(5,6-dimethoxy-1-methyl-1H-indol-3-yl)-1H-pyrrolo[2,3-b]pyrid-4-carbaldehyde oxime is obtained, the characteristics of which are as follows:

$^1$H NMR spectrum (300 MHz, $(CD_3)_2SO$ d6, δ in ppm): 3.82 (s, 3H); 3.87 (s, 3H); 3.89 (s, 3H); 7.07 (d, J=2.0 Hz, 1H); 7.12 (s, 1H); 7.09 (d, J=5.0 Hz, 1H); 7.45 (s, 1H); 7.80 (s, 1H); 8.11 (d, J=5.0 Hz, 1H); 8.54 (s, 1H); 11.58 (s, 1H); 11.9 (broad s, 1H).

Mass spectrum (EI): m/z=350 M⁺ base peak; m/z=332 $(M-H_2O)^+$; m/z=306 $(M-CH_2NO)^+$

EXAMPLE 210

N-[2-(5,6-dimethoxy-1-methyl-1H-indol-3-yl)-1H-pyrrolo[2,3-b]pyrid-4-ylmethyl]-4-trifluoromethoxy-benzenesulfonamide (A003453139 (P-32989-120-2))

N-[2-(5,6-Dimethoxy-1-methyl-1H-indol-3-yl)-1H-pyrrolo[2,3-b]pyrid-4-ylmethyl]-4-trifluoromethoxybenzenesulfonamide may be prepared in the following manner:

0.053 g of para-toluenesulfonic acid is added to a solution of 0.050 g of N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide in 2 cm³ of dichloromethane and 5 cm³ of toluene, at a temperature in the region of 20° C. The reaction medium is stirred at this same temperature for 24 hours, at room temperature, and then heated at a temperature in the region of 60° C. for 24 hours. After cooling, the reaction medium is concentrated under reduced pressure. 5 cm³ of water and 10 cm³ of dichloromethane are added. The reaction medium is basified to pH 9 with 1N sodium hydroxide. After separation of the phases by settling, the organic phase is dried over magnesium sulfate, filtered and then concentrated under reduced pressure. The residue obtained is purified on preparative LC/MS (water/acetonitrile/TFA). The solid obtained is taken up in 5 cm³ of dichloromethane and 2 cm³ of water, and then basified with 1N sodium hydroxide to pH 9. 0.008 g of N-[2-(5,6-dimethoxy-1-methyl-1H-indol-3-yl)-1H-pyrrolo[2,3-b]pyrid-4-ylmethyl]-4-trifluoromethoxybenzenesulfonamide is obtained, the characteristics of which are as follows:

$^1$H NMR spectrum (300 MHz, $(CD_3)_2SO$ d6, δ in ppm): 3.82 (s, 3H); 3.88 (s, 3H); 3.90 (s, 3H); 4.38 (broad s, 2H); 6.87 (d, J=5.0 Hz, 1H); 6.95 (d, J=2.0 Hz, 1H); 7.13 (s, 1H); 7.50 (s, 1H); 7.55 (broad d, J=8.5 Hz, 2H); 7.78 (s, 1H); 7.96 (broad d, J=8.5 Hz, 2H); 8.00 (d, J=5.0 Hz, 1H); 8.50 (m, 1H); 11.75 (broad s, 1H).

Mass spectrum (EI): m/z=560 M⁺ base peak; m/z=335 $(M-C_7H_4SO_3F_3)^+$

EXAMPLE 211

N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide (A003423534 (P-32989-083-2))

a) N-(2,4-Dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide is prepared as described in Example 179a starting with 0.070 g of N-(2,4-dimethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]-4-trifluoromethoxybenzenesulfonamide instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.40 cm³ of 5N potassium hydroxide. 0.030 g of N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide is obtained, the characteristics of which are as follows:

$^1$H NMR spectrum (300 MHz, $(CD_3)_2SO$ d6, δ in ppm): 3.46 (s, 3H); 3.63 (s, 3H); 3.83 (s, 3H); 3.87 (s, 6H); 4.28 (broad s, 2H); 4.79 (broad s, 2H); from 6.20 to 6.26 (m, 2H); 6.78 (d, J=5.0 Hz, 1H); 6.88 (d, J=8.5 Hz, 1H); 6.99 (broad s, 1H); 7.12 (s, 1H); 7.48 (s, 1H); 7.50 (broad d, J=8.5 Hz, 2H); 7.78 (s, 1H); 7.88 (broad d, J=8.5 Hz, 2H); 7.98 (d, J=5.0 Hz, 1H); 11.75 (broad s, 1H).

Mass spectrum (ES): m/z=711 (M+H)⁺ base peak b) N-(2,4-Dimethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]-4-trifluoromethoxybenzenesulfonamide may be prepared in the following manner:

0.052 cm³ of triethylamine and 0.265 cm³ of 4-(trifluoromethoxy)benzenesulfonyl chloride are added to a solution of 0.200 g of (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine in 6 cm³ of dichloromethane, under an argon atmosphere, at a temperature in the region of 20° C. The reaction medium is stirred at this same temperature for 24 hours. 2 cm³ of water are added. After separation of the phases by settling, the organic phase is dried over magnesium sulfate, filtered and then concentrated under reduced pressure. After purification by flash-pack chromatography (SiO2, dichloromethane/methanol 98/02 by volume as eluent), 0.210 g of N-(2,4-dim ethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]-4-trifluoromethoxybenzenesulfonamide is obtained, the characteristics of which are as follows:

Mass spectrum (ES): m/z=865 (M+H)⁺ base peak

EXAMPLE 212

Thiophene-2-sulfonic acid [2-(5,6-dimethoxy-1-methyl-1H-indol-3-yl)-1H-pyrrolo[2,3-b]pyrid-4-ylmethyl]-amide (A0013453971 (P-32989-122-3))

a) Thiophene-2-sulfonic acid [2-(5,6-dimethoxy-1-methyl-1H-indol-3-yl)-1H-pyrrolo[2,3-b]pyrid-4-ylmethyl]amide is prepared as described in Example 210 starting with 0.1 g of thiophene-2-sulfonic acid (2,4-dimethoxybenzyl)[2-(5,6-dimethoxy-1-methyl-1H-indol-3-yl)-1H-pyrrolo[2,3-b]pyrid-4-ylmethyl]amide instead of the N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide used in Example 210 and 0.110 g of para-toluenesulfonic acid. 0.025 g of thiophene-2-sulfonic acid [2-(5,6-dimethoxy-1-methyl-1H-indol-3-yl)-1H-pyrrolo[2,3-b]pyrid-4-ylmethyl]amide is obtained, the characteristics of which are as follows:

$^1$H NMR spectrum (300 MHz, $(CD_3)_2SO$ d6, δ in ppm): 3.81 (s, 3H); 3.87 (s, 3H); 3.89 (s, 3H); 4.40 (broad s, 2H); 6.89 (d, J=5.0 Hz, 1H); 6.91 (d, J=2.0 Hz, 1H); 7.11 (s, 1H); 7.19 (dd, J=3.5 and 5.0 Hz, 1H); 7.48 (s, 1H); 7.66 (dd, J=1.0 and 3.5 Hz, 1H); 7.77 (s, 1H); 7.92 (dd, J=1.0 and 5.0 Hz, 1H); 8.02 (d, J=5.0 Hz, 1H); 8.51 (broad m, 1H); 11.75 (broad s, 1H).

Mass spectrum (EI): m/z=482 M$^+$; m/z=320 (M-C$_4$H$_4$NO$_2$S$_2$)$^+$ base peak b) Thiophene-2-sulfonic acid (2,4-dimethoxybenzyl)[2-(5,6-dimethoxy-1-methyl-1H-indol-3-yl)-1H-pyrrolo[2,3-b]pyrid-4-ylmethyl]amide is prepared as described in Example 179a starting with 0.150 g of thiophene-2-sulfonic acid (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amide instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1 cm$^3$ of 5N potassium hydroxide. 0.100 g of thiophene-2-sulfonic acid (2,4-dimethoxybenzyl)[2-(5,6-dimethoxy-1-methyl-1H-indol-3-yl)-1H-pyrrolo[2,3-b]pyrid-4-ylmethyl]amide is obtained, the characteristics of which are as follows:

Mass spectrum (ES): m/z=633 (M+H)$^+$ base peak c) Thiophene-2-sulfonic acid (2,4-dimethoxybenzyl) [2-(5,6-dimethoxy-1-methyl-1H-indol-3-yl)-1-(toluene-4-sulfonyl)-1H-pyrrolo[2,3-b]pyrid-4-ylmethyl]amide is prepared as described in Example 211b starting with 0.80 g of (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine and 0.114 g of 2-thiophenesulfonyl chloride instead of the 4-(trifluoromethoxy)benzenesulfonyl chloride used in Example 211b. 0.150 g of thiophene-2-sulfonic acid (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amide is obtained, the characteristics of which are as follows:

Mass spectrum (EI): m/z=786 M$^+$; m/z=631 (M-C$_7$H$_7$SO$_2$)$^+$ base peak; m/z=320 (m/z=631-C$_{13}$H$_{13}$NO$_4$S$_2$)$^+$

EXAMPLE 213

N-[2-(5,6-dimethoxy-1-methyl-1H-indol-3-yl)-1H-pyrrolo[2,3-b]pyrid-4-ylmethyl]benzenesulfonamide trifluoroacetate (A003454170A (P-32989-126-3))

a) N-[2-(5,6-Dimethoxy-1-methyl-1H-indol-3-yl)-1H-pyrrolo[2,3-b]pyrid-4-ylmethyl]benzenesulfonamide trifluoroacetate is prepared as described in Example 210 starting with 0.04 g of N-(2,4-dimethoxybenzyl)-N-[2-(5,6-dimethoxy-1-methyl-1H-indol-3-yl)-1H-pyrrolo[2,3-b]pyrid-4-ylmethyl]benzenesulfonamide instead of the N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide used in Example 210 and 0.045 g of para-toluenesulfonic acid. 0.011 g of N-[2-(5,6-dimethoxy-1-methyl-1H-indol-3-yl)-1H-pyrrolo[2,3-b]pyrid-4-ylmethyl]benzenesulfonamide trifluoroacetate is obtained, the characteristics of which are as follows:

$^1$H NMR spectrum (300 MHz, (CD$_3$)$_2$SO d6, δ in ppm): 3.81 (s, 3H); 3.87 (s, 3H); 3.89 (s, 3H); 4.33 (d, J=6.5 Hz, 2H); 6.91 (d, J=5.0 Hz, 1H); 6.93 (d, J=2.0 Hz, 1H); 7.11 (s, 1H); 7.49 (s, 1H); from 7.52 to 7.68 (m, 3H); 7.78 (s, 1H); 7.87 (broad d, J=7.5 Hz, 2H); 8.01 (d, J=5.0 Hz, 1H); 8.31 (broad t, J=6.5 Hz, 1H); 11.8 (broad s, 1H).

Mass spectrum (ES): m/z=477; (M+H)$^+$ b) N-(2,4-Dimethoxybenzyl)-N-[2-(5,6-dimethoxy-1-methyl-1H-indol-3-yl)-1H-pyrrolo[2,3-b]pyrid-4-ylmethyl]benzenesulfonamide is prepared as described in Example 179a starting with 0.090 g of N-(2,4-dimethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]benzenesulfonamide instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 0.6 cm$^3$ of 5N potassium hydroxide. 0.100 g of N-(2,4-dimethoxybenzyl)-N-[2-(5,6-dimethoxy-1-methyl-1H-indol-3-yl)-1H-pyrrolo[2,3-b]pyrid-4-ylmethyl]benzenesulfonamide is obtained, the characteristics of which are as follows:

Mass spectrum (ES): m/z=627 (M+H)$^+$ base peak c) N-(2,4-Dimethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]benzenesulfonamide is prepared as described in Example 211b starting with 0.80 g of (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine and 0.110 g of benzenesulfonyl chloride instead of the 4-(trifluoromethoxy)benzenesulfonyl chloride used in Example 211b. 0.060 g of N-(2,4-dimethoxybenzyl)-N-[2-(5,6-dimethoxy-1-methyl-1H-indol-3-yl)-1-(toluene-4-sulfonyl)-1H-pyrrolo[2,3-b]pyrid-4-ylmethyl]benzenesulfonamide is obtained, the characteristics of which are as follows:

Mass spectrum (ES): m/z 781 (M+H)$^+$ base peak

EXAMPLE 214

1-[2-(5,6-dimethoxy-1-methyl-1H-indol-3-yl)-1H-pyrrolo[2,3-b]pyrid-4-ylmethyl]-3-(4-trifluoromethoxyphenyl)urea trifluoroacetate (A003454230A (P-32989-128'-2))

a) 1-[2-(5,6-Dimethoxy-1-methyl-1H-indol-3-yl)-1H-pyrrolo[2,3-b]pyrid-4-ylmethyl]-3-(4-trifluoromethoxyphenyl)urea trifluoroacetate is prepared as described in Example 210 starting with 0.04 g of 1-(2,4-dimethoxybenzyl)-1-[2-(5,6-dimethoxy-1-methyl-1H-indol-3-yl)-1H-pyrrolo[2,3-b]pyrid-4-ylmethyl]-3-(4-trifluoromethoxyphenyl)urea instead of the N-(2,4-dimethoxybenzyl)-N-[2-(5,6-dimethoxy-1-methyl-1H-indol-3-yl)-1H-pyrrolo[2,3-b]pyrid-4-ylmethyl]-4-trifluoromethoxybenzenesulfonamide used in Example 210 and 0.045 g of para-toluenesulfonic acid. 0.0015 g of 1-[2-(5,6-dimethoxy-1-methyl-1H-indol-3-yl)-1H-pyrrolo[2,3-b]pyrid-4-ylmethyl]-3-(4-trifluoromethoxyphenyl)urea trifluoroacetate is obtained, the characteristics of which are as follows:

$^1$H NMR spectrum (300 MHz, (CD$_3$)$_2$SO d6, δ in ppm): 3.78 (s, 3H); 3.80 (s, 3H); 3.86 (s, 3H); 4.63 (broad d, J=6.5 Hz, 2H); 6.78 (broad t, J=6.5 Hz, 1H); 6.83 (broad s, 1H); 6.93 (d, J=5.0 Hz, 1H); 7.10 (s, 1H); 7.22 (broad d, J=8.5 Hz, 2H); 7.43 (s, 1H); 7.52 (broad d, J=8.5 Hz, 2H); 7.77 (s, 1H); 8.06 (d, J=5.0 Hz, 1H); 8.82 (s, 1H); 11.75 (broad s, 1H).

Mass spectrum (ES): m/z=540 (M+H)$^+$ base peak b) 1-(2,4-Dimethoxybenzyl)-1-[2-(5,6-dimethoxy-1-methyl-1H-indol-3-yl)-1H-pyrrolo[2,3-b]pyrid-4-ylmethyl]-3-(4-trifluoromethoxyphenyl)urea is prepared as described in Example 179a starting with 0.150 g of 1-(2,4-dimethoxybenzyl)-1-[2-(5,6-dimethoxy-1-methyl-1H-indol-3-yl)-1-(toluene-4-sulfonyl)-1H-pyrrolo[2,3-b]pyrid-4-ylmethyl]-3-(4-trifluoromethoxyphenyl)urea instead of the [2-(5,6-dimethoxy-1-methyl-1H-indol-3-yl)-1-(toluene-4-sulfonyl)-1H-pyrrolo[2,3-b]pyrid-4-ylmethyl](4-trifluoromethylsulfanylbenzyl)amine used in Example 179a and 1 cm$^3$ of 5N potassium hydroxide. 0.040 g of 1-(2,4-dimethoxybenzyl)-1-[2-(5,6-dimethoxy-1-methyl-1H-indol-3-yl)-1H-pyrrolo[2,3-b]pyrid-4-ylmethyl]-3-(4-trifluoromethoxyphenyl)urea is obtained, the characteristics of which are as follows:

Mass spectrum (ES): m/z=690 (M+H)+ base peak c) 1-(2,4-Dimethoxybenzyl)-1-[2-(5,6-dimethoxy-1-methyl-1H-indol-3-yl)-1-(toluene-4-sulfonyl)-1H-pyrrolo[2,3-b]pyrid-4-ylmethyl]-3-(4-trifluoromethoxyphenyl)urea may be prepared in the following manner:

0.094 cm$^3$ of 4-(trifluoromethoxy)phenyl isocyanate is added to a solution of 0.080 g of (2,4-dimethoxybenzyl)[2-(5,6-dimethoxy-1-methyl-1H-indol-3-yl)-1-(toluene-4-sulfonyl)-1H-pyrrolo[2,3-b]pyrid-4-ylmethyl]amine in 6 cm$^3$ of dichloromethane, under an argon atmosphere, at a temperature in the region of 20° C. The reaction medium is stirred at this same temperature for 24 hours. 2 cm$^3$ of water are added. After separation of the phases by settling, the organic phase is dried over magnesium sulfate, filtered and then concentrated under reduced pressure. After purification by flash-pack chromatography (SiO2, dichloromethane/methanol 98/02 by volume as eluent), 0.150 g of 1-(2,4-dimethoxybenzyl)-1-[2-(5,6-dimethoxy-1-methyl-1H-indol-3-yl)-1-(toluene-4-sulfonyl)-1H-pyrrolo[2,3-b]pyrid-4-ylmethyl]-3-(4-trifluoromethoxyphenyl)urea is obtained, the characteristics of which are as follows:

Mass spectrum (EI): m/z=843 (M)+; m/z=640 (M-C$_8$H$_4$NO$_2$F$_3$)+; m/z=485 (m/z=640-C$_7$H$_7$SO$_2$)+; m/z=203 (C$_8$H$_4$NO$_2$F$_3$+) base peak

EXAMPLE 215

2-[5,6-dimethoxy-1-methyl-1H-indol-3-yl]-4-methyl-1H-pyrrolo[2,3-b]pyridine (A003338710 (P-31376-043-1))

a) 2-[5,6-Dimethoxy-1-methyl-1H-indol-3-yl]-4-methyl-1H-pyrrolo[2,3-b]pyridine is prepared in the following manner:

1.3 cm$^3$ of aqueous 5N potassium hydroxide solution are added to a solution of 0.13 g of 2-[5,6-dimethoxy-1-methyl-1H-indol-3-yl]-1-(toluene-4-sulfonyl)-4-methyl-1H-pyrrolo[2,3-b]pyridine in 15 cm$^3$ of methanol, at a temperature in the region of 20° C. The reaction medium is refluxed for about 18 hours. The reaction mixture is evaporated under reduced pressure and the residue thus obtained is dissolved in 100 cm$^3$ of ethyl acetate, transferred into a separating funnel and washed with 50 cm$^3$ of distilled water. The aqueous phase is re-extracted with twice 50 cm$^3$ of ethyl acetate, and the combined organic phases are washed successively with 50 cm$^3$ of saturated aqueous sodium chloride solution and 50 cm$^3$ of distilled water. The organic extract is dried over magnesium sulfate, filtered and evaporated under reduced pressure to give the crude compound, which is purified by chromatography on a Flash Chromabond RS 6 SiOH cartridge (3 g of silica). The elution was performed at a flow rate of 10 cm$^3$/min with a heptane/isopropanol mixture (70/30 by volume). The fractions containing the expected compound are combined and evaporated to give 2-[5,6-dimethoxy-1-methyl-1H-indol-3-yl]-4-methyl-1H-pyrrolo[2,3-b]pyridine in the form of a pasty yellow solid (0.008 g, 8%), the characteristics of which are as follows:

$^1$H NMR spectrum (300 MHz, (CD$_3$)$_2$SO d6, δ in ppm): 2.55 (s, 3H); 3.81 (s, 3H); 3.86 (s, 3H); 3.89 (s, 3H); 6.73 (d, J=2.0 Hz, 1H); 6.82 (d, J=5.0 Hz, 1H); 7.10 (s, 1H); 7.47 (s, 1H); 7.75 (s, 1H); 7.98 (d, J=5.0 Hz, 1H); 11.65 (broad s, 1H).

Mass spectrum (ES): m/z=322 (M+H)+ b) 2-[5,6-Dimethoxy-1-methyl-1H-indol-3-yl]-1-(toluene-4-sulfonyl)-4-methyl-1H-pyrrolo[2,3-b]pyridine is prepared in the following manner:

0.017 g of sodium hydride (60%) is added to a solution of 0.17 g of 2-[5,6-dimethoxy-1H-indol-3-yl]-1-(toluene-4-sulfonyl)-4-methyl-1H-pyrrolo[2,3-b]pyridine in 7 cm$^3$ of anhydrous dimethylformamide, under an inert atmosphere of argon at a temperature in the region of 20° C. After stirring for one hour at the same temperature, 0.025 cm$^3$ of methyl iodide is added. Stirring is continued at this temperature for 4 hours. The reaction mixture is taken up in 50 cm$^3$ of water and then extracted with 100 cm$^3$ of ethyl acetate, and the aqueous phase is re-extracted with 2×50 cm$^3$ of ethyl acetate. The combined organic phases are washed successively with 50 cm$^3$ of saturated aqueous sodium chloride solution and then with 50 cm$^3$ of distilled water. After separation of the phases by settling, the organic phase is dried over magnesium sulfate, filtered and then concentrated under reduced pressure. The residue obtained is purified on a Flash Chromabond RS 6 SiOH cartridge (3 g of silica). The elution was performed at a flow rate of 10 cm$^3$/min with a dichloromethane/methanol mixture (95/05 by volume). The fractions containing the expected compound are combined and evaporated to give 2-[5,6-dimethoxy-1-methyl-1H-indol-3-yl]-1-(toluene-4-sulfonyl)-4-methyl-1H-pyrrolo[2,3-b]pyridine in the form of a beige-colored solid (0.130 g, 72%), the characteristics of which are as follows:

Mass spectrum (ES): m/z=476 (M+H)+ c) 2-[5,6-Dimethoxy-1H-indol-3-yl]-1-(toluene-4-sulfonyl)-4-methyl-1H-pyrrolo[2,3-b]pyridine is prepared in the following manner:

0.475 g of 1-tert-butyloxycarbonyl-5,6-dimethoxyindol-3-boronic acid and 4.5 cm$^3$ of saturated aqueous sodium bicarbonate solution are added successively to a solution of 0.61 g of 1-(toluene-4-sulfonyl)-1H-2-iodo-4-methylpyrrolo[2,3-b]pyridine in 14 cm$^3$ of anhydrous dimethylformamide. The reaction mixture is purged with argon using a sparge tube for 30 minutes, and 0.085 g of tetrakis(triphenylphosphine)palladium is added. The reaction medium is heated at 120° C. for 4 hours. After cooling, the reaction medium is filtered through Celite and the filtrate is concentrated under reduced pressure. The oil obtained is taken up in 100 cm$^3$ of water and extracted with 2×100 cm$^3$ of ethyl acetate, the organic phase is washed successively with 2×50 cm$^3$ of distilled water, 50 cm$^3$ of saturated aqueous sodium chloride solution and 50 cm$^3$ of distilled water. The organic phase is dried over magnesium sulfate in the presence of animal charcoal, filtered through Celite and then concentrated under reduced pressure. The residue obtained is purified on a Flash Chromabond RS 70 SiOH cartridge (35 g of silica). The elution was performed at a flow rate of 10 cm$^3$/minute with a heptane/isopropanol mixture (90/10 by volume). The fractions containing the expected compound are combined and evaporated under reduced pressure. 2-[5,6-Dimethoxy-1H-indol-3-yl]-1-(toluene-4-sulfonyl)-4-methyl-1H-pyrrolo[2,3-b]pyridine is thus obtained in the form of a beige-colored powder (0.17 g, 25%), the characteristics of which are as follows:

Mass spectrum (ES): m/z=462 (M+H)+

1-tert-Butyloxy-carbonyl-5,6-dimethoxyindol-3-boronic acid is prepared according to the process described in patent WO 03/000688 A1.

d) 1-(Toluene-4-sulfonyl)-1H-2-iodo-4-methylpyrrolo[2,3-b]pyridine is prepared in the following manner:

1.1 cm$^3$ of n-BuLi (2.5 M in hexane) are added dropwise to a solution of 0.5 g of 1-(toluene-4-sulfonyl)-1H-4-methylpyrrolo[2,3-b]pyridine in 8 cm$^3$ of anhydrous tetrahydrofuran, under an inert atmosphere of argon at a temperature in the region of −70° C. The reaction medium is stirred at this same temperature for 1 hour, and a solution of 0.8 g of iodine in 4 cm³ of tetrahydrofuran is then added dropwise. The reaction medium is stirred at −78° C. for 15 minutes. The reaction medium is stirred for 20 hours. 50 cm³ of water are added and the reaction medium is extracted with 3×100 cm³ of ethyl acetate. The organic phase is washed successively with 100 cm³ of distilled water, 100 cm³ of saturated aqueous sodium chloride solution, and 100 cm³ of distilled water. The organic phase is dried over magnesium sulfate, filtered and then concentrated under reduced pressure. The residue obtained is purified on a Macherey-Nagel cartridge (15 g of silica). The elution was performed at a flow rate of 10 cm³/minute with a (cyclohexane/ethyl acetate) mixture (75/25, V/V). The fractions containing the expected compound are combined and evaporated under reduced pressure. 1-(Toluene-4-sulfonyl)-1H-2-iodo-4-methylpyrrolo[2,3-b]pyridine is thus obtained in the form of a brown oil (0.61 g, 43%), the characteristics of which are as follows:

Mass spectrum (EI): m/z=412 (M)⁺; m/z=348 (M-SO₂)⁺; m/z=221 (m/z=348-I)⁺; m/z=91; (C₇H₇)⁺ base peak e) 1-(Toluene-4-sulfonyl)-1H-4-methylpyrrolo[2,3-b]pyridine is prepared in the following manner:

4.020 g of triphenylphosphine, 5.4 g of lithium chloride, 2.115 g of bis(triphenylphosphine)palladium(II) chloride and 18.19 g of tetramethyltin are added to a solution of 10 g of 1-(toluene-4-sulfonyl)-1H-4-iodo-pyrrolo[2,3-b]pyridine in 120 cm³ of dimethylformamide, under an inert atmosphere of argon at a temperature in the region of 20° C. The reaction medium is heated at a temperature in the region of 120° C. for 20 hours. After cooling, the reaction medium is concentrated under reduced pressure. The residue obtained is taken up in 200 cm³ of ethyl acetate and extracted with 2×50 cm³ of water. The organic phase is dried over magnesium sulfate in the presence of animal charcoal, filtered through Celite and then concentrated under reduced pressure. The residue obtained is taken up in 50 ml of methanol. The solid obtained is filtered off through a sinter funnel. 5.1 g of 1-(toluene-4-sulfonyl)-1H-4-methylpyrrolo[2,3-b]pyridine are thus obtained in the form of a yellow solid, the characteristics of which are as follows:

Mass spectrum (EI): m/z=286 (M)⁺; m/z=222 (M-SO₂)⁺ base peak; m/z=91; (C₇H₇)⁺ f) 1-(Toluene-4-sulfonyl)-1H-4-iodo-pyrrolo[2,3-b]pyridine is prepared in the following manner:

10.6 g of para-toluenesulfonyl chloride and 0.331 g of tetrabutylammonium hydrogen sulfate are added to a solution of 12 g of 1H-4-iodo-pyrrolo[2,3-b]pyridine in 425 cm³ of toluene, under an inert atmosphere of argon at a temperature in the region of 20° C., followed by dropwise addition of a 3.1N sodium hydroxide solution. The reaction medium is stirred at a temperature in the region of 20° C. for 16 hours. After separation of the phases by settling, the organic phase is dried over sodium sulfate, filtered and then concentrated under reduced pressure. 19.3 g of 1-(toluene-4-sulfonyl)-1H-4-iodo-pyrrolo[2,3-b]pyridine are thus obtained, the characteristics of which are as follows:

Mass spectrum (EI): m/z=398; (M)⁺; m/z=334 (M-S₂)⁺ base peak; m/z=91 (C₇H₇)⁺

The compound 1H-4-iodo-pyrrolo[2,3-b]pyridine is prepared according to the process described in Synlett, 2001, 5, 609-612.

EXAMPLE 216

Pharmaceutical Composition

Tablets corresponding to the following formula were prepared:

| | |
|---|---|
| Compound of Example 94 | 0.2 g |
| Excipient for a finished tablet weighing (excipient details: lactose, talc, starch, magnesium stearate). | 1 g |

EXAMPLE 217

Pharmaceutical Composition

Tablets corresponding to the following formula were prepared:

| | |
|---|---|
| Compound of Example 101 | 0.2 g |
| Excipient for a finished tablet weighing (excipient details: lactose, talc, starch, magnesium stearate). | 1 g |

EXAMPLE 218

Pharmaceutical Composition

Tablets corresponding to the following formula were prepared:

| | |
|---|---|
| Compound of Example 193 | 0.2 g |
| Excipient for a finished tablet weighing (excipient details: lactose, talc, starch, magnesium stearate) | 1 g |

What is claimed is:
1. A compound of formula (I):

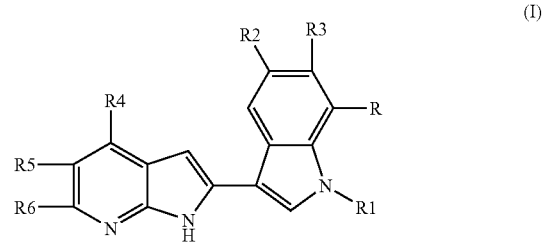

wherein:
R represents hydrogen or is selected from the values of R2 and R3,
R1 represents alkenyl or alkyl substituted with —CO—NR7R8, —NR7R8, hydroxyl, or a halogen atom, R2 and R3, which may be identical or different, represent alkyl or —O—alkyl optionally substituted with —CO—NR7R8, —NR7R8, alkoxy, alkoxy-NR7R8, free or esterified carboxyl, or phenyl, which is itself optionally substituted, R4, R5 and R6, which may be identical or different, are selected from a hydrogen atom, a halogen atom and cyano, amino, and optionally substituted alkoxy or alkyl radicals, R4 also being selected from the group consisting of carboxaldehyde —CH=O, formaldoxime —CH=N—OH and methylhydroxylamine —CH2NHOH;

R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted, all the above alkyl, alkenyl, cycloalkyl, cycloalkenyl, heterocycloalkyl, aryl and heteroaryl radicals, which may be monocyclic or bicyclic, and also the heterocyclic radical formed by R7 and R8 with the nitrogen atom to which they are attached, being optionally substituted with one or more radicals, which may be identical or different, selected from a halogen atom and cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)—C(=O)—R9, —N(R11)—C(=O)—OR10, —NR12R13, —C(=O)—NR12R13, —N(R11)—C(=O)—NR12R13, —S(O)n—R9, —N(R11)—S(O)n—R9, —S(O)n—NR12R13 and —N(R11)—S(O)n—NR12R13 radicals, n represents an integer from 0 to 2, the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from a halogen atom and hydroxyl, alkyl, alkoxy, —NR12R13, free or esterified carboxyl, CF3, nitro, cyano, phenyl and phenylalkyl radicals in which the phenyl radical is itself optionally substituted with one or more radicals, which may be identical or different, selected from a halogen atom and hydroxyl, alkyl, alkoxy, free or esterified carboxyl, CF3, nitro, cyano and pyridyl radicals;

R9 represents alkyl, alkenyl, cycloalkyl, heterocycloalkyl, aryl, heteroaryl, cycloalkylalkyl, heterocycloalkylalkyl, arylalkyl or heteroarylalkyl, all these radicals being optionally substituted, R10 represents the values of R9 or hydrogen, R11 represents hydrogen or optionally substituted alkyl, R12 and R13, which may be identical or different, represent hydrogen, acyl, alkyl, cycloalkyl, heterocycloalkyl, heteroaryl, SO2-heteroaryl, —SO2-alkyl, —SO2-phenyl, —CO—NH-phenyl and phenyl radicals, all these radicals being optionally substituted, or alternatively R12 and R13 form, with the nitrogen atom to which they are attached, an unsaturated or partially or totally saturated 3- to 10-membered heterocyclic radical containing one or more hetero atoms selected from O, S, N and NR14, this radical being optionally substituted, R14 represents the values of R9, hydrogen, acyl or free or esterified carboxyl, the radicals R9, R10, R11, R12, R13 and R14 above, and also the cyclic radical that may be formed by R12 and R13 with the nitrogen atom to which they are attached, being optionally substituted with one or more radicals, which may be identical or different, selected from a halogen atom and alkyl, alkyl-NH2, alkyl-NHCO2alkyl, NH2, NHCO2alkyl, hydroxyl, alkoxy, hydroxyalkoxy, free or esterified carboxyl, CF3, SCF3, OCF3, OCHF2, SO2CF3, nitro, cyano, heterocycloalkyl, heteroaryl and phenyl radicals, the latter cyclic radicals themselves being optionally substituted with one or more radicals, which may be identical or different, selected from a halogen atom and alkyl, hydroxyl, alkoxy, free or esterified carboxyl, CF3, SCF3, OCF3, OCHF2, SO2CF3, NH2, NHCO2alkyl, nitro and cyano radicals, all the above aryl, heteroaryl and heterocycloalkyl radicals being, in addition, optionally substituted with an alkylenedioxy radical, all the above alkyl, alkenyl, alkoxy or —O-alkyl and alkylthio radicals being linear or branched and containing no more than 6 carbon atoms, all the above cycloalkyl radicals containing no more than 7 carbon atoms, all the above aryl, heteroaryl and heterocycloalkyl radicals containing no more than 10 carbon atoms;

or a stereoisomer, a racemate, an enantiomer or a diastereoisomer of said compound of formula (I), or a pharmaceutically acceptable addition salt of said compound of formula (I) with a mineral or organic acid or a mineral or organic base.

2. The compound of formula (I) according to claim 1, wherein:

R represents hydrogen or is selected from the values of R2 and R3,

R1 represents alkenyl or alkyl substituted with —CO—NR7R8, —NR7R8, hydroxyl, or a halogen atom, R2 and R3, which may be identical or different, represent alkyl or —O-alkyl optionally substituted with —CO—NR7R8, —NR7R8, alkoxy, alkoxy-NR7R8, free or esterified carboxyl, or phenyl, which is itself optionally substituted, R4, R5 and R6, which may be identical or different, are selected from a hydrogen atom, a halogen atom and cyano, amino, and optionally substituted alkoxy or alkyl radicals, R4 also being selected from the group consisting of carboxaldehyde —CH=O, formaldoxime —CH=N—OH and methylhydroxylamine —CH2NHOH;

R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted, all the above alkyl, alkenyl, cycloalkyl, cycloalkenyl, heterocycloalkyl, aryl and heteroaryl radicals, which may be monocyclic or bicyclic, and also the heterocyclic radical formed by R7 and R8 with the nitrogen atom to which they are attached, being optionally substituted with one or more radicals, which may be identical or different, selected from a halogen atom and cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)—C(=O)—R9, —N(R11)—C(=O)—OR10, —NR12R13, —C(=O)—NR12R13, —N(R11)—C(=O)—NR12R13, —S(O)n—R9, —N(R11)—S(O)n—R9, —S(O)n—NR12R13 and —N(R11)—S(O)n—NR12R13 radicals, n represents an integer from 0 to 2, the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from a halogen atom and hydroxyl, alkyl, alkoxy, —NR12R13, free or esterified carboxyl, CF3, nitro, cyano, phenyl and phenylalkyl radicals in which the phenyl radical is itself optionally substituted with one or more radicals, which may be identical or different, selected from a halogen atom and hydroxyl, alkyl, alkoxy, free or esterified carboxyl, CF3, nitro, cyano and pyridyl radicals;

R9 represents alkyl, alkenyl, cycloalkyl, heterocycloalkyl, aryl, heteroaryl, cycloalkylalkyl, heterocycloalkylalkyl, arylalkyl or heteroarylalkyl, all these radicals being optionally substituted, R10 represents the values of R9 or hydrogen, R11 represents hydrogen or optionally substituted alkyl, R12 and R13, which may be identical or different, represent hydrogen, acyl, alkyl, cycloalkyl, piperidyl, piperazinyl, pyrrolidinyl, azetidinyl, pyrazolyl, pyridyl, imidazolyl, pyrimidyl, thiazolyl, thiazolidinyl, —SO2-thienyl, —SO2-pyridyl, —SO2-alkyl, —SO2-phenyl, —CO—NH-phenyl and phenyl radicals, all these radicals being optionally substituted, or alternatively R12 and R13 form, with the nitrogen atom to which they are attached, an unsaturated or partially or totally saturated 3- to 10-membered heterocyclic radical containing one or more hetero atoms selected from O, S, N and NR14, this radical being optionally substituted, R14 represents the values of R9 or hydrogen, acyl or free or esterified carboxyl, the radicals R9, R10, R11, R12, R13 and R14 above, and also the cyclic radical that may be formed by R12 and R13 with the nitrogen atom to which they are attached, being optionally substituted with one or more radicals, which may be identical or different, selected from a halogen atom and alkyl, —CH2—NH2, —CH2—NHCO2alkyl, NH2, NHCO2alkyl, hydroxyl, alkoxy, hydroxyalkoxy, free or esterified carboxyl, CF3, SCF3, OCF3, OCHF2, SO2CF3, nitro, cyano, piperidyl, morpholinyl, piperazinyl, thienyl, pyridyl, imidazolyl, thiazolyl, thiazolidinyl and phenyl radicals, the latter cyclic radicals themselves being optionally substituted with one or more radicals, which may be identical or different, selected from a halogen atom and alkyl, hydroxyl, alkoxy, free or esterified carboxyl, CF3, SCF3, OCF3, OCHF2, SO2CF3, NH2, NHCO2alkyl, nitro and cyano radicals, all the above aryl, heteroaryl and heterocycloalkyl radicals being, in addition, optionally substituted with an alkylenedioxy radical, all the above alkyl, alkenyl, alkoxy or —O-alkyl and alkylthio radicals being linear or branched and containing no more than 6 carbon atoms, all the above cycloalkyl radicals containing no more than 7 carbon atoms, all the above aryl, heteroaryl and heterocycloalkyl radicals containing no more than 10 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

3. The compound of formula (I):

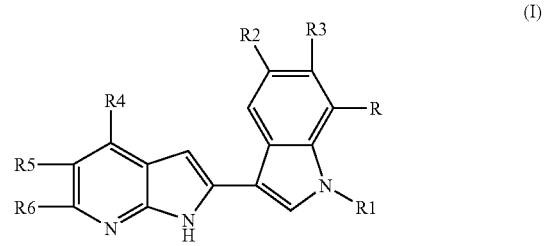

(I)

wherein:

R represents hydrogen or is selected from the values for R2 and R3,

R1 represents alkenyl or alkyl optionally substituted with —CO—NR7R8, —NR7R8, free or esterified carboxyl, hydroxyl, alkoxy or a halogen atom, one of R2 and R3 represents alkyl or —O-alkyl optionally substituted with —CO—NR7R8, —NR7R8, alkoxy, alkoxy—NR7R8, free or esterified carboxyl, or phenyl which is itself optionally substituted, and the other of R2 and R3 independently represents alkyl or —O-alkyl substituted with —CO—NR7R8, —NR7R8, alkoxy, alkoxy-NR7R8, free or esterified carboxyl, or phenyl which is itself optionally substituted;

R4, R5 and R6, which may be identical or different, are selected from a hydrogen atom, a halogen atom and the radicals: cyano, amino, and optionally substituted alkoxy or alkyl, R7 and R8, which may be identical or different, are selected from hydrogen, alkyl, alkenyl, cycloalkyl, cycloalkenyl, heterocycloalkyl, aryl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted, all the above radicals: alkyl, alkenyl, cycloalkyl, cycloalkenyl, heterocycloalkyl, aryl and heteroaryl, which may be monocyclic or bicyclic, and also the heterocyclic radical formed by R7 and R8 with the nitrogen atom to which they are attached, being optionally substituted with one or more radicals, which may be identical or different, selected from a halogen atom and the radicals: cyano, hydroxyl, alkyl, alkoxy, alkylthio, nitro, oxo, cycloalkyl, heterocycloalkyl, aryl, heteroaryl, cycloalkylalkyl, heterocycloalkylalkyl, arylalkyl, heteroarylalkyl, —C(=O)—R9, —C(=O)—OR10, —N(R11)—C(=O)—R9, —N(R11)—C(=O)—OR10, —NR12R13, —C(=O)—NR12R13, —N(R11)—C(=O)—NR12R13, —S(O)n—R9, —N(R11)—S(O)n—R9, —S(O)n—NR12R13 and —N(R11)—S(O)n—NR12R13, n represents an integer from 0 to 2, the latter alkyl, alkoxy, cycloalkyl, heterocycloalkyl, aryl, heteroaryl, cycloalkylalkyl, heterocycloalkylalkyl, arylalkyl and heteroarylalkyl radicals themselves being optionally substituted with one or more radicals, which may be identical or different, selected from a halogen atom and hydroxyl, alkyl, alkoxy, —NR12R13, pyrrolidinyl, free or esterified carboxyl, $CF_3$, nitro, cyano, and phenyl and phenylalkyl radicals in which the phenyl radical is itself optionally substituted with one or more radicals, which may be identical or different, selected from a halogen atom and hydroxyl, alkyl, alkoxy, free or esterified carboxyl, $CF_3$, nitro, cyano and pyridyl radicals, R9 represents alkyl, alkenyl, cycloalkyl, heterocycloalkyl, aryl, heteroaryl, cycloalkylalkyl, heterocycloalkylalkyl, arylalkyl, or heteroarylalkyl, all these radicals being optionally substituted, R10 represents the values of R9 or hydrogen, R11 represents hydrogen or optionally substituted alkyl, R12 and R13, which may be identical or different, represent hydrogen, acyl, alkyl, cycloalkyl and phenyl radicals, these radicals being optionally substituted, or alternatively R12 and R13 form, with the nitrogen atom to which they are attached, an unsaturated or partially or totally saturated 3- to 10-membered heterocyclic radical containing one or more hetero atoms selected from O, S, N and NR14, this radical being optionally substituted, R14 represents the values for R9 or hydrogen, acyl or free or esterified carboxyl, the radicals R9, R10, R11, R12, R13 and R14 above being optionally substituted with one or more radicals, which may be identical or different, selected from a halogen atom and the radicals: alkyl, hydroxyl, alkoxy, hydroxyalkoxy, free or esterified carboxyl, $CF_3$, nitro, cyano and phenyl, itself optionally substituted with one or more radicals, which may be identical or different, selected from a halogen atom and the radicals: alkyl, hydroxyl, alkoxy, free or esterified carboxyl, $CF_3$, nitro and cyano, all the above aryl, heteroaryl and heterocycloalkyl radicals above being, in addition, optionally substituted with an alkylenedioxy radical, all the alkyl, alkenyl, alkoxy or —O-alkyl and alkylthio radicals above being linear or branched and containing no more than 6 carbon atoms, all the cycloalkyl radicals above containing no more than 7 carbon atoms, all the above aryl, heteroaryl and heterocycloalkyl radicals containing no more than 10 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

4. The compound of formula (I) according to claim 1, wherein R2 and R3, which may be identical or different, represent —O-alkyl containing no more than 4 carbon atoms, optionally substituted with —CO—NR7R8, —NR7R8, alkoxy, alkoxy- NR7R8 or free or esterified carboxyl;

R, R1, R4, R5, R6, R7 and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

5. The compound of formula (I) according to claim 1, wherein R2 and R3, which may be identical or different, represent —O-alkyl containing no more than 4 carbon atoms, optionally substituted with —CO—NR7R8, —NR7R8, alkoxy, or alkoxy-NR7R8;

R, R1, R4, R5, R6, R7 and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

6. The compound of formula (I) according to claim 1, wherein R2 and R3, which may be identical or different, represent —O-alkyl containing no more than 4 carbon atoms, optionally substituted with —CO—NR7R8 or —NR7R8;

R, R1, R4, R5, R6, R7 and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

7. The compound of formula (I) according to claim 1, wherein R1 represents alkyl substituted with —CO—NR7R8, —NR7R8, hydroxyl, or a halogen atom;

R, R2, R3, R4, R5, R6, R7 and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

8. The compound of formula (I) according to claim 1, wherein R1 represents alkyl containing no more than 4 carbon atoms, substituted with —CO—NR7R8, —NR7R8, or hydroxyl;

R, R2, R3, R4, R5, R6, R7, and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

9. The compound of formula (I) according to claim 1, wherein R1 represents alkyl containing no more than 4 carbon atoms, substituted with —CO—NR7R8, —NR7R8 or hydroxyl;

R, R2, R3, R4, R5, R6, R7, and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

10. The compound of formula (I) according to claim 1, wherein R1 represents alkyl containing no more than 4 carbon atoms, substituted with —CO—NR7R8 or —NR7R8;

R, R2, R3, R4, R5, R6, R7, and R8 are as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

11. The compound of formula (I) according to claim 1, wherein R1 represents alkyl containing no more than 4 carbon atoms, substituted with NR7R8, R, R2, R3, R4, R5, R6, R7, and R8 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

12. The compound of formula (I) according to claim 1, wherein
R4, R5 and R6 are such that one represents hydrogen and the others, which may be identical or different, are selected from a hydrogen atom, a halogen atom and the radicals: cyano, amino or alkyl which may be optionally substituted;
R, R1, R2, and R3 are as defined in claim 1; or a stereoisomer, a racemate, an enantiomer or a diastereoisomer of said compound of formula (I);
or a pharmaceutically acceptable addition salt of said compound of formula (I) with a mineral or organic acid or a mineral or organic base.

13. The compound of formula (I) according to claim 1, wherein
R5 and R6, which may be identical or different, are selected from a hydrogen atom and a halogen atom,
R4, which may be identical to or different from R5 and R6, is selected from a halogen atom and amino, carboxaldehyde —CH=O, formaldoxime —CH=N—OH, methylhydroxylamine —CH2NHOH and alkyl radicals, optionally substituted with one or more radicals, which may be identical or different, selected from a halogen atom and cyano, hydroxyl, alkoxy, cycloalkyl, heterocycloalkyl, phenyl, heteroaryl and —NR12R13 radicals;
R, R1, R2, R3, R12 and R13 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

14. The compound of formula (I) according to claim 1, wherein
R4, R5 and R6 represent hydrogen or are such that two of them represent hydrogen and the third represents a halogen atom or a cyano radical;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

15. The compound of formula (I) according to claim 1, wherein R4, R5 and R6 represent hydrogen;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

16. The compound of formula (I) according to claim 1, wherein R4, R5 and R6 are such that two of them represent hydrogen and the third represents a halogen atom or a cyano radical;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

17. The compound of formula (I) according to claim 1, wherein R4, R5 and R6 are such that two of them represent hydrogen and the third represents a halogen atom;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

18. The compound of formula (I) according to claim 1, wherein R4, R5 and R6 are such that two of them represent hydrogen and the third represents a chlorine or fluorine atom;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

19. The compound of formula (I) according to claim 1, wherein R4, R5 and R6 are such that two of them represent hydrogen and the third represents a cyano radical;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

20. The compound of formula (I) according to claim 1, wherein R6 represents hydrogen;
R, R1, R2, R3, R4, and R5 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

21. The compound of formula (I) according to claim 1, wherein R5 and R6 represent hydrogen and R4 represents a halogen atom or a cyano radical;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

22. The compound of formula (I) according to claim 1, wherein R4 and R6 represent hydrogen and R5 represents a fluorine atom;
R, R1, R2, and R3 are as defined in claim 1;
or a stereoisomer, a racemate, an enantiomer or a diastereoisomer of said compound of formula (I);
or a pharmaceutically acceptable addition salt of said compound of formula (I) with a mineral or organic acid or a mineral or organic base.

23. The compound of formula (I) according to claim 1, wherein R, R1, R2, R3, R4, R5 and R6 are as defined in claim 1,
wherein the radical —NR12R13 is such that
R12 and R13, which may be identical or different, represent a hydrogen atom; and acyl, alkyl, cycloalkyl, piperidyl, piperazinyl, pyrrolidinyl, azetidinyl, pyrazolyl, pyridyl, imidazolyl, pyrimidyl, thiazolyl, thiazolidinyl, —SO2-thienyl, —SO2-pyridyl, —SO2-alkyl, —SO2-phenyl, —CO—NH-phenyl and phenyl radicals, all these radicals being optionally substituted with one or more radicals, which may be identical or different, selected from a halogen atom and the following radicals: alkyl; CH2—NH2; CH2—NHCO2alkyl; NH2; NHCO2alkyl; hydroxyl; alkoxy; hydroxyalkoxy; free or esterified carboxyl; CF3; SCF3; OCF3; OCHF2; SO2CF3; nitro; cyano; thienyl; piperidyl; morpholino, which is itself optionally substituted with one or two alkyl radicals; and phenyl, which is itself optionally substituted with one or more radicals, which may be identical or different, selected from a halogen atom and alkyl, hydroxyl, alkoxy, free or esterified carboxyl, CF3, SCF3, OCH3, OCHF2, SO2CF3, NH2, NHCO2alkyl, nitro and cyano radicals;

or alternatively R12 and R13 form, with the nitrogen atom to which they are attached, an unsaturated or partially or totally saturated 3- to 10-membered heterocyclic radical containing one or more hetero atoms selected from O, S, N and NR11, this radical being optionally substituted with one or more radicals, which may be identical or different, selected from a halogen atom and the following radicals: alkyl; —CH2—NH2; CH2—NHCO2alkyl; NH2; NHCO2alkyl; hydroxyl; alkoxy; hydroxyalkoxy; free or esterified carboxyl; CF3; SCF3; OCF3; OCHF2; SO2CF3; nitro; cyano; piperidyl; morpholinyl; piperazinyl; thienyl; pyridyl, imidazolyl, thiazolyl, thiazolidinyl and phenyl radicals, which are themselves optionally substituted with one or more radicals, which may be identical or different, selected from a halogen atom and alkyl, hydroxyl, alkoxy, free or esterified carboxyl, CF3, SCF3, NH2, NHCO2alkyl, nitro and cyano radicals;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

24. The compound of formula (I) according to claim 1, wherein R, R1, R2, R3, R4, R5 and R6 are as defined in claim 1, and R7 and R8, which may be identical or different, are selected from hydrogen, alkyl, cycloalkyl, phenyl, heterocycloalkyl and heteroaryl, which may be monocyclic or bicyclic, all these radicals being optionally substituted, or alternatively R7 and R8 form, with the nitrogen atom to which they are attached, an unsaturated or partially or totally saturated 3- to 10-membered heterocyclic radical containing one or more hetero atoms selected from O, S, N and NR14, this radical being optionally substituted, all the above radicals: alkyl, cycloalkyl, phenyl, heterocycloalkyl and heteroaryl, which may be monocyclic or bicyclic, and also the heterocyclic radical formed by R7 and R8 with the nitrogen atom to which they are attached, being optionally substituted with one or more radicals, which may be identical or different, selected from a halogen atom and the radicals: hydroxyl, alkyl, alkoxy, alkylthio, nitro, oxo, cycloalkyl, phenyl, heterocycloalkyl, heteroaryl, —C(=O)—R9, —C(=O)—OR10, —N(R11)—C(=O)—R9, —N(R11)—C(=O)—OR10, —NR12R13, —C(=O)—NR12R13, and —N(R11)—C(=O)—NR12R13, the latter alkyl, alkoxy, cycloalkyl, heterocycloalkyl and heteroaryl radicals themselves being optionally substituted with one or more radicals, which may be identical or different, selected from a halogen atom and the radicals: hydroxyl, alkyl, alkoxy, —NR12R13, free or esterified carboxy, pyrrolidinyl, phenyl and phenylalkyl in which the phenyl radical is itself optionally substituted with one or more radicals, which may be identical or different, selected from a halogen atom and the radicals: hydroxyl, alkyl, alkoxy, free or esterified carboxy, CF3, nitro, cyano and pyridyl, R9 represents alkyl, cycloalkyl, phenyl, heterocycloalkyl or heteroaryl, all these radicals being optionally substituted, R10 represents the values of R9 or hydrogen, R11 represents hydrogen or optionally substituted alkyl, R12 and R13, which may be identical or different, represent hydrogen, acyl, alkyl, cycloalkyl and phenyl, these radicals being optionally substituted, or alternatively R12 and R13 form, with the nitrogen atom to which they are attached, an unsaturated or partially or totally saturated 3- to 10-membered heterocyclic radical containing one or more hetero atoms selected from O, S, N and NR11, the radical being optionally substituted, R14 represents hydrogen, acyl, free or esterified carboxyl, alkyl, cycloalkyl or phenyl, optionally substituted, the radicals R9, R10, R11, R12, R13 and R14 above being optionally substituted with one or more radicals, which may be identical or different, selected from a halogen atom and the radicals: alkyl, hydroxyl, alkoxy, hydroxyalkoxy, free or esterified carboxyl, CF3, nitro, cyano and phenyl, itself optionally substituted with one or more radicals, which may be identical or different, selected from a halogen atom and the radicals: alkyl, hydroxyl, alkoxy, free or esterified carboxyl, CF3, nitro and cyano, all the phenyl and heteroaryl radicals above being, in addition, optionally substituted by a dioxol radical, all the above alkyl, alkenyl, alkoxy or —O-alkyl and alkylthio radicals being linear or branched and containing no more than 4 carbon atoms, all the above cycloalkyl radicals containing no more than 7 carbon atoms, all the above heteroaryl and heterocycloalkyl radicals containing no more than 10 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

25. The compound of formula (I) according to claim 1, wherein R, R1, R2, R3, R4, R5 and R6 are as defined in claim 1; and R7 and R8, which may be identical or different, are selected from hydrogen, cycloalkyl, optionally substituted alkyl, optionally substituted phenyl, heterocycloalkyl and monocyclic or bicyclic heteroaryl, which may be optionally substituted, or alternatively R7 and R8 form, with the nitrogen atom to which they are attached, an optionally substituted heterocyclic radical containing one or more hetero atoms, all the alkyl, phenyl and heterocyclic radicals above, and also the heterocyclic radical that R7 and R8 may form with the nitrogen atom to which they are attached, being optionally substituted with one or more radicals selected from a halogen atom and the radicals: hydroxyl; oxo; nitro; cycloalkyl; alkoxy; OCF3; hydroxyalkoxy; alkylthio; acyl; free or esterified carboxyl; optionally substituted phenyl; optionally substituted amino; alkyl optionally substituted with one or more radicals selected from a halogen atom and the radicals: hydroxyl, alkoxy, pyrrolidinyl, phenyl and amino, themselves optionally substituted; and pyrrolidinyl, piperidyl, pyridyl and piperazinyl, themselves optionally substituted with one or more radicals selected from the radicals: hydroxyl, alkyl, alkoxy, free or esterified carboxyl, phenyl and phenylalkyl, themselves optionally substituted, the amino radicals being optionally substituted with one or two radicals, which may be identical or different, selected from alkyl, hydroxyalkyl, alkoxyalkyl, acyl, phenyl and phenylalkyl, themselves optionally substituted, the phenyl and phenylalkyl radicals being optionally substituted with one or more radicals selected from a halogen atom and the radicals: hydroxyl, alkyl, alkoxy, $CF_3$, free or esterified carboxyl, pyridyl and dioxol, all the alkyl and alkoxy radicals being linear or branched and containing no more than 4 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

26. The compound of formula (I) according to claim 1, wherein R, R1, R2, R3, R4, R5 and R6 are as defined in claim 1, and R7 and R8, which may be identical or different, are selected from hydrogen and alkyl, cycloalkyl, phenyl and heterocyclic radicals selected from the group consisting of pyrrolidinyl, piperidyl, pyrimidinyl, thienyl, thiazolyl, pyran, furyl, tetrahydrofuryl, tetrahydrofuran-2-yl, imidazolinyl, piperazinyl, indolyl, pyrrole, benzopyran, quinolyl, pyridyl, purinyl and morpholinyl, these radicals being optionally substituted, or alternatively R7 and R8 form, with the nitrogen atom to which they are attached, a heterocyclic radical selected from pyrrolidinyl, imidazolyl, morpholinyl, piperazinyl, piperidyl, thiazolyl, diazepine, spiro [4.5]decane, pyrrolyl, dihydropyrrolyl, tetrahydropyrrolyl, tetrahydropyrrolo [3,4-c]pyrrolyl, piperidinyl, indolinyl, pyrindolinyl, tetrahydroquinolyl, thiazolidinyl, naphthyridyl, azetidine or quinazolinyl radicals, these radicals all being optionally substituted, all the above alkyl, phenyl and heterocyclic radicals being optionally substituted with one or more radicals selected from a halogen atom and the radicals: hydroxyl; oxo; nitro; cycloalkyl; alkoxy; $OCF_3$; hydroxyalkoxy; alkylthio; acyl; free or esterified carboxyl; optionally substituted phenyl; optionally substituted amino; alkyl optionally substituted with one or more radicals selected from a halogen atom and the radicals: hydroxyl, alkoxy, pyrrolidinyl, phenyl and amino, themselves optionally substituted; and pyrrolidinyl, piperidyl, pyridyl and piperazinyl, themselves optionally substituted with one or more radicals selected from the radicals: hydroxyl, alkyl, alkoxy, free or esterified carboxyl, phenyl and phenylalkyl, themselves optionally substituted, the amino radicals being optionally substituted with one or two radicals, which may be identical or different, selected from alkyl, hydroxyalkyl, alkoxyalkyl, acyl, phenyl and phenylalkyl, themselves optionally substituted, the phenyl and phenylalkyl radicals being optionally substituted with one or more radicals selected from a halogen atom and the radicals: hydroxyl, alkyl, alkoxy, $CF_3$, free or esterified carboxyl, pyridyl and dioxol, all the alkyl and alkoxy radicals being linear or branched and containing no more than 4 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

27. The compound of formula (I) according to claim 1, wherein R, R1, R2, R3, R4, R5 and R6 are as defined in claim 1, and R7 and R8, which may be identical or different, are selected from hydrogen, cycloalkyl radicals and alkyl, phenyl and heterocyclic radicals selected from the group consisting of pyrrolidinyl, piperidyl, furyl, tetrahydrofuryl, tetrahydrofuran-2-yl, imidazolinyl, piperazinyl, indolyl, pyrrolyl, benzopyranyl, benzopyran-8-carboxylic, pyridyl, purinyl and morpholinyl, all these radicals being optionally substituted, or alternatively R7 and R8 form, with the nitrogen atom to which they are attached, a heterocyclic radical selected from pyrrolidinyl, imidazolyl, morpholinyl, piperazinyl, piperidyl, thiazolyl, diazepine, spiro [4.5]decane, pyrrolyl, dihydropyrrolyl, tetrahydropyrrolyl and tetrahydropyrrolo [3,4-c]pyrrolyl radicals, all these radicals being optionally substituted, all the above alkyl, phenyl and heterocyclic radicals that R7 and R8 represent or that R7 and R8 may form with the nitrogen atom to which they are attached being optionally substituted with one or more radicals selected from the radicals: hydroxyl; oxo; cycloalkyl; alkoxy; hydroxyalkoxy; alkylthio; CO-alkyl; —CO-furyl; free or esterified carboxyl; optionally substituted phenyl; alkyl optionally substituted with a radical selected from hydroxyl, alkoxy, pyrrolidinyl, optionally substituted phenyl and amino optionally substituted with one or two radicals selected from alkyl and optionally substituted phenyl; amino optionally substituted with one or two radicals, which may be identical or different, selected from alkyl, hydroxyalkyl, alkoxyalkyl, CO-alkyl and phenyl, itself optionally substituted; pyrrolidinyl, piperidyl, pyridyl and piperazinyl, optionally substituted with one or more radicals selected from hydroxyl, alkyl, alkoxy, free or esterified carboxyl, phenylalkyl and optionally substituted phenyl, all the phenyl radicals being optionally substituted with one or more radicals, which may be identical or different, selected from a halogen atom and the radicals: hydroxyl, alkyl, alkoxy, $CF_3$, free or esterified carboxyl, pyridyl and dioxol;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

28. The compound of formula (I) according to claim 1, wherein R, R1, R2, R3, R4, R5 and R6 are as defined in claim 1, and R7 and R8, which may be identical or different, are selected from the following radicals:

hydrogen;

benzopyran;

pyridyl itself optionally substituted with hydroxyl;

piperidyl optionally substituted with alkyl, itself optionally substituted with phenyl;

purinyl;

alkyl optionally substituted with one or more radicals selected from hydroxyl; alkoxy; alkylthio; pyridyl; imidazolinyl, indolyl; pyrrolyl; furyl; tetrahydrofuryl; amino optionally substituted with one or two radicals, which may be identical or different, selected from alkyl, hydroxyalkyl, alkoxyalkyl and phenyl, itself optionally substituted with alkyl; pyrrolidinyl, itself optionally substituted with an alkyl radical; piperidyl, itself optionally substituted with alkyl or phenylalkyl; piperazinyl, itself optionally substituted with alkyl; phenyl optionally substituted with dioxol or free or esterified carboxyl;

phenyl optionally substituted with one or more radicals selected from alkoxy, piperidyl and piperazinyl, itself optionally substituted with an alkyl radical;

or alternatively R7 and R8 form, with the nitrogen atom to which they are attached, a heterocyclic radical selected from the following radicals:

imidazolyl;
dihydropyrrolyl;
1,4-dioxa-8-azaspiro [4.5]decane;
thiazolyl;
tetrahydropyrrolo [3,4-c]pyrrol-2-one;
tetrahydropyrrolo [3,4-c]pyrrole-1,3-dione;
pyrrolidinyl optionally substituted with a radical selected from pyridyl; amino, itself optionally substituted with an alkyl radical and an acyl radical;
and alkyl, itself optionally substituted with a radical selected from hydroxyl, alkoxy, pyrrolidinyl and amino, itself optionally substituted with a phenyl radical;
morpholinyl optionally substituted with one or more alkyl radicals;
piperazinyl optionally substituted with one or more radicals, which may be identical or different, selected from the radicals: oxo; cycloalkyl; acyl; carboxyl; pyridyl; alkyl containing no more than 4 carbon atoms, itself optionally substituted with a radical: hydroxyl, alkoxy, hydroxyalkoxy containing no more than 4 carbon atoms and phenyl, itself optionally substituted with a dioxol radical; phenyl, itself optionally substituted with one or more radicals selected from a halogen atom and hydroxyl, alkoxy and CF3 radicals;
piperidyl optionally substituted with one or more substituents selected from hydroxyl, alkyl, hydroxyalkyl and piperidyl;
diazepine or perhydro-1,4-diazepine optionally substituted with an alkyl radical; itself optionally substituted with pyrrolidinyl;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

29. The compound of formula (I) according to claim 1, wherein R, R1, R2, R3, R4, R5 and R6 are as defined in claim 1, and R7 and R8, which may be identical or different, are selected from the radicals: hydrogen, alkyl, itself optionally substituted with a pyrrolidinyl or piperidyl radical and phenyl, itself optionally substituted with one or more radicals selected from the piperazinyl radical, itself optionally substituted with an alkyl radical, or alternatively R7 and R8 form, together with the nitrogen atom to which they are attached, a radical selected from the following radicals: morpholinyl; thiazolyl; diazepine or perhydro-1,4-diazepine optionally substituted with an alkyl radical; 1-tetrahydropyrrolo[3,4-c]pyrrol-2-one; piperazinyl optionally substituted with one or more radicals, which may be identical or different, selected from the radicals: oxo and alkyl, itself optionally substituted with a hydroxyl, alkoxy or hydroxyalkoxy radical; piperidyl optionally substituted with hydroxyl, alkyl, hydroxyalkyl or piperidyl;

the alkyl and alkoxy radicals containing no more than 4 carbon atoms;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

30. The compound of formula (I) according to claim 26, wherein:

R and R6 represent a hydrogen atom,
R1 represents alkyl containing no more than 2 carbon atoms, substituted with —CO—NR7R8 or —NR7R8,
R2 and R3, which may be identical or different, represent —O-alkyl containing no more than 3 carbon atoms, optionally substituted with —CO—NR7R8 or —NR7R8,
R4 and R5 are such that one represents hydrogen and the other represents a halogen atom or a cyano radical,
R7 and R8 are as defined in claim 26;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

31. The compound of formula (I) according to claim 1, wherein R, R1, R2, R3, R4, R5, R6, R7 and R8 are as defined in claim 1, wherein R7 and R8 do not both represent hydrogen;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

32. The compound of formula (I) according to claim 1, wherein R, R1, R2, R3, R4, R5 and R6 are as defined in claim 1, and R7 and R8 are such that either one of R7 and R8 represents hydrogen or alkyl and the other is selected from the values for R7 and R8 as defined in claim 1, or R7 and R8 form, with the nitrogen atom to which they are attached, a heterocyclic radical as defined in claim 1;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

33. A compound selected from the group consisting of:
2-{5,6-dimethoxy-1-[2-(4-methylpiperazin- 1 -yl)ethyl]-1H-indol-3 -yl}-1H-pyrrolo[2,3- b]pyridine;
2-(4- {2-[5,6-dimethoxy-3-(1H-pyrrolo[2,3-b]pyrid-2-yl)indol-1-yl]ethyl}piperazin-1- yl)ethanol;
2-(1- {2-[5,6-dimethoxy-3-(1H-pyrrolo[2,3-b]pyrid-2-yl)indol-1-yl]ethyl}piperid-4-yl)ethanol;
1'-{2-[5,6-dimethoxy-3-(1H-pyrrolo[2,3-b]pyrid-2-yl)indol-1-yl]ethyl}-[1,4']bipiperidyl;
1-{2-[5,6-dimethoxy-3-(1H-pyrrolo[2,3-b]pyrid-2-yl)indol-1-yl]ethyl}piperid-3-ol;
2-{5,6-dimethoxy-1-[2-(4-methylperhydro-1,4-diazepin-1-yl)ethyl]-1H-indol-3-yl}-1H- pyrrolo[2,3-b]pyridine;
2-[5,6-dimethoxy-3-(1H-pyrrolo[2,3-b]pyrid-2-yl)indol-1-yl]-1-(4-hydroxypiperid-1- yl)ethanone;
2-[5,6-dimethoxy-3-(1H-pyrrolo[2,3-b]pyrid-2-yl)indol-1-yl]-1-thiazolidin-3-ylethanone;
4-{[5,6-dimethoxy-3-(1H-pyrrolo[2,3-b]pyrid-2-yl)indol-1-yl]acetyl}-1-methylpiperazin-2- one;

4-Chloro-2-(5,6-dimethoxy-1-methyl-1H-indol-3-yl)-1H-pyrrolo[2,3-b]pyridine;

2-(5,6-dimethoxy-1-methyl-1H-indol-3-yl)-1H-pyrrolo[2,3-b]pyridine-4-carbonitrile;

4-chloro-2-[5,6-dimethoxy-1-(2-morpholin-4-ylethyl)-1H-indol-3-yl]-1H-pyrrolo[2,3-b]pyridine;

2-(1-{2-[3-(4-chloro-1H-pyrrolo[2,3-b]pyrid-2-yl)-5,6-dimethoxyindol-1-yl]ethyl}piperid-4-yl)ethanol;

4-chloro-2-{5,6-dimethoxy-1-[2-(4-methylpiperazin-1-yl)ethyl]-1H-indol-3-yl}-1H-pyrrolo[2,3-b]pyridine;

2-{5,6-dimethoxy-1-[2-(4-methylpiperazin-1-yl)ethyl]-1H-indol-3-yl}-1H-pyrrolo[2,3-b]pyridine-4-carbonitrile;

2-(5,6-dimethoxy-1-methyl-1H-indol-3-yl)-5-fluoro-1H-pyrrolo[2,3-b]pyridine;

2-[5,6-dimethoxy-1-(2-morpholin-4-ylethyl)-1H-indol-3-yl]-5-fluoro-1H-pyrrolo[2,3-b]pyridine;

2-{5,6-dimethoxy-1-[2-(4-methylpiperazin-1-yl)ethyl]-1H-indol-3-yl}-5-fluoro-1H-pyrrolo[2,3-b]pyridine;

2-[5-Methoxy-1-methyl-3-(1H-pyrrolo[2,3-b]pyrid-2-yl)-1H-indol-6-yloxy]-1-morpholin-4-ylethanone;

2-[5-Methoxy-1-methyl-3-(1H-pyrrolo[2,3-b]pyrid-2-yl)-1H-indol-6-yloxy]-1-(4-methyl[1,4]diazepan-1-yl)ethanone;

2-[5-Methoxy-1-methyl-3-(1H-pyrrolo[2,3-b]pyrid-2-yl)-1H-indol-6-yloxy]-N-[4-(4-methylpiperazin-1-yl)phenyl]acetamide;

2-[5-Methoxy-1-methyl-3-(1H-pyrrolo[2,3-b]pyrid-2-yl)-1H-indol-6-yloxy]-1-(4-methylpiperazin-1-yl)ethanone;

1-{4-[2-(2-Hydroxyethoxy)ethyl]piperazin-1-yl}-2-[5-methoxy-1-methyl-3-(1H-pyrrolo[2,3-b]pyrid-2-yl)-1H-indol-6-yloxy]ethanone;

(3aS,6aS)-5-{2-[5-Methoxy-1-methyl-3-(1H-pyrrolo[2,3-b]pyrid-2-yl)-1H-indol-6-yloxy]acetyl}hexahydropyrrolo[3,4-c]pyrrol-1-one trifluoroacetate;

2-{5-Methoxy-1-methyl-6-[3-(4-methylperhydro-1,4-diazepin-1-yl)propoxy]-1H-indol-3-yl}-1H-pyrrolo[2,3-b]pyridine;

4-Chloro-2-{1-methyl-5-methoxy-6-[2-(4-methylpiperazin-1-yl)ethoxy]-1H-indol-3-yl}-1H-pyrrolo[2,3-b]pyridine;

4-Chloro-2-{1-methyl-5-methoxy-6-[2-(4-piperidylpiperid-1-yl)ethoxy]-1H-indol-3-yl}-1H-pyrrolo[2,3-b]pyridine;

4-Chloro-2-{5-methoxy-1-methyl-6-[2-(2-pyrrolidinethylamino)ethoxy]-1H-indol-3-yl}-1H-pyrrolo[2,3-b]pyridine; and 4-Chloro-2-{1-methyl-5-methoxy-6-[2-(2-piperidinethylamino)ethoxy]-1H-indol-3-yl}-1H-pyrrolo[2,3-b]pyridine;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

34. A compound selected from the group consisting of:

2-{5,6-Dimethoxy-1-[2-(4-methylpiperazin-1-yl)ethyl]-1H-indol-3-yl}-1H-pyrrolo[2,3-b]pyridine;

2-(4-{2-[5,6-Dimethoxy-3-(1H-pyrrolo[2,3-b]pyridin-2-yl)indol-1-yl]ethyl}piperazin-1-yl)ethanol;

2-(1-{2-[5,6-Dimethoxy-3-(1H-pyrrolo[2,3-b]pyridin-2-yl)indol-1-yl]ethyl}piperidin-4-yl)ethanol;

1'-{2-[5,6-Dimethoxy-3-(1H-pyrrolo[2,3-b]pyridin-2-yl)indol-1-yl]ethyl}-[1,4']bipiperidinyl;

1-{2-[5,6-Dimethoxy-3-(1H-pyrrolo[2,3-b]pyridin-2-yl)indol-1-yl]ethyl}piperidin-3-ol;

2-{5,6-Dimethoxy-1-[2-(4-methylperhydro-1,4-diazepin-1-yl)ethyl]-1H-indol-3-yl}-1H-pyrrolo[2,3-b]pyridine;

2-[5,6-Dimethoxy-3-(1H-pyrrolo[2,3-b]pyridin-2-yl)indol-1-yl]-1-(4-hydroxypiperidin-1-yl)ethanone;

2-[5,6-Dimethoxy-3-(1H-pyrrolo[2,3-b]pyridin-2-yl)indol-1-yl]-1-thiazolidin-3-ylethanone;

4-{[5,6-Dimethoxy-3-(1H-pyrrolo[2,3-b]pyridin-2-yl)indol-1-yl]acetyl}-1-methylpiperazin-2-one;

4-Chloro-2-(5,6-dimethoxy-1-methyl-1H-indol-3-yl)-1H-pyrrolo[2,3-b]pyridine;

2-(5,6-Dimethoxy-1-methyl-1H-indol-3-yl)-1H-pyrrolo[2,3-b]pyridine-4-carbonitrile;

4-Chloro-2-[5,6-dimethoxy-1-(2-morpholin-4-ylethyl)-1H-indol-3-yl]-1H-pyrrolo[2,3-b]pyridine;

2-(1-{2-[3-(4-chloro-1H-pyrrolo[2,3-b]pyridin-2-yl)-5,6-dimethoxyindol-1-yl]ethyl}piperidin-4-yl)ethanol;

4-Chloro-2-{5,6-dimethoxy-1-[2-(4-methylpiperazin-1-yl)ethyl]-1H-indol-3-yl}-1H-pyrrolo[2,3-b]pyridine;

2-{5,6-Dimethoxy-1-[2-(4-methylpiperazin-1-yl)ethyl]-1H-indol-3-yl}-1H-pyrrolo[2,3-b]pyridine-4-carbonitrile;

2-{5,6-Dimethoxy-1-methyl-1H-indol-3-yl)-5-fluoro-1H-pyrrolo[2,3-b]pyridine;

2-[5,6-Dimethoxy-1-[2-morpholin-4-ylethyl)-1H-indol-3-yl]-5-fluoro-1H-pyrrolo[2,3-b]pyridine;

2-{5,6-Dimethoxy-1-[2-(4-methylpiperazin-1-yl)ethyl]-1H-indol-3-yl}-5-fluoro-1H-pyrrolo[2,3-b]pyridine;

2-[5-Methoxy-1-methyl-3-(1H-pyrrolo[2,3-b]pyridin-2-yl)-1H-indol-6-yloxy]-1-morpholin-4-ylethanone;

2-[5-Methoxy-1-methyl-3-(1H-pyrrolo[2,3-b]pyridin-2-yl)-1H-indol-6-yloxy]-1-(4-methyl-[1,4]diazepan-1-yl)ethanone;

2-[5-Methoxy-1-methyl-3-(1H-pyrrolo[2,3-b]pyridin-2-yl)-1H-indol-6-yloxy]-N-[4-(4-methylpiperazin-1-yl)phenyl]acetamide;

2-[5-Methoxy-1-methyl-3-(1H-pyrrolo[2,3-b]pyridin-2-yl)-1H-indol-6-yloxy]-1-(4-methylpiperazin-1-yl)ethanone;

1-{4-[2-(2-Hydroxyethoxy)ethyl]piperazin-1-yl}-2-[5-methoxy-1-methyl-3-(1H-pyrrolo[2,3-b]pyridin-2-yl)-1H-indol-6-yloxy]ethanone;

(3aS,6aS)-5-{2-[5-Methoxy-1-methyl-3-(1H-pyrrolo[2,3-b]pyridin-2-yl)-1H-indol-6-yloxy]acetyl}hexahydropyrrolo[3,4-c]pyrrol-1-one trifluoroacetate;

2-{5-Methoxy-1-methyl-6-[3-(4-methylperhydro-1,4-diazepin-1-yl)propoxy]-1H-indol-3-yl}-1H-pyrrolo[2,3-b]pyridine;

4-Chloro-2-{1-methyl-1-methoxy-6-[2-(4-methylpiperazin-1-yl)ethoxy-1H-indol-3-yl}-1H-pyrrolo[2,3-b]pyridine;

4-Chloro-2-{1-methyl-5-methoxy-6-[2-(4-piperidylpiperidin-1-yl)ethoxy-1H-indol-3-yl}-1H-pyrrolo[2,3-b]pyridine;

4-Chloro-2-{5-methoxy-1-methyl-6-[2-(2-pyrrolidinethylamino)ethoxy]-1H-indol-3-yl}-1H-pyrrolo[2,3-b]pyridine; and 4-Chloro-2-{1-methyl-5-methoxy-6-[2-(2-piperidinethylamino)ethoxy]-1H-indol-3-yl}-1H-pyrrolo[2,3-b]pyridine;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

35. A pharmaceutical composition comprising at least one compound according to claim 1 and one or more pharmaceutically acceptable excipients.

36. A pharmaceutical composition comprising at least one compound according to claim 33 and one or more pharmaceutically acceptable excipients.

37. A pharmaceutical composition comprising at least one compound according to claim 34 and one or more pharmaceutically acceptable excipients.

38. The pharmaceutical composition according to claim 35 further comprising one or more antiproliferative agents.

39. The compound of formula (I) according to claim 3, wherein one of R2 and R3 represents —O-alkyl containing no more than 4 carbon atoms, substituted with —CO—NR7R8, —NR7R8, alkoxy, alkoxy-NR7R8 or free or esterified carboxyl;

R, R1, R4, R5, R6, R7 and R8 are as defined in claim 3;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

40. The compound of formula (I) according to claim 3, wherein one of R2 and R3 represents —O-alkyl containing no more than 4 carbon atoms, substituted with —CO—NR7R8, —NR7R8, alkoxy, or alkoxy—NR7R8;

R, R1, R4, R5, R6, R7 and R8 are as defined in claim 3;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

41. The compound of formula (I) according to claim 3, wherein one R2 and R3 represents —O-alkyl containing no more than 4 carbon atoms, substituted with —CO—NR7R8 or —NR7R8;

R, R1, R4, R5, R6, R7 and R8 are as defined in claim 3;

or a stereoisomer, a racemate, an enantiomer or a diastereoisomer of said compound of formula (I);

or a pharmaceutically acceptable addition salt of said compound of formula (I) with a mineral or organic acid or a mineral or organic base.

42. A pharmaceutical composition comprising at least one compound according to claim 3 and one or more pharmaceutically acceptable excipients.

* * * * *

UNITED STATES PATENT AND TRADEMARK OFFICE
CERTIFICATE OF CORRECTION

PATENT NO. : 7,528,147 B2
APPLICATION NO. : 11/541051
DATED : May 5, 2009
INVENTOR(S) : Sylvie Wentzler et al.

It is certified that error appears in the above-identified patent and that said Letters Patent is hereby corrected as shown below:

In column 16, line 35, delete "phenyl-CO-pyrazolyl-CO—," and insert -- phenyl-CO—, pyrazolyl-CO— --, therefor.

In column 20, line 40-41, delete "compounds;" and insert -- compounds --, therefor.

In column 27, line 5, delete "(F) may be prepared" and insert -- (F1) may be prepared --, therefor.

In column 53-54, line 6, delete "ethy}" and insert -- ethyl} --, therefor.

In column 56, line 63, delete "yl)ethylamino}" and insert -- yl}ethylamino) --, therefor.

In column 57, line 60, delete "[5,6-" and insert -- {5,6- --, therefor.

In column 57, line 61, delete "yl]propyl)" and insert -- yl}propyl) --, therefor.

In column 60, line 31, delete "1M" and insert -- 5M --, therefor.

In column 62, line 52, delete "[2,3-pyridine" and insert -- [2,3-b]pyridine --, therefor.

In column 68, line 12, delete "1-methyl 1H-indol" and insert -- 1-methyl-1H-indol --, therefor.

In column 74, line 25, delete "[M-I]" and insert -- [M-I]$^+$ --, therefor.

In column 76, line 20, delete "10b:" and insert -- 100b: --, therefor.

In column 77, line 47, delete "[M-SO2]$^+$;" and insert -- [M-SO$_2$]$^+$; --, therefor.

In column 78, line 39, delete "yl)-5" and insert -- yl}-5 --, therefor.

In column 85, line 24, delete "5-6" and insert -- 56 --, therefor.

Signed and Sealed this

Twenty-seventh Day of July, 2010

David J. Kappos
*Director of the United States Patent and Trademark Office*

CERTIFICATE OF CORRECTION (continued)
U.S. Pat. No. 7,528,147 B2

In column 94, line 60, delete "[1" and insert -- {1 --, therefor.

In column 94, line 62, delete "3-yl)" and insert -- 3-yl} --, therefor.

In column 96, line 13, delete "expected:" and insert -- expected --, therefor.

In column 100, line 17, delete "11.5" and insert -- 1.5 --, therefor.

In column 104, line 15, delete "hydroxyl" and insert -- hydroxy] --, therefor.

In column 105, line 1, delete "hydroxyl" and insert -- hydroxy] --, therefor.

In column 105, line 17, delete "189a," and insert -- 89a, --, therefor.

In column 108, line 27, delete "(2-(2" and insert -- [2-(2 --, therefor.

In column 108, line 66, delete "10.240 g" and insert -- 0.240 g --, therefor.

In column 109, line 42, delete "plus," and insert -- plus --, therefor.

In column 111, line 45, delete "sulfonyl]" and insert -- sulfonyl) --, therefor.

In column 113, line 8, delete "μg" and insert -- g --, therefor.

In column 124, line 4, delete "m/z=60.1" and insert -- m/z=601 --, therefor.

In column 124, line 36, delete "ethoxyethyl)" and insert -- methoxyethyl) --, therefor.

In column 129, line 10, delete "Dimethoxy-" and insert -- Dimethoxy-1- --, therefor.

In column 130, line 12, delete "[2,33-b]" and insert -- [2,3-b] --, therefor.

In column 140, line 41, delete "0.2107 g" and insert -- 0.207 g --, therefor.

In column 142, line 37, delete "dim ethoxybenzyl)" and insert -- dimethoxybenzyl) --, therefor.

In column 150, line 38, in Claim 2, delete "hydroxyl,or" and insert -- hydroxyl, or --, therefor.

In column 152, line 30, in Claim 3, delete "R3represents" and insert -- R3 represents --, therefor.

In column 152, line 37, in Claim 3, delete "—NR7R8. alkoxy. alkoxy-NR7R8." and insert -- —NR7R8, alkoxy, alkoxy-NR7R8, --, therefor.

In column 152, line 38, in Claim 3, delete "carboxyl." and insert -- carboxyl, --, therefor.